(12) United States Patent
Morris et al.

(10) Patent No.: US 7,390,833 B2
(45) Date of Patent: Jun. 24, 2008

(54) METHOD FOR TREATING ADAMTS-5-ASSOCIATED DISEASE

(75) Inventors: Elisabeth A. Morris, Sherborn, MA (US); Sonya Glasson, Belmont, MA (US); Jason Shaoyun Xiang, Winchester, MA (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 10/983,981

(22) Filed: Nov. 8, 2004

(65) Prior Publication Data

US 2006/0004066 A1 Jan. 5, 2006

Related U.S. Application Data

(60) Provisional application No. 60/526,883, filed on Dec. 4, 2003.

(51) Int. Cl.
| | |
|---|---|
| A01N 41/02 | (2006.01) |
| A01N 37/34 | (2006.01) |
| A01N 37/30 | (2006.01) |
| A01N 37/12 | (2006.01) |
| A01N 37/44 | (2006.01) |
| A61K 31/275 | (2006.01) |
| A61K 31/205 | (2006.01) |
| A61K 31/195 | (2006.01) |
| A61K 31/255 | (2006.01) |

(52) U.S. Cl. ............ 514/518; 514/520; 514/555; 514/562

(58) Field of Classification Search ........... 514/520, 514/555, 562
See application file for complete search history.

(56) References Cited

U.S. PATENT DOCUMENTS

| | | | |
|---|---|---|---|
| 6,376,665 B1 | 4/2002 | Duan | |
| 6,391,610 B1 * | 5/2002 | Apte et al. | 435/226 |
| 6,451,575 B1 | 9/2002 | Arner et al. | 435/226 |
| 6,566,381 B1 * | 5/2003 | Cheng et al. | 514/365 |

FOREIGN PATENT DOCUMENTS

WO    WO 03-066822    8/2003

OTHER PUBLICATIONS

Collins-Racie et al., 2004, Matrix Biol. 23:219-230.
Glasson et al., 2004, Arthritis & Rhuem, 50:2547-2558.
Clements et al., 2003, Arthritis & Rhuem 48:3452-3463.
Somerville et al., 2003, Biol. Chem. 278:9503-9513.
Little et al., 2002, Arthritis & Rhuem 46:124-129.
Bau et al., 2002, Arthritis & Rhuem 46:2648-2657.
Tortorella et al., 2002, Matrix Biol. 21:499-511.
Rodriguez-Manzaneque et al., 2002, Biochem Biophys. Res. Commun. 293:501-508.
Yamanashi et al., 2002, J. Immunol. 168:1405-1412.
Tortorella et al., 2001, Osteoarthritis Cartilage 9:539-552.
Chambers et al., 2001, Arthritis & Rhuem 44:1455-1465.
Curtis et al., 2000, J. Biol. Chem 275:721-724.
Tortorella et al., 2000, J. Biol. Chem. 275:18566-18573.
Kuno et al., 2000, FEBS Letters 478:241245.
M.A. Abramov, W. Dehaen, B. D'hooge, M.L. Petrov, S. Smeets, S. Toppet and M. Voets Tetrahedron, 2000, 56, 3933-3940.
Tortorella et al., 1999, Science 284:1664-1666.
Abbaszade et al., 1999, J. Biol. Chem. 274:23443-23450.
Lohmander, Neame and Sandy, 1993, Arthritis & Rhuem 36:1214-1223.
Farndale et al., 1986, Biochim Biophys Acta 883:173-177.
Sandy et al., 1991, J. Biol. Chem. 266:8683-8685.
Database HCAPLUS on STN (DN 134:305005, Biorg. & Med. Chem. Let., 2001, 11(2)91-94, abstract).
Database HCAPLUS on STN (DN 137:183746, J. Biol. Chem., 2002, 277(25)22201-208, abstract).
Database HCAPLUS on STN (DN 139:175864, WO 2003066822).

* cited by examiner

*Primary Examiner*—Ardin Marschel
*Assistant Examiner*—Amy A Lewis
(74) *Attorney, Agent, or Firm*—Fitzpatrick, Cella, Harper & Scinto

(57) ABSTRACT

The present invention relates to methods of treating ADAMTS-5-associated diseases and particularly osteoarthritis comprising administering an agent capable of modulating ADMATS-5 activity to a subject afflicted with the disease. The agent is preferably a biaryl sulfonamide compound. The invention is based, in part, on the discovery that transgenic animals that do not express functional ADAMTS-5 show a reduction in the degree of osteoarthritis after the induction of osteoarthritis as compared to WT animals. Furthermore, the ADAMTS-5 transgenic animals have reduced aggrecanase activity in articular tissue as compared to WT animals. These animals are good models for ADAMTS-5-associated diseases, and for screening of drugs useful in the treatment and/or prevention of these diseases. There are no other animal models in which the deletion of the activity of a single gene is capable of abrogating the course of osteoarthritis. Accordingly, these animals also show that osteoarthritis can be prevented and/or treated by administering to a subject an ADAMTS-5 inhibitory agent and particularly an agent capable of inhibiting the aggrecanase activity of ADAMTS-5.

29 Claims, 8 Drawing Sheets

METHOD FOR TREATING ADAMTS-5-ASSOCIATED DISEASE

CROSS REFERENCE TO RELATED APPLICATIONS

This application claims priority under 35 U.S.C. § 119(e) to U.S. Provisional Application No. 60/526,883, filed Dec. 4, 2003.

FIELD OF THE INVENTION

The present invention relates to a method of treating an ADAMTS-5-associated disease, and particularly, osteoarthritis. As employed herein, the term "ADAMTS" means a disintegrin and metalloprotease with thrombosondin type I motifs. As employed herein, the term "KO" refers to animals carrying a mutation resulting in substantial reduction or absence of expression of a gene product, such as the ADAMTS-5 gene product in the cells of the transgenic animal.

BACKGROUND OF THE INVENTION

Osteoarthritis is a pathologic condition in synovial joints characterized by cartilage extracellular matrix degradation. A major component of cartilage extracellular matrix is the proteoglycan aggrecan. Pathologic cleavage of aggrecan occurs at 2 primary sites within the interglobular domain of the protein backbone which results in release of the functional entity from the extracellular matrix. One site ($N^{341-342}F$) is cleaved by matrix metalloproteases (MMPs), while a second, non-MMP cleavage site within aggrecan is at $E^{373-374}A$. The $E^{373-374}A$ cleavage site has been identified as an important site of degradation in osteoarthritic synovial fluid samples (Lohmander, Neame and Sandy, 1993, *Arthritis & Rhuem* 36:1214) and cytokine stimulated cartilage cultures (Sandy et al., 1991, *J. Biol. Chem.* 266:8683). Several ADAMTS enzymes have been demonstrated to be capable of cleaving aggrecan at the $E^{373-374}A$, or "aggrecanase" site (Kuno et al., 2000, *FEBS Letters* 478 :241; Rodriquez-Manzaneque et al., 2002, *Biochem. Biophys. Res. Commun.* 293:501; Somerville et al., 2003, *Biol. Chem.* 278:9503; U.S. Pat. No. 6,451,575). ADAMTS-4 and ADAMTS-5, or Aggrecanase-1 and Aggrecanase-2, respectively, appear to be the two enzymes capable of being synthesized by articular cartilage with by far (>1000 fold) the most efficient "aggrecanase" activity (Tortorella et al., 1999, *Science* 284:1664; and Abbaszade et al., 1999, *J. Biol. Chem.* 274:23443). However, it is not clear whether these enzymes, either collectively or independently, are responsible for the aggrecan degradation in osteoarthritis.

Evidence of ADAMTS-4 in joint disease is found in several reports of increased expression of ADAMTS-4 after stimulation of articular tissues with inflammatory cytokines. Bau et al., 2002, *Arthritis & Rhuem* 46:2648-2657; Curtis et al., 2000, *J. Biol. Chem.* 275:721-724; Tortorella et al., 2001, *Osteoarthritis Cartilage* 9:539-552; Little et al., 2002, *Arthritis & Rhuem* 46:124-129; and Yamanashi et al., 2002, *J. Immunol.* 168:1405-1412. In vitro findings indicate that ADAMTS-4 is one of the few enzymes that can efficiently cleave aggrecan at the site that is cleaved in naturally occurring disease. Tortorella et al., 2000, *J. Biol. Chem.* 275:18566-18573; Tortorella et al., 2002, *Matrix Biol.* 21:499-511.

In addition, aggrecanases are known to play a role in other disorders in which extracellular protein degradation or destruction occurs, such as cancer, asthma, chronic obstructive pulmonary disease ("COPD"), atherosclerosis, age-related macular degeneration, myocardial infarction, corneal ulceration and other ocular surface diseases, hepatitis, aortic aneurysms, tendonitis, central nervous system diseases, abnormal wound healing, angiogenesis, restenosis, cirrhosis, multiple sclerosis, glomerulonephritis, graft versus host disease, diabetes, inflammatory bowel disease, shock, invertebral disc degeneration, stroke, osteopenia, and periodontal diseases.

The generation of the ADAMTS-4 knockout (KO) has previously been reported (Glasson et al., 2004, *Arthritis and Rheum,* 50:2547-2558). While many reports showed at least some evidence that ADAMTS-4 is involved in the development of osteoarthritis, surprisingly this mouse did not show any differences in the onset of osteoarthritis than wild-type (WT) and did not exhibit any difference in aggrecanase activity. Although, it is still possible that ADAMTS-4 is involved in osteoarthritis in other animals, including humans, to date, the aggrecanase activity associated with the pathological accumulation of aggrecan degradation products has not been identified.

SUMMARY OF THE INVENTION

The present invention provides a method for treating an ADAMTS-5-associated disease, and particularly osteoarthritis, comprising administering to a subject an effective amount of an ADAMTS-5 inhibitory agent. In one embodiment, the ADAMTS-5 inhibitory agent inhibits the metalloproteinase activity of ADAMTS-5. In another embodiment, the agent inhibits the aggrecanase activity of ADAMTS-5. Particularly preferred agents that are useful for treating ADAMTS-5-associated diseases, and particularly osteoarthritis, include biaryl sulfonamide compounds and antibodies that bind to and inhibit ADAMTS-5.

Preferred biaryl sulfonamide compounds of the invention are those of the formula I:

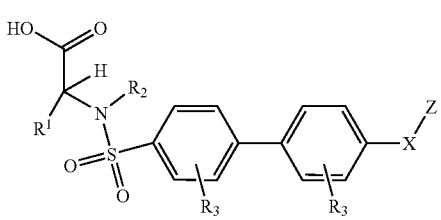

wherein:
R$^1$ is H or C1-C6 alkyl;
R$^2$ is H, C1-C6 alkyl, $(CH_2)_nR^{2'}$, phenyl, or benzyl;
n is 0-6;
R$^{2'}$ is aryl, heteroaryl, cycloalkyl, or heterocycloalkyl;
R$^3$ is, independently with respect to each occurrence, H, halogen, OC(halogen)$_3$, C(halogen)$_3$, alkoxy, or C1-C6 alkyl;
X is selected from $CH_2O$, $OCH_2$, $C(R^3)=C(R^3)$, $C(R^3)_2—C(R^3)_2$, $CH_2NHC(=O)$, $O(C=O)NH$, O, $C(=O)CH_2$, $SO_2CH_2C(=O)NH$, $SO_2NH$, $OC(=O)$, $CH_2S(O)$, and $CH_2S(O)_2$; and
Z is at least one aryl or heteroaryl moiety.

Particularly preferred biaryl sulfonamides of the invention are listed in Table 1 below in Example 4.

In addition, the present invention provides a method for identifying agents useful for the treatment of osteoarthritis using the transgenic animals of the invention, and cells isolated therefrom. In a particularly embodiment, the methods comprise administering to an ADAMTS-5 transgenic animal of the invention and an animal having ADAMTS-5 activity a potential therapeutic agent and determining whether the potential therapeutic agent is capable of abrogating the onset of induced osteoarthritis in the WT type animal but not in the ADAMTS-5 transgenic animal. In another embodiment, the methods comprise contacting a cell derived from an ADAMTS-5 transgenic animal and a cell derived from an animal having ADAMTS-5 activity, with a potential therapeutic agent, and determining whether the agent inhibits metalloproteinase activity in the cell having ADAMTS-5 activity but not in the ADAMTS-5 transgenic animal cell. Both methods may further comprise determining whether the agent inhibits ADAMTS-5 metalloproteinase activity and/or aggrecanase activity.

In a further embodiment, the methods of identifying potential agents useful for the treatment of ADAMTS-5-associated diseases, and particularly osteoarthritis, comprise identifying agents that inhibit ADAMTS-5 by contacting ADAMTS-5 and determining whether the agent inhibits ADAMTS-5. In a preferred embodiment, the agent inhibits the metalloproteinase activity of ADAMTS-5. In a particularly preferred embodiment, the agent inhibits the aggrecanase activity of ADAMTS-5.

BRIEF DESCRIPTION OF THE DRAWINGS

These and other aspects of the invention will be more clearly understood by reference to the following detailed description of exemplary embodiments in conjunction with the accompanying drawings, in which.

DETAILED DESCRIPTION OF THE INVENTION

Figure 1:
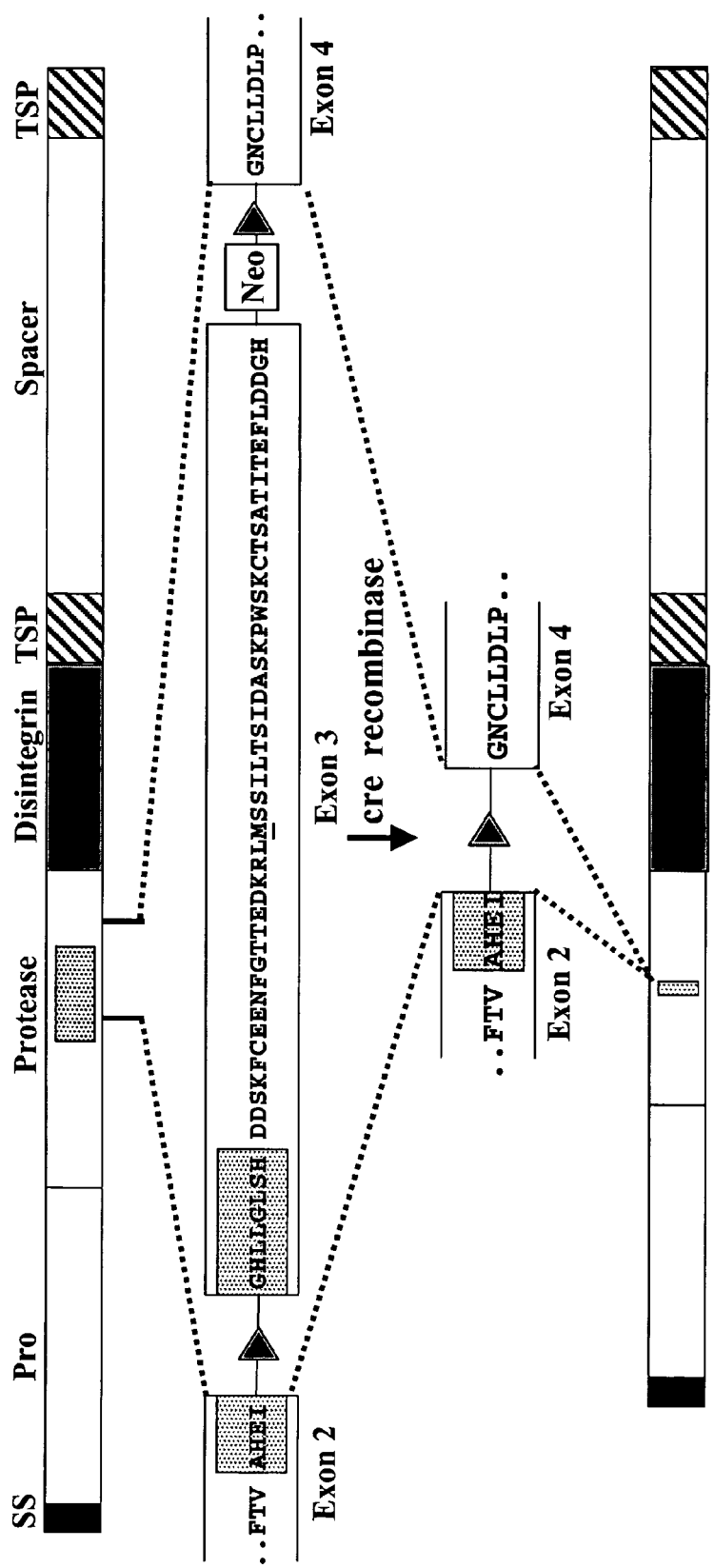
FIG. 1 illustrates the targeted disruption of the murine ADAMTS-5 gene (A) shows a map of the amino acid sequence of ADAMTS-5, (B) shows the allelic characterization of the ADAMTS-5 KO animal and the location of primers used to generate PCR products, (C) shows PCR products generated using primers 1 and 2 shown in 1B, and PCR products generated using primers 3 and 4 shown in 1B, (D) shows a map of the site of primers used in reverse transcriptase (RT) PCR to identify mRNA in WT and KO animals, (E) shows RT-PCR products generated using primers 4 and 5, and (G) shows RT-PCR products generated using primers 4 and 6.
Figure 1:
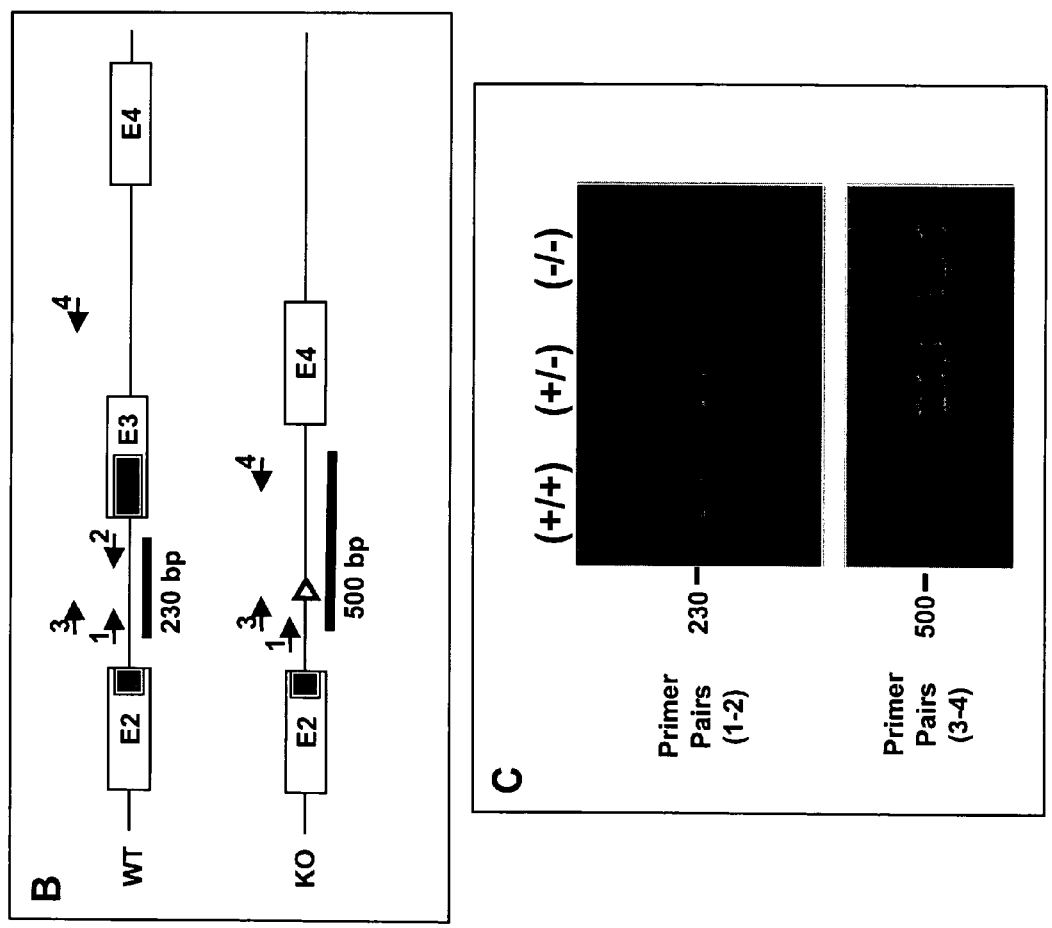
Figure 1:
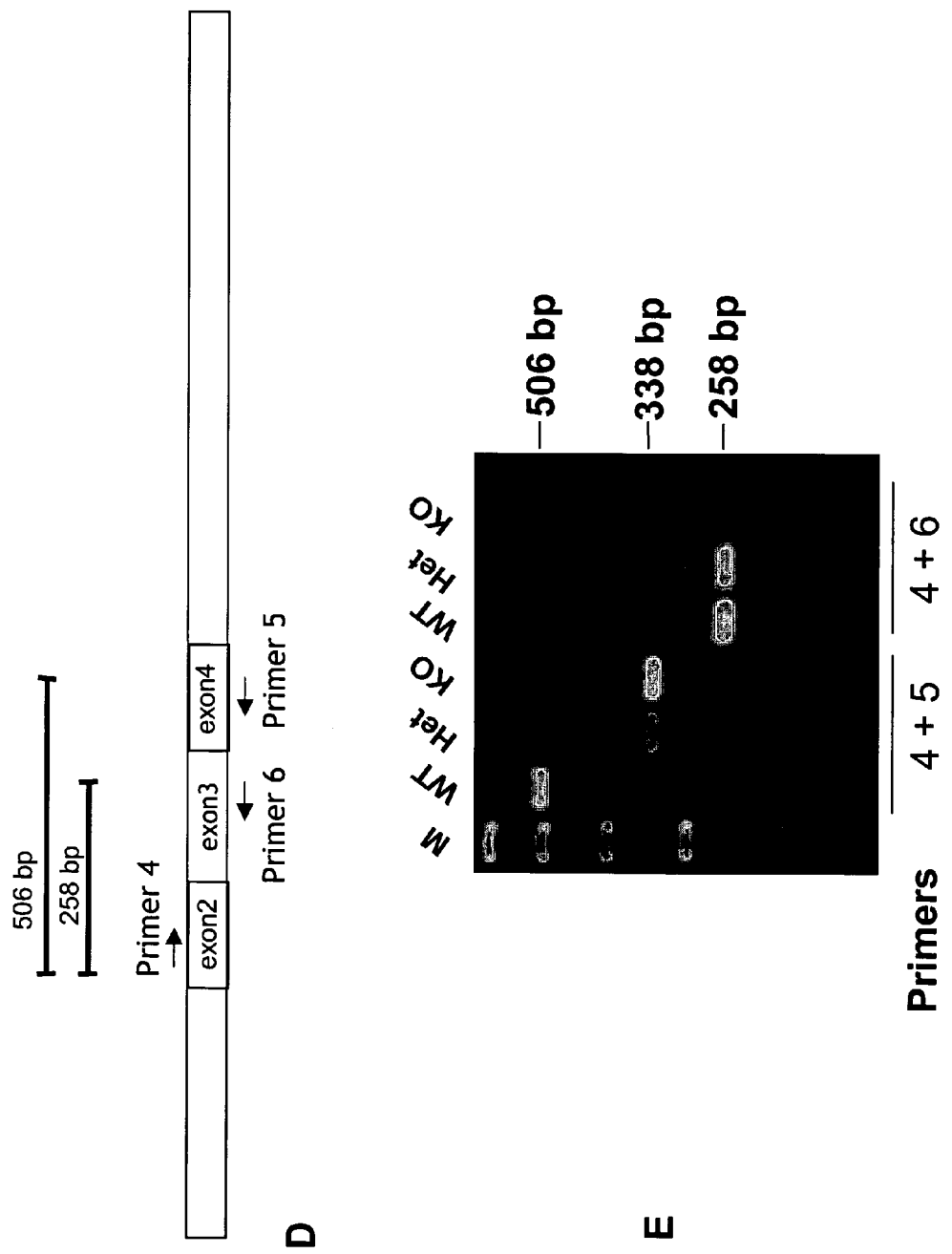

The present invention relates to the discovery that the expression of ADAMTS-5 is directly involved in osteoarthritis. Transgenic ADAMTS-5 KO mice are resistant to the onset of osteoarthritis when stimulated to develop osteoarthritis. These transgenic animals represent the first animal model in which the disruption in a single gene has resulted in resistance to osteoarthritis. Accordingly, this discovery has led to the determination that ADAMTS-5 is a drug target molecule for the treatment of osteoarthritis and that inhibitors, preferably aggrecanase inhibitors, of ADAMTS-5 can be used to treat osteoarthritis.

Therefore, the present invention relates to a method of preventing and/or treating osteoarthritis comprising administering to a subject an effective amount of an agent that inhibits ADAMTS-5. Such agents include, but are not limited to antisense RNA, drug compounds, particularly those that bind to and inhibit the metalloproteinase site of ADAMTS-5, peptides and proteins, and antibodies capable of binding to and inhibiting ADAMTS-5.

The term "effective amount," as used herein, refers to the amount of an agent, that when administered to a subject, is effective to at least partially ameliorate (and in preferred embodiments, prevent and/or cure) a condition from which the subject is suspected to suffer.

In one preferred embodiment, the agent is an anti-ADAMTS-5 antibody that is capable of inhibiting ADAMTS-5 metalloproteinase activity and/or aggrecanase activity. In a particularly preferred embodiment, the antibody inhibits ADAMTS-5. Such antibodies are further discussed below in Example 5.

In another preferred embodiment, the agent is a biaryl sulfonamide compound which has been found to act as a metalloproteinase inhibitor and/or an aggrecanase inhibitor. In a particularly preferred embodiment the agent is a biaryl sulfonamide compound that has been found to act as an ADAMTS-5 inhibitor and is capable of inhibiting the aggrecanase activity of ADAMTS-5.

In a preferred embodiment, the biaryl sulfonamide compound is of the formula I:

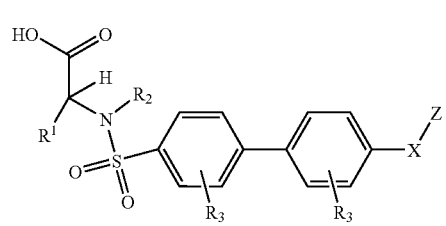

wherein:

$R^1$ is H or C1-C6 alkyl;

$R^2$ is H, C1-C6 alkyl, $(CH_2)_nR^{2'}$, phenyl, or benzyl;

n is 0-6;

$R^{2'}$ is aryl, heteroaryl, cycloalkyl, or heterocycloalkyl;

$R^3$ is, independently with respect to each occurrence, H, halogen, $OC(halogen)_3$, $C(halogen)_3$, alkoxy, or C1-C6 alkyl;

X is selected from $CH_2O$, $OCH_2$, $C(R^3)=C(R^3)$, $C(R^3)_2$—$C(R^3)_2$, $CH_2NHC(=O)$, $O(C=O)NH$, O, $C(=O)CH_2$, $SO_2CH_2C(=O)NH$, $SO_2NH$, $OC(=O)$, $CH_2S(O)$, and $CH_2S(O)_2$; and Z is at least one aryl or heteroaryl moiety.

It is understood that the foregoing definition includes pharmaceutically acceptable salts and pro-drugs of these compounds.

In one embodiment, Z is pyridine, pyrimidine, pyrazine, pyridazine, phenyl, naphthalene, furan, thiophene, pyrrole, pyrazole, imidazole, oxazole, isoxazole, thiazole, benzothiazole, quinoline, or isoquinoline, or

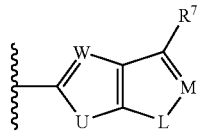

wherein:
U is selected from S, O, $C(R^3)=C(R^3)$, $C(R^3)=N$, and $N(R^4)$;
W is selected from $C(R^3)$, and N;
M is selected from $C(R^3)$, and N;
L is selected from S, O, $C(R^3)=C(R^3)$, $C(R^3)=N$, and $N(R^4)$;
$R^4$ and $R^5$ are, independently with respect to each occurrence, a bond to the other, H, C1-C6 alkyl, or phenyl;
$R^7$ is selected from a bond to $R^3$, H, halogen, $C(halogen)_3$, $NR^4R^5$, $N[(CH_2)_2]_2O$, $N[(CH_2)_2]_2NR^4$, $NHSO_2R^4$, $NR^4C(=O)R^5$, $NHC(=O)OR^4$, $NO_2$, $SO_2NR^4R^5$, $SO_2R^4$, $OR^4$, $C(=O)R^4$, $COOR^4$, $CONR^4R^5$, CN, phenyl, heteroaryl, C1-C6 alkyl, C2-C6 alkenyl, or C2-C6 alkynyl; and
$R^8$ is selected from H, phenyl, heteroaryl, and C1-C6 alkyl.
$R^7$, when substituted, is preferably substituted with $NR^4R^5$, $N[(CH_2)_2]_2O$, $N[(CH_2)_2]_2NR^4$, $NHSO_2R^4$, $NR^4C(=O)R^5$, $NHC(=O)OR^4$, $NO_2$, $SO_2NR^4R^5$, $SO_2R^4$, $OR^8$, $C(=O)R^4$, $COOR^4$, $CONR^4R^5$, CN, phenyl, or heteroaryl.
$R^8$, when substituted, is preferably substituted with $NR^4R^5$, $N[(CH_2)_2]_2O$, $N[(CH_2)_2]_2NR^4$, $NR^4SO_2R^5$, $NR^4C(=O)R^5$, $NHC(=O)OR^4$, $NO_2$, $SO_2NR^4R^5$, $SO_2R^4$, $C(=O)R^4$, $COOR^4$, $CONR^4R^5$, CN, phenyl, or heteroaryl.

Preferred among the above noted $R^1$ groups are H and branched alkyl, and more preferably isopropyl.

Preferred among the above noted $R^3$ groups are halogen, $CF_3$, $OCH_3$, and $CH_3$.

Preferred among the above noted X groups are $CH_2O$, $OCH_2$, $C(R^3)=C(R^3)$, and $CH_2NHC(=O)$.

Preferred among the above noted $R^7$ groups are $CH_3$, ethyl, isopropyl, $CF_3$, CN, and $OCH_3$.

Preferred among the above noted $R^8$ groups are CH3, phenyl, and benzyl.

In one embodiment, X is $CH_2O$, and Z is aryl or heteroaryl, preferably bicyclic.

A preferred biarylsulfanomide is shown in Formula 2 which follows:

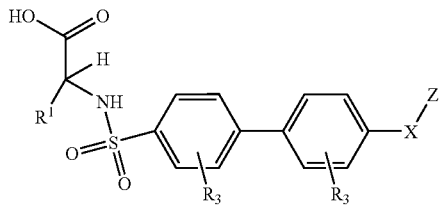

wherein
R1 is H or $C_1$-$C_6$ alkyl
Rc is H, Halogen, or $C_1$-$C_6$ alkyl

X is O, $CH_2O$ or $OCH_2$; and
Z is at least one aryl or heteroaryl moiety.

When Z is aryl, preferred moieties include substituted phenyl. Substituents for the phenyl group preferably include OH, halogen, $C_1$-$C_6$ alkoxy, benzoyl, $C_1$-$C_6$ alkyl or $C_1$-$C_6$ alkoyl.

When Z is a heteroaryl, preferred moieties include benzyfuranyl, pyridyl, indolyl.

In another embodiment, X is $OCH_2$, and Z is aryl or heteroaryl, preferably bicyclic.

In a further embodiment, X is $C(R^3)=C(R^3)$, and Z is aryl or heteroaryl, preferably bicyclic. More preferably, X is a trans carbon-carbon double bond.

In yet another embodiment, X is $C(R^3)_2$—$C(R^3)_2$, Z is aryl or heteroaryl, preferably bicyclic.

In one embodiment, X is $CH_2NHCO$, Z is aryl or heteroaryl, preferably bicyclic.

When X is carbamate O—CO—NH, Z is preferably aryl or heteroaryl, preferably bicyclic.

In one embodiment X is $CO_2$, Z is aryl or heteroaryl, preferably bicyclic.

In another embodiment, X is O, Z is aryl or heteroaryl, preferably bicyclic.

In a further embodiment, X is $C(=O)CH_2$, Z is aryl or heteroaryl, preferably bicyclic.

In one embodiment, X is $SO_2CH_2$, Z is aryl or heteroaryl, preferably bicyclic.

In one embodiment, X is $OCH_2$, Z is aryl or heteroaryl, preferably bicyclic. Preferably, if substituted, the substitution is on the second phenyl ring.

In one embodiment, X is $OCH_2$, Z is aryl or heteroaryl, preferably bicyclic. Preferably, if substituted, the substitution is on the first phenyl ring.

In one embodiment, X is $CH_2OCH_2$, Z is aryl or heteroaryl, preferably bicyclic. Preferably, if substituted, the substitution is on the first phenyl ring.

The term "alkyl", as used herein, whether used alone or as part of another group, refers to a substituted or unsubstituted aliphatic hydrocarbon chain and includes, but is not limited to, straight and branched chains containing from 1 to 12 carbon atoms, preferably 1 to 6 carbon atoms, unless explicitly specified otherwise. For example, methyl, ethyl, propyl, isopropyl, butyl, i-butyl and t-butyl are encompassed by the term "alkyl." C1-C6 alkyl includes straight and branched chain aliphatic groups having from 1 to 6 carbons. Specifically included within the definition of "alkyl" are those aliphatic hydrocarbon chains that are optionally substituted.

The carbon number as used in the definitions herein refers to carbon backbone and carbon branching, but does not include carbon atoms of the substituents, such as alkoxy substitutions and the like.

The term "alkenyl", as used herein, whether used alone or as part of another group, refers to a substituted or unsubstituted aliphatic hydrocarbon chain and includes, but is not limited to, straight and branched chains having 2 to 8 carbon atoms and containing at least one double bond. Preferably, the alkenyl moiety has 1 or 2 double bonds. Such alkenyl moieties may exist in the E or Z conformations and the compounds of this invention include both conformations. C2-C6 alkenyl includes a 1 to 6 carbon straight or branched chain having at least one carbon-carbon double bond. Specifically included within the definition of "alkenyl" are those aliphatic hydrocarbon chains that are optionally substituted. Heteroatoms, such as O, S or N—R1, attached to an alkenyl should not be attached to a carbon atom that is bonded to a double bond.

The term "alkynyl" refers to a hydrocarbon moiety containing at least one carbon-carbon triple bond. C2-C6 alkynyl includes a 1 to 6 carbon straight or branched chain having at least one carbon-carbon triple bond.

The term "cycloalkyl" refers to a monocyclic, bicyclic, tricyclic, fused, bridged, or spiro monovalent saturated hydrocarbon moiety, wherein the carbon atoms are located inside or outside of the ring system. Any suitable ring position of the cycloalkyl moiety may be covalently linked to the defined chemical structure. Examples of cycloalkyl moieties include, but are not limited to, chemical groups such as cyclopropyl, cyclopropylmethyl, cyclobutyl, cyclopentyl, cyclohexyl, cyclohexylmethyl, cyclohexylethyl, cycloheptyl, norbornyl, adamantyl, spiro[4.5]decanyl, and homologs, isomers, and the like. C3-C6 cycloalkyl includes monocyclic, saturated rings of 3 to 6 carbons, optionally substituted with $R^3$, or spiro unsaturated hydrocarbon moiety. Examples are cyclopentane, cyclohexane, and cyclohexadiene.

The term "cycloalkenyl" refers to a monocyclic, bicyclic, tricyclic, fused, bridged, or spiro monovalent saturated hydrocarbon moiety, wherein the carbon atoms are located inside or outside of the ring system. Any suitable ring position of the cycloalkyl moiety may be covalently linked to the defined chemical structure. Examples of cycloalkyl moieties include, but are not limited to, chemical groups such as cyclopropyl, cyclopropylmethyl, cyclobutyl, cyclopentyl, cyclohexyl, cyclohexylmethyl, cyclohexylethyl, cycloheptyl, norbornyl, adamantyl, spiro[4.5]decanyl, and homologs, isomers, and the like. C3-C6 cycloalkyl includes monocyclic, saturated rings of 3 to 6 carbons, optionally substituted with $R^3$.

"Aryl" refers to an unsaturated cyclic hycrocarbons with one or more rings, and may be fused with a carbocyclic or heterocyclic ring at any possible position. Aryl compounds generally have molecules with the ring structure characteristic of benzene, naphthalene, or the like.

"Heteroaryl" refers to a 5 to 6 membered aryl heterocyclic ring which contains from 1 to 3 heteroatoms selected from the group consisting of oxygen, nitrogen, and sulfur atoms in the ring and may be fused with a carbocyclic or heterocyclic ring at any possible position. Including unsaturated hetrocyclics that are not aromatic, such as theinyl, furyl, pyrrolyl and the like.

"Heterocycloalkyl" refers to a 5 to 7-membered saturated ring containing carbon atoms and from 1 to 2 heteroatoms selected from N, O, and S.

The term "phenyl", as used herein, whether used alone or as part of another group, refers to a substituted or unsubstituted phenyl group.

An optionally substituted moiety may be substituted with one or more substituents. Suitable optionally substituents may be selected independently from H, halogen, C1-C6 alkyl, C2-C6 alkenyl, C2-C6 alkynyl, $NR^4R^5$, $N[(CH_2)_2]_2O$, $N[(CH_2)_2]_2NR^4$, $NHSO_2R^4$, $NR^4C(\!=\!O)R^5$, $NHC(\!=\!O)OR^4$, $NO_2$, $SO_2NR^4R^5$, $SO_2R^4$, $OR^4$, $C(\!=\!O)R^4$, $COOR^4$, $CONR^4R^5$, and CN.

When such moieties are substituted, for example, they may typically be mono-, di-, tri- or persubstituted. Examples for a halogen substituent include 1-bromo vinyl, 1-fluoro vinyl, 1,2-difluoro vinyl, 2,2-difluorovinyl, 1,2,2-trifluorovinyl, 1,2-dibromo ethane, 1,2 difluoro ethane, 1-fluoro-2-bromo ethane, $CF_2CF_3$, $CF_2CF_2CF_3$, and the like.

The term halogen includes bromine, chlorine, fluorine, and iodine.

For the sake of simplicity, connection points ("-") are not depicted. When an atom or compound is described to define a variable, it is understood that it is intended to replace the variable in a manner to satisfy the valency of the atom or compound. For example, when L is $C(R^3)\!=\!C(R^3)$, both carbon atoms form a part of the ring in order to satisfy their respective valences.

The term "pharmaceutically acceptable salt", as used herein, refers to salts derived form organic and inorganic acids such as, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, camphorsulfonic, and similarly known acceptable acids when a compound of this invention contains a basic moiety. Salts may also be formed from organic and inorganic bases, preferably alkali metal salts, for example, sodium, lithium, or potassium, when a compound of this invention contains a carboxylate or phenolic moiety, or similar moiety capable of forming base addition salts.

The term "subject", as used herein, refers to a mammal, preferably a human.

The terms "administer", "administering", or "administration", as used herein, refer to either directly administering a compound or composition to a patient, or administering a prodrug derivative or analog of the compound to the patient, which will form an equivalent amount of the active compound or substance within the patient's body.

The term "carrier", as used herein, shall encompass carriers, excipients, and diluents.

The compounds of this invention may contain an asymmetric carbon atom and some of the compounds of this invention may contain one or more asymmetric centers and may thus give rise to optical isomers and diastereomers. While shown without respect to stereochemistry in formula I, the present invention includes such optical isomers and diastereomers; as well as the racemic and resolved, enantiomerically pure R and S stereoisomers; as well as other mixtures of the R and S stereoisomers and pharmaceutically acceptable salts thereof. Where a stereoisomer is preferred, it may in some embodiments be provided substantially free of the corresponding enantiomer. Thus, an enantiomer substantially free of the corresponding enantiomer refers to a compound that is isolated or separated via separation techniques or prepared free of the corresponding enantiomer. "Substantially free", as used herein, means that the compound is made up of a significantly greater proportion of one stereoisomer, preferably less than about 50%, more preferably less than about 25%, and even more preferably less than about 10% of the corresponding enantiomer.

The present invention thus provides pharmaceutical compositions comprising at least one biaryl sulfonamide compound and one or more pharmaceutically acceptable carriers, excipients, or diluents.

Examples of such carriers are well known to those skilled in the art and are prepared in accordance with acceptable pharmaceutical procedures, such as, for example, those described in Remington's Pharmaceutical Sciences, 17th edition, ed. Alfonoso R. Gennaro, Mack Publishing Company, Easton, Pa. (1985), which is incorporated herein by reference in its entirety. Pharmaceutically acceptable carriers are those that are compatible with the other ingredients in the formulation and biologically acceptable.

The compounds of this invention may be administered orally or parenterally, alone or in combination with conventional pharmaceutical carriers. Applicable solid carriers can include one or more substances which may also act as flavoring agents, lubricants, solubilizers, suspending agents, fillers, glidants, compression aids, binders or tablet-disintegrating agents or encapsulating materials. They are formulated in conventional manner, for example, in a manner similar to that used for known antihypertensive agents, diuretics and β-blocking agents. Oral formulations containing the active compounds of this invention may comprise any conventionally used oral forms, including tablets, capsules, buccal forms, troches, lozenges and oral liquids, suspensions or solutions. In powders, the carrier is a finely divided solid, which is an admixture with the finely divided active ingredient. In tablets, the active ingredient is mixed with a carrier having the necessary compression properties in suitable proportions and compacted in the shape and size desired. The powders and tablets preferably contain up to 99% of the active ingredient.

Capsules may contain mixtures of the active compound(s) with inert fillers and/or diluents such as the pharmaceutically acceptable starches (e.g. corn, potato or tapioca starch), sugars, artificial sweetening agents, powdered celluloses, such as crystalline and microcrystalline celluloses, flours, gelatins, gums, and the like.

Useful tablet formulations may be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, sodium lauryl sulfate, talc, sugars, lactose, dextrin, starch, gelatin, cellulose, methyl cellulose, microcrystalline cellulose, sodium carboxymethyl cellulose, carboxymethylcellulose calcium, polyvinylpyrrolidine, alginic acid, acacia gum, xanthan gum, sodium citrate, complex silicates, calcium carbonate, glycine, sucrose, sorbitol, dicalcium phosphate, calcium sulfate, lactose, kaolin, mannitol, sodium chloride, low melting waxes and ion exchange resins. Preferred surface modifying agents include nonionic and anionic surface modifying agents. Representative examples of surface modifying agents include, but are not limited to, POLOAXEMER 188, a block copolymer of ethylene glycol and propylene glycol, benzalkonium chloride, calcium stearate, cetostearl alcohol, cetomacrogol emulsifying wax, sorbitan esters, colliodol silicon dioxide, phosphates, sodium dodecylsulfate, magnesium aluminum silicate, and triethanolamine. Oral formulations herein may utilize standard delay or time release formulations to alter the absorption of the active compound(s). The oral formulation may also consist of administering the active ingredient in water or fruit juice, containing appropriate solubilizers or emulsifiers as needed.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellant.

Liquid pharmaceutical compositions, which are sterile solutions or suspensions, can be utilized by, for example, intramuscular, intraperitoneal or subcutaneous injection. Sterile solutions can also be administered intravenously. Compositions for oral administration may be in either liquid or solid form.

Preferably the pharmaceutical composition is in unit dosage form, e.g. as tablets, capsules, powders, solutions, suspensions, emulsions, granules, or suppositories. In such form, the composition is sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form. Such unit dosage form may contain from about 1 mg/kg to about 250 mg/kg, and may given in a single dose or in two or more divided doses. Such doses may be administered in any manner useful in directing the active compounds herein to the recipient's bloodstream, including orally, via implants, parenterally (including intravenous, intraperitoneal and subcutaneous injections), rectally, vaginally, and transdermally. Such administrations may be carried out using the present compounds, or pharmaceutically acceptable salts thereof, in lotions, creams, foams, patches, suspensions, solutions, and suppositories (rectal and vaginal).

When administered for the treatment or inhibition of a particular disease state or disorder, it is understood that the effective dosage may vary depending upon the particular compound utilized, the mode of administration, the condition, and severity thereof, of the condition being treated, as well as the various physical factors related to the individual being treated. In therapeutic application, compounds of the present invention are provided to a patient already suffering from a disease in an amount sufficient to cure or at least partially ameliorate the symptoms of the disease and its complications. An amount adequate to accomplish this is defined as a "therapeutically effective amount". The dosage to be used in the treatment of a specific case must be subjectively determined by the attending physician. The variables involved include the specific condition and the size, age and response pattern of the patient.

In some cases it may be desirable to administer the compounds directly to the airways in the form of an aerosol. For administration by intranasal or intrabrachial inhalation, the compounds of this invention may be formulated into an aqueous or partially aqueous solution.

The compounds of this invention may be administered parenterally or intraperitoneally. Solutions or suspensions of these active compounds as a free base or pharmaceutically acceptable salt may be prepared in water suitably mixed with a surfactant such as hydroxyl-propylcellulose. Dispersions may also be prepared in glycerol, liquid polyethylene glycols and mixtures thereof in oils. Under ordinary conditions of storage and use, these preparations contain a preservative to inhibit the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

The compounds of this invention can be administered transdermally through the use of a transdermal patch. For the purposes of this disclosure, transdermal administrations are understood to include all administrations across the surface of the body and the inner linings of bodily passages including epithelial and mucosal tissues. Such administrations may be carried out using the present compounds, or pharmaceutically acceptable salts thereof, in lotions, creams, foams, patches, suspensions, solutions, and suppositories (rectal and vaginal).

Transdermal administration may be accomplished through the use of a transdermal patch containing the active compound and a carrier that is inert to the active compound, is non-toxic to the skin, and allows delivery of the agent for systemic absorption into the blood stream via the skin. The carrier may take any number of forms such as creams and ointments, pastes, gels and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream, such as a semi-permeable membrane covering a reservoir containing the active ingredient with or without a carrier, or a matrix containing the active ingredient. Other occlusive devices are known in the literature.

The compounds of this invention may be administered rectally or vaginally in the form of a conventional suppository. Suppository formulations may be made from traditional materials, including cocoa butter, with or without the addition of waxes to alter the suppository's melting point, and glycerin. Water soluble suppository bases, such as polyethylene glycols of various molecular weights, may also be used.

In certain embodiments, the present invention is directed to prodrugs of biaryl sulfonamide compounds. Various forms of prodrugs are known in the art, for example, as discussed in, for example, Bundgaard, (ed.), Design of Prodrugs, Elsevier (1985); Widder, et al. (ed.), Methods in Enzymology, vol. 4, Academic Press (1985); Krogsgaard-Larsen, et al. (ed.), "Design and Application of Prodrugs", Textbook of Drug Design and Development, Chapter 5, 113-191 (1991), Bundgaard, et al., Journal of Drug Deliver reviews, 8:1-38 (1992), Bundgaard, J. of Pharmaceutical Sciences, 77:285 et seq. (1988); and Higuchi and Stella (eds.) Prodrugs as Novel Drug Delivery Systems, American Chemical Society (1975), each of which is incorporated by reference in its entirety.

It is understood that the dosage, regimen and mode of administration of the compounds of the invention will vary according to the malady and the individual being treated and will be subject to the judgment of the medical practitioner involved. It is preferred that the administration of one or more of the compounds herein begin at a low dose and be increased until the desired effects are achieved.

The compounds of the current invention were prepared according to the following general synthetic scheme from commercially available starting materials, materials prepared as described in literature procedures, or new intermediates described in the schemes and experimental procedures. This general scheme covers most of the examples. For more detailed information, please refer to the schemes in the Examples section below.

General Synthetic Scheme

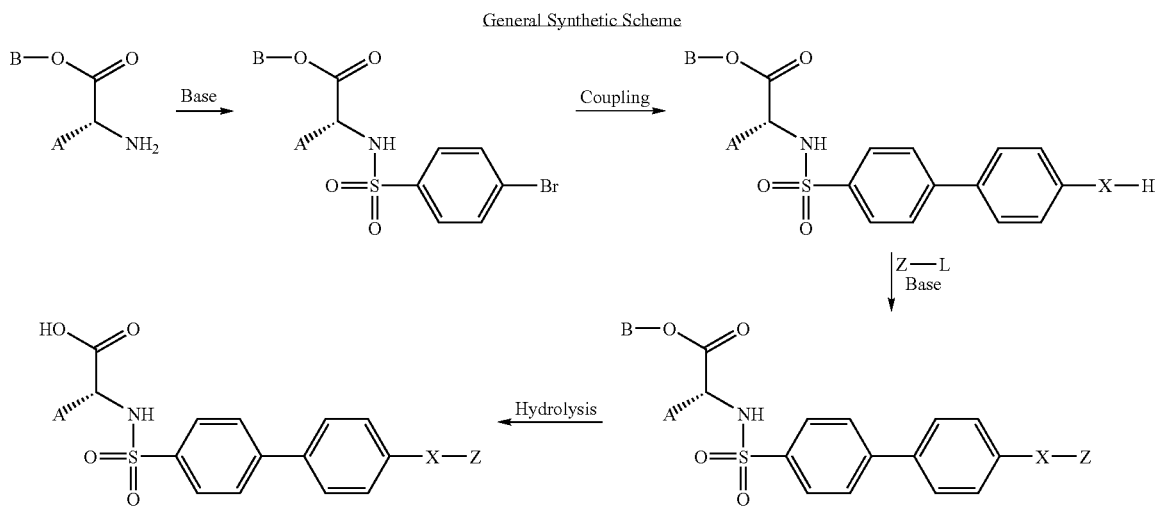

Bases used here are triethylamine, potassium carbonate, NaH, Hunig base, etc. Coupling was generally concluded by Suzuki coupling or Stille coupling. Hydrolysis was carried out using TFA, NaOH, LiOH, $K_2CO_3$, etc.

More specific synthetic routes to many of the compounds of the invention are included in the following Schemes. It is understood by those skilled in the art that protection and deprotection steps not shown in the Schemes may be required for these syntheses, and that the order of steps may be changed to accommodate functionality in the target molecules.

In Scheme 1 the compounds of the invention, 1, are prepared in 4 steps. Sulfonylation of valine methyl ester with 4-bromo-benzenesulfonyl chloride was carried out in the presence of Hunig base to give sulfonamide Intermediate 1. This 4-bromo-benzenesulfonamide was furthered coupled with boronate ester using Palladium catalyst under Suzuki coupling condition to provide biphenyl sulfonamide Intermediate 2. Biphenyl sulfonamide Intermediate 2 was then alkylated with various alkylating reagents to provide biphenyl sulfonamide ester (Intermediate 3). Hydrolysis of Intermediate 3 was carried out using bases such as NaOH, or LiOH to form the final product 1.

diate 4) under basic condition in DMF. Pinacolborane was then coupled with 4-bromo-benzenesulfonamide under Suzuki condition to provide biphenyl sulfonamide Intermediate 5, which was hydrolyzed to final product under basic conditions.

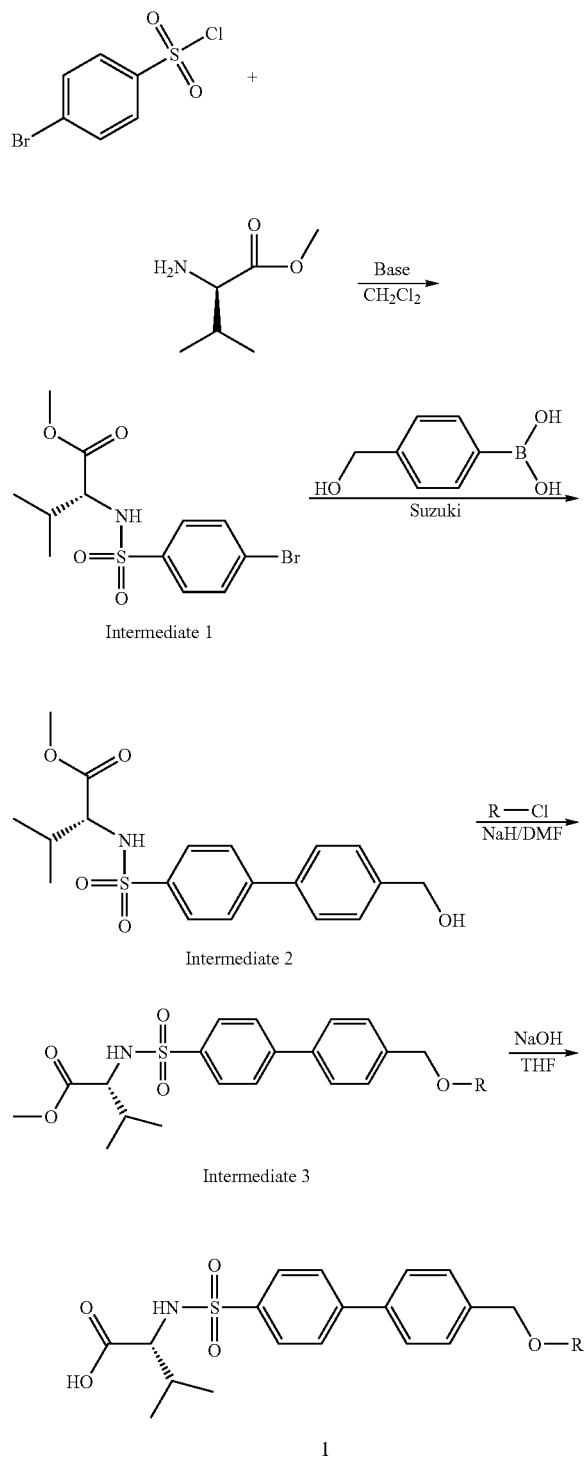

An alternative route to compounds 1 is shown in Scheme 2. Phenol derivative was converted to pinacolborane (Interme- A third option to make compounds of the invention, 1, are carried out based on Scheme 3. The synthetic sequence in Scheme 3 is similar to that in Scheme 1 but using a different starting material, valine tert-butyl ester. Therefore, the final step to form the product 1 was carried out by using TFA to deprotect the tert-butyl ester group of Intermediate 8.

Scheme 3

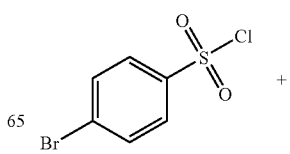

-continued

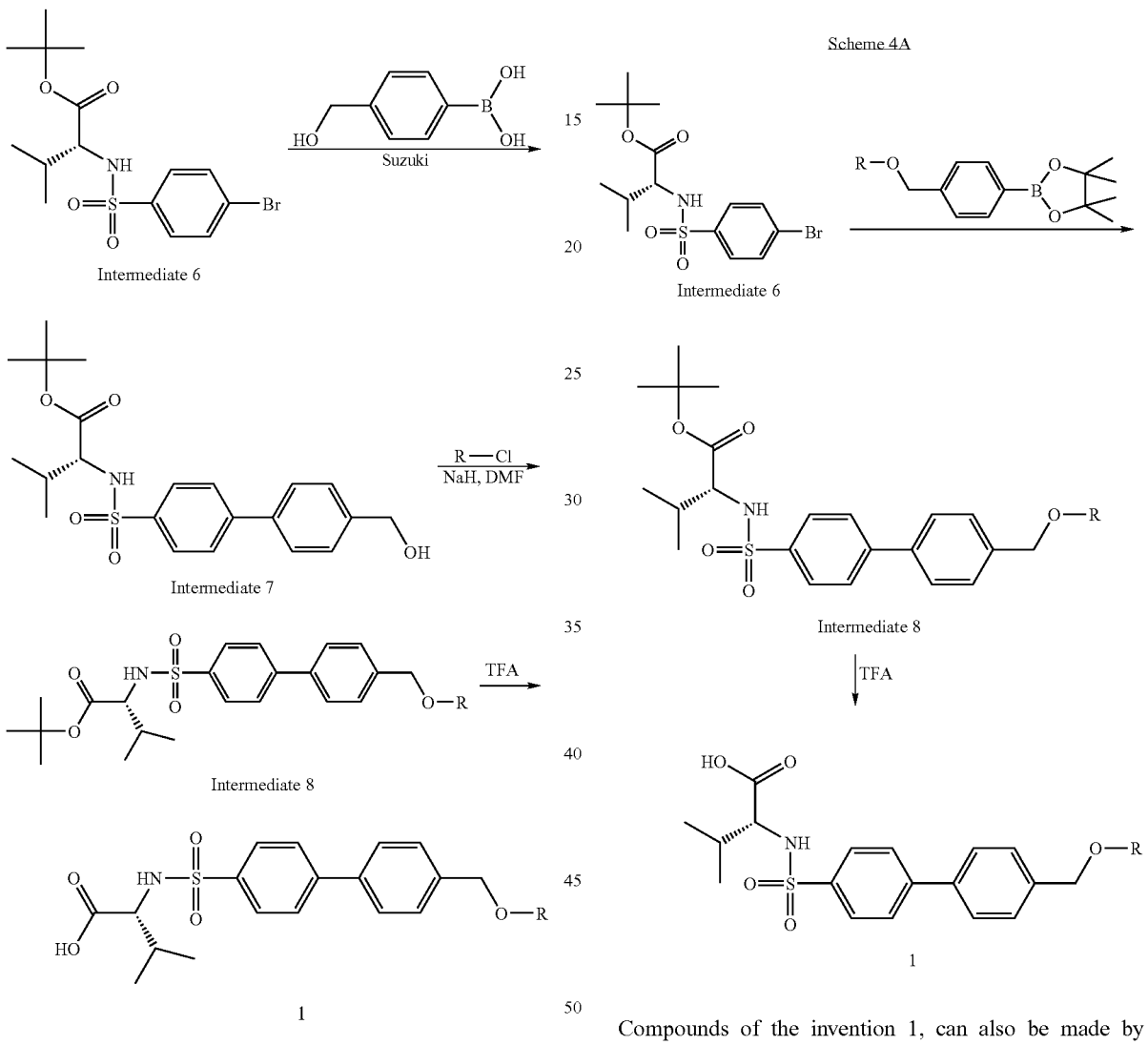

A slight modification of Scheme 3 can be made to produce the compounds of invention 1. This is illustrated in Scheme 4A. In this case, boronate esters with suitable ether moiety are purchased from a commercial source and used for Suzuki coupling to provide Intermediate 8. TFA deprotection of tert-butyl ester from Intermediate 8 resulted the desired final product 1.

Compounds of the invention 1, can also be made by hydrolysis of a suitable ester, such as Intermediate 10.

Scheme 4B

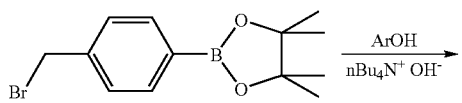

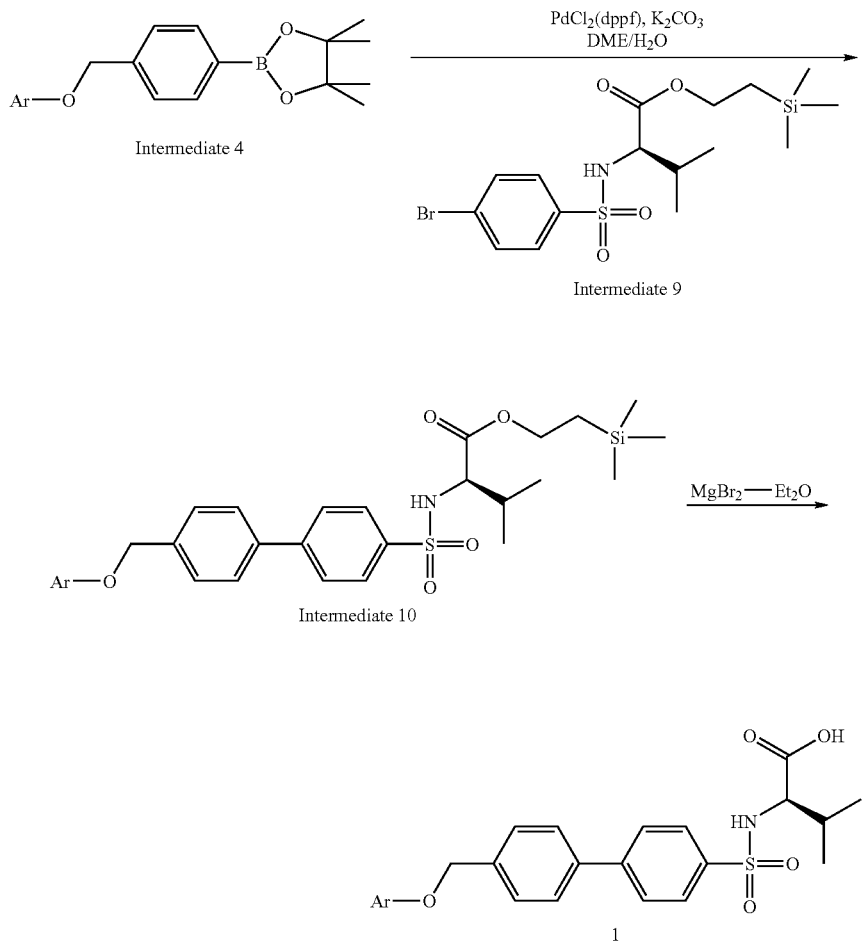

Scheme 4B features an alkylation, a Suzuki coupling and a deprotection step as follows.

Alkylation: The phenol derivative (4.14 mmol) is dissolved in methanol (6 mL) and treated with tetrabutylammonium hydroxide (4.14 mmol.) The mixture is stirred for 10 minutes, and the solvent is removed under reduced pressure. The residue is dissolved in THF (10 mL) and treated with a solution of the benzylic bromide (4.14 mmol) in THF (5 mL.) The reaction is stirred at room temperature overnight. The solvent is removed under reduced pressure and redissolved in dichloromethane (5 mL) and ether (50 mL.) The organic solution is washed with water (4×50 mL) and saturated sodium chloride solution (50 mL,) and dried over magnesium sulfate. The organic solution is filtered and concentrated under reduced pressure. The crude material is purified by flash silica gel chromatography to yield the purified product in 53% yield, which is Intermediate 4 a boronate ester.

Suzuki Coupling: The boronate ester (1.07 mmol) and aryl bromide (1.07 mmol) are dissolved in ethylene glycol dimethyl ether (10 mL) and the resulting solution is treated with tetrakis(triphenylphosphine)palladium(0) (0.054 mmol.) A solution of potassium carbonate (2.14 mmol) in water (3.5 mL) is added, and the reaction is heated to reflux for 1 h. The reaction is cooled, filtered to remove solids, diluted with water (10 mL) and concentrated under reduced pressure. The residue is extracted with dichloromethane (3×25 mL) and the organic layers are washed with water (25 mL) and saturated sodium chloride solution (25 mL). The organic solution is dried over magnesium sulfate, filtered and concentrated under reduced pressure. Purification by flash silica gel chromatography furnishes the product Intermediate 10, a (triemthylsilyl)ethyl ester of the desired product, in 57% yield. In some cases, PdCl2(dppf) was used as the catalyst instead of tetrakis(triphenylphosphine)palladium(0).

Deprotection with $MgBr_2$: The 2-(trimethylsilyl)ethyl ester (0.0621 mmol) is dissolved in dichloromethane (58 mL) and treated with magnesium bromide etherate (0.186 mmol). The mixture is stirred vigorously overnight or until reaction is complete and then shaken with 10% HCl (3×25 mL) and saturated sodium chloride solution (25 mL). The organic solution is then dried over magnesium sulfate, filtered and concentrated under reduced pressure to yield the product in 95% yield. The crude product could be purified by HPLC when required.

As shown in Scheme 4C Suzuki coupling can be carried out on free acid with boronate ester. Therefore, hydrolysis of the esters (as in Intermediate 10) is avoided. This results in direct preparation of compounds 1.

Scheme 4C

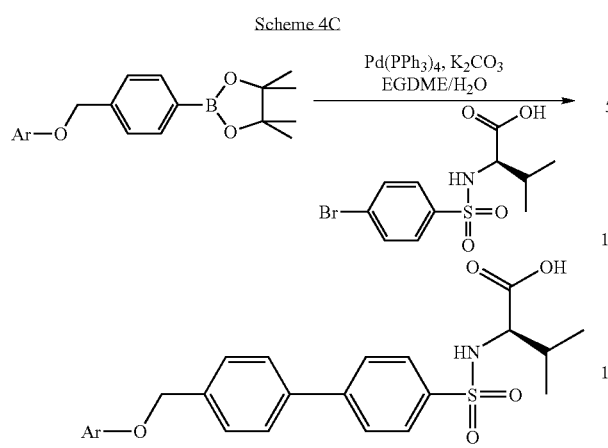

Suzuki coupling with free acid: The boronate ester (1.36 mmol) and bromoacid (1.36 mmol) are dissolved in ethylene glycol dimethyl ether (13.8 mL) and the resulting solution is treated with tetrakis(triphenylphosphine)palladium(0) (0.068 mmol). After stirring at room temperature for 10 minutes, a solution of potassium carbonate (4.08 mmol) in water (4.8 mL) are added. The solution is heated to reflux for 2 h, and then allowed to cool to room temperature overnight. The mixture is concentrated to an aqueous residue under reduced pressure and ethyl acetate (50 mL) is added. The organic mixture is washed with 10% HCl (2×25 mL) and saturated sodium chloride (25 mL). The organic solution is dried over magnesium sulfate, filtered and concentrated to a crude residue, which is purified using flash silica gel chromatography to obtain the product in 64% yield.

In Scheme 5 the compounds of the invention, 2, are prepared in 3 steps. Boronate ester (Intermediate 11) is prepared by alkylation under basic condition. Intermediate 11 thus obtained can be easily coupled with 4-bromo-benzenesulfonamide derivative to provide biphenyl sulfonamide analog (Intermediate 12).

The ester functional group in Intermediate 12 can be hydrolyzed under various conditions to yield the desired biphenyl sulfonamide product 2.

Scheme 5

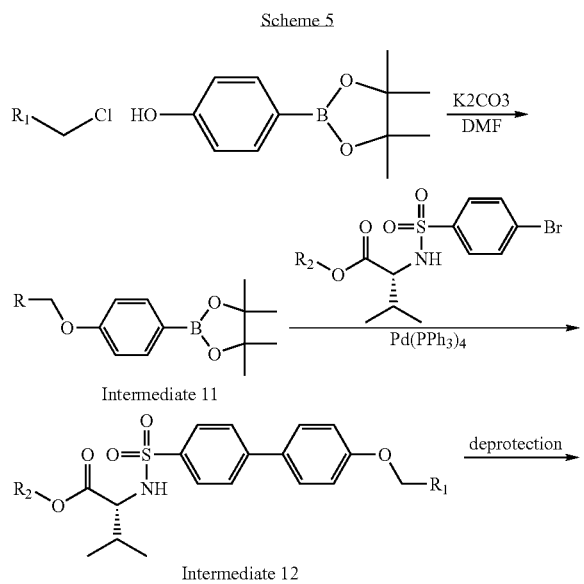

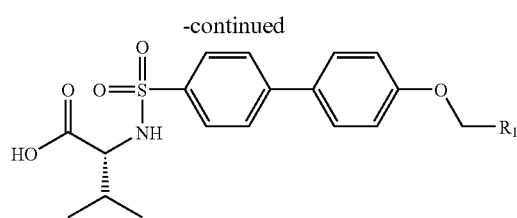

Alternate route to provide compounds, 2, is shown in Scheme 6. Starting material 4-hydroxybiphenyl sulfonamide derivative was readily available through Suzuki coupling. Alkylation of 4-hydroxybiphenyl sulfonamide under basic condition provides biphenyl sulfonamide ester Intermediate 13 with an ether linker. Hydrolysis of ester (Intermediate 13) using aqueous NaOH provides the desired product of the invention, 2.

Scheme 6

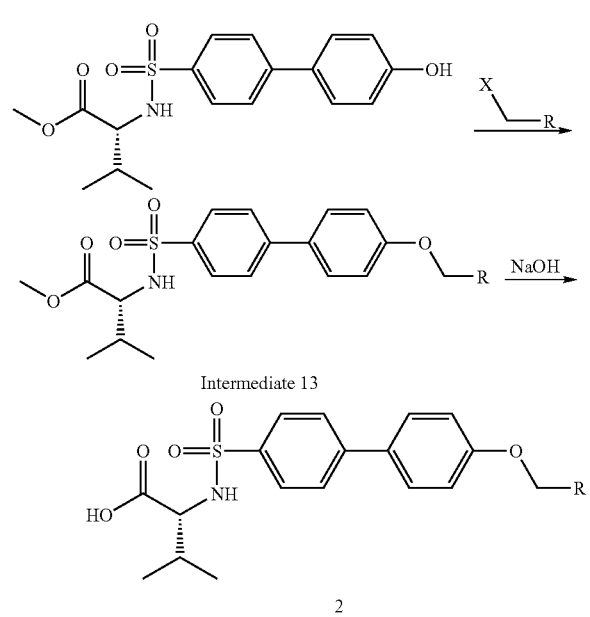

Deprotection of esters, such as methyl esters, shown in Scheme 6 can be conducted employing the route shown in Scheme 6A.

Scheme 6A

Deprotection of Methyl esters:

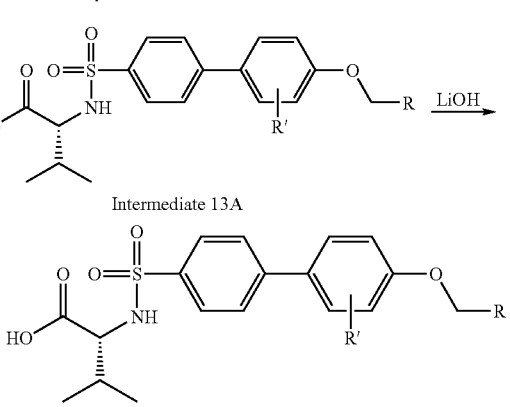

Intermediate 13A methyl ester, (0.294 mmol) was dissolved in THF:MeOH (2:1)(2 mL) and 1M LiOH (0.881 mmol) was added. The reaction mix was stirred for 3 days. The solvent was removed and the remaining white solid was dissolved in H$_2$O. The H$_2$O was extracted with ether. The ether layer was removed and the aqueous layer was acidified to pH 2 with HCl (conc.) forming a cloudy solution. This solution was extracted with CH$_2$Cl$_2$. The resulting aqueous layer was removed and the remaining organic layer was washed with brine. The solvent was removed and the remaining solid was dissolved in minimal CH$_2$Cl$_2$ and then hexane was added thus precipitating a white solid. The solid was filtered and dried at reduced pressure to provide the desired product.

Compounds of the invention, 3, are prepared based on Synthesis Scheme 7. 4-Vinylphenylboronic acid and 4-bromobenzene sulfonamide derivative were reacted via Suzuki coupling catalyzed by palladium catalyst to provide Intermediate 14. Heck reaction of Intermediate 14 with aryl halide generated Intermediate 15. Intermediate 15 is a biphenyl sulfonamide derivative with a double bond as a linker connected to an aryl ring. Regular TFA deprotection of the tert-butyl ester of Intermediate 15 provides desired product 3 in high yield.

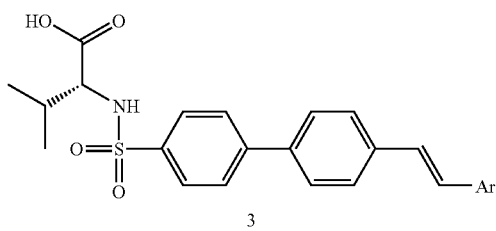

Scheme 8 shows the a multiple step synthesis leading to the compounds of invention, 4. A regular Suzuki coupling followed by the alkylation with triflic anhydride furnishes triflate Intermediate 16. Triflate Intermediate 16 was converted into alkynylation product 17 through a Sonagoshira reaction. TBDMS protecting group in 17 was removed by TBAF followed by another Sonagoshira reaction to provide Intermediate 18 with a triple bond linking the biphenyl group with aryl moiety. Intermediate 18 was then reduced by hydrogenation then TFA deprotection removed the ester group to give the desired product 4.

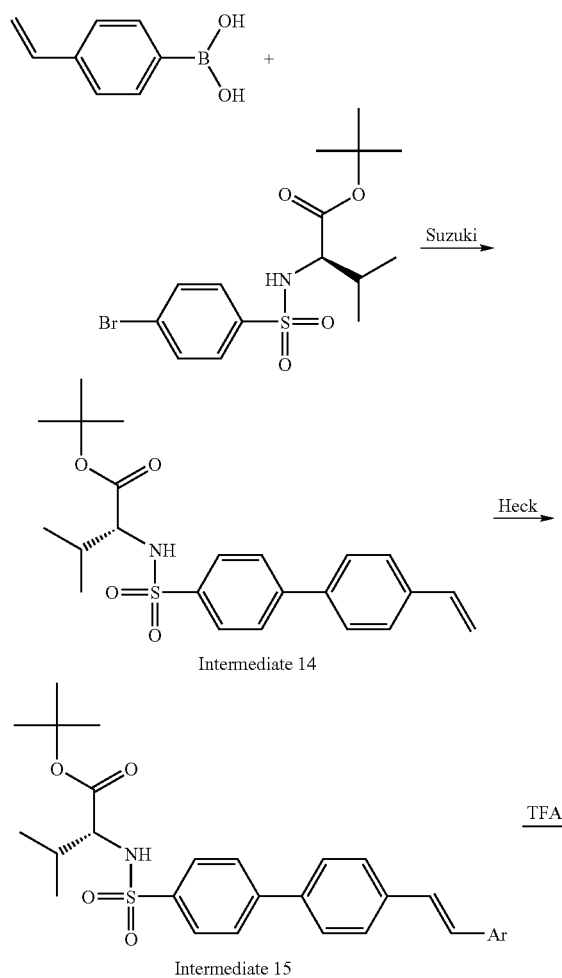

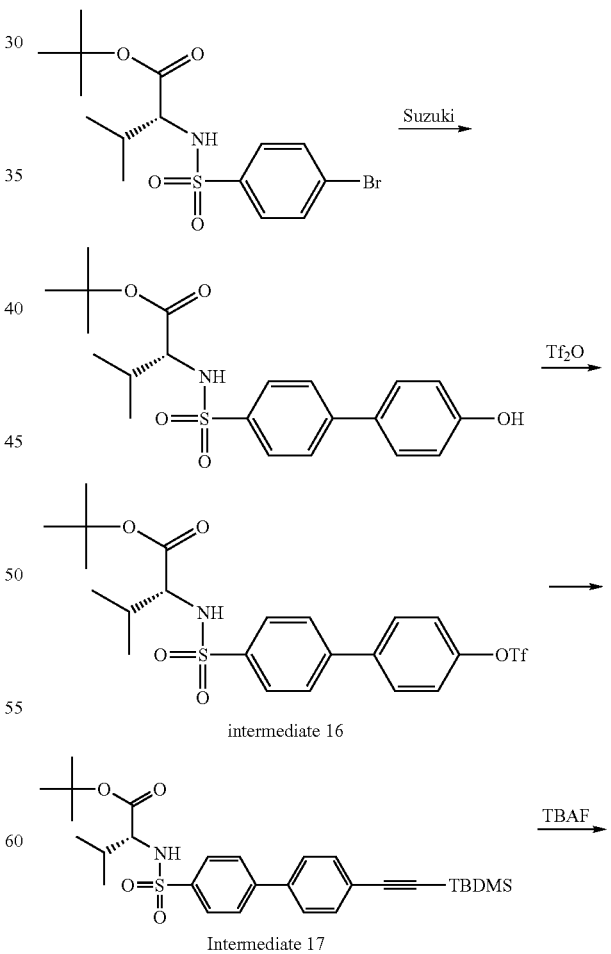

-continued

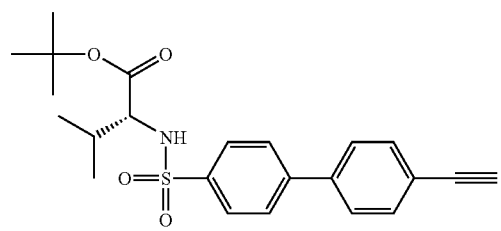

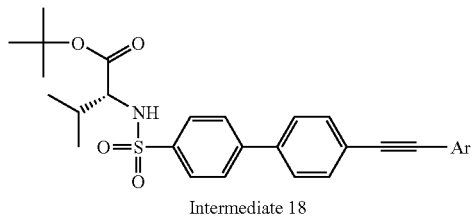
Intermediate 18

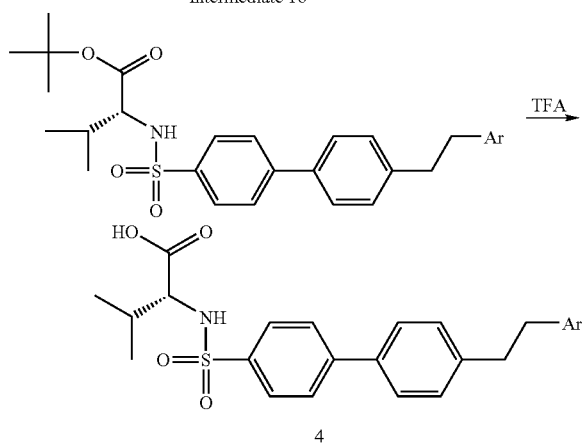
4

Routes to compounds of structure 5 are shown in Scheme 9. 4-aminomethyl phenyl boronic acid was used for Suzuki coupling to produce the Intermediate 19. Acylation of Intermediate 19 with acetic anhydride, followed by the TFA deprotection provided compounds with structure 5.

Scheme 9

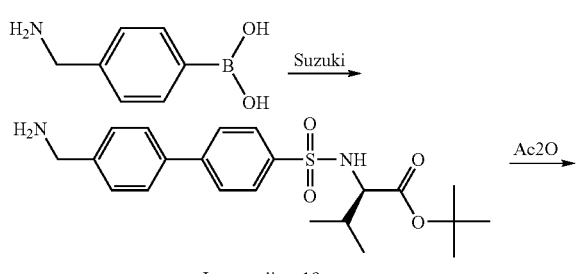
Intermediate 19

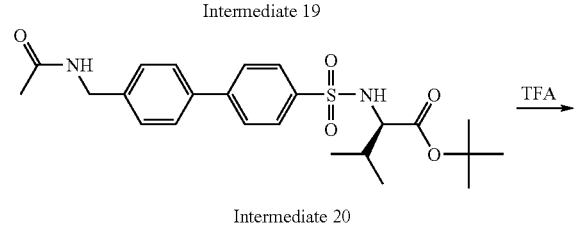
Intermediate 20

-continued

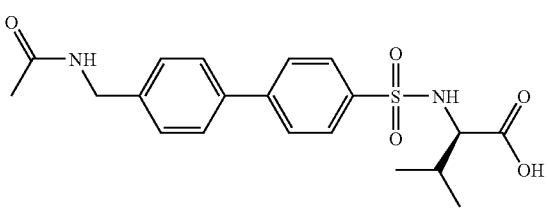
5

An alternate route to make structures of 5 is presented in Scheme 10. Intermediate 21 was formed by EDCL coupling of 4-bromophenylacetic acid with phenylamine in DMF. Stille coupling of Intermediate 21 with corresponding tin reagent followed by TFA deprotection provided product 5.

Scheme 10

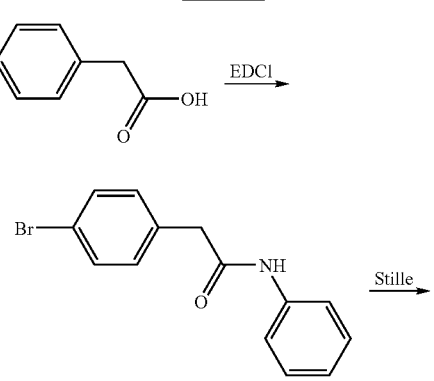
Intermediate 21

Intermediate 22

5

In Scheme 11 the compounds of the invention, 6, are prepared by reacting 4-hydroxybiphenyl sulfonamide derivative with an isocyanate in the presence of triethylamine. Carbamate (Intermediate 24) thus obtained was treated with TFA to remove the tert-butyl ester protecting group to provide compounds 6.

Scheme 11

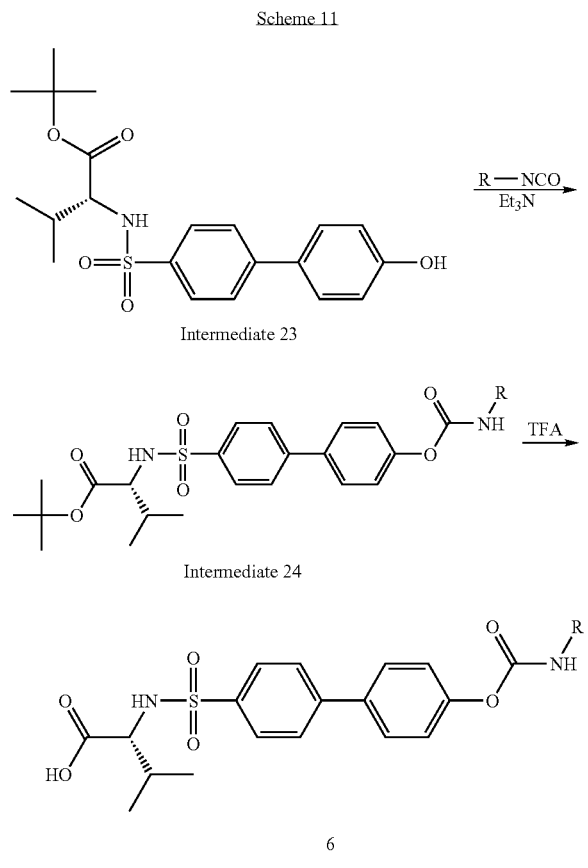

An alternate route to make compounds 6 is shown in Scheme 12 using 4-hydroxybiphenyl sulfonamide free acid to react with isocyanate in the presence of triethylamine. Compounds 6 are obtained thereby directly, without a deprotection step.

Scheme 12

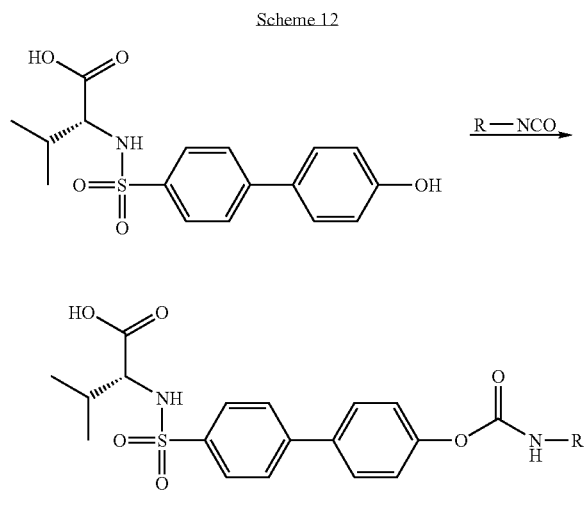

Routes to compounds of structure 7 are shown in Scheme 13. Intermediate 23 was coupled with carboxylic acid using DCC reagent to provide ester 24. Intermediate 24 was treated with TFA to selectively remove the tert-butyl group to provide compound 7.

Scheme 13

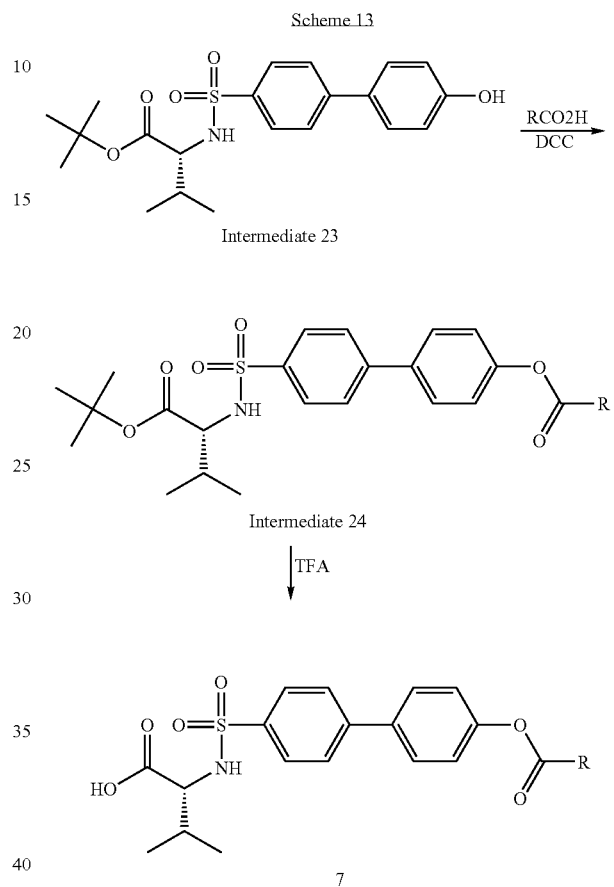

In Scheme 14, the compounds of the invention, 8, are prepared from Intermediate 23 by alkylation followed by the deprotection (removal of protecting tert-butyl group) with TFA.

Scheme 14

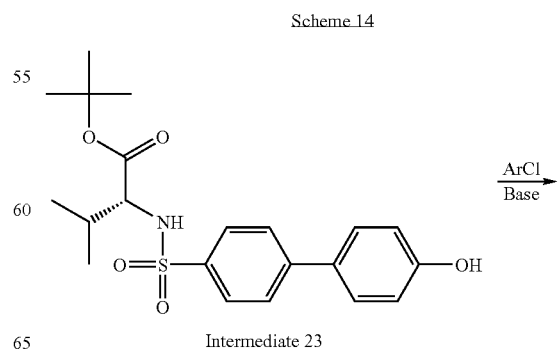

-continued

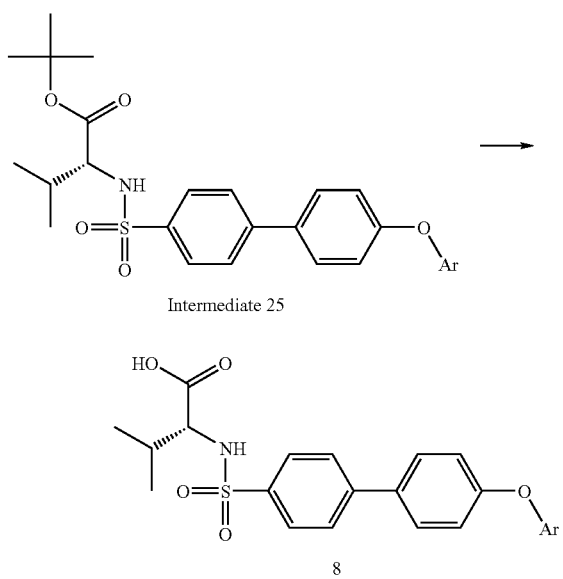

In Scheme 15 the compounds of the invention, 9, are prepared in a multiple step synthesis. Intermediate 26 was prepared based on known literature procedure. Stille coupling followed by TFA deprotection provided the desired product 9.

Scheme 16

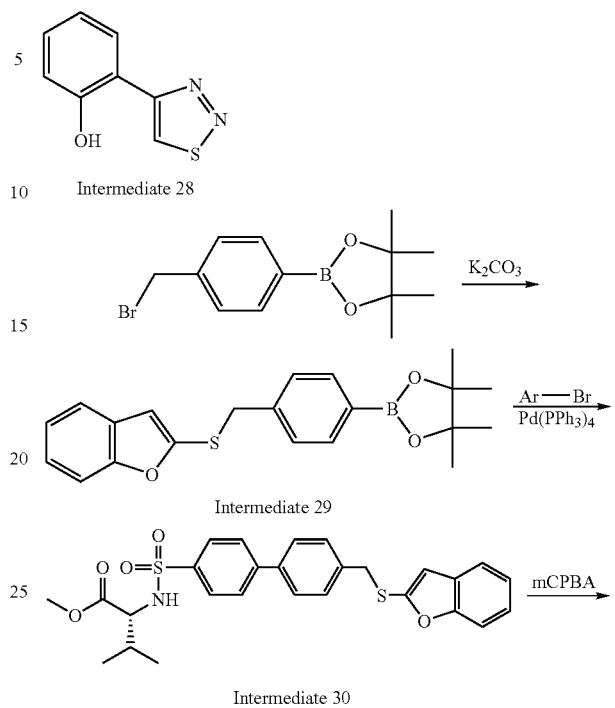

Scheme 15

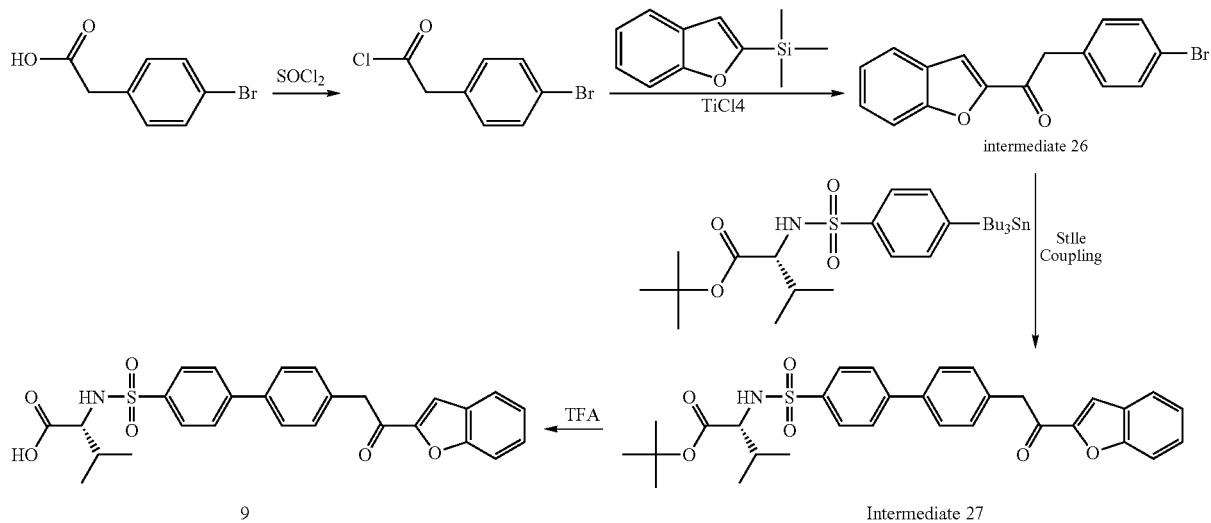

Routes to compounds of structure 10 are shown in Scheme 16. Intermediate 28 (2-[1,2,3]thiazol-4-yl-phenol) was prepared according to literature procedure. Alkylation with benzyl bromide derivative followed by condensation resulted in thioether intermediate 29. Suzuki coupling of 29 with 4-bromobenzene sulfonamide generated Intermediate 30. Oxidation with mCPBA followed by hydrolysis provided compound 10.

-continued

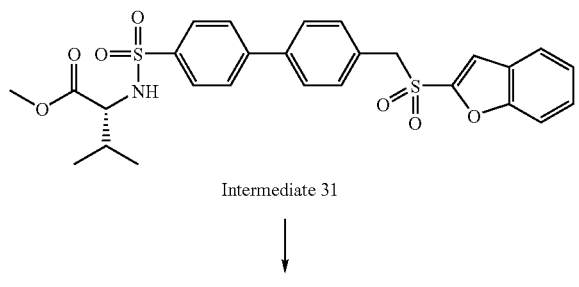

-continued

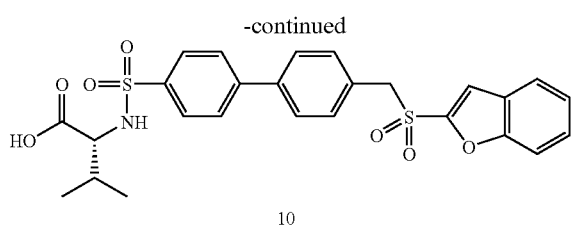

10

Removal of t-butyl Ester Protecting Group with TFA

Scheme 17

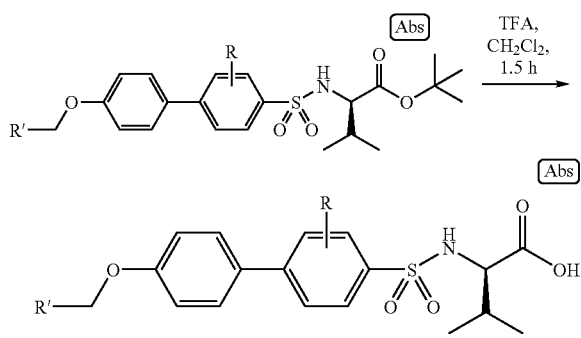

The t-butyl ester protected biphenylsulfonamide (0.505 mmol) was dissolved in $CH_2Cl_2$ (2.5 mL). TFA (2.5 mL) was dissolved in $CH_2Cl_2$ (2.5 mL), and this was slowly added to the dissolved ester and stirred for 1.5 h. The solvent was removed at reduced pressure and the remaining oil dissolved in toluene, and the toluene removed. Finally, the oil was dissolved in a minimal amount of $CH_2Cl_2$ and hexane was added to precipitate a white solid. Solvent was removed at reduced pressure, and, after vacuum pump drying, a solid dried to give a 98% yield.

The present invention further relates to methods of identifying agents useful for the treatment of osteoarthritis. The methods of identifying agents useful for the treatment of osteoarthritis comprise determining whether a particular agent has ADAMTS-5-specific aggrecanase inhibitory activity. The methods may also comprise using ADAMTS-5 transgenic animals to determine whether a potential agent useful for the treatment of osteoarthritis is effective in an animal having ADAMTS-5 activity but is not effective in an animal not exhibiting ADAMTS-5 activity.

As further described in the Examples below, the ADAMTS-5 gene allele is functionally disrupted in a cell by homozygous recombination between the allele and a mutant ADAMTS-5 gene, or a portion thereof. The cell can be a differentiated cell type that normally expresses ADAMTS-5, such as a macrophage or monocyte, or a macrophage-like or monocyte-like cell line. Alternatively, the cell can be a pluripotent progenitor cell that can develop into an animal, such as an embryonic stem cell. In a preferred embodiment, an embryonic stem cell is used. The embryonic stem cell can be introduced into a blastocyst and the blastocyst introduced into a pseudopregnant animal to produce an animal having somatic and germ cells in which an ADAMTS-5 gene allele is functionally disrupted. Such an animal is a "homologous recombinant" animal. A preferred homologous recombinant animal of the invention is a mouse. Mice are a preferred animal because they are more easily utilized for laboratory studies and because they provide an art recognized model, as further described in the Examples below. However, any animal may be used, including, but not limited to, pigs, cows, sheep, goats, and other animals. In a particularly preferred embodiment, the animal is an inbred mouse.

To create a homologous recombinant cell or animal, a targeting vector can be prepared which contains DNA encoding an ADAMTS-5 protein, or a portion thereof, having a mutation introduced therein. The targeting vector may include a nonhomologous ADAMTS-5 replacement portion, which preferably includes Cre/Lox-P sites; a first homology region located upstream of the nonhomologous portion which has substantial identity to a first ADAMTS-5 gene sequence; and a second homology region located downstream of the nonhomologous portion which has substantial identity to a second ADAMTS-5 gene sequence. As used herein, "substantial identity" is intended to describe a nucleotide sequence having sufficient homology to an ADAMTS-5 gene to allow for homologous recombination between the nucleotide sequence and an endogenous sequence to allow for homologous recombination between the nucleotide sequence and the endogenous ADAMTS sequence in a host cell. Typically, the nucleotide sequences of the flanking homology regions are from about 80% to about 100% identical to the endogenous sequences. In a particularly preferred embodiment, they are 100% identical. The homology regions are also of sufficient length to allow for homologous recombination with the endogenous gene in a host cell, i.e., at least 1 kilobase in length, and more preferably at least several kilobases in length.

The targeting vector may further include positive and negative selection cassettes. These cassettes include nucleotide sequences encoding positive and negative selection markers operatively linked to regulatory elements that control expression of the selection marker.

To functionally disrupt an endogenous ADAMTS-5 gene allele in a host cell, a targeting vector is introduced into the host cell, e.g., a differentiated cell or an embryonic stem cell. The targeting vector may be introduced into the cell by any technique known in the art, including, but not limited to, calcium phosphate precipitation, DEAE-dextran transfection, microinjection, lipofection, electroporation and the like. After introduction of the vector into the host cell, the cell is cultured for a period of time and under conditions sufficient to allow for homologous recombination between the introduced targeting vector and the endogenous ADAMTS-5 gene. Host cells are selected (e.g. by positive and/or negative selection) and screened for homologous recombination at the endogenous ADAMTS-5 gene locus by standard techniques known in the art (e.g. Southern hybridizations or PCR using probes/primers which distinguish the normal endogenous allele from the homologous recombinant allele.)

To create a homologous recombinant animal, an embryonic cell having at least one ADAMTS-5 gene allele functionally disrupted is introduced into a blastocyst, the blastocyst is implanted into a pseudopregnant foster mother, and the embryo is allowed to develop to term. The resultant animal is a chimera having cells descendent from the embryonic stem cell. Chimeric animals in which the embryonic stem cell has contributed to the germ cells of the animal can be mated with WT animals to produce animals heterozygous for the ADAMTS-5 gene disruption in all somatic and germ cells. The heterozygous animals can then be mated to create animals homozygous for the ADAMTS-5 gene disruption (i.e. having both ADAMTS-5 gene alleles functionally disrupted). Any sort of mutation may be introduced into a transgenic animal, including null mutations and point mutations. A point mutation may result in normal expression of the ADAMTS-5 gene product but the product may have aberrant activity, e.g. it may not have aggrecanase activity.

In addition, cells from the animal homozygous for the ADAMTS-5 gene disruption can be isolated from the animals and cultured in vitro for various studies, including for screening assays.

ADAMTS-5 transgenic animals and cells derived therefrom are useful as positive controls by which to evaluate the efficacy of ADAMTS-5 inhibitors. The homozygous and heterozygous animals provide such standards. In a screening assay to identify and assess the efficacy of ADAMTS-5 inhibitors, a WT animal (or cells derived therefrom) not treated with inhibitor is used as the 0% inhibition standard, an animal homozygous for an ADAMTS-5 disruption is used as the 100% inhibition standard, while an animal heterozygous for an ADAMTS-5 gene disruption is used as standard for less than 100% inhibition but more than 0% inhibition. The amount of ADAMTS-5 activity in a subject treated with an ADAMTS-5 inhibitor is then assessed relative to these standards. The inhibition may be measured by the % inhibition of aggrecanase activity or the % reduction in osteoarthritic symptoms.

The transgenic animals and cells derived therefrom also can be used to screen ADAMTS-5 inhibitors for side effects or toxicity resulting from the inhibitor's action on a target(s) other than ADAMTS-5 (e.g. ADAMTS-5 isoforms or ADAMTS-4). For example, an ADAMTS-5 inhibitor may be administered to an ADAMTS-5 animal of the invention to evaluate side effects or toxicity of the inhibitor. Because the ADAMTS-5 transgenic animal lacks the normal target for the inhibitor, an effect observed upon administration of the inhibitor to the ADAMTS-5 null mutant can be attributed to a side effect of the ADAMTS-5 inhibitor on other target(s). Accordingly, ADAMTS-5 transgenic animals are useful for distinguishing these side effects from the direct effects of the inhibitor on ADAMTS-5 activity.

The transgenic animals may also be used for in vivo screening assays to identify diseases in which ADAMTS-5 plays a role in the pathogenesis of the disease condition. Such screening assays are further useful for identifying other diseases that may be treated with ADAMTS-5 inhibitors. For example, the transgenic animals may be useful in evaluating the role of ADAMTS-5 in other disorders in which extracellular protein degradation or destruction occurs, such as cancer, asthma, chronic obstructive pulmonary disease ("CODP"), atherosclerosis, age-related macular degeneration, myocardial infarction, corneal ulceration and other ocular surface diseases, hepatitis, aortic aneurysms, tendonitis, central nervous system diseases, abnormal would healing, angiogenesis, restenosis, cirrhosis, multiple sclerosis, glomerulonephritis, graft versus host disease, diabetes, inflammatory bowel disease, shock, invertebral disc degeneration, stroke, osteopenia, rheumatoid arthritis and other forms of arthritis, and periodontal disease. A stimulus may be administered to the transgenic animals of the invention to induce the disease condition, as further described below in the Examples for osteoarthritis. Alternatively the transgenic animals of the invention may be bred with an animal genetically prone to a particular disease. Following induction of the disease in the ADAMTS-4 or ADAMTS-5 null mutant animal, the susceptibility or resistance of the animal to the disease condition is determined. Resistance of the animal to the disease condition, relative to WT, is indicative that the pathology of the disease condition involves the action of ADAMTS-4 or ADAMTS-5, and thus the disease condition is treatable with an inhibitor of ADAMTS-4 or ADAMTS-5, respectively. As an example of this utility, Example 1 below and FIG. 3A and FIG. 3B demonstrate that homozygous and heterozygous ADAMTS-5 transgenic animals are resistant to induced osteoarthritis.

ADAMTS-5 transgenic animals homozygous ADAMTS-5 null mutation, or a cell derived therefrom, can be reconstituted with a human equivalent of the gene to create a nonhuman cell or animal that expresses a human ADAMTS-5 gene product. These cells and animals can be used to screen compounds to identify agents that inhibit the activity of human ADAMTS-5, either in cultured cells or in vivo. Such animals and cells can be made by techniques well known to the skilled artisan. A nonhuman animal having cells expressing human ADAMTS-5 polypeptide, and/or cells derived therefrom, can be used to screen and identify agents that can inhibit human ADAMTS-5 in vivo.

ADAMTS-5 transgenic animals are also useful to determine whether a particular substance is a substrate for ADAMTS-5. ADAMTS-5 are metalloproteinases having aggrecanase activity. To assess whether a precursor form of a putative substrate is cleaved by ADAMTS-5, the presence or absence of cleaved product in the ADAMTS-5 animals may be assessed. The cleaved product will be substantially reduced or absent in the transgenic animals.

The following examples are offered to illustrate, but not to limit the present invention.

EXAMPLES

Example 1

Materials and Methods

Generation of ADAMTS5 KO Mice

ADAMTS-5 KO mice used in these studies were generated from inbred 129SvEvBrd mice carrying a Cre/LoxP type conditional KO allele of the ADAMTS5 gene (Lexicon Genetics, The Woodlands, Tex.). The conditional allele contained LoxP sites flanking exon 3 so that Cre recombination resulted in deletion of exon 3, which encodes the majority of the enzyme active site, as shown in FIG. 1A. In FIG. 1A, exons 2, 3 and 4 are presented in the Sequence Listing as SEQ ID NOS: 1, 2 and 3, respectively.

Mice carrying the ADAMTS-5 conditional KO allele were created by homologous recombination in ES cells followed by blastocyst injection to generate chimeric mice. The ADAMTS-5 KO mouse line was produced by crossing conditional KO mice with Protamine-Cre transgenic mice (provided by Lexicon Genetics) which resulted in Cre mediated deletion of exon 3 in the sperm of male offspring carrying both the mutant ADAMTS-5 and Prot-Cre alleles, as shown in FIG. 1B.

Genotyping for ADAMTS5 WT, Conditional KO and KO Alleles

Genotyping for alleles of the ADAMTS-5 gene was performed by PCR using DNA template from crude proteinase K digest of tail biopsies. The wild type and heterozygous KO alleles were identified by PCR using a forward primer of the sequence (5'TGT TCA CCC AAA GCA ACT AC3') (primer 1, SEQ ID NO:4) and a reverse primer of the sequence (5'TAG AGG AGA GGA GAG GAG G3') (primer 2, SEQ ID NO:5). These primers flanked the insertion site of the (5') LoxP site producing a 230 bp amplicon in the WT and heterozygous animals and no amplicon in the KO animals (FIGS. 1B, C). The knockout allele was identified using the forward primer (5'GTG AAC CAC ATG GAC TTT GG3') (primer 3, SEQ ID NO:6) and the reverse primer (5'TCG TAG CAA ACA CCC ACC TG3') (primer 4, SEQ ID NO:7) resulting in a 500 bp PCR product of the exon 3 deleted (KO) allele (FIGS. 1B, C).

Preparation of RNA for RT-PCR:

Total RNA was prepared from WT and KO mice spleen using the RNAeasy kit (Qiagen, Valencia, Calif.) according to the manufacturer's instructions. The quality of the RNA samples were confirmed in an RNA 6000 Nano assay using a Bioanalyzer (Agilent Technologies, Palo Alto, Calif.). PCR primers were designed and synthesized (BioSource International, Camarillo, Calif.) as follows:

```
Primer 5'CGACCCTCAAGAACTTTTGC3';    SEQ ID NO:8
5,
Primer 5'CTCAGGCCCAAATGTCAAGT3';    SEQ ID NO:9
6,
Primer 5'CGTCATGAGAAAGGCCAAGT3';    SEQ ID NO:10.
7,
```

RT-PCR was performed by using Qiagen OneStep RT-PCR kit with a 600 nM concentration of each primer and 200 ng of total RNA in a DNA Engine Dyad thermal cycler (MJ Research, Waltham, Mass.). The RT-PCR was run for 30 min at 50° C., 15 min at 95° C., and 35 cycles of 15 seconds at 95° C., 1 min at 59° C., and 30 seconds at 72° C. The RT-PCR primers are shown in FIG. 1D and the RT-PCR products are shown in FIGS. 1E and 1F. Using primers 5 and 6, FIG. 1E shows that the mRNA of the WT is 506 bp and the KO is 338 bp. Using primers 5, 4 and 7, FIG. 1E shows that the mRNA of the WT is 258 bp and there is no product, as expected, in the KO because primer 7 is located in exon 3 which is deleted in the KO.

Histology and Pathologic Assessment of Young and Aged Mice:

Complete necropsies were performed on 22 WT and 20 ADAMTS-5 KO males at 18 weeks of age. Necropsies included macroscopic observations, body and organ weights, hematology, complete serum chemistry and microscopic examination of brain, joints, heart, lungs, thymus, spleen, liver, kidneys, salivary glands, mandibular lymph nodes, testes, epididymides, eyes, harderian glands, lacrimal glands, sternum, and humerus. All tissues were fixed in 10% neutral buffered formalin, decalcified if mineralized, routinely processed, paraffin-embedded and prepared as routine hematoxylin and eosin-stained sections. All slides were evaluated by a board-certified veterinary pathologist (BS) for presence or absence of pathologic lesions.

Surgical Induction of Osteoarthritis:

All studies were performed with approval of the Wyeth Institutional Animal Care and Use committee. Surgical induction of osteoarthritis in mice is an art recognized model for the study of osteoarthritis. Accordingly, ten week old mice were anesthetized with 250 mg/kg intraperitoneal tribromoethanol (Sigma-Aldrich, St. Louis, Mo.), and knees were prepared for aseptic surgery. A medial para-patellar incision was made to expose and transect the meniscotibial ligament (anchoring the medial meniscus to the tibial plateau), resulting in destabilization of the medial meniscus (DMM). The joint capsule and subcutaneous layer were sutured closed with 8-0 and 9-0 Vicryl (Ethicon, Inc. Somerville, N.J.) respectively, and the skin closed with Nexaband®S/C tissue adhesive (Abbott Laboratories, North Chicago, Ill.). Buprenorphine (Buprenex, Reckitt and Coleman Products, Hull, England) was provided at 0.03 mg/kg pre- and postoperatively. Four weeks after DMM surgery, 19 WT and 19 KO mice were sacrificed by carbon dioxide. Eight weeks after surgery, 33 WT, 20 heterozygous, and 28 homozygous KO mice were sacrificed. A small subset of animals underwent sham surgery to determine the effect of inflammation secondary to arthrotomy on disease progression. Histologic scores of animals 4 or 8 weeks following sham surgery were not statistically different than animals that did not undergo any surgery.

Assessment of Progression and Severity of Osteoarthritis:

Intact knee joints were placed into 4% paraformaldehyde for 24 hours, then decalcified in 20% EDTA for 5 days. Joints were embedded in paraffin and 6 µm frontal sections taken through the entire joint. Slides were stained with Safranin-O/Fast green and graded at 70 µm intervals through the joint by three blinded, independent scorers. The semi-quantitative scoring system was modified from Chambers et al. (Chambers et al, 2001, *Arthritis & Rhuem* 44:1455) where 0 represents normal cartilage; 0.5 is loss of Safranin-O without structural changes; 1 represents roughened articular surface and small fibrillations; 2 represents fibrillation down to the layer immediately below the superficial layer and some loss of surface lamina; 3 is mild (<20%), 5 is moderate (20-80%) and 6 is severe (>80%) loss of non-calcified cartilage. All quadrants of the joint (medial tibial plateau (MTP), medial femoral condyle, lateral tibial plateau, and lateral femoral condyle) were scored separately. Approximately 12 levels were scored for each knee joint, with scoring continuing until articular cartilage was no longer observed in any quadrant. Scores were expressed as the maximum histologic score found from all levels of the entire joint, as shown in FIG. 3A. Scores were added from all levels of all four quadrants to obtain the summed histologic score, as shown in FIG. 3B, to reflect OA lesion severity as well the surface area affected.

Figure 4:
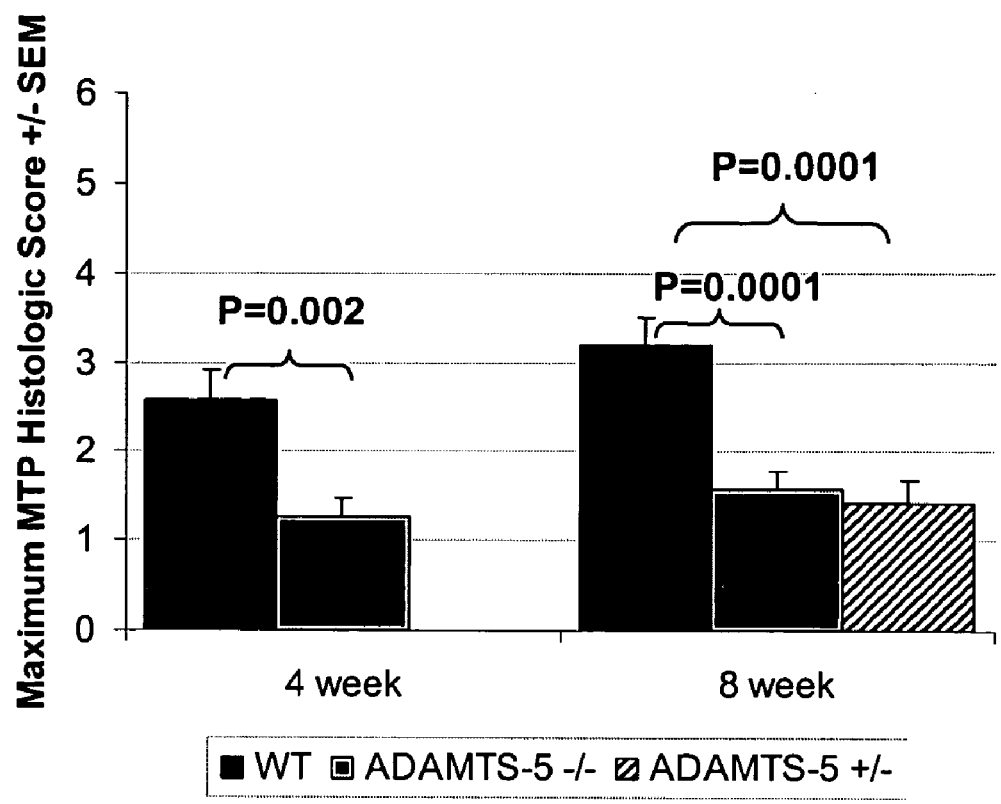
FIG. 4 illustrates the mean maximal histologic scores of the medial tibial plateau of WT, homozygous ADAMTS-5 KO and heterozygous ADAMTS-5 KO animals 4 and 8 weeks after induction of joint instability.

In order to compare the results with those published results examining the progression of osteoarthritis in IL-1β, IL-1βr, INOS, and ICE KO mice (Clements et al., 2003, *Arthritis & Rhuem* 48:3452) the results as mean scores of the medial tibial plateau of each experimental group were also expressed. FIG. 4 shows that these scores also were significantly reduced in the ADAMTS-5 homozygous and heterozygous KO animals.

Preparation and Culture of Cartilage Explants:

Femoral heads were harvested from 4 week old WT and KO mice, and the cartilage was separated from the underlying subchondral bone. Cartilage samples were cultured as explants at 37° C. in a humidified atmosphere of 5% $CO_2$ and 95% air in Dulbecco's modified Eagle's medium (DMEM) containing 1% antimycotic-antibiotic (Sigma, Aldrich), 2 mM glutamine, 10 mM Hepes, 50 mg/ml of ascorbate and 10% FBS for 48 hours. Explants were then washed 3 times and cultured for an additional 72 hours in serum-free DMEM+10 ng mouseIL-1α/ml (Sigma, Aldrich) and $10^{-5}$ M retinoic acid (Sigma, Aldrich). Conditioned media was collected and cartilage harvested at the end of the culture period.

Quantitation of Proteoglycan

The proteoglycan content in the medium was measured as sulphated glucosaminoglycan (GAG) by a colorimetric assay using dimethylmethylene blue (DMMB) and chondroitin sulphate C from shark cartilage (Sigma, Aldrich) as a standard according to a previously reported procedure (Farndale et al., 1986, *Biochim Biophys Acta* 883:173). Harvested cartilage samples were digested with proteinase K (Sigma, Aldrich) for 16 h, centrifuged and supernatant collected. Proteoglycan content in the digested cartilage was also measured to provide the total proteoglycan content in the cartilage and enable calculation of per cent release of proteoglycan during the experimental protocol.

Western Analysis

Aggrecan fragments in conditioned medium were analyzed by western analysis using neoepitope antibodies designed to recognize aggrecanase-generated fragments. Conditioned medium was dialyzed against 50 mM Tris-acetate (pH 6.5) and digested with Chondroitinase ABC (Sigma; 1 mU/µg of GAG), Keratinase I (Seikagaku America, Falmouth, Mass.; 1 mU/µg GAG) and Keratinase II (Seikagaku; 0.02 mU/µg GAG) for 2 h at 37° C. Samples were concentrated by YM-10 centrifugal filter device (Millipore Corp., Bedford, Mass.), lyophilized and reconstituted with water at a concentration of 1 mg/ml of GAG as measured by DMMB. Equal amount of GAG for each sample was separated under reducing conditions on 4-12% gradient Tris-glycine gels (Invitrogen, Carlsbad, Calif.) and transferred to nitrocellulose membranes. Immunoblotting was performed using monoclonal antibody (MAb) AGG-C1 (0.04 µg/ml) (Collins-Racie et al., 2004, *Matrix Biol.* 23:219-230) recognizing the aggrecanase-generated C-terminal interglobular neoepitope NITEGE$^{373}$. Incubation with primary and alkaline-phosphatase-conjugated secondary goat anti-mouse IgG (Promega Corp., Madison, Wis.; 1:7500) was performed overnight at 4° C. and at room temperature for 1 h, respectively. The immunoblots were incubated with NBT/BCIP substrate (Promega) at room temperature for 2-15 minutes to achieve optimum color development.

Immunohistochemical Identification of TEGE$^{373}$ Neoepitope in Murine Articular Cartilage The polyclonal antibody TEGE$^{373}$ was synthesized by standard polyclonal antibody technology (Glasson et al., 2004, *Arthritis & Rheum.* 50:2547-2558.). The antibody reacted with G1-TEGE$^{373}$ generated by ADAMTS-4 digestion of bovine aggrecan, but did not react with intact (undigested) aggrecan validating it as a "neoepitope" antibody. Positive serum was purified by affinity chromatography using the immunizing peptide.

For immunostaining of TEGE$^{373}$ neoepitope in murine articular cartilage, femoral heads from ADAMTS-4 KO, ADAMTS-5 KO and WT animals were harvested after 3 days of tissue culture in the presence or absence of 10 ng IL-1α/ml [is this γ or α] (Sigma) and 10$^{-5}$M retinoic acid (Sigma). Tissues were frozen in OCT and 5 micron sections were cut. Endogenous peroxidase activity was blocked with hydrogen peroxidase (DakoCytomation, Carpinteria, Calif.) and the sections were deglycosylated with 0.1 U Chondroitinase ABC/ml (Sigma), 0.1 U keratanase I/ml (Seikagaku Corp., Tokyo, Japan) and 0.1 U Keratinase II/ml (Seikagaku Corp., Tokyo, Japan) for 1 hour at 37° C. Primary antibody or normal rabbit serum was added to sections for 12 hours, and secondary antibody (donkey anti-rabbit, Rockland, Inc, Gilbertsville Pa.) was added for 30 minutes. Sections were incubated with ABC-peroxidase followed by DAB substrate (Vector Laboratories, Burlingame, Calif.). The sections were counterstained with hematoxylin.

Example 2

Results and Discussion

The ADAMT-4 knock out (KO) was generated (Glasson et al., 2004, *Arthritis & Rheum.* 50:2547-2558.). As detailed above, the ADAMTS-5 KO was created by Cre-Lox mediated recombination resulting in deletion of 56 amino acids encoded by exon 3, including disruption of the zinc binding site and the deletion of the "met turn" (FIG. 1A). PCR products from WT and heterozygous mice using primers 1 and 2 generated a 230 bp product. Primer 2 was located within the deleted portion encompassing exon 3 and therefore did not generate a PCR product in the homozygous KO animals. Primers 3 and 4 generated a 500 bp product in the heterozygous and homozygous KO animals doe to deletion of exon 3. The use of two forward primers (1 and 3) was required for optimal amplification with respect to the reverse primers (2 and 4). Because of differences in amplification efficiency between long and short amplicons, the use of short, allele-specific amplicons provided superior reliability of genotyping as compared to the use of one short (deletion) amplicon and one long (wt) amplicon generated from a single primer pair (i.e. 3 and 4). FIG. 1E shows RT-PCR from spleen total RNA demonstrated mRNA generated by PCR products made from primers spanning exon 3 reduced in size in the KO. The presence of mRNA indicates that this in-frame deletion did not cause instability of the message. Presence of a translated protein lacking the catalytic domain could not be confirmed.

Male and female WT and homozygous KO mice were allowed to age for 14-18 weeks. Animals were examined for any gross abnormality, blood samples were drawn for complete blood count and serum chemistry, and 17 tissues were harvested and examined by a board certified veterinary pathologist (BS). Tissues examined included heart, lung, thymus, spleen, liver, kidney, brain, salivary glands, mandibular lymph node, testis, epididymis, eye, harderian gland, lacrimal gland, whole sternum, femur, and whole paw. There were no abnormalities in total body weight, any blood or serum analysis or histologic appearance of any tissue examined indicating activity of the ADAMTS-5 enzyme was not required for normal development and growth.

Figure 2:
FIG. 2 shows the immunohistochemical localization of the aggrecanase generated TEGE$^{373}$ neoepitope in growth plates of 14-18 week old WT animals (top), ADAMTS-4 KO animals (left bottom) and, ADAMTS-5 KO animals (right bottom)

Aggrecan is a plentiful component of cartilage within the growth plate as well as the articular cartilage of the joints. FIG. 2 shows an analysis of growth plates from WT, ADAMTS-4 and ADAMTS-5 KO animals by immunostaining of the proximal tibial growth plates with a polyclonal antibody raised against the new C terminus of aggrecan after cleavage by aggrecanases, G1-TEGE$^{373}$.

As shown in FIG. 2, WT mice demonstrated significant hybridization of the antibody within the cells of the proximal tibial growth plate, and this staining was no longer present in the ADAMTS-4 KO animals. In contrast, hybridization of the anti-TEGE$^{373}$ antibody within the growth plate of the ADAMTS-5 KO mice resembled closely the staining of the WT growth plates. These results suggest that aggrecan turnover in the growth plate is a result of enzymatic activity of ADAMTS-4 and not ADAMTS-5. It is notable that the gross appearance of the animals, length of long bones and histologic appearance of the growth plates in both KO animals were identical to the WT. It is therefore likely that any aggrecan degrading activity attributed to ADAMTS-4 in the growth plate can be compensated for adequately by other enzymes in the absence of ADAMTS-4.

Figure 3:
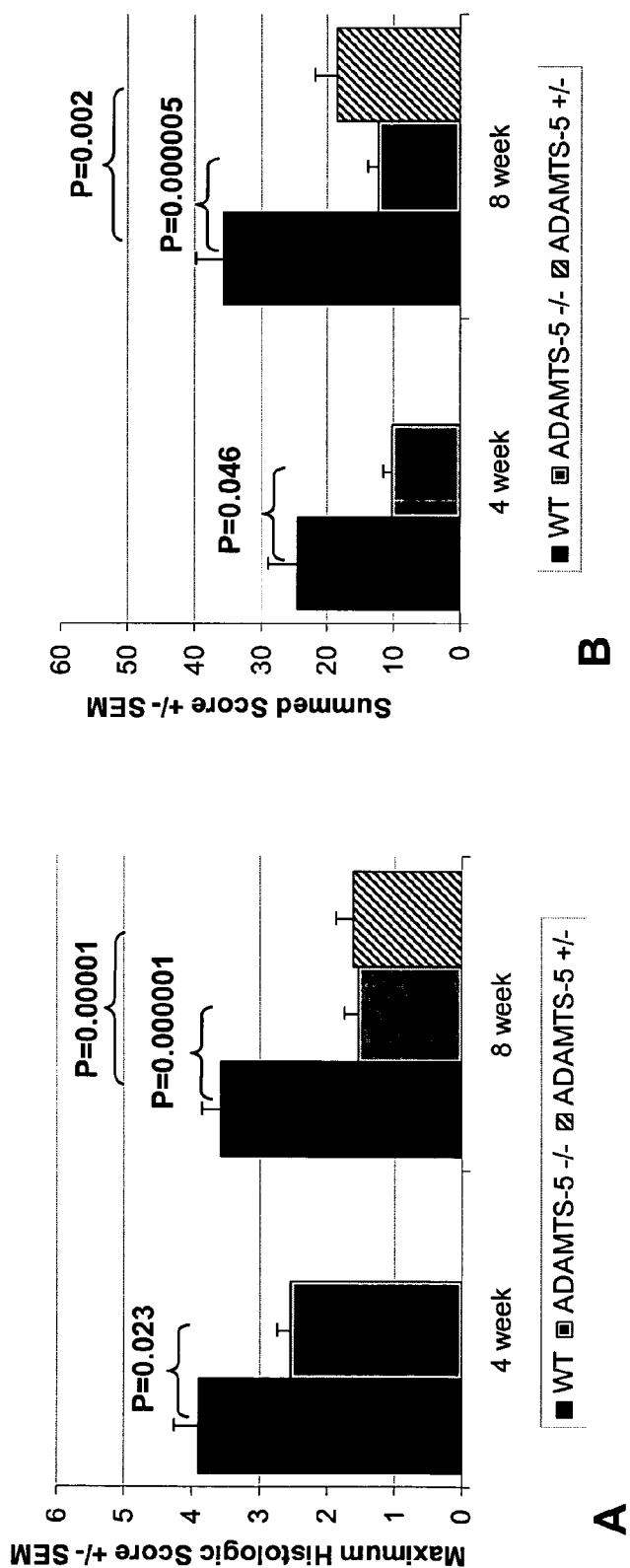
FIG. 3 illustrates the histologic scores of joints from WT, ADAMTS-5 homozygous KO and ADAMTS-5 heterozygous mice 4 and 8 weeks after induction of surgical joint in stability (A) shows the histologic scores expressed as the mean maximal score from each joint, and (B) shows the histologic scores expressed as the mean of the sum of the scores form each histologic section through the joints.

As described in detail in Example 1 above, unilateral joint instability was generated by surgical transection of the anterior menisco-tibial ligament resulting in destabilization of the medial meniscus (DMM), the data are represented in FIG. 3A and FIG. 3B. Mice were sacrificed 4 and 8 weeks after surgery, and sections through the joint were scored using a reported scoring system (Chambers et al., 2001, *Arthritis & Rheum* 44:1455). Scores were reported as mean maximal score from WT and ADAMTS-5 homozygous KO and heterozygous KO. In addition, the scores from each section through the joint were added to express the severity of OA as the mean of the summed scored for each treatment group at each time point. This second method of scoring takes into account severity of the lesion as well as the surface area of the joint affected. As shown in FIGS. 3A and 3B, both methods of analysis revealed significant reduction (p<0.05) in the scores of the ADAMTS-5 homozygous and heterozygous KO compared to WT mice (FIG. 3). The summed scores of the ADAMTS-5 KO animals were reduced to less than 50% of the WT indicating reduced severity as well as surface area involvement. It is notable that we previously reported no difference in the scores in the identical surgical model performed on ADAMTS-4 KO mice. In addition, similar studies in the literature describing induction of OA in IL-1β, IL-1βr, INOS, and ICE KO mice reported increased severity of pathology in the genetically manipulated mice (Clements et al., 2003, *Arthritis & Rhuem* 48:3452). In order to compare the results with those published results examining the progression of osteoarthritis in IL-1β, IL-1βr, INOS, and ICE KO mice the results as mean scores of the medial tibial plateau of each experimental group were also expressed. FIG. 4 shows that these scores also were significantly reduced in the ADAMTS-5 homozygous and heterozygous KO animals.

Figure 5:
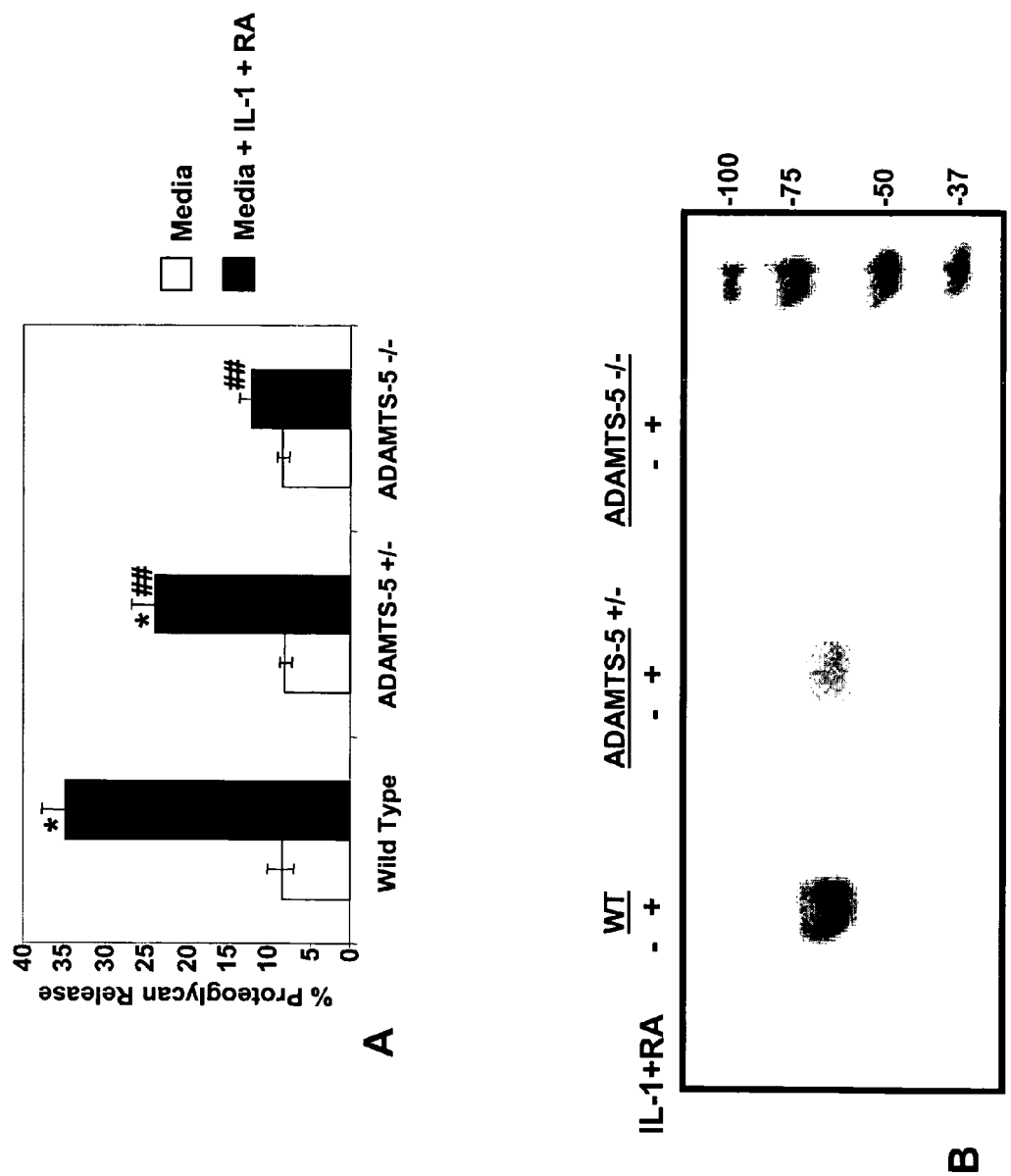
FIG. 5 illustrates proteoglycan release from articular cartilage from WT and ADAMTS-5 KO animals (A) shows the percent total proteoglycan released from cultured articular cartilage, (B) shows a western analysis of TEGE$^{373}$ neoepitope released from articular cartilage, and (C) shows immunostaining of femoral head articular cartilage from WT (top), ADAMTS-4 KO (center) and ADAMTS-5 KO (bottom) articular cartilage.
Figure 5:
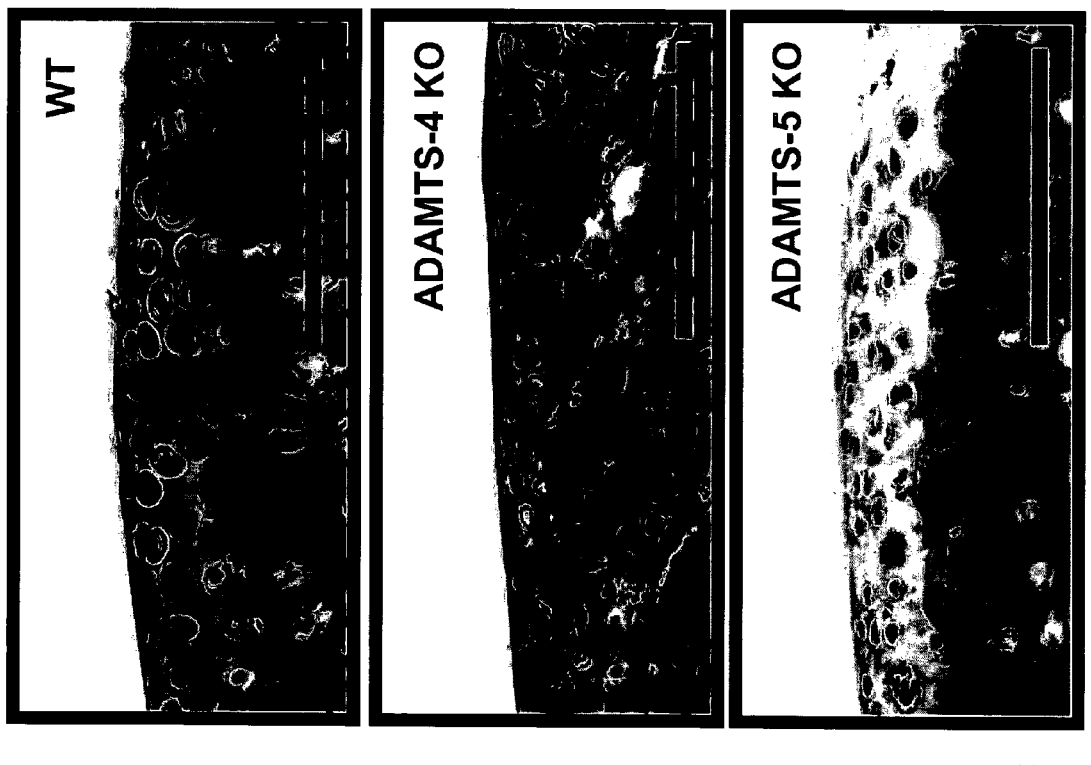

Femoral head articular cartilage was removed from ADAMTS-4 KO, ADAMTS-5 KO and WT mice and placed into tissue culture. Inflammatory cytokines (IL-1 and retinoic acid) were added to the culture system to induce degradative enzyme activity, and analysis of the aggrecan degradation products released from the cartilage were evaluated by quantitation of total proteoglycan release and by western blots using a monoclonal neoepitope antibody generated against the new C terminus of aggrecan after cleavage by an "aggrecanase" (G1-TEGE$^{373}$) (Collins-Racie et al., 2004, Matrix Biology 23:219-230). Results depicted in FIGS. 5A and 5B demonstrated equivalent total proteoglycan release, and equivalent generation of the TEGE$^{373}$ neoepitope in articular cartilage from WT and ADAMTS-4 KO mice, while there was no evidence of aggrecanase-generated fragments in conditioned media from the articular cartilage of the ADAMTS-5 KO mice. FIG. 5C shows immunohistochemical analysis of these femoral heads using a polyclonal antibody generated against the TEGE$^{373}$ neoepitope demonstrated significant hybridization to the aggrecanase generated aggrecan neoepitope in articular cartilage from WT and ADAMTS-4 KO mice, and negligible hybridization in the ADAMTS-5 KO cartilage.

This work examined the affect of deletion of the activity of ADAMTS-5 (aggrecanase-2) on normal murine development, growth and physiology. Similar to reports previously examining the ADAMTS-4 KO mouse, deletion of ADAMTS-5 activity did not negatively affect any of these functions. Deletion of ADAMTS-5 activity did not affect aggrecanase-generated aggrecan turnover in the growth plates. However, surprisingly, deletion of ADAMTS-5 activity significantly abrogated the progression of osteoarthritis in these mice, while deletion of ADAMTS-4 activity had no such affect. This inability to cleave aggrecan at the "aggrecanase" site within the interglobular domain of the substrate in the ADAMTS-5 knockout was further substantiated by lack of appearance of these fragments after cytokine stimulation of articular cartilage in vitro in the ADAMTS-5 knockout mouse. Several enzymes have been reported to be capable of cleavage of aggrecan at the E$^{373-374}$A site within the interglobular domain of aggrecan including ADAMTS-1, ADAMTS-4, ADAMTS-5 and ADAMTS-9. The present invention shows that ADAMTS-5 is the enzyme responsible for articular cartilage extracellular matrix degradation in osteoarthritis. This is the first report of a single gene deletion capable of abrogating the course of osteoarthritis in an animal model. It is clear from these results that ADAMTS-5 is the primary "aggrecanase" responsible for aggrecan degradation in murine osteoarthritis.

Example 3

Preparation of Biaryl Sulfanomides

Examples 3.1 and 3.2 were made based on Scheme 1

Example 3.1

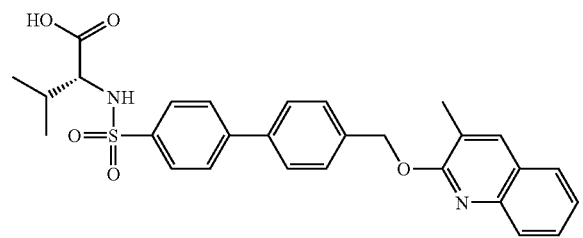

3-Methyl-2-[4'-(3-methyl-quinolin-2-yloxymethyl)-biphenyl-4-sulfonylamino]-butyric acid Step 1A [Intermediate 1] To a dry round-bottom flask was added 4-Bromo-benzenesulfonyl chloride (12.2 g, 47.7 mmol, 1 equiv.), anhydrous methylene chloride (170 mL), and H-D-Val-OMe (8.0 g, 47.7 mmol, 1 equiv.). The mixture was cooled to 0° C. in an ice bath followed by the addition of Hunig base (19.11 mL, 109.7 mmol, 2.3 equiv.). The reaction mixture was allowed to warm to room temperature and was stirred overnight. Reaction was complete as determined by TLC. The reaction mixture was then diluted with dichloromethane (100 mL) and washed with brine. The organic layer was dried over anhydrous MgSO$_4$, solvent evaporated to yield 2-(4-Bromo-benzenesulfonylamino)-3-methyl-butyric acid methyl ester in 96% yield (16.0 g). 1H NMR (400 MHz, CHLOROFORM-D) δ ppm 0.87 (d, J=6.82 Hz, 3 H) 0.96 (d, J=6.82 Hz, 3 H) 2.04 (m, 1 H) 3.49 (s, 3 H) 3.74 (d, J=14.40 Hz, 1 H) 5.10 (d, J=9.85 Hz, 1 H) 7.66 (m, 4 H Step 1B [Intermediate 2: 2-($^4$-Bromo-benzenesulfonylamino)-3-methyl-butyric acid methyl ester (3.4 g, 9.71 mmol), 4-hydroxymethyl phenyl boronic acid (1.48 g, 9.71 mmol, 1 equiv.), Pd(PPh$_3$)$_4$ (561 mg, 0.48 mmol, 0.05 equiv.) were dissolved in ethylene glycol dimethyl ether (90 mL) under N$_2$ atmosphere and stirred at room temperature for 30 min. Then K$_2$CO$_3$ (2.68 g, 19.4 mmol, 2 equiv.) in H$_2$O (30 mL) was introduced to the reaction mixture and heat to reflux overnight. After TLC confirmation of reaction completion, solvent was removed by rotovap, residue partitioned between EtOAc and brine, organic layer dried over MgSO$_4$, solvent removed, crude residue was triturated with EtOAc to give 2-(4'-Hydroxymethyl-biphenyl-4-sulfonylamino)-3-methyl-butyric acid methyl ester in 67% yield (2.46 g).

1 H NMR (400 MHz, CHLOROFORM-D) δ ppm 0.90 (d, J=7.07 Hz, 3 H) 0.97 (d, J=6.82 Hz, 3 H) 1.57 (s, 1 H) 2.04 (m, 1 H) 3.43 (s, 3 H) 3.79 (dd, J=10.11, 5.05 Hz, 1 H) 4.78 (s, 2 H) 5.11 (d, J=10.36 Hz, 1 H) 7.49 (d, J=8.34 Hz, 2 H) 7.60 (d, J=8.34 Hz, 2 H) 7.70 (d, J=8.84 Hz, 2 H) 7.88 (d, J=8.59 Hz, 2 H).

Step 1C [Intermediate 3: 2-(4'-Hydroxymethyl-biphenyl-4-sulfonylamino)-3-methyl-butyric acid methyl ester (1.2 g, 3.2 mmol, 1.0 equiv.), 2-chloro-3-methyl quinoline (2.26 g, 12.7 mmol, 4 equiv.) were dissolved in DMF (30 mL) followed by the addition of NaH (382 mg, 60% in oil, 9.54 mmol, 3 equiv.). The mixture was stirred at 100° C. for 5 hrs, then at room temperature overnight. The reaction mixture was then poured into cold water, solid precipitated from the mixture was collected by filtration and washed with water. Regular column chromatography (Silica gel, 1% MeOH/$CH_2Cl_2$) to yield 203 mg of 3-Methyl-2-[4'-(3-methyl-quinolin-2-yloxymethyl)-biphenyl-4-sulfonylamino]-butyric acid methyl ester in 12% yield.

H NMR (400 MHz, CHLOROFORM-D) δ ppm 0.89 (d, J=6.82 Hz, 3 H) 0.97 (d, J=6.82 Hz, 3 H) 2.04 (m, 1 H) 2.40 (s, 3 H) 3.43 (s, 3 H) 3.78 (dd, J=10.11, 5.31 Hz, 1 H) 5.09 (d, J=10.11 Hz, 1 H) 5.64 (s, 2 H) 7.37 (m, 1 H) 7.64 (m, 8 H) 7.86 (m, 4 H).

Step 1D: 3-Methyl-2-[4'-(3-methyl-quinolin-2-yloxymethyl)-biphenyl-4-sulfonylamino]-butyric acid methyl ester (203 mg, 0.39 mmol, 1 equiv.) was dissolved in THF (8 mL) and MeOH (4 mL) and hydrolyzed with 1N NaOH (5.83 mL, 5.83 mmol, 13 equiv.). After stirring for 3 days, solvent was removed and the residue was dissolved in $H_2O$. The mixture was then acidified to pH 3 using 1N HCl. Solid precipitated from the mixture was collected by filtration and washed with water. After drying in vacuum oven, 101 mg of 3-Methyl-2-[4'-(3-methyl-quinolin-2-yloxymethyl)-biphenyl-4-sulfonylamino]-butyric acid was obtained in 76.3% yield.

1H NMR (400 MHz, DMSO-D6) δ ppm 0.81 (d, J=6.57 Hz, 3 H) 0.84 (d, J=6.82 Hz, 3 H) 1.95 (m, 1 H) 2.36 (s, 3 H) 3.56 (dd, J=9.09, 5.81 Hz, 1 H) 5.61 (s, 2 H) 7.42 (t, J=7.45 Hz, 1 H) 7.61 (t, J=7.71 Hz, 1 H) 7.67 (d, J=7.83 Hz, 2 H) 7.83 (m, 8 H) 8.08 (d, J=8.34 Hz, 2 H) 12.58 (s, 1 H).

Example 3.2

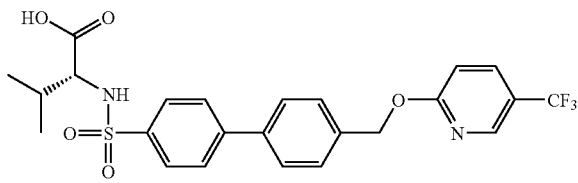

3-Methyl-2-[4'-(5-trifluoromethyl-pyridin-2-yloxymethyl)-biphenyl-4-sulfonylamino]-butyric acid The title compound, 3-Methyl-2-[4'-(5-trifluoromethyl-pyridin-2-yloxymethyl)-biphenyl-4-sulfonylamino]-butyric acid, was prepared according to the procedures similar to that described for Example 3.1.

Step 1C: 2-(4'-Hydroxymethyl-biphenyl-4-sulfonylamino)-3-methyl-butyric acid methyl ester (350 mg, 0.93 mmol, 1 equiv), 2-chloro-5-trifluoromethylpyridine (841 mg, 4.64 mmol, 5 equiv.) were dissolved in DMF (7 mL) followed by the addition of NaH (111 mg, 2.78 mmol, 3 equiv.) under $N_2$ atmosphere. The mixture was heat to 100° C. for 2 hrs and cool to room temperature. Reaction mixture poured onto cold water and the resulting solid collected by filtration. Further purification by column chromatography (Silica gel, 20% EtOAc/Hexane) to afford 259 mg of G9058-182-2 in 54% yield.

1H NMR (400 MHz, CHLOROFORM-D) δ ppm 0.82 (d, J=6.82 Hz, 3 H) 0.90 (d, J=6.82 Hz, 3 H) 1.98 (m, 1 H) 3.36 (s, 3 H) 3.72 (dd, J=10.11, 5.05 Hz, 1 H) 5.02 (d, J=10.11 Hz, 1 H) 5.43 (s, 2 H) 6.84 (d, J=8.84 Hz, 1 H) 7.52 (m, 4 H) 7.64 (d, J=6.82 Hz, 2 H) 7.74 (d, J=8.84 Hz, 1 H) 8.40 (s, 1 H).

Step 1D: 3-Methyl-2-[4'-(5-trifluoromethyl-pyridin-2-yloxymethyl)-biphenyl-4-sulfonylamino]-butyric acid (86.4% yield, 210 mg) was prepared according to procedures in Step 1D for Example 1A, using 3-Methyl-2-[4'-(5-trifluoromethyl-pyridin-2-yloxymethyl)-biphenyl-4-sulfonylamino]-butyric acid methyl ester (250 mg) as the starting material.

1H NMR (400 MHz, DMSO-D6) δ ppm 0.81 (d, J=6.82 Hz, 3 H) 0.84 (d, J=6.57 Hz, 3 H) 1.95 (m, 1 H) 3.56 (m, 1 H) 5.51 (d, 2 H) 7.12 (d, J=8.84 Hz, 1 H) 7.59 (d, J=8.34 Hz, 2 H) 7.77 (d, J=8.34 Hz, 2 H) 7.86 (m, 4 H) 8.11 (m, 2 H) 8.63 (m, 1 H) 12.57 (s, 1 H).

Example 3.3 and 3.4 were made based on Scheme 2.

Example 3.3

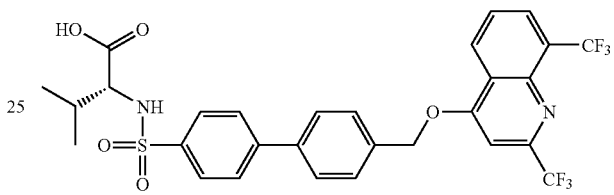

2-[4'-(2,8-Bis-trifluoromethyl-quinolin-4-yloxymethyl)-biphenyl-4-sulfonylamino]-3-methyl-butyric acid Step 2A [Intermediate 4, G9591-157-1]: To a solution of 2,8-Bis-trifluoromethyl-quinolin-4-ol (3.85 g, 13.7 mmol, 1.1 equiv.) in DMF (40 mL) was added 2-(4-Bromomethyl-phenyl)-4,4,5,5-tetramethyl-[1,3,2]dioxaborolane (3.7 g, 12.5 mmol, 1.0 equiv.) and $K_2CO_3$ (3.45 g, 24.92 mmol, 2.2 equiv.) under $N_2$ atmosphere. The reaction mixture was stirred at room temperature overnight. The reaction was complete as determined by TLC. The reaction mixture was poured into cold water, the white precipitate formed was collected by filtration, washed with water, dried under vacuum to yield 4-[4-(4,4,5,5-Tetramethyl-[1,3,2]dioxaborolan-2-yl)-benzyloxy]-2,8-bis-trifluoromethyl-quinoline in 73% yield (4.95 g).

1H NMR (400 MHz, CHLOROFORM-D) δ ppm 1.36 (s, 12 H) 5.38 (s, 2 H) 7.21 (s, 1 H) 7.51 (d, J=8.34 Hz, 2 H) 7.65 (t, J=7.83 Hz, 1 H) 7.90 (d, J=8.08 Hz, 2 H) 8.14 (d, J=7.33 Hz, 1 H) 8.50 (d, J=8.59 Hz, 1 H).

Step 2B [Intermediate 5, G9591-162]: To 4-[4-(4,4,5,5-Tetramethyl-[1,3,2]dioxaborolan-2-yl)-benzyloxy]-2,8-bis-trifluoromethyl-quinoline (1.5 g, 3.0 mmol, 1 equiv.) in 45 mL of ethylene glycol dimethyl ether was added 2-(4-Bromo-benzenesulfonylamino)-3-methyl-butyric acid methyl ester (1.06 g, 3.0 mmol, 1.0 equiv.) and $Pd(PPh_3)_4$ (174 mg, 0.15 mmol, 0.05 equiv.) under $N_2$. The reaction mixture was stirred for 0.5 hr, then an aqueous solution of $K_2CO_3$ (834 mg, 6.0 mmol, 2 equiv.) was added. The mixture was heat to reflux overnight. After cooling to room temperature, solvent was removed under vacuum. The residue was diluted with EtOAc (100 mL) and washed with brine solution. The organic layer was dried over anhydrous $MgSO_4$, solvent evaporated under vacuum, and the crude product was purified on silica gel column (30% EtOAc/Hexane) to give 1.026 g of 2-[4'-(2,8-

Bis-trifluoromethyl-quinolin-4-yloxymethyl)-biphenyl-4-sulfonylamino]-3-methyl-butyric acid methyl ester in 53% yield.

1H NMR (400 MHz, CHLOROFORM-D) δ ppm 0.90 (d, J=6.82 Hz, 3 H) 0.98 (d, J=6.82 Hz, 3 H) 2.07 (m, 1 H) 3.45 (s, 3 H) 3.81 (dd, J=10.1 1, 5.05 Hz, 1 H) 5.12 (d, J–10.11 Hz, 1 H) 5.44 (s, 2 H) 7.25 (s, 1 H) 7.70 (m, 7 H) 7.92 (d, J=8.84 Hz, 2 H) 8.16 (d, J=7.33 Hz, 1 H) 8.52 (d, J=8.59 Hz, 1 H).

Step 2C: 2-[4'-(2,8-Bis-trifluoromethyl-quinolin-4-yloxymethyl)-biphenyl-4-sulfonylamino]-3-methyl-butyric acid methyl ester (1.026 g, 1.6 mmol, 1 equiv.) was dissolved in THF (15 mL) and MeOH (6 mL) and 1N NaOH (17.6 mL, 11 equiv.) was added. The reaction was monitored by TLC. It was complete in 3 days. Solvent was removed by rotovap and the residue was dissolved in H₂O. The mixture was then acidified to pH 3 with 1N HCl. The resulting precipitate was collected by filtration and washed with cold water and dried overnight. 460 mg of white solid was obtained in 46% yield.

1H NMR (400 MHz, DMSO-D6) δ ppm 0.82 (d, J=6.82 Hz, 3 H) 0.85 (d, J=6.82 Hz, 3 H) 1.96 (m, 1 H) 3.57 (dd, J=9.35, 6.32 Hz, 1 H) 5.66 (s, 2 H) 7.83 (m, 10 H) 8.11 (d, J=9.35 Hz, 1 H) 8.35 (d, J=7.33 Hz, 1 H) 8.58 (d, J=7.83 Hz, 1 H) 12.57 (s, 1 H).

Example 3.4

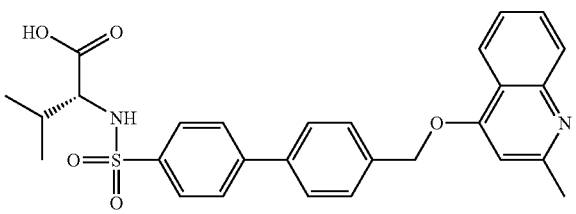

D-3-Methyl-2-[4'-(2-methyl-quinolin-4-yloxymethyl)-biphenyl-4-sulfonylamino]-butyric acid The title compound, D-3-Methyl-2-[4'-(2-methyl-quinolin-4-yloxymethyl)-biphenyl-4-sulfonylamino]-butyric acid, was prepared according to the procedures similar to that described for Example 3.3.

Step 2A: Alkylation of 2-Methyl-quinolin-4-ol with 2-(4-Bromomethyl-phenyl)-4,4,5,5-tetramethyl-[1,3,2]dioxaborolane was carried out according to procedures in Step 2A for Example 1C to give 2-Methyl-4-[4-(4,4,5,5-tetramethyl-[ 1,3,2]dioxaborolan-2-yl)-benzyloxy]-quinoline in 28% yield. 1H NMR (400 MHz, DMSO-D6) δ ppm 1.3 (s, 12 H) 2.6 (s, 3 H) 5.4 (s, 2 H) 7.0 (s, 1 H) 7.5 (m, 1 H) 7.6 (d, J=8.1 Hz, 2 H) 7.7 (d, J=8.1 Hz, 2 H) 7.9 (d, J=8.1 Hz, 1 H) 8.1 (dd, J=8.3, 0.8 Hz, 1 H).

Step 2B: Suzuki coupling of D-2-(4-Bromo-benzenesulfonylamino)-3-methyl-butyric acid methyl ester with 2-Methyl-4-[4-(4,4,5,5-tetramethyl-[1,3,2]dioxaborolan-2-yl)-benzyloxy]-quinoline was carried out according to procedures in Step 2B for Example 3.3 in 80% yield. 1H NMR (400 MHz, DMSO-D6) δ ppm 0.8 (dd, J=15.0, 6.7 Hz, 6 H) 1.9 (m, 1 H) 2.6 (s, 3 H) 3.3 (s, 3 H) 3.6 (dd, J=9.3, 7.1 Hz, 1 H) 5.5 (s, 2 H) 7.1 (s, 1 H) 7.5 (t, J=7.6 Hz, 1 H) 7.7 (m, 3 H) 7.8 (d, J=7.6 Hz, 4 H) 7.9 (m, 1 H) 7.9 (m, 2 H) 8.1 (d, J=8.3 Hz, 1 H) 8.3 (d, J=9.3 Hz, 1 H).

Step 2C: Hydrolysis of D-3-Methyl-2-[4'-(2-methyl-quinolin-4-yloxymethyl)-biphenyl-4-sulfonylamino]-butyric acid methyl ester was carried out according to procedures in Step 2C for Example 3.3 in quantitative yield. 1H NMR (400 MHz, DMSO-D6) δ ppm 0.8 (dd, J=40.2, 6.8 Hz, 6 H) 2.0 (m, 1 H) 2.6 (s, 3 H) 3.0 (s, 1 H) 5.4 (s, 2 H) 7.1 (s, 1 H) 7.5 (t, J=8.1 Hz, 1 H) 7.7 (t, J=7.7 Hz, 3 H) 7.8 (m, 7 H) 8.1 (d, J=9.3 Hz, 1 H).

Example 3.5 was made based on Scheme 3.

Example 3.5

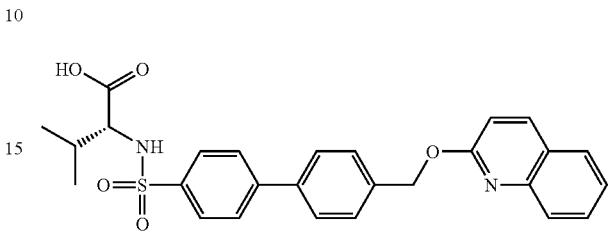

Step 3A. To a round-bottom flask was added 4-Bromo-benzenesulfonyl chloride (24.37 g, 95.4 mmol, 1 equiv), anhydrous methylene chloride (350 mL), and H-D-Val-OtBu (20 g, 95.4 mmol, 1 equiv.). The mixture was cool to 0° C. followed by the addition of Hunig's base (38.2 mL, 219 mmol, 2.3 equiv.). The cooling bath was then removed and the reaction mixture was allowed to warm to room temperature and stirred overnight. Starting material was consumed as determined by TLC. The reaction mixture was then diluted with methylene chloride (200 mL) and washed with H₂O (500 mL), brine (250 mL). The organic layer was dried over anhydrous MgSO₄, evaporated under vacuum to yield 2-(4-Bromo-benzenesulfonylamino)-3-methyl-butyric acid tert-butyl ester in quantitative yield (35.0 g).

1H NMR (400 MHz, DMSO-D6) δ ppm 0.82 (d, J=6.82 Hz, 3 H) 0.84 (d, J=6.82 Hz, 3 H) 1.19 (s, 9 H) 1.93 (m, 1 H) 3.46 (dd, J=9.35, 6.06 Hz, 1 H) 7.69 (d, J=8.59 Hz, 2 H) 7.79 (m, 2 H) 8.24 (d, J=9.60 Hz, 1 H).

Step 3B: 2-(4-Bromo-benzenesulfonylamino)-3-methyl-butyric acid tert-butyl ester (11.96 g, 30.47 mmol, 1 equiv.), 4-(Hydroxymethylbenzene) boronic acid (4.63 g, 30.5 mmol, 1 equiv) and Pd(PPh₃)₄ (1.76 g, 1.52 mmol, 0.05 equiv.) were charged to a reaction flask and added with ethylene glycol dimethyl ether (300 mL). The mixture was stirred at room temperature for 10 min., then a solution of K₂CO₃ (8.43 g, 60.9 mmol, 2 equiv.) dissolved in 100 mL H₂O was introduced. The reaction mixture was heat to reflux overnight. After cooling to room temperature, solvent was removed by rotavap and the residue partitioned between EtOAc and brine. Organic layer was separated and dried over MgSO₄. After removing solvent by rotavap, 8.3 g of white solid 2-(4'-Hydroxymethyl-biphenyl-4-sulfonylamino)-3-methyl-butyric acid tert-butyl ester was obtained in 65% yield.

1H NMR (400 MHz, MeOD) δ ppm 1.05 (d, J=6.82 Hz, 3 H) 1.12 (d, J=6.82 Hz, 3 H) 1.33 (s, 9 H) 2.16 (m, 1 H) 3.73 (d, J=5.56 Hz, 1 H) 4.81 (s, 2 H) 7.62 (d, J=8.59 Hz, 2 H) 7.78 (d, J=8.34 Hz, 2 H) 7.92 (d, J=8.84 Hz, 2 H) 8.04 (m, 2 H).

Step 3C 2-(4'-Hydroxymethyl-biphenyl-4-sulfonylamino)-3-methyl-butyric acid tert-butyl ester (700 mg, 1.68 mmol, 1 equiv), 2-chloroquinoline (1.1 g, 6.7 mmol, 4 equiv) were dissolved in DMF (20 mL) and added with and NaH (202 mg, 60% in oil, 5.04 mmol, 3 equiv). The mixture was heat to 100° C. for 2 hrs. After cooling to room temperature, the reaction mixture was quenched with sat. NH₄Cl (aq). After stirring for 0.5 h, solid precipitated from the mixture. Solid was collected by filtration and washed with water and dried overnight to produce 793 mg of 2-[4'-(Isoquinolin-3- yloxymethyl)-biphenyl-4-sulfonylamino]-3-methyl-butyric acid tert-butyl ester in 87% yield.

1H NMR (400 MHz, CHLOROFORM-D) δ ppm 0.87 (d, J=6.82 Hz, 3 H) 1.03 (d, J=6.82 Hz, 3 H) 1.19 (s, 9 H) 2.05 (m, 1 H) 3.66 (dd, J=9.85, 4.55 Hz, 1 H) 5.14 (d, J=9.85 Hz, 1 H) 5.62 (s, 2 H) 6.98 (d, J=8.84 Hz, 1 H) 7.40 (m, 1 H) 7.66 (m, 9 H) 7.89 (m, 2 H) 8.03 (d, J=8.59 Hz, 1 H).

Step 3D: 2-[4'-(Isoquinolin-3-yloxymethyl)-biphenyl-4-sulfonylamino]-3-methyl-butyric acid tert-butyl ester (480 mg, 0.88 mmol) was dissolved in 15 mL of dichloromethane. The solution was cool to 0° C. followed by the addition of 5 mL of TFA. The resulting mixture was stirred at room temperature for 4 hrs. Solvent was removed by rotavap and the residue was washed with MeOH. Solid thus obtained was dried overnight under vacuum to afford 60 mg of 2-[4'-(Isoquinolin-3-yloxymethyl)-biphenyl-4-sulfonylamino]-3-methyl-butyric acid in 14% yield.

1H NMR (400 MHz, DMSO-D6) δ ppm 0.81 (d, J=6.82 Hz, 3 H) 0.84 (d, J=6.82 Hz, 3 H) 1.95 (m, 1 H) 3.56 (dd, J=9.35, 6.06 Hz, 1 H) 5.58 (s, 2 H) 7.11 (d, J=8.84 Hz, 1 H) 7.46 (dd, J=7.58, 6.32 Hz, 1 H) 7.79 (m, 11 H) 8.08 (d, J=9.35 Hz, 1 H) 8.29 (d, J=8.59 Hz, 1 H) 12.57 (s, 1 H).

Example 3.6 was made based on Scheme 4.

Example 3.6

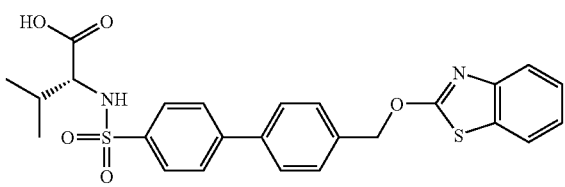

2-[4'-(Benzothiazol-2-yloxymethyl)-biphenyl-4-sulfonylamino]-3-methyl-butyric acid To 2-[4-(4,4,5,5-tetramethyl-[1,3,2]dioxaborolan-2-yl)-benzyloxy]-benzothiazole (300 mg, 0.604 mmol, 1 equiv.) in 9 mL of dimethoxy ethane was added 2-(4-Bromo-benzenesulfonylamino)-3-methyl-butyric acid tert-butyl ester (237 mg, 0.604 mmol, 1 equiv.) and Pd(PPh3)4 (35 mg, 0.03 mmol, 0.05 equiv). The mixture was stirred at room temperature for 20 min followed by the addition of K2CO3 (167 mg, 1.208 mmol, 2 equiv.) in H2O (3 mL). The mixture was heat to reflux overnight. After cooling to room temperature, solvent was removed by rotavap. Residue was dissolved in methylene chloride and washed with water, brine. Organic layer dried over MgSO4, solvent removed under vacuum, crude mixture purified by column chromatography (30% EtOAc/Hexane) to give 285 mg of in 85% yield.

1H NMR (400 MHz, CHLOROFORM-D) δ ppm 1.07 (d, J=6.82 Hz, 3 H) 1.23 (d, J=6.82 Hz, 3 H) 1.39 (s, 9 H) 1.47 (t, J=7.20 Hz, 1 H) 3.86 (dd, J=9.85, 4.55 Hz, 1 H) 5.42 (s, 2 H) 6.99 (s, 1 H) 7.22 (d, J=7.07 Hz, 1 H) 7.39 (m, 2 H) 7.61 (d, J=8.59 Hz, 2 H) 7.67 (d, J=6.32 Hz, 1 H) 7.72 (m, 2 H) 7.84 (d, J=8.84 Hz, 2 H) 8.09 (d, J=8.59 Hz, 2 H).

Step 4B 2-[4'-(Benzothiazol-2-yloxymethyl)-biphenyl-4-sulfonylamino]-3-methyl-butyric acid tert-butyl ester (140 mg, 0.25 mml) was dissolved in 6 mL of methylene chloride followed by the addition of TFA (3 mL) The reaction was complete in 6 hrs as determined by TLC. Solvent was removed and the residue was dissolved in EtOAc. n-Hexane was added into the solution and solid precipitated from the mixture. The precipitate was collected and dried to afford 86 mg of in 68% yield.

1H NMR (400 MHz, DMSO-D6) δ ppm 0.80 (d, J=6.82 Hz, 3 H) 0.83 (d, J=6.82 Hz, 3 H) 1.93 (m, 1 H) 3.54 (dd, J=9.35, 6.06 Hz, 1 H) 5.26 (s, 2 H) 7.21 (m, 1 H) 7.33 (m, 2 H) 7.44 (d, J=8.59 Hz, 2 H) 7.71 (t, J=8.46 Hz, 3 H) 7.82 (s, 4 H) 8.07 (d, J=9.35 Hz, 1 H) 12.55 (s, 1 H).

Examples 3.7, 3.8, 3.9, 3.10, 3.11, 3.12, 3.13, 3.14, 3.15, 3.16, 3.17, 3.18 were made based on Scheme 4B.

Example 3.7

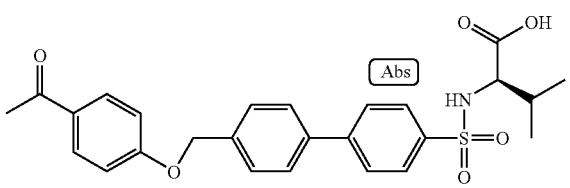

ES–480.1 (M–H)–HRMS: 482.16311 (M+Na)+; 482.16319 Calc'd

Example 3.8

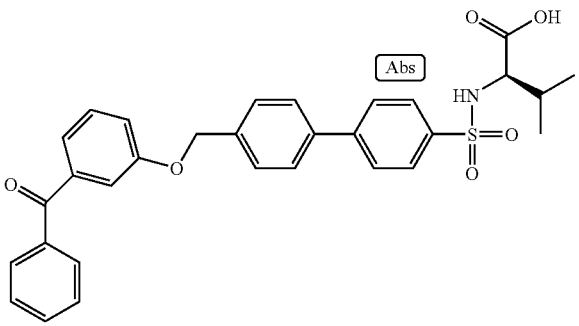

ES+544.2 (M+H)+HRMS: 544.17694 (M+H); 544.17884 Calc'd

Example 3.9

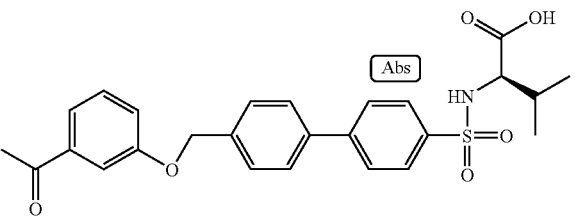

ES–480.2 (M–H)–HRMS: 482.1635 (M+H)+; 482.16319 Calc'd

Example 3.10
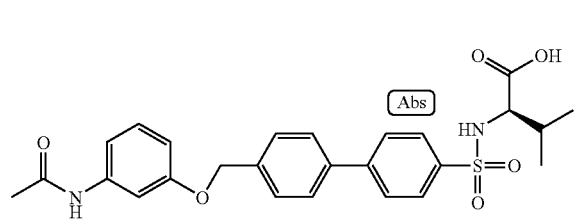
ES–495.2 (M–H)–HRMS: 497.17284 (M+H)+; 497.17409 Calc'd
Example 3.11
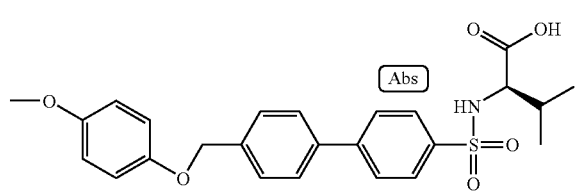
ES–468.2 (M–H)–HRMS: 470.16231 (M+H)+; 470.16319 Calc'd
Example 3.12
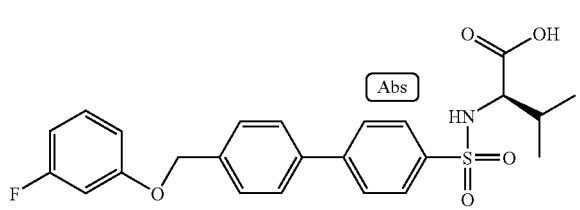
ES–456.1 (M–H)–HRMS: 458.14323 (M+H)+; 458.1432 Calc'd
Example 3.13
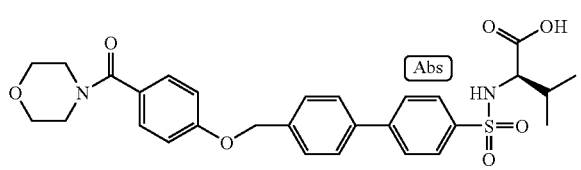
ES–551.2 (M–H)–HRMS: 553.19849 (M+H)+; 553.2003 Calc'd
Example 3.14
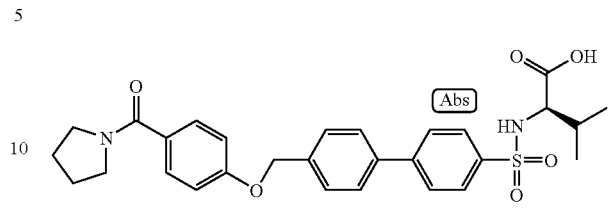
ES–535.2 (M–H)–HRMS: 537.20469 (M+H)+; 537.20539 Calc'd
Example 3.15
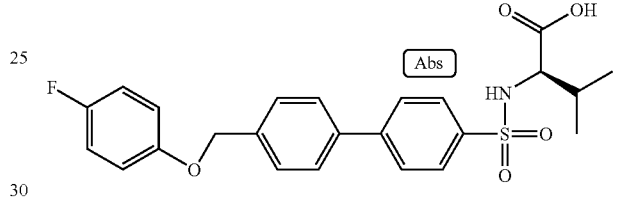
ES–456.1 (M–H)–HRMS: 458.14389 (M+H)+; 458.1432 Calc'd
Example 3.16
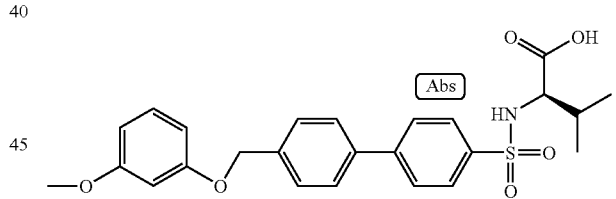
ES–468.2 (M–H)–HRMS: 470.16151 (M+H)+; 470.16319 Calc'd
Example 3.17
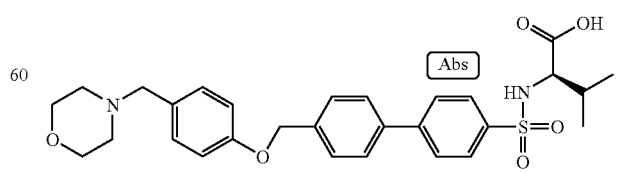
ES+539.1 (M+H)+HRMS: 539.2202 1 (M+H)+; 539.22104 Calc'd

Example 3.18

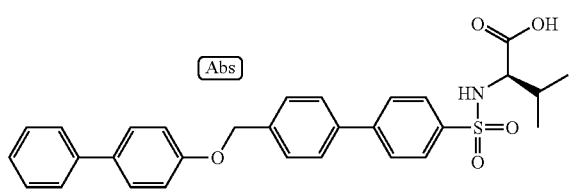

ES–514.1 (M−H)–HRMS: 516.18313 (M+H)+; 516.18392 Calc'd

Examples 3.19, 3.20, 3.21, 3.22, 3.23, 3.24, 3.25, 3.26, 3.27, 3.28, 3.29, 3.30, 3.32 were made based on Scheme 4C.

Example 3.19

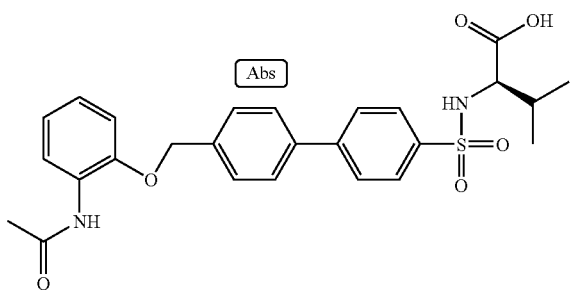

ES–495.1 (M−H)–HRMS: 497.17429 (M+H)+; 497.17409 Calc'd

Example 3.20

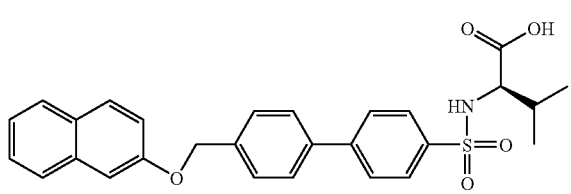

ES–488.1 (M−H)–HRMS: 490.16864 (M+H)+; 490.16827 Calc'd

Example 3.21

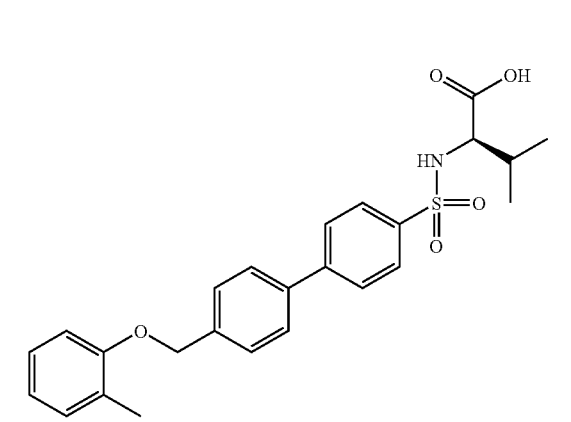

ES+ m/z 452.1 (M−H)–HRMS: 454.16745 (M+H)+; 454.16827 Calc'd $^1$H NMR (400 MHz, CDCl$_3$): δ 0.82 (d, 3H, J=6.8 Hz), 0.94 (d, 3H, J=6.8 Hz), 2.06 (m, 1H), 2.31 (s, 3H), 3.80 (dd, 1H, J=4.4, 10 Hz), 5.13 (m, 3H), 6.90 (m, 2H), 7.17 (m, 2H), 7.55 (d, 2H, J=8 Hz), 7.60 (d, 2H, J=8 Hz), 7.66 (d, 2H, J=8 Hz), 7.86 (d, 2H, J=8 Hz).

Example 3.22

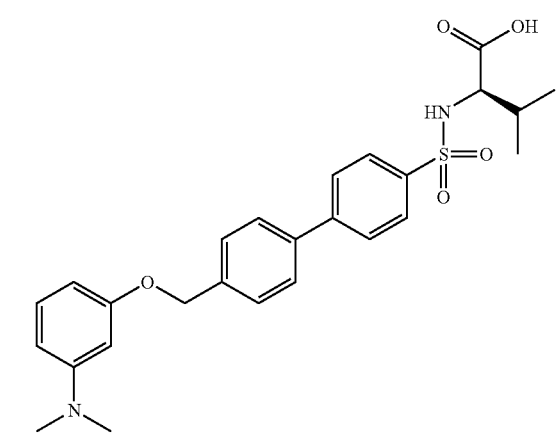

ES+m/z 481.2 (M+H)+HRMS: 483.19410 (M+H)+; 483.19482 Calc'd $^1$H NMR (400 MHz, CD$_3$OD): δ 0.90 (d, 3H, J=6.8 Hz), 0.99 (d, 3H, J=6.8 Hz), 2.06 (m, 1H), 2.92 (s, 6H), 3.42 (s, 3H), 3.70 (d, 1H, J=5.6, 10 Hz), 5.14 (s, 2H), 6.41 (m, 3H), 7.11 (m, 1H), 7.57 (d, 2H, 8 Hz), 7.71 (d, 2H, J=8 Hz), 7.80 (d, 2H, J=8 Hz), 7.92 (d, 2H, J=8 Hz).

Example 3.23

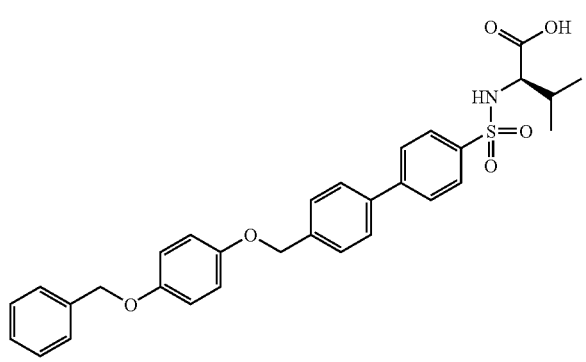

ES+ m/z 544.1 (M+H)+HRMS: 546.19448 (M+H)+; 546.19449 Calc'd $^1$H NMR (400 MHz, CD$_3$OD): δ 0.93 (d, 3H, J=6.8 Hz), 0.99 (d, 3H, J=6.8 Hz), 2.07 (m, 1H), 3.70 (d, 1H, J=5.6), 5.03 (s, 2H), 5.10 (s, 2H), 6.94 (s, 4H), 7.31 (m, 2H), 7.37 (m, 2H), 7.43 (m, 2H), 7.55 (d, 2H, 8 Hz), 7.71 (d, 2H, J=8 Hz), 7.80 (d, 2H, J=8 Hz) 7.92 (d, 2H, J=8 Hz).

Example 3.24

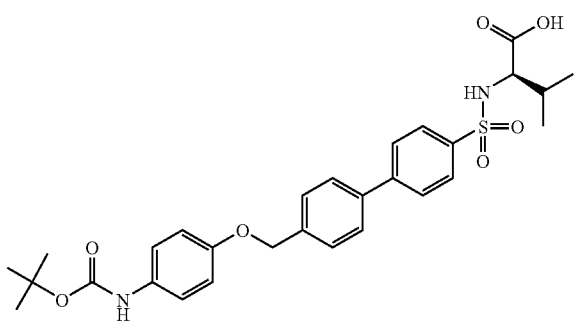

ES+ m/z 553.2 (M−H)−HRMS: 577.19777 (M+Na)+; 577.19789 Calc'd
¹H NMR (400 MHz, CD₃OD): δ 0.91 (d, 3H, J=6.8 Hz), 0.97 (d, 3H, J=6.8 Hz), 1.50 (s, 9H), 2.04 (m, 1H), 3.68 (d, 1H, J=5.6 Hz), 5.10 (s, 2H), 6.92 (s, 2H), 7.28 (d, 2H, J=8 Hz), 7.54 (d, 2H, J=8 Hz), 7.70 (d, 2H, J=8 Hz), 7.79 (d, 2H, J=8 Hz), 7.91 (d, 2H, J=8 Hz).

Example 3.25

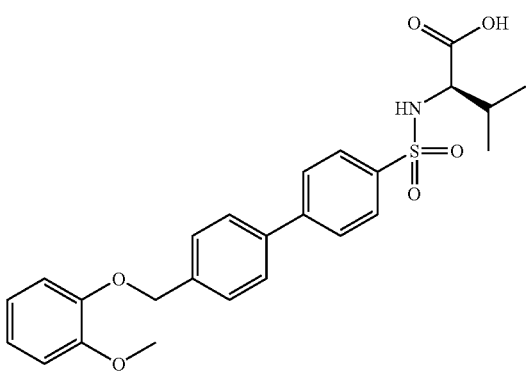

ES+ m/z 470.2 (M+H)+HRMS: 470.16364 (M+H)+; 470.16319 Calc'd
¹H NMR (400 MHz, CDCl₃): δ 0.89 (d, 3H, J=6.8 Hz), 0.96 (d, 3H, J=6.8 Hz), 2.10 (m, 1H), 3.82 (m, 1H), 3.90 (s, 3H), 5.07 (d, 1H, J=9.6 Hz), 5.21 (s, 2H), 6.93 (m, 4H), 7.54 (d, 2H, J=8 Hz), 7.58 (d, 2H, J=8 Hz), 7.65 (d, 2H, J=8 Hz), 7.89 (d, 2H, J=8 Hz).

Example 3.26

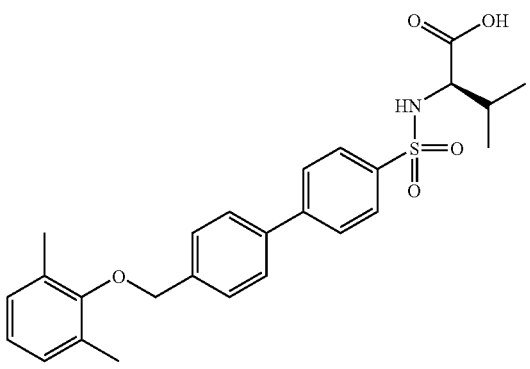

ES+ m/z 466.2 (M−H)−HRMS: 468.18540 (M+H)+; 468.18392 Calc'd
¹H NMR (400 MHz, CDCl₃): δ 0.83 (d, 3H, J=6.8 Hz), 0.95 (d, 3H, J=6.8 Hz), 2.05 (m, 1H), 2.33 (s, 6H), 3.82 (dd, 1H, J=5.2, 10 Hz), 4.88 (s, 2H), 5.07 (d, 1H, J=10 Hz), 6.97 (m, 1H), 7.05 (m, 2H), 7.64 (m, 4H), 7.67 (d, 2H, J=8 Hz), 7.87 (d, 2H, J=8 Hz).

Example 3.27

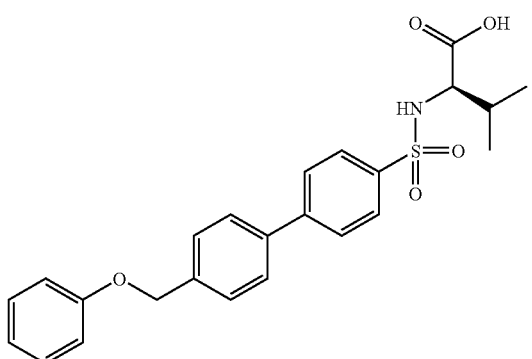

ES+ m/z 454.1 (M−H)−HRMS: 456.14707 (M+H)+; 456.14754 Calc'd
¹H NMR (400 MHz, acetone(d₆)): δ 0.92 (d, 3H, J=6.8 Hz), 0.98 (d, 3H, J=6.8 Hz), 2.10 (m, 1H), 3.16 (m, 1H), 5.16 (s, 2H), 6.45 (d, 1H, J=8 Hz), 6.53 (m, 2H), 7.10 (t, 1H, J=8 Hz), 7.61 (d, 2H, J=8 Hz), 7.76 (d, 2H, J=8 Hz), 7.86 (d, 2H, J=8 Hz), 7.94 (d, 2H, J=8 Hz).

Example 3.28

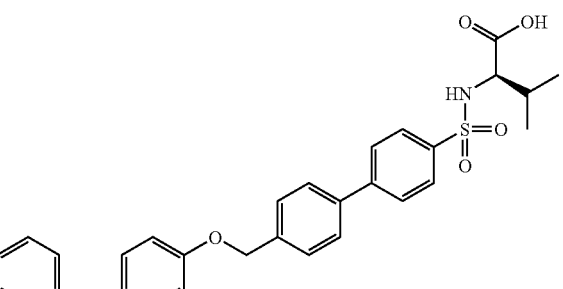

ES+ m/z 530.1 (M−H)−HRMS: 532.17709 (M+H)+; 532.17884 Calc'd
¹H NMR (400 MHz, CD₃OD): δ 0.93 (d, 3H, J=6.8 Hz), 0.99 (d, 3H, J=6.8 Hz), 2.06 (m, 1H), 3.70 (d, 1H, J=5.6, 10 Hz), 5.16 (s, 2H), 6.93 (m, 3H), 7.04 (m, 3H), 7.31 (m, 2H), 7.58 (d, 2H, J=8 Hz), 7.72 (d, 2H, J=8 Hz), 7.81 (d, 2H, J=8 Hz), 7.93 (d, 2H, J=8 Hz).

Example 3.29

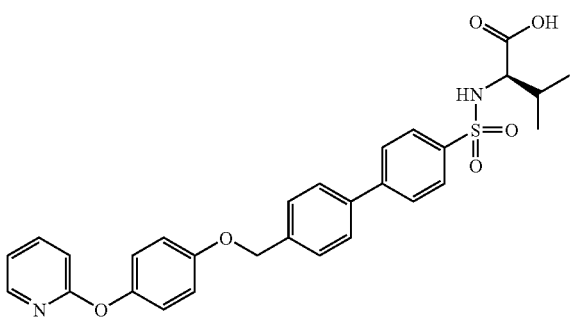

ES+ m/z 531.1 (M−H)−HRMS: 533.17293 (M+H)+; 533.17409 Calc'd

¹H NMR (400 MHz, CDCl₃): δ 0.88 (d, 3H, J=6.8 Hz), 1.00 (d, 3H, J=6.8 Hz), 2.13 (m, 1H), 3.83 (m, 1H), 5.13 (m, 3H), 6.82 (m, 1H), 7.02 (m, 5H), 7.56 (m, 4H), 7.67 (m, 3H), 7.89 (m, 2H), 8.16 (m, 1H).

Example 3.30

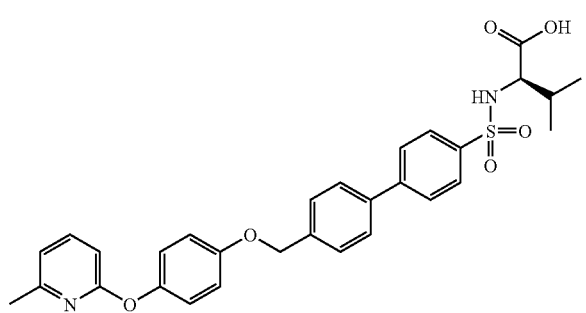

ES+ m/z 545.2 (M−H)−HRMS: 547.19006 (M+H)+; 547.18974 Calc'd

¹H NMR (400 MHz, CDCl₃): δ 0.89 (d, 3H, J=6.8 Hz), 1.01 (d, 3H, J=6.8 Hz), 2.19 (m, 1H), 2.44 (s, 3H), 3.83 (m, 1H), 5.04 (s, 2H), 6.39 (d, 1H, J=8 Hz), 6.83 (m, 1H), 6.90 (m, 2H, J=8 Hz), 6.97 (d, 2H, J=8 Hz), 7.52 (m, 5H), 7.60 (d, 2H, J=8 Hz), 7.90 (d, 2H, J=8 Hz).

Example 3.31

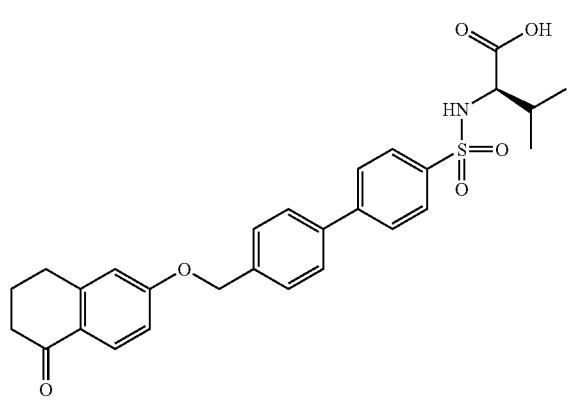

ES+ m/z 506.2 (M−H)−HRMS: 508.17782 (M+H)+; 508.17884 Calc'd

¹H NMR (400 MHz, DMSO): δ 0.81 (d, 3H, J=6.8 Hz), 0.84 (d, 3H, J=6.8 Hz), 1.98 (m, 3H), 2.64 (d, 2H), 2.91 (t, 2H, J=6 Hz), 3.56 (dd, 1H, J=6, 9.2 Hz), 5.27 (s, 2H), 6.99 (d, 2H, J=8 Hz), 7.59 (d, 2H, J=8 Hz), 7.78 (d, 2H, J=8 Hz), 7.85 (m, 4H), 8.08 (d, 1H, 8 Hz).

Examples 3.32, 3.33, 3.34, 3.35, 3.36, 3.37, 3.38, 3.39, 3.40, 3.41 were made based on Scheme 5.

Example 3.32

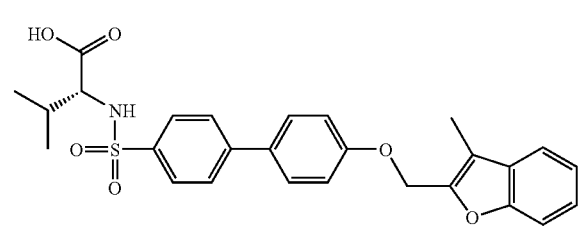

D-3-Methyl-2-[4'-(3-methyl-benzofuran-2-yl-methoxy)-biphenyl-4-sulfonylamino]-butyric acid Step 5A: A mixture of 2-Chloromethyl-3-methyl-benzofuran (675.9 mg, 3.75 mmol), 4-(4,4,5,5-Tetramethyl-[1,3,2] dioxaborolan-2-yl)-phenol (825 mg, 3.75 mmol, 1 eq), K₂CO₃ (2.1 g, 15.2 mmol, 4 eq) in 20 mL of CH₃CN was heat to reflux under nitrogen atmosphere. Reaction was complete after 12 hrs. Regular work-up and column purification (5% EtOAc/hexane) to give 3-Methyl-2-[4-(4,4,5,5-tetramethyl-[1,3,2]dioxaborolan-2-yl)-phenoxymethyl]-benzofuran in 44% yield (601 mg). 1H NMR (400 MHz, CHLOROFORM-D) δ ppm 1.3 (s, 12 H) 2.3 (s, 3 H) 5.2 (s, 2 H) 7.0 (d, J=8.6 Hz, 2 H) 7.3 (m, 2 H) 7.5 (dd, J=21.6, 7.7 Hz, 2 H) 7.8 (d, J=8.8 Hz, 2 H).

Step 5B: A mixture of D-2-(4-Bromo-benzenesulfonylamino)-3-methyl-butyric acid methyl ester (568.07 mg, 1.62 mmol), 3-Methyl-2-[4-(4,4,5,5-tetramethyl-[1,3,2]dioxaborolan-2-yl)-phenoxymethyl]-benzofuran (590.7 mg, 1.62 mmol, 1 eq), Pd(PPh₃)₄ (93.7 mg, 0.08 mmol, 0.05 eq), and K₂CO₃ (448.35 mg, 3.24 mmol, 2 eq) in 5 mL of DME and 5 mL of H₂O was heat to reflux for 12 hrs. After cool to room temperature, the mixture was loaded onto column for purification. 616 mg of product G8475-146 was obtained in 75% yield. 1H NMR (400 MHz, MeOD) δ ppm 0.8 (d, J=6.8 Hz, 6 H) 1.9 (m, 1 H) 2.2 (s, 3 H) 3.2 (s, 3 H) 3.5 (d, J=6.6 Hz, 1 H) 5.1 (s, 2 H) 7.0 (m, J=9.1 Hz, 2 H) 7.1 (m, 1 H) 7.2 (m, 1 H) 7.3 (m, 1 H) 7.4 (m, 1 H) 7.5 (d, J=9.1 Hz, 2 H) 7.6 (d, J=8.8 Hz, 2 H) 7.7 (m, 2 H).

Step 5C: To D-3-Methyl-2-[4'-(3-methyl-benzofuran-2-ylmethoxy)-biphenyl-4-sulfonylamino]-butyric acid methyl ester (364 mg) was dissolved in THF (10 mL) and MeOH (3 mL). 1N LiOH (3 mL) was added and the mixture was stirred overnight. Regular work-up and column purification to give D-3-Methyl-2-[4'-(3-methyl-benzofuran-2-ylmethoxy)-biphenyl-4-sulfonylamino]-butyric acid in quantitative. 1H NMR (400 MHz, MeOD) δ ppm 0.8 (dd, J=30.3, 6.8 Hz, 6 H) 2.0 (m, 1 H) 2.2 (s, 3 H) 3.5 (d, J=5.3 Hz, 1 H) 5.1 (s, 2 H) 7.1 (d, J=9.1 Hz, 2 H) 7.1 (m, 1 H) 7.2 (m, 1 H) 7.3 (d, J=8.3 Hz, 1 H) 7.5 (d, J=8.3 Hz, 1 H) 7.5 (d, J=9.1 Hz, 3 H) 7.6 (d, J=8.6 Hz, 2 H) 7.8 (d, J=8.8 Hz, 2 H).

Example 3.33

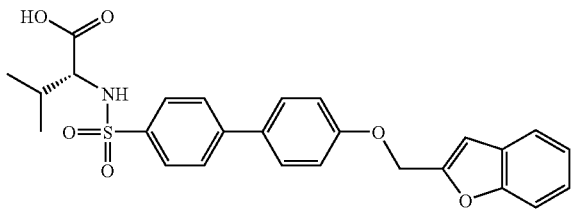

D-2-[4'-(Benzofuran-2-ylmethoxy)-biphenyl-4-sulfonylamino]-3-methyl-butyric acid The title compound, D-2-[4'-(Benzofuran-2-ylmethoxy)-biphenyl-4-sulfonylamino]-3-methyl-butyric acid, was prepared according to procedures similar to that of Example 3.32.

Step 5A: To 2-Bromomethyl-benzofuran (1.5 g, 7.1 mmol, 1 eq.), 4-(4,4,5,5-Tetramethyl-[1,3,2]dioxaborolan-2-yl)-phenol (1.56 g, 7.1 mmol, 1 eq.), potassium carbonate (1.96 g, 14.2 mmol, 2 eq.) was dissolved in acetonitrile (50 mL) under argon and heated at 70° C. for 16 hours. After work-up and flash column chromatography, 2-[4-(4,4,5,5-Tetramethyl-[1,3,2]dioxaborolan-2-yl)-phenoxymethyl]-benzofuran is obtained. Yield: 63%. 1H NMR (400 MHz, DMSO-D6) δ ppm 1.3 (s, 12 H) 5.3 (s, 2 H) 7.1 (m, 3 H) 7.3 (m, 1 H) 7.3 (m, 1 H) 7.6 (m, 4 H).

Step 5B: Coupling of 2-[4-(4,4,5,5-Tetramethyl-[1,3,2]dioxaborolan-2-yl)-phenoxymethyl]-benzofuran with D-$^2$-($^4$-Bromo-benzenesulfonylamino)-3-methyl-butyric acid tert-butyl ester to obtain D-$^2$-[$^{4'}$-(Benzofuran-2-ylmethoxy)-biphenyl-4-sulfonylamino]-3-methyl-butyric acid tert-butyl ester was done according to procedures in Step 5B for Example 3.32. Yield: 33%. 1H NMR (400 MHz, DMSO-D6) δ ppm 0.8 (dd, J=8.3, 7.1 Hz, 6 H) 1.2 (s, 9 H) 1.9 (m, 1 H) 3.5 (dd, J=9.7, 6.2 Hz, 1 H) 5.3 (s, 2 H) 7.1 (s, 1 H) 7.2 (d, J=8.6 Hz, 2 H) 7.3 (m, 1 H) 7.3 (m, 1 H) 7.6 (dd, J=8.2, 0.6 Hz, 1 H) 7.7 (m, 3 H) 7.8 (d, J=3.3 Hz, 4 H) 8.1 (d, J=9.9 Hz, 1 H).

Step 5C: D-$^2$-[$^{4'}$-(Benzofuran-2-ylmethoxy)-biphenyl-4-sulfonylamino]-3-methyl-butyric acid tert-butyl ester (126 mg, 0.23 mmol, 1 eq.), cerium chloride heptahydrate (175 mg, 0.47 mmol, 2 eq.), potassium iodide (51 mg, 0.30 mmol, 1.3 eq.) in acetonitrile (10 mL) were heated at 70 C for 16 hours. After work-up and flash column chromatography, D-2-[4'-(Benzofuran-2-ylmethoxy)-biphenyl-4-sulfonylamino]-3-methyl-butyric acid was obtained. Yield: 25%. NMR: 1H NMR (400 MHz, DMSO-D6) δ ppm 0.8 (dd, J=12.5, 6.7 Hz, 6 H) 2.0 (m, 1 H) 3.5 (dd, J=9.2, 5.9 Hz, 1 H) 5.3 (s, 2 H) 7.1 (s, 1 H) 7.2 (d, J=8.8 Hz, 2 H) 7.3 (dd, J=8.1, 0.8 Hz, 1 H) 7.3 (m, 1 H) 7.6 (d, J=8.1 Hz, 1 H) 7.7 (m, 1 H) 7.7 (d, J=8.8 Hz, 2 H) 7.8 (d, 4 H) 8.0 (d, J=9.3 Hz, 1 H).

Example 3.34

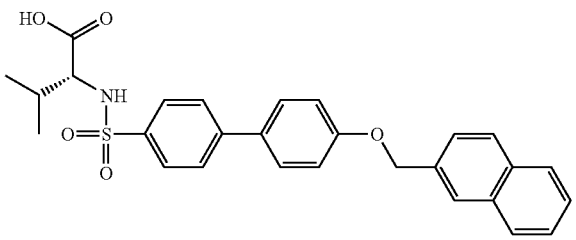

D-3-Methyl-2-[4'-(naphthalen-2-ylmethoxy)-biphenyl-4-sulfonylamino]-butyric acid The title compound, D-3-Methyl-2-[4'-(naphthalen-2-ylmethoxy)-biphenyl-4-sulfonylamino]-butyric acid, was prepared according to procedures similar to that of Example 3.32.

Step 5A: Alkylation of 2-Bromomethyl-naphthalene with 4-(4,4,5,5-Tetramethyl-[1,3,2]dioxaborolan-2-yl)-phenol was carried out according to procedures in Step 5A in Example 3.32 to give 4,4,5,5-Tetramethyl-2-[4-(naphthalen-2-ylmethoxy)-phenyl]-[1,3,2]dioxaborolane in 85% yield. 1H NMR (400 MHz, CHLOROFORM-D) δ ppm 1.3 (s, 12 H) 5.3 (s, 2 H) 7.0 (d, J=8.6 Hz, 2 H) 7.5 (m, 2 H) 7.5 (dd, J=8.3, 1.8 Hz, 1H) 7.8 (d, J=8.6 Hz, 2H) 7.9 (m, 4H).

Step 5B: Suzuki coupling of 4,4,5,5-Tetramethyl-2-[4-(naphthalen-2-ylmethoxy)-phenyl]-[1,3,2]dioxaborolane with D-2-(4-Bromo-benzenesulfonylamino)-3-methyl-butyric acid methyl ester was carried out according to procedures in Step 5B for Example 3.32 to give D-3-Methyl-2-[4'-(naphthalen-2-ylmethoxy)-biphenyl-4-sulfonylamino]-butyric acid methyl ester in 44% yield. 1H NMR (400 MHz, CHLOROFORM-D) δ ppm 0.9 (dd, J=32.1, 6.8 Hz, 6 H) 2.0 (m, 1 H) 3.4 (s, 3 H) 3.8 (dd, J=10.2, 5.2 Hz, 1 H) 5.1 (d, J=10.1 Hz, 1 H) 5.3 (s, 2 H) 7.1 (d, J=9.1 Hz, 2 H) 7.5 (m, 2 H) 7.6 (m, 3 H) 7.7 (d, J=8.6 Hz, 2 H) 7.9 (m, 6 H).

Step 5C: Hydrolysis of D-3-Methyl-2-[4'-(naphthalen-2-ylmethoxy)-biphenyl-4-sulfonylamino]-butyric acid methyl ester was carried out according to procedures in Step 5C for Example 3.32 in quantitative yield. 1H NMR (400 MHz, MeOD) δ ppm 0.8 (dd, J=32.6, 6.8 Hz, 6 H) 1.9 (m, 1 H) 3.5 (d, J=5.3 Hz, 1 H) 5.2 (s, 2 H) 7.1 (d, J=8.8 Hz, 2 H) 7.4 (m, 2 H) 7.5 (dd, J=8.6, 1.8 Hz, 1 H) 7.5 (d, J=8.8 Hz, 2 H) 7.6 (d, J=8.8 Hz, 2 H) 7.8 (m, 5 H) 7.8 (s, 1 H).

Example 3.35

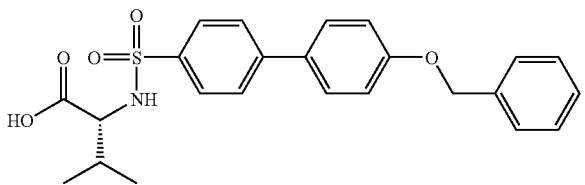

D-2-(4'-Benzyloxy-biphenyl-4-sulfonylamino)-3-methyl-butyric acid

The title compound, D-2-(4'-Benzyloxy-biphenyl-4-sulfonylamino)-3-methyl-butyric acid, was prepared according to procedures similar to that of Example 3.32.

Step 5B: Suzuki coupling of 4-benzyloxyphenylboronic acid with D-2-(4-Bromo-benzenesulfonylamino)-3-methyl-butyric acid tert-butyl ester was carried out according to procedures in Step 5B for Example 3.32 to give D-2-(4'-Benzyloxy-biphenyl-4-sulfonylamino)-3-methyl-butyric acid tert-butyl ester in 73% yield. 1H NMR (400 MHz, MeOD) δ ppm 0.8 (dd, J=29.7, 6.7 Hz, 6 H) 1.1 (s, 9 H) 1.9 (m, 1 H) 3.5 (d, J=5.8 Hz, 1 H) 5.0 (s, 2 H) 7.0 (d, J=8.8 Hz, 2 H) 7.2 (t, J=7.3 Hz, 1 H) 7.3 (m, 2 H) 7.4 (d, J=6.8 Hz, 2 H) 7.5 (d, J=9.1 Hz, 2 H) 7.6 (d, J=8.6 Hz, 2 H) 7.8 (d, J=8.8 Hz, 2 H).

Step 5C: D-2-(4'-Benzyloxy-biphenyl-4-sulfonylamino)-3-methyl-butyric acid was prepared according to procedures in Step 5C for Example 3.32 in quantitative yield. 1H NMR (400 MHz, DMSO-D6) δ ppm 0.8 (dd, J=12.3, 6.7 Hz, 6 H) 1.9 (m, 1 H) 3.5 (dd, J=9.3, 6.1 Hz, 1 H) 5.2 (s, 2 H) 7.1 (d, J=9.1 Hz, 2 H) 7.4 (m, 3 H) 7.5 (m, 2 H) 7.7 (d, J=8.8 Hz, 2 H) 7.8 (s, 4 H) 8.0 (d, J=9.3 Hz, 1 H).

Example 3.36

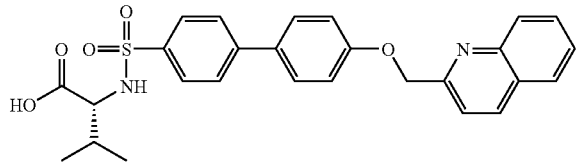

D-3-Methyl-2-[4'-(quinolin-2-ylmethoxy)-biphenyl-4-sulfonylamino]-butyric acid

The title compound, D-3-Methyl-2-[4'-(quinolin-2-ylmethoxy)-biphenyl-4-sulfonylamino]-butyric acid, was prepared according to procedures similar to that of Example 3.32.

Step 5A: Alkylation of 2-Chloromethyl-quinoline with 4-(4,4,5,5-Tetramethyl-[1,3,2]dioxaborolan-2-yl)-phenol was carried out according to procedures in Step 5A for Example 3.32 to give 2-[4-(4,4,5,5-Tetramethyl-[1,3,2]dioxaborolan-2-yl)-phenoxymethyl]-quinoline in 90% yield. 1H NMR (400 MHz, MeOD) δ ppm 1.2 (s, 12 H) 5.3 (s, 2 H) 7.0 (d, J=8.6 Hz, 2 H) 7.5 (m, 1 H) 7.6 (dd, J=11.4, 8.6 Hz, 3 H) 7.7 (m, 1 H) 7.8 (dd, J=8.1, 1.5 Hz, 1 H) 7.9 (d, J=8.6 Hz, 1 H) 8.3 (d, J=8.6 Hz, 1 H).

Step 5B: Suzuki coupling of 2-[4-(4,4,5,5-Tetramethyl-[1,3,2]dioxaborolan-2-yl)-phenoxymethyl]-quinoline with D-2-(4-Bromo-benzenesulfonylamino)-3-methyl-butyric acid tert-butyl ester was carried out according to procedures in Step 5B for Example 3.32 to give D-3-Methyl-2-[4'-(quinolin-2-ylmethoxy)-biphenyl-4-sulfonylamino]-butyric acid tert-butyl ester in 70% yield. 1H NMR (400 MHz, MeOD) δ ppm 0.8 (dd, J=29.8, 6.8 Hz, 6 H) 1.1 (s, 9 H) 1.9 (m, 1 H) 3.5 (d, J=5.6 Hz, 1 H) 5.3 (s, 2 H) 7.1 (d, J=8.8 Hz, 2 H) 7.5 (m, 3 H) 7.6 (t, J=8.6 Hz, 3 H) 7.7 (m, 1 H) 7.8 (d, J=8.8 Hz, 2 H) 7.9 (dd, J=8.2, 0.9 Hz, 1 H) 8.0 (m, 1 H) 8.3 (d, J=8.8 Hz, 1 H).

Step 5C: Removal of t-butyl ester was done according to procedures in Step 5C for Example 3.32 in quantitative yield. 1H NMR (400 MHz, DMSO-D6) δ ppm 0.8 (dd, J=12.5, 6.7 Hz, 6 H) 1.9 (m, 1 H) 3.5 (dd, J=9.3, 6.1 Hz, 1 H) 5.5 (s, 2 H) 7.2 (d, J=8.8 Hz, 2 H) 7.7 (m, 1 H) 7.7 (dd, J=8.7, 1.9 Hz, 3 H) 7.8 (s, 5 H) 8.0 (m, 3 H) 8.5 (d, J=8.6 Hz, 1 H).

Example 3.37

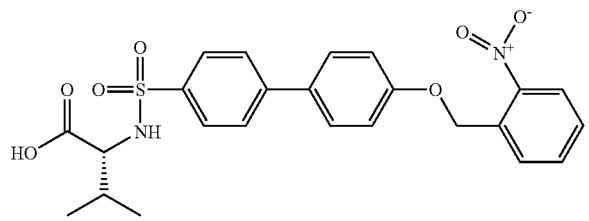

D-3-Methyl-2-[4'-(2-nitro-benzyloxy)-biphenyl-4-sulfonylamino]-butyric acid

The title compound, D-3-Methyl-2-[4'-(2-nitro-benzyloxy)-biphenyl-4-sulfonylamino]-butyric acid, was prepared according to procedures similar to that of Example 3.32.

Step 5A: Alkylation of 1-Bromomethyl-2-nitro-benzene with 4-(4,4,5,5-Tetramethyl-[1,3,2]dioxaborolan-2-yl)-phenol was carried out according to procedures in Step 5A for Example 3.32 to give 4,4,5,5-Tetramethyl-2-[4-(2-nitro-benzyloxy)-phenyl]-[1,3,2]dioxaborolane in 62% yield. 1H NMR (400 MHz, CHLOROFORM-D) δ ppm 1.3 (s, 12 H) 5.5 (s, 2 H) 7.0 (d, J=8.6 Hz, 2 H) 7.5 (m, 1 H) 7.7 (m, 1 H) 7.8 (d, J=8.6 Hz, 2 H) 7.9 (dd, J=7.8, 1.0 Hz, 1 H) 8.2 (dd, J=8.1, 1.3 Hz, 1 H).

Step 5B: Suzuki coupling of 4,4,5,5-Tetramethyl-2-[4-(2-nitro-benzyloxy)-phenyl]-[1,3,2]dioxaborolane with D-2-(4-Bromo-benzenesulfonylamino)-3-methyl-butyric acid tert-butyl ester was carried out according to procedures in Step 5B for Example 3.32 to give D-3-Methyl-2-[4'-(2-nitro-benzyloxy)-biphenyl-4-sulfonylamino]-butyric acid tert-butyl ester in 20% yield. 1H NMR (400 MHz, MeOD) δ ppm 0.8 (dd, J=30.1, 6.8 Hz, 6 H) 1.1 (s, 9 H) 1.9 (m, 1 H) 3.5 (d, J=5.6 Hz, 1 H) 5.4 (s, 2 H) 7.0 (d, J=8.8 Hz, 2 H) 7.5 (m, 1 H) 7.5 (d, J=8.8 Hz, 2 H) 7.6 (m, 3 H) 7.8 (d, J=8.6 Hz, 3 H) 8.1 (dd, J=8.1, 1.3 Hz, 1 H).

Step 5C: Removal of t-butyl ester was done according to procedures in Step 5C for Example 3.32 in quantitative yield. 1H NMR (400 MHz, MeOD) δppm 0.8 (dd, J=24.3, 6.8 Hz, 6 H) 2.0 (m, 1 H) 3.6 (d, J=5.8 Hz, 1 H) 5.4 (s, 2 H) 7.0 (d, J=8.6 Hz, 2 H) 7.5 (t, J=7.7 Hz, 1 H) 7.6 (d, J=8.8 Hz, 2 H) 7.7 (m, 3 H) 7.8 (m, 3 H) 8.1 (d, J=9.6 Hz, 1 H).

Example 3.38

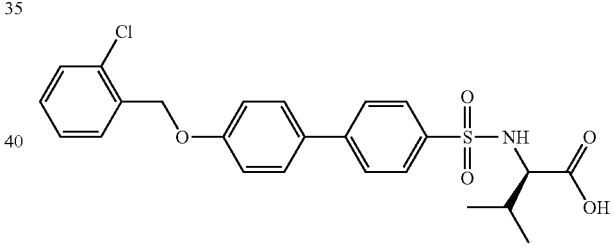

D-2-[4'-(2-Chloro-benzyloxy)-biphenyl-4-sulfonylamino]-3-methyl-butyric acid

The title compound, D-2-[4'-(2-Chloro-benzyloxy)-biphenyl-4-sulfonylamino]-3-methyl-butyric acid, was prepared according to procedures similar to that of Example 3.32.

Step 5A: Coupling of 2-chlorobenzyl bromide with 4-hydroxyphenyl boronic ester to obtain 2-[4-(2-Chloro-benzyloxy)-phenyl]-4,4,5,5-tetramethyl-[1,3,2]dioxaborolane was done according to procedures in Step 5A for Example 2A. Yield: 85%. 1H NMR (400 MHz, DMSO-D6) δ ppm 1.3 (s, 12 H) 5.2 (s, 2 H) 7.0 (d, J=8.8 Hz, 2 H) 7.4 (m, 2 H) 7.5 (m, 1 H) 7.6 (m, 1 H) 7.6 (d, J=8.8 Hz, 2 H).

Step 5B: Coupling 2-[4-(2-Chloro-benzyloxy)-phenyl]-4,4,5,5-tetramethyl-[1,3,2]dioxaborolane with D-2-(4-Bromo-benzenesulfonylamino)-3-methyl-butyric acid methyl ester to obtain D-2-[4'-(2-Chloro-benzyloxy)-biphenyl-4-sulfonylamino]-3-methyl-butyric acid methyl ester was done according to procedures in Step 5B for Example 3.32. Yield: 73%. 1H NMR (400 MHz, DMSO-D6) δppm 0.8 (dd, J=15.4, 6.6 Hz, 6 H) 1.9 (m, 1 H) 3.3 (s, 3 H) 3.6 (dd, J=9.3, 7.1 Hz, 1 H)

5.2 (s, 2 H) 7.2 (d, J=8.8 Hz, 2 H) 7.4 (m, 2 H) 7.5 (m, 1 H) 7.6 (m, 1 H) 7.7 (d, J=8.8 Hz, 2 H) 7.8 (d, J=8.6 Hz, 2 H) 7.8 (m, 2 H) 8.3 (d, J=9.3 Hz, 1 H).

Step 5C: Hydrolysis of D-2-[4'-(2-Chloro-benzyloxy)-biphenyl-4-sulfonylamino]-3-methyl-butyric acid methyl ester to D-2-[4'-(2-Chloro-benzyloxy)-biphenyl-4-sulfonylamino]-3-methyl-butyric acid was done according to procedures in Step 5C for Example 3.32. Yield: 55%. 1H NMR (400 MHz, DMSO-D6) δ ppm 0.8 (dd, J=12.6, 6.8 Hz, 6 H) 1.9 (m, 1 H) 3.5 (dd, J=9.2, 5.9 Hz, 1 H) 5.2 (s, 2 H) 7.2 (d, J=8.8 Hz, 2 H) 7.4 (m, 2 H) 7.5 (m, 1 H) 7.7 (d, J=8.8 Hz, 2 H) 7.8 (s, 4 H) 8.0 (d, J=9.3 Hz, 1 H) 12.6 (s, 1 H).

Example 3.39

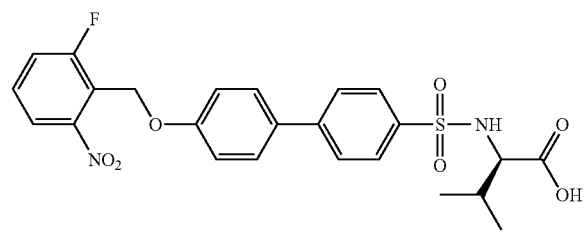

D-2-[4'-(2-Fluoro-6-nitro-benzyloxy)-biphenyl4-sulfonylamino]-3-methyl-butyric acid The title compound, D-2-[4'-(2-Fluoro-6-nitro-benzyloxy)-biphenyl-4-sulfonylamino]-3-methyl-butyric acid, was prepared according to procedures similar to that of Example 3.32.

Step 5A: Coupling of 2-fluoro-6-nitrobenzyl bromide with 4-hydroxyphenyl boronic ester to obtain 2-[4-(2-Fluoro-6-nitro-benzyloxy)-phenyl]-4,4,5,5-tetramethyl-[1,3,2]dioxaborolane was done according procedures in Step 5A for Example 3.32. Yield: 95%. 1H NMR (400 MHz, DMSO-D6) δ ppm 1.3 (s, 12 H) 5.3 (d, J=1.3 Hz, 2 H) 7.0 (d, J=8.8 Hz, 2 H) 7.6 (d, J=8.8 Hz, 2 H) 7.7 (m, 2 H) 7.9 (m, 1 H).

Step 5B: Coupling 2-[4-(2-Fluoro-6-nitro-benzyloxy)-phenyl]-4,4,5,5-tetramethyl-[1,3,2]dioxaborolane with D-2-(4-Bromo-benzenesulfonylamino)-3-methyl-butyric acid methyl ester to obtain D-2-[4'-(2-Fluoro-6-nitro-benzyloxy)-biphenyl-4-sulfonylamino]-3-methyl-butyric acid methyl ester was done according to procedures in Step 5B for Example 3.32. Yield: 49%. 1H NMR (400 MHz, DMSO-D6) δ ppm 0.8 (dd, J=15.2, 6.8 Hz, 6 H) 1.9 (m, 1 H) 3.3 (s, 3 H) 3.6 (dd, J=9.5, 7.2 Hz, 1 H) 5.4 (d, J=1.3 Hz, 2 H) 7.1 (d, J=8.8 Hz, 2 H) 7.8 (m, 6H) 7.8 (m, 2H) 7.9 (m, 1 H) 8.3 (m, J=9.3 Hz, 1 H).

Step 5C: Hydrolysis of D-2-[4'-(2-Fluoro-6-nitro-benzyloxy)-biphenyl-4-sulfonylamino]-3-methyl-butyric acid methyl ester to D-2-[4'-(2-Fluoro-6-nitro-benzyloxy)-biphenyl-4-sulfonylamino]-3-methyl-butyric acid was done according to procedures in Step 5C for Example 3.32, except purification through prep-HPLC. Yield: 30%. 1H NMR (400 MHz, DMSO-D6) δ ppm 0.8 (dd, J=12.9, 6.8 Hz, 6 H) 1.9 (m, 1 H) 3.5 (dd, J=9.2, 5.9 Hz, 1 H) 5.4 (d, J=1.3 Hz, 2 H) 7.1 (d, J=8.8 Hz, 2 H) 7.7 (m, 4 H) 7.8 (d, J=0.8 Hz, 4 H) 7.9 (m, 2 H) 8.0 (d, J=9.1 Hz, 1 H).

Example 3.40

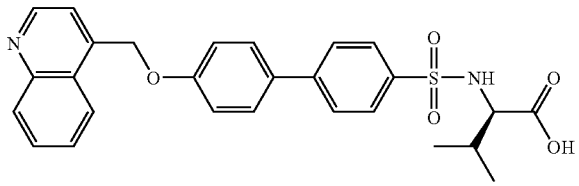

D-3-Methyl-2-[4'-(quinolin-4-ylmethoxy)-biphenyl-4-sulfonylamino]-butyric acid

The title compound, D-3-Methyl-2-[4'-(quinolin-4-ylmethoxy)-biphenyl-4-sulfonylamino]-butyric acid, was prepared according to procedures similar to that of Example 3.32.

Step 5A: Coupling of 4-Chloromethyl-quinoline with 4-hydroxyphenyl boronic ester to obtain 4-[4-(4,4,5,5-Tetramethyl-[1,3,2]dioxaborolan-2-yl)-phenoxymethyl]-quinoline was done according to procedures in Step 5A for Example 3.32. Yield: 62%. 1H NMR (400 MHz, DMSO-D6) δ ppm 1.3 (s, 12 H) 5.7 (d, J=0.5 Hz, 2 H) 7.1 (d, J=8.8 Hz, 2 H) 7.7 (m, 4 H) 7.8 (m, 1 H) 8.1 (dd, J=8.5, 0.9 Hz, 1 H) 8.2 (d, J=8.3 Hz, 1 H) 8.9 (d, J=4.5 Hz, 1 H).

Step 5B: Coupling of 4-[4-(4,4,5,5-Tetramethyl-[1,3,2]dioxaborolan-2-yl)-phenoxymethyl]-quinoline with D-2-(4-Bromo-benzenesulfonylamino)-3-methyl-butyric acid methyl ester to obtain D-3-Methyl-2-[4'-(quinolin-4-ylmethoxy)-biphenyl-4-sulfonylamino]-butyric acid methyl ester was done according to procedures in Step 5B for example 3.32. Yield: 47%. 1H NMR (400 MHz, DMSO-D6) δppm 0.8 (dd, J=15.2, 6.8 Hz, 6 H) 1.9 (m, 1 H) 3.3 (s, 3 H) 3.6 (dd, J=9.3, 7.1 Hz, 1 H) 5.8 (s, 2 H) 7.3 (d, J=8.8 Hz, 2 H) 7.8 (m, 9 H) 8.1 (d, J=8.6 Hz, 1 H) 8.2 (d, J=8.6 Hz, 1 H) 8.3 (d, J=9.3 Hz, 1 H) 8.9 (d, J=4.3 Hz, 1 H).

Step 5C: Hydrolysis of D-3-Methyl-2-[4'-(quinolin-4-ylmethoxy)-biphenyl-4-sulfonylamino]-butyric acid methyl ester to D-3-Methyl-2-[4'-(quinolin-4-ylmethoxy)-biphenyl-4-sulfonylamino]-butyric acid was done according to procedures in Step 5C for Example 3.32. Yield: 54%. 1H NMR (400 MHz, DMSO-D6) δ ppm 0.8 (dd, J=43.6, 6.9 Hz, 6 H) 2.0 (m, 1 H) 3.0 (d, J=3.0 Hz, 1 H) 5.8 (d, 2 H) 7.3 (d, J=8.8 Hz, 2 H) 7.7 (m, 4 H) 7.8 (m, 5 H) 8.1 (m, 1 H) 8.2 (dd, J=8.3, 0.8 Hz, 1 H) 8.9 (d, J=4.5 Hz, 1 H).

Example 3.41

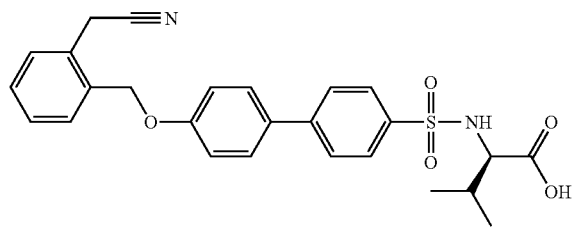

D-2-[4'-(2-Cyanomethyl-benzyloxy)-biphenyl-4-sulfonylamino]-3-methyl-butyric acid The title compound, D-3-Methyl-2-[4'-(quinolin-4-yl-methoxy)-biphenyl-4-sulfonylamino]-butyric acid, was prepared according to procedures similar to that of Example 3.32.

Step 5C: Hydrolysis of D-2-[4'-(2-Cyanomethyl-benzyloxy)-biphenyl-4-sulfonylamino]-3-methyl-butyric acid methyl ester (prepared according to step 3) to D-2-[4'-(2-Cyanomethyl-benzyloxy)-biphenyl-4-sulfonylamino]-3-methyl-butyric acid was done according to procedures in Step 5C for Example 3.32. Prep-HPLC was used for purification. Yield: 75%. 1H NMR (400 MHz, DMSO-D6) δ ppm 0.8 (dd, J=23.7, 6.8 Hz, 6 H) 2.0 (m, 1 H) 2.8 (d, J=6.6 Hz, 1 H) 4.1 (s, 2 H) 5.2 (s, 2 H) 7.2 (d, J=9.1 Hz, 2 H) 7.4 (m, 2 H) 7.5 (m, 1 H) 7.6 (m, 1 H) 7.7 (d, J=8.8 Hz, 2 H) 7.8 (d, J=2.0 Hz, 4 H).

Examples 3.42, 3.43, 3.44, 3.45, 3.46, 3.47, 3.48, 3.49 were made based on Scheme 6.

Example 3.42

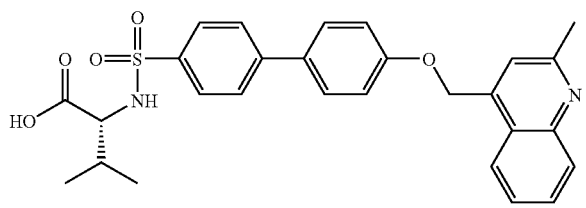

D-3-Methyl-2-[4'-(2-methyl-quinolin-4-ylmethoxy)-biphenyl-4-sulfonylamino]-butyric acid Step: A mixture of 4-Chloromethyl-2-methyl-quinoline (165 mg, 0.86 mmol, 1 eq), D-2-(4'-Hydroxy-biphenyl-4-sulfonylamino)-3-methyl-butyric acid methyl ester (314 mg, 0.86 mmol, 1 eq), and $K_2CO_3$ (270 mg, 1.13 mmol, 1.3 eq) in 8 mL of DMF under nitrogen was heat to 90° C. for 12 hrs. After work up and column chromatography (30-60% EtOAc in hexane), D-3-Methyl-2-[4'-(2-methyl-quinolin-4-yl-methoxy)-biphenyl-4-sulfonylamino]-butyric acid methyl ester was obtained in 34% yield (150 mg). 1H NMR (400 MHz, DMSO-D6) δ ppm 0.8 (dd, J=15.0, 6.7 Hz, 6 H) 1.9 (m, 1 H) 2.7 (s, 3 H) 3.3 (s, 3 H) 3.6 (dd, J=9.2, 7.2 Hz, 1 H) 5.7 (s, 2 H) 7.3 (d, J=8.8 Hz, 2 H) 7.6 (m, 2 H) 7.8 (m, 4 H) 7.8 (m, 2 H) 8.0 (d, J=9.3 Hz, 1 H) 8.1 (d, J=8.3 Hz, 1 H) 8.1 (none, 1 H) 8.3 (d, J=9.6 Hz, 1 H).

Step 6B: D-3-Methyl-2-[4'-(2-methyl-quinolin-4-ylmethoxy)-biphenyl-4-sulfonylamino]-butyric acid methyl ester (150 mg) was dissolved in THF (8 mL) and MeOH (4 mL) and added with 1N LiOH (3 mL, 3 mmol). The resulting solution was stirred at room temperature overnight. Reaction was complete as determined by TLC. Solvents removed and regular work-up and column chromatography to afford 148 mg of in quantitative yield. 1H NMR (400 MHz, DMSO-D6) δ ppm 0.8 (dd, J=31.8, 6.8 Hz, 6 H) 2.0 (m, 1 H) 2.7 (s, 3 H) 3.2 (s, 1 H) 5.7 (s, 2 H) 7.3 (d, J=8.8 Hz, 2 H) 7.6 (m, 2 H) 7.8 (m, 7 H) 8.0 (d, J=7.6 Hz, 1 H) 8.1 (d, J=6.8 Hz, 1 H).

Example 3.43

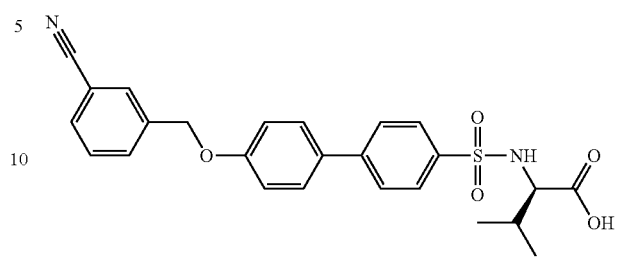

D-2-[4'-(3-Cyano-benzyloxy)-biphenyl-4-sulfonylamino]-3-methyl-butyric acid

The title compound, D-2-[4'-(3-Cyano-benzyloxy)-biphenyl-4-sulfonylamino]-3-methyl-butyric acid, was prepared according to procedures similar to that of Example 3.42.

Step 6A: Coupling of α-Bromo-m-tolunitrile with D-2-(4'-Hydroxy-biphenyl-4-sulfonylamino)-3-methyl-butyric acid methyl ester to obtain D-2-[4'-(3-Cyano-benzyloxy)-biphenyl-4-sulfonylamino]-3-methyl-butyric acid methyl ester was done according to procedures in Step 6A for Example 3.42. Yield: 25%. 1H NMR (400 MHz, DMSO-D6) δ ppm 0.8 (dd, J=14.9, 6.8 Hz, 6 H) 1.9 (m, 1 H) 3.3 (s, 3 H) 3.6 (dd, J=9.5, 7.2 Hz, 1 H) 5.3 (s, 2 H) 7.2 (d, J=9.1 Hz, 2 H) 7.6 (t, J=8.0 Hz, 1 H) 7.7 (m, 4 H) 7.8 (m, 4 H) 8.0 (s, 1 H) 8.3 (d, J=9.3 Hz, 1 H).

Step 6B: Hydrolysis of D-2-[4'-(3-Cyano-benzyloxy)-biphenyl-4-sulfonylamino]-3-methyl-butyric acid methyl ester to D-2-[4'-(3-Cyano-benzyloxy)-biphenyl-4-sulfonylamino]-3-methyl-butyric acid was done according to procedures in Step 6B for Example 3.42. Yield: 24%. 1H NMR (400 MHz, DMSO-D6) δ ppm 0.8 (dd, J=26.0, 6.8 Hz, 6 H) 2.0 (m, 1 H) 2.7 (s, 1 H) 5.2 (s, 2 H) 7.2 (d, J=8.8 Hz, 2 H) 7.6 Hz, 1 H) 7.7 (d, J=8.8 Hz, 2 H) 7.8 (m, 6 H) 8.0 (s, 1 H).

Example 3.44

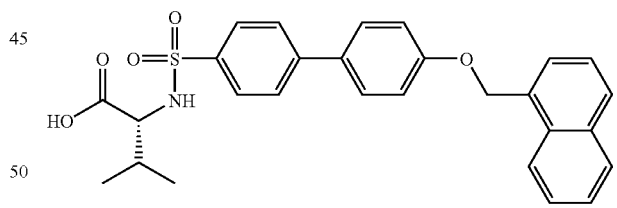

D-3-Methyl-2-[4'-(naphthalen-1-ylmethoxy)-biphenyl-4-sulfonylamino]-butyric acid The title compound, D-3-Methyl-2-[4'-(naphthalen-1-ylmethoxy)-biphenyl-4-sulfonylamino]-butyric acid, was prepared according to procedures similar to that of Example 3.42.

Step 6A: Alkylation of 1-Chloromethyl-naphthalene with D-2-(4'-Hydroxy-biphenyl-4-sulfonylamino)-3-methyl-butyric acid methyl ester was carried out according to procedures in Step 6A for Example 3.42 to give D-3-Methyl-2-[4'-(naphthalen-1-ylmethoxy)-biphenyl-4-sulfonylamino]-butyric acid methyl ester in 34% yield. 1H NMR (400 MHz, CHLOROFORM-D) δ ppm 0.9 (dd, J=32.3, 6.8 Hz, 6 H) 2.0

(m, 1 H) 3.4 (s, 3 H) 3.8 (dd, J=10.1, 5.1 Hz, 1 H) 5.1 (d, J=10.1 Hz, 1 H) 5.6 (s, 2 H) 7.2 (d, J=8.8 Hz, 2 H) 7.5 (dd, J=8.2, 6.9 Hz, 1 H) 7.6 (m, 4 H) 7.6 (d, J=6.6 Hz, 1 H) 7.7 (d, J=8.6 Hz, 2 H) 7.9 (m, 4 H) 8.1 (dd, J=8.5, 1.4 Hz, 1 H).

Step 6B: Hydrolysis of D-3-Methyl-2-[4'-(naphthalen-1-ylmethoxy)-biphenyl-4-sulfonylamino]-butyric acid methyl ester was carried out according to procedures in Step 6B for Example 3.42 in quantitative yield. 1H NMR (400 MHz, DMSO-D6) δ ppm 0.8 (dd, J=15.4, 6.8 Hz, 6 H) 2.0 (m, 1 H) 3.5 (s, 1 H) 5.6 (s, 2 H) 7.2 (d, J=8.8 Hz, 2 H) 7.6 (m, 3 H) 7.7 (m, 3 H) 7.8 (d, J=2.8 Hz, 4 H) 8.0 (m, 3 H) 8.1 (m, 1 H).

Example 3.45

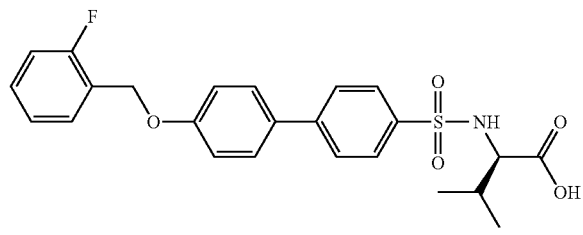

D-2-[4'-(2-Fluoro-benzyloxy)-biphenyl-4-sulfonylamino]-3-methyl-butyric acid

The title compound, D-2-[4'-(2-Fluoro-benzyloxy)-biphenyl-4-sulfonylamino]-3-methyl-butyric acid, was prepared according to procedures similar to that of Example 3.42.

Step 6A: Coupling of 2-fluorobenzyl bromide with D-2-(4'-Hydroxy-biphenyl-4-sulfonylamino)-3-methyl-butyric acid methyl ester to obtain D-2-[4'-(2-Fluoro-benzyloxy)-biphenyl-4-sulfonylamino]-3-methyl-butyric acid methyl ester was done according to procedures in Step 6A for Example 3.42. Yield: 47%. 1H NMR (400 MHz, DMSO-D6) δ ppm 0.8 (dd, J=15.2, 6.8 Hz, 6 H) 1.9 (dd, 1 H) 3.3 (s, 3 H) 3.6 (dd, J=9.3, 7.1 Hz, 1 H) 5.2 (s, 2 H) 7.2 (d, J=8.8 Hz, 2 H) 7.3 (m, 2 H) 7.4 (m, 1 H) 7.6 (m, 1 H) 7.7 (m, 4 H) 7.8 (m, 2 H) 8.3 (d, J=9.3 Hz, 1 H).

Step 6B: Hydrolysis D-2-[4'-(2-Fluoro-benzyloxy)-biphenyl-4-sulfonylamino]-3-methyl-butyric acid methyl ester to D-2-[4'-(2-Fluoro-benzyloxy)-biphenyl-4-sulfonylamino]-3-methyl-butyric acid was done according to procedures in Step 6B for Example 3.42. Yield: 67%. 1H NMR (400 MHz, DMSO-D6) δ ppm 0.8 (dd, J=43.7, 6.8 Hz, 6 H) 2.0 (m, 1 H) 2.9 (d, J=2.8 Hz, 1 H) 5.2 (s, 2 H) 6.8 (s, 1 H) 7.2 (d, J=8.8 Hz, 2 H) 7.3 (m, 2 H) 7.4 (m, 1 H) 7.6 (m, 1 H) 7.7 (d, J=8.8 Hz, 2 H) 7.8 (s, 4 H).

Example 3.46

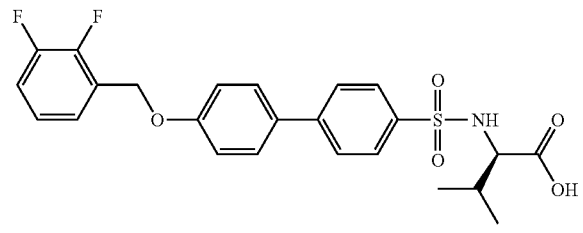

D-2-[4'-(2,3-Difluoro-benzyloxy)-biphenyl-4-sulfonylamino]-3-methyl-butyric acid The title compound, D-2-[4'-(2,3-Difluoro-benzyloxy)-biphenyl-4-sulfonylamino]-3-methyl-butyric acid, was prepared according to procedures similar to that of Example 3.42.

Step 6A: Coupling of 2,3-difluorobenzyl bromide with D-2-(4'-Hydroxy-biphenyl-4-sulfonylamino)-3-methyl-butyric acid methyl ester to obtain D-2-[4'-(2,3-Difluoro-benzyloxy)-biphenyl-4-sulfonylamino]-3-methyl-butyric acid methyl ester was done according to procedures in Step 6A for Example 3.42 but at room temperature for 16 hours. Yield: 42%. 1H NMR (400 MHz, DMSO-D6) δ ppm (s, 2 H) 7.2 (d, J=8.8 Hz, 2 H) 7.3 (m, 1 H) 7.5 (m, 2 H) 7.7 (m, 4 H) 7.8 (m, 2 H) 8.3 (d, J=9.3 Hz, 1 H).

Step 6B: Hydrolysis D-2-[4'-(2,3-Difluoro-benzyloxy)-biphenyl-4-sulfonylamino]-3-methyl-butyric acid methyl ester to D-2-[4'-(2,3-Difluoro-benzyloxy)-biphenyl-4-sulfonylamino]-3-methyl-butyric acid was done according to procedures in Step 6B for Example 3.42. Yield: 63%. 1H NMR (400 MHz, DMSO-D6) δ ppm 0.8 (dd, J=12.4, 6.8 Hz, 6 H) 1.9 (m, 1 H) 3.5 (dd, J=9.3, 6.1 Hz, 1 H) 5.3 (s, 2 H) 7.2 (d, J=9.1 Hz, 2 H) 7.3 (m, 1 H) 7.5 (m, 2 H) 7.7 (d, J=9.1 Hz, 2 H) 7.8 (d, J=1.8 Hz, 4 H) 8.0 (d, J=9.3 Hz, 1 H) 12.6 (s, 1 H).

Example 2P

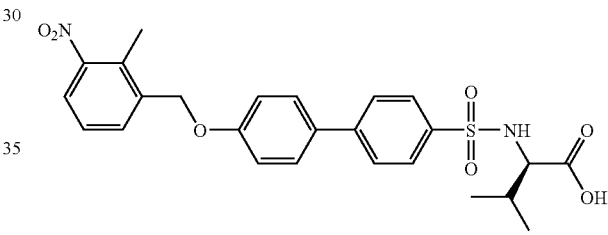

D-3-Methyl-2-[4'-(2-methyl-3-nitro-benzyloxy)-biphenyl-4-sulfonylamino]-butyric acid The title compound, D-3-Methyl-2-[4'-(2-methyl-3-nitro-benzyloxy)-biphenyl-4-sulfonylamino]-butyric acid, was prepared according to procedures similar to that of Example 3.42.

Step 6A: Coupling of 2-methyl-3-nitrobenzyl bromide with D-2-(4'-Hydroxy-biphenyl-4-sulfonylamino)-3-methyl-butyric acid methyl ester to obtain D-3-Methyl-2-[4'-(2-methyl-3-nitro-benzyloxy)-biphenyl-4-sulfonylamino]-butyric acid methyl ester was done according to procedures in Step 6A for Example 3.42 but at room temperature for 16 hours. Product further purified by recrystallization (EtOAc/hexane). Yield: 26%. 1H NMR (400 MHz, DMSO-D6) δ ppm 0.8 (dd, J=15.2, 6.8 Hz, 6 H) 1.9 (m, 1 H) 2.4 (s, 3 H) 3.3 (s, 3 H) 3.6 (m, 1 H) 5.3 (s, 2 H) 7.2 (d, J=8.8 Hz, 2 H) 7.5 (t, J=7.8 Hz, 1 H) 7.8 (m, 8 H) 8.3 (d, J=9.3 Hz, 1 H).

Step 6B: Hydrolysis D-3-Methyl-2-[4'-(2-methyl-3-nitro-benzyloxy)-biphenyl-4-sulfonylamino]-butyric acid methyl ester to D-3-Methyl-2-[4'-(2-methyl-3-nitro-benzyloxy)-biphenyl-4-sulfonylamino]-butyric acid was done according to procedures in Step 6B for Example 3.42. Yield: 33%. 1H NMR (400 MHz, DMSO-D6) δ ppm 0.8 (dd, J=12.4, 6.8 Hz, 6 H) 1.9 (dd, J=9.3, 6.1 Hz, 1 H) 5.3 (s, 2 H) 7.2 (d, J=9.1 Hz, 2 H) 7.3 (m, 1 H) 7.5 (m, 2 H) 7.7 (d, J=9.1 Hz, 2 H) 7.8 (d, J=1.8 Hz, 4 H) 8.0 (d, J=9.3 Hz, 1 H) 12.6 (s, 1 H).

Example 3.48

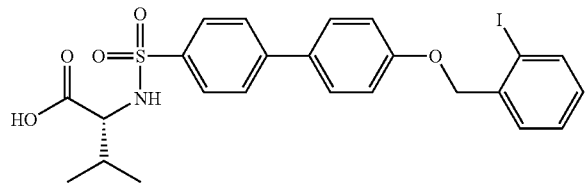

D-2-[4'-(2-Iodo-benzyloxy)-biphenyl-4-sulfonylamino]-3-methyl-butyric acid

The title compound, D-2-[4'-(2-Iodo-benzyloxy)-biphenyl-4-sulfonylamino]-3-methyl-butyric acid, was prepared according to procedures similar to that of Example 3.42.

Step 6A: Alkylation of 1-Chloromethyl-2-iodo-benzene with D-2-(4'-Hydroxy-biphenyl-4-sulfonylamino)-3-methyl-butyric acid methyl ester was carried out according to procedures in Step 6A for Example 3.42 to give D-2-[4'-(2-Iodo-benzyloxy)-biphenyl-4-sulfonylamino]-3-methyl-butyric acid methyl ester in 55% yield. 1H NMR (400 MHz, DMSO-D6) δ ppm 0.8 (dd, J=15.3, 6.7 Hz, 6 H) 1.9 (m, 1 H) 3.3 (s, 3 H) 3.6 (dd, J=9.5, 7.2 Hz, 1 H) 7.1 (m, 3 H) 7.5 (m, 1 H) 7.6 (m, 1 H) 7.7 (m, 4 H) 7.8 (m, 2 H) 7.9 (dd, J=8.0, 1.1 Hz, 1 H) 8.3 (d, J=9.3 Hz, 1 H).

Step 6B: Hydrolysis of D-2-[4'-(2-Iodo-benzyloxy)-biphenyl-4-sulfonylamino]-3-methyl-butyric acid methyl ester was carried out according to procedures in Step 6A for Example 3.42 in quantitative yield. 1H NMR (400 MHz, DMSO-D6) δ ppm 0.8 (dd, J=12.1, 6.8 Hz, 6 H) 1.9 (m, 1 H) 3.5 (dd, J=9.3, 6.1 Hz, 1 H) 5.1 (s, 2 H) 7.1 (d, J=8.8 Hz, 2 H) 7.5 (m, 1H) 7.6 (d, J=7.6 Hz, 1 H) 7.7 (d, J=8.8 Hz, 2 H) 7.8 (s, 4 H) 7.9 (dd, J=7.8 Hz, 1 H) 8.0 (d, J=9.3 Hz, 1 H).

Example 3.49

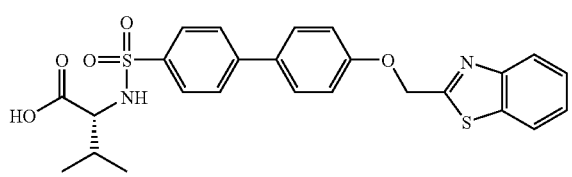

D-2-[4'-(Benzothiazol-2-ylmethoxy)-biphenyl-4-sulfonylamino]-3-methyl-butyric acid The title compound, D-2-[4'-(Benzothiazol-2-ylmethoxy)-biphenyl-4-sulfonylamino]-3-methyl-butyric acid, was prepared according to procedures similar to that of Example 3.42.

Step 6A: Alkylation of 2-Bromomethyl-benzothiazole with D-2-(4'-Hydroxy-biphenyl-4-sulfonylamino)-3-methyl-butyric acid methyl ester was carried out according to procedures in Step 6A for Example 3.42 to give D-2-[4'-(Benzothiazol-2-ylmethoxy)-biphenyl-4-sulfonylamino]-3-methyl-butyric acid methyl ester in 20% yield. 1H NMR (400 MHz, DMSO-D6) δ ppm 0.8 (dd, J=15.0, 6.7 Hz, 6 H) 1.9 (m, 1 H) 3.6 (dd, J=9.5, 7.2 Hz, 1 H) 5.7 (s, 2 H) 7.2 (m, J=8.8 Hz, 2 H) 7.5 (m, 1 H) 7.6 (m, 1 H) 7.7 (m, 4 H) 7.8 (m, 2 H) 8.0 (d, J=7.3 Hz, 1 H) 8.1 (d, J=7.8 Hz, 1 H) 8.3 (d, J=9.6 Hz, 1 H).

Step 6B: Hydrolysis of D-2-[4'-(Benzothiazol-2-ylmethoxy)-biphenyl-4-sulfonylamino]-3-methyl-butyric acid methyl ester was carried out according to procedures in Step 6B for Example 3.42 in quantitative yield. 1H NMR (400 MHz, DMSO-D6) δ ppm 0.8 (dd, J=12.4, 6.8 Hz, 6 H) 1.9 (m, 1 H) 3.5 (dd, J=9.3, 5.8 Hz, 1 H) 5.7 (s, 2 H) 7.2 (d, J=8.8 Hz, 2 H) 7.5 (m, 1 H) 7.6 (m, 1 H) 7.7 (d, J=8.8 Hz, 2 H) 7.8 (d, J=2.3 Hz, 4 H) 8.0 (dd, J=9.1, 4.5 Hz, 2 H) 8.1 (d, J=8.6 Hz, 1 H). 97%.

Examples 3.50, 3.51, 3.52, 3.53, 3.54, 3.55, 3.56 were made based on Scheme 6B.

Example 3.50

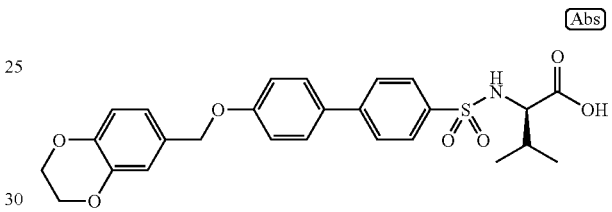

2-[4'-(2,3-Dihydro-benzo[1,4]dioxin-6-ylmemethoxy)-biphenyl-4-sulfonylamino]-3-methyl-butyric acid 1H NMR (400 MHz, DMSO): δ 0.778(d, 3H), 0.845(d, 3H), 1.99(dd, 1H), 3.17(bs, 1H), 4.24(s, 4H), 5.04(s, 2H), 6.91(m, 3H), 7.10(d, 2H), 7.68(d, 2H); ES+ m/z 496.0 (M−H); HRMS (C26H27NO7S): calcd; 520.14004; found; 520.13995 (M+Na).

Example 3.51

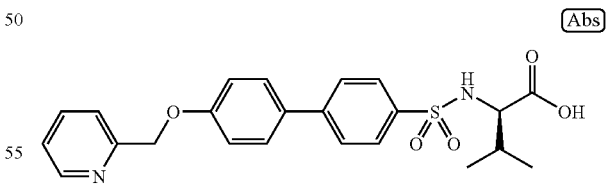

3-Methyl-2-[4'-(pyridin-2-ylmethoxy)-biphenyl-4-sulfonylamino]-butyric acid

1H NMR (400 MHz, DMSO): δ 0.800(d, 3H), 0.803(d, 3H), 1.94(m, 1H), 3.51(bs, 1H), 5.25(s, 2H), 7.15(d, 2H), 7.36(m, 1H), 7.54(d, 2H), 7.71(d, 2H), 7.83(m, 3H), 8.59(d, 2H); ES+ m/z 441.2 (M+H); HRMS (C23H24N205S): calcd; 440.14004; found; 440.14037 (M+H).

Example 3.52

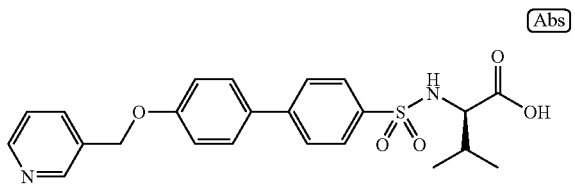

3-Methyl-2-[4'-(pyridin-3-ylmethoxy)-biphenyl-4-sulfonylamino]-butyric acid $^1$H NMR (400 MHz, DMSO): δ 0.800(d, 3H), 0.803(d, 3H), 1.95(m, 1H), 3.49(bs, 1H), 5.23(s, 2H), 7.16(d, 2H), 7.45(m, 1H), 7.71(d, 2H), 7.80(m, 3H), 7.90(d, 2H), 8.56(d, 1H), 8.70(bs, 1H); ES$^+$m/z 441.1 (M+H); HRMS (C23H24N2O5S): calcd; 441.14787; found; 441.14617 (M+H).

Example 3.53

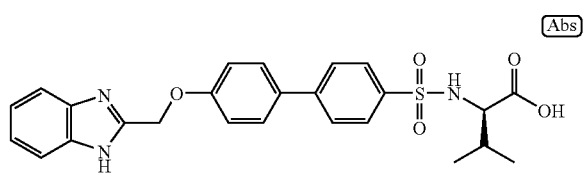

2-[4'-(1H-Benzoimidazol-2-ylmethoxy)-biphenyl-4-sulfonylamino]-3-methyl-butyric acid $^1$H NMR (400 MHz, DMSO): δ 0.802(d, 3H), 0.833(d, 3H), 1.94(m, 1H), 3.54(m, 1H), 5.51(s, 2H), 6.88(d, 2H), 7.24(d, 1H), 7.34(m, 1H), 7.58(d, 2H), 7.66(m, 1H), 7.78(m, 4H), 8.03(d, 1H); ES$^+$ m/z 480.1 (M+H); HRMS (C25H25N3O5S): calcd; 480.15877; found; 480.15787 (M+H).

Example 3.54

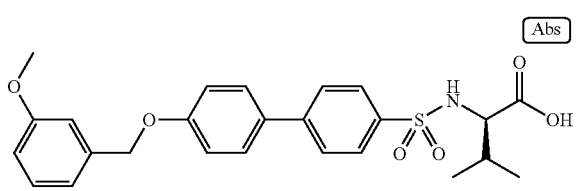

2-[4'-(3-Methoxy-benzyloxy)-biphenyl-4-sulfonylamino]-3-methyl-butyric acid $^1$H NMR (400 MHz, DMSO): δ 0.804(d, 3H), 0.835(d, 3H), 1.95(m, 1H), 3.54(m, 1H), 3.77(s, 3H), 5.15(s, 2H), 6.89(m, 2H), 7.04(m, 2H), 7.13(m, 2H), 7.32(m, 1H), 7.58(d, 1H), 7.69(d, 2H), 7.80(m, 1H), 8.01(d, 1H); ES$^+$ m/z 470.1 (M+H); HRMS (C25H27NO6S): calcd; 470.16319; found; 470.16183 (M+H).

Example 3.55

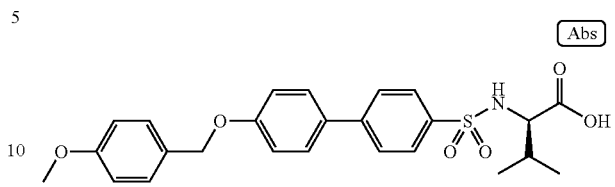

2-[4'-(4-Methoxy-benzyloxy)-biphenyl-4-sulfonylamino]-3-methyl-butyric acid $^1$H NMR (400 MHz, DMSO): δ 0.805(d, 3H), 0.836(d, 3H), 1.94(m, 1H), 3.54(m, 1H), 3.76(s, 3H), 5.09(s, 2H), 6.96(d, 2H), 7.12(d, 2H), 7.40(d, 2H), 7.69(d, 2H), 7.80(s, 3H), 8.01(d, 1H); ES$^+$ m/z 468.2 (M−H); HRMS (C25H27NO6S): calcd; 470.16319; found; 470.16248 (M+H)

Example 3.56

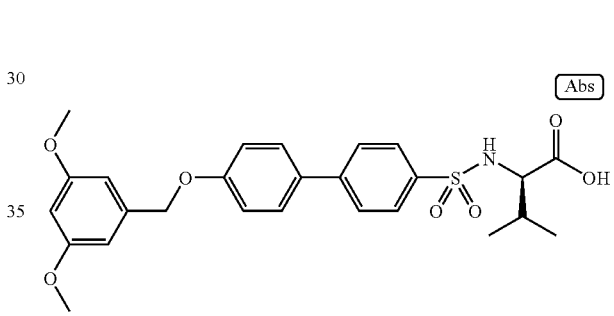

2-[4'-(3,5-Dimethoxy-benzyloxy)-biphenyl-4-sulfonylamino]-3-methyl-butyric acid $^1$H NMR (400 MHz, DMSO): δ 0.804(d, 3H), 0.835(d, 3H), 1.95(m, 1H), 3.55(m, 1H), 3.75(s, 6H), 5.11(s, 2H), 6.45(bs, 1H), 6.62(bs, 2H), 7.12(d, 2H), 7.70(d, 2H), 7.80(s, 3H), 8.01(d, 1H); ES$^+$ m/z 498.2 (M−H); HRMS (C26H29NO7S): calcd; 500.17375; found; 500.17223 (M+H).

Example 3.57 was made based on Scheme 7.

Example 3.57

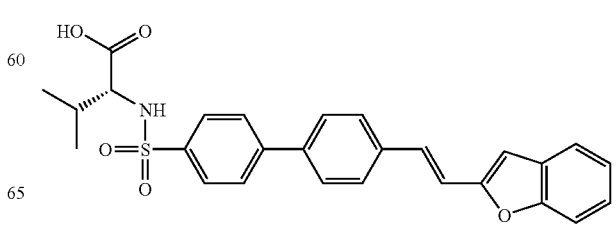

3-Methyl-2-(4'-vinyl-biphenyl-4-sulfonylamino)-butyric acid tert-butyl ester Step 7A: 4-Vinylphenylboronic acid (1.89 g, 12.7 mmol, 1 equiv.) and 2-(4-Bromo-benzenesulfonylamino)-3-methyl-butyric acid tert-butyl ester (5 g, 12.7 mmol, 1 equiv.) were dissolved in ethylene glycol dimethyl ether (180 mL) and added with Pd(Ph$_3$)$_4$ (736.0 mg, 0.64 mmol) and stirred at room temperature for 20 min. Then to the reaction mixture was introduced an aqueous solution of K$_2$CO$_3$ (3.52 g, 25.5 mmol, 2 equiv.) and heat to reflux overnight. After cool to room temperature, solvent was evaporated and the residue partitioned between EtOAC and H$_2$O. Organic layer washed with brine, dried over MgSO$_4$, and purified by column chromatography (Silica gel, 10% EtOAc/Hexane) to yield 808 mg of G9058-169 in 15.2% yield.

$^1$H NMR (400 MHz, CHLOROFORM-D) δ ppm 0.80 (d, J=6.82 Hz, 3 H) 0.95 (d, J=6.82 Hz, 3 H) 1.12 (s, 9 H) 1.99 (m, 1 H) 3.59 (dd, J=9.85, 4.55 Hz, 1 H) 5.06 (d, J=10.11 Hz, 1 H) 5.25 (d, J=10.86 Hz, 1 H) 5.75 (d, J=16.93 Hz, 1 H) 6.70 (m, 1 H) 7.45 (m, 4 H) 7.61 (d, J=8.84 Hz, 2 H) 7.82 (d, J=8.84 Hz, 2 H).

Step 7B: 3-Methyl-2-(4'-vinyl-biphenyl-4-sulfonylamino)-butyric acid tert-butyl ester (300 mg, 0.72 mmol, 1.2 equiv.), Pd$_2$(dba)$_3$ (11 mg, 0.012 mmol, 0.02 equiv.), Tri-t-tetrafluoroborate (14 mg, 0.048 mmol, 0.08 equiv.) and dioxane (1.5 mL) were placed in a microwave tube under N$_2$. 2-Bromo-1-Benzofuran (118 mg, 0.6 mmol, 1 equiv) and dicyclohexyl methyl amine (0.15 mL, 0.72 mmol, 1.2 equiv.) were injected. The mixture was then irradiated in microwave reactor at 180° C. for 30 min. The mixture was partitioned between EtOAc and H$_2$O, organic layer dried over MgSO$_4$. Crude residue purified by column chromatography (silica gel, 20% EtOAc/Hexane) to afford 80 mg of 2-[4'-(2-Benzofuran-2-yl-vinyl)-biphenyl-4-sulfonylamino]-3-methyl-butyric acid tert-butyl ester. (G9058-171) in 25% yield.

$^1$H NMR (400 MHz, CHLOROFORM-D) δ ppm 0.80 (d, J=6.82 Hz, 3 H) 0.96 (d, J=6.82 Hz, 3 H) 1.14 (s, 9 H) 2.01 (m, 1 H) 3.60 (dd, J=9.98, 4.42 Hz, 1 H) 5.07 (d, J=9.85 Hz, 1 H) 6.66 (s, 1 H) 7.01 (d, J=15.92 Hz, 1 H) 7.14 (m, 1 H) 7.25 (m, 2 H) 7.42 (d, J=8.08 Hz, 1 H) 7.52 (m, 5 H) 7.64 (d, J=8.59 Hz, 2 H) 7.84 (d, J=8.59 Hz, 2 H).

Step 7C: 2-[4'-(2-Benzofuran-2-yl-vinyl)-biphenyl-4-sulfonylamino]-3-methyl-butyric acid tert-butyl ester (80 mg) in dichloroethane (4.5 mL) was added with to TFA (1.5 mL) and stirred at room temperature. The reaction was complete after 3 hrs as determined by TLC. After removing solvent, the crude residue was then purified by column chromatography (5-10% MeOH/CH$_2$Cl$_2$) to give 22 mg of 2-[4'-(2-Benzofuran-2-yl-vinyl)-biphenyl-4-sulfonylamino]-3-methyl-butyric acid G9058-172 in 30.7% yield.

1H NMR (400 MHz, DMSO-D6) δ ppm 0.79 (d, J=6.82 Hz, 3 H) 0.86 (d, J=6.82 Hz, 3 H) 1.23 (s, 2 H) 2.02 (m, 1 H) 3.18 (m, 1 H) 7.01 (s, 1 H) 7.25 (t, J=7.07 Hz, 1 H) 7.33 (m, 1 H) 7.38 (d, J=14.65 Hz, 1 H) 7.59 (d, J=8.08 Hz, 1 H) 7.64 (d, J=8.08 Hz, 1 H) 7.79 (d, J=6.57 Hz, 4 H) 7.83 (d, J=8.59 Hz, 2 H) 7.90 (m, 2 H).

Example 3.58 was made based on Scheme 8.

Example 3.58

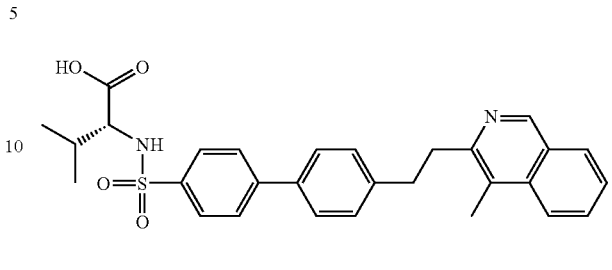

N-({4'-[2-4-methylisoquinolin-3-yl)ethyl]-1,1'-biphenyl-4-yl}sulfonyl)-D-valine

Step 8A2-(4-Bromo-benzenesulfonylamino)-3-methyl-butyric acid tert-butyl ester (10.65 g, 27.1 mmol, 1 equiv.), 4-(4,4,5,5-Tetramethyl-1,3,2-dioxaborolan-2-yl)phenol (5.97 g, 27.1 mmol, 1 equiv), Pd(PPh$_3$)$_4$ (1.57 g, 1.4 mmol, 0.05 equiv.) were dissolved in ethylene glycol dimethyl ether (210 mL) under N$_2$ atmosphere and stirred at room temperature for 30 min. Then K$_2$CO$_3$ (7.5 g, 54.3 mmol, 2 equiv.) in H$_2$O (70 mL) was introduced to the reaction mixture and heat to reflux overnight. Reaction was complete as determined by TLC. Solvent was removed by rotovap and the residue partitioned between dichloromethane and brine. Organic layered dried over MgSO$_4$, solvent removed, crude purified by column chromatography (silica gel, 30% EtOAc/n-Hexane) to give 7.1 g of 2-(4'-Hydroxy-biphenyl-4-sulfonylamino)-3-methyl-butyric acid tert-butyl ester in 65% yield.

1H NMR (400 MHz, CHLOROFORM-D) δ ppm 0.79 (d, J=6.82 Hz, 3 H) 0.95 (d, J=6.57 Hz, 3 H) 1.13 (s, 9 H) 1.51 (s, 1 H) 1.99 (m, 1 H) 3.59 (dd, J=10.11, 4.55 Hz, 1 H) 5.06 (d, J=9.85 Hz, 1 H) 6.86 (d, J=8.84 Hz, 2 H) 7.38 (d, J=8.84 Hz, 2 H) 7.55 (d, J=8.59 Hz, 2 H) 7.79 (d, J=8.59 Hz, 2 H).

Step 8B: 2-(4'-Hydroxy-biphenyl-4-sulfonylamino)-3-methyl-butyric acid tert-butyl ester (330 mg, 0.81 mmol) was dissolved in 20 mL of dry methylene chloride and cool to 0° C. NaH (83 mg, 60% in oil, 2.0 mmol, 2.5 equiv.) was added under N2 and the mixture was stirred for 15 min. Triflic anhydride (251 mg, 0.89 mmol, 1.1 equiv.) was injected and the mixture was warm to room temperature for 1 h. TLC indicated the reaction was complete. The reaction mixture was diluted with methylene chloride and neutralized with 1N HCl. Mixture was washed with water, brine, and dried over MgSO4. Regular column chromatography (40% EtOAc/hexane) to afford 314 mg of desired product in 72% yield.

1H NMR (400 MHz, CHLOROFORM-D) δ ppm 0.87 (d, J=6.82 Hz, 3 H) 1.03 (d, J=6.82 Hz, 3 H) 1.21 (s, 9 H) 2.01-2.20 (m, 1 H) 3.68 (dd, J=9.85, 4.55 Hz, 1 H) 5.18 (d, J=10.11 Hz, 1 H) 7.39 (d, J=8.84 Hz, 2 H) 7.64 (dd, J=13.52, 8.72 Hz, 4 H) 7.93 (d, J=8.59 Hz, 2 H).

Step 8C: The reaction tube was filled with triflate (300 mg, 0.56 mmol) from Step 8B, lithium chloride (24 mg, 0.56 mmol, 1 eq.), CuI (11 mg, 0.05 mmol, 10%), and PdCl$_2$(PPh$_3$)$_2$ (19.6 mg, 0.028 mmol, 5%) under nitrogen followed by the addition of DMF (5 mL). t-butyldimethylacetylene (235 mg, 1.68 mmol, 3 eq.) and diethylamine (409 mg, 5.6 mmol, 10 eq.) were injected. The tube was irradiated in microwave reactor at 125° C. for 10 min. Starting materials were consumed as determined by TLC. Mixture was partitioned between ethyl acetate and water. Organic phase collected and regular work-up and column chromatography to give 270 mg of desired acetylenic product tert-butyl N-[(4'-{[tert-butyl(dimethyl)silyl]ethynyl}-1,1'-biphenyl-4-yl)sulfonyl]-D-valinate in 92% yield. 1H NMR (400 MHz, CHLOROFORM-D) δ ppm 0.00 (s, 6 H) 0.66 (d, J=6.82 Hz, 3 H) 0.81 (s, 9 H) 0.82 (d, J=6.82 Hz, 3 H) 0.98 (s, 9 H) 1.75-1.98 (m, 1 H) 3.46 (dd, J=9.85, 4.55 Hz, 1 H) 4.93 (d, J=9.85 Hz, 1 H) 7.27-7.32 (m, 2 H) 7.33-7.39 (m, 2 H) 7.47 (d, J=8.84 Hz, 2 H) 7.70 (d, J=8.84 Hz, 2 H).

Step 8D: tert-butyl N-[(4'-{[tert-butyl(dimethyl)silyl]ethynyl}-1,1'-biphenyl-4-yl)sulfonyl]-D-valinate (600 mg, 1.14 mmol) was dissolved in THF (8 mL) and added with TBAF (1.7 mL, 1M, 1.7 mmol, 1.5 eq). The solution was stirred at room temperature for half hour and the reaction was complete. Solvent removed and the residue was purified with column chromatography (silica gel, 20% EtOAc/hexane). 469 mg of product tert-butyl N-[(4'-ethyny-1,1'-biphenyl-4-yl)sulfonyl]-D-valinate was isolated in quantitative yield. 1H NMR (400 MHz, CHLOROFORM-D) δ ppm 0.86 (d, J=6.82 Hz, 2 H) 1.02 (d, J=6.82 Hz, 2 H) 1.20 (s, 9 H) 1.88-2.29 (m, 1 H) 3.17 (s, 1 H) 3.67 (dd, J=9.85, 4.55 Hz, 1 H) 5.14 (d, J=10.1 1 Hz, 1 H) 7.52 (d, J=8.59 Hz, 2 H) 7.56-7.62 (m, 2 H) 7.67 (d, J=8.84 Hz, 2 H) 7.91 (d, J=8.59 Hz, 2 H).

Step 8E tert-butyl N-[(4'-ethyny-1,1'-biphenyl-4-yl)sulfonyl]-D-valinate (117 mg, 0.28 mmol), 2-chloro-3-methylisoquinoline (60 mg, 0.34 mmol, 1.2 eq), CuI (5.3 mg, 0.028 mmol, 10%), and PdC12(PPh3)2 (9.8 mg, 0.014 mmol, 5%) were placed in a reaction tube under N₂ and added with DMF (4 mL) and 10 eq. of diethyl amine. The mixture was irradiated at 125° C. for 10 min. Reaction was complete as determined by LCMS. Dilute the mixture with EtOAc and washed with water 3 times, brine once then dried over MgSO4. Column chromatography (silica gel, 30% EtOAc/hexane) to provide 120 mg of desired product tert-butyl N-({4'-[(4-methylisoquinolin-3-yl)ethynyl]-1,1'-biphenyl-4-yl}sulfonyl)-D-valinate in 76% yield. 1H NMR (400 MHz, DMSO-D6) δ ppm 0.86 (dd, J=8.59, 6.82 Hz, 6 H) 1.17 (s, 9 H) 1.94 (m, 1 H) 2.67 (s, 3 H) 3.50 (dd, J=10.61, 7.33 Hz, 1 H) 7.62 (t, J=7.45 Hz, 1 H) 7.69-7.78 (m, 1 H) 7.80-7.85 (m, 4 H) 7.87 (d, J=8.59 Hz, 2 H) 7.90-7.97 (m, 2 H) 8.00 (d, J=8.59 Hz, 1 H) 8.20 (d, J=9.60 Hz, 1 H) 8.30 (s, 1 H).

Step 8F: tert-butyl N-({4'-[(4-methylisoquinolin-3-yl)ethynyl]-1,1'-biphenyl-4-yl}sulfonyl)-D-valinate (46 mg, 0.08 mmol) was dissolved in 25 mL of methanol and added with catalytic amount of Pd/C (8.5 mg, 10% weight on Carbon, 0.008 mmol). The hydrogenation was carried out in a Parr shaker bottle under H₂ (50 PSI). Reaction was terminated after 5 hours and LCMS indicated the reaction was complete. The mixture was filtered through Celite and concentrated to the desired product G8594-178 in quantitative yield (46 mg). 1H NMR (400 MHz, DMSO-D6) δ ppm 0.77-0.93 (m, 6 H) 1.15 (s, 9 H) 1.85-2.06 (m, 1 H) 2.51 (s, 3 H) 3.13-3.28 (m, 2 H) 3.25-3.39 (m, 2 H) 3.47 (d, J=8.84 Hz, 1 H) 7.47 (d, J=8.08 Hz, 2 H) 7.52 (t, J=7.45 Hz, 1 H) 7.59-7.71 (m, 3 H) 7.76-7.90 (m, 4 H) 7.97 (d, J=8.34 Hz, 1 H) 8.06 (s, 1 H) 8.15 (s, 1 H).

Step 8G: tert-butyl N-({4'-[2-(4-methylisoquinolin-3-yl)ethyl]-1,1'-biphenyl-4-yl}sulfonyl-D-valinate (46 mg, 0.08 mmol) was dissolved in 5 mL of dry methylene chloride followed by the addition of 2.5 mL of TFA. The mixture was stirred at room temperature for 3 hrs and TLC indicated the reaction was complete. Solvent was removed by rotavap and the product dried in vacuum oven overnight. 44 mg of product N-({4'-[2-(4-methylisoquinolin-3-yl)ethyl]-1,1'-biphenyl-4-yl}sulfonyl-D-valine was obtained in 95% yield.

1H NMR (400 MHz, MeOD) δ ppm 0.83 (d, J=6.82 Hz, 3 H) 0.88 (d, J=6.82 Hz, 3 H) 1.80-2.13 (m, 1 H) 2.57 (s, 3 H) 3.15 (t, J=7.83 Hz, 2 H) 3.45-3.55 (m, 2 H) 3.60 (d, J=5.56 Hz, 1 H) 7.25 (d, J=8.08 Hz, 2 H) 7.53 (d, J=8.08 Hz, 2 H) 7.65 (d, J=8.34 Hz, 2 H) 7.81 (d, J=8.59 Hz, 3 H) 7.98 (t, J=7.58 Hz, 1 H) 8.02-8.09 (m, 1 H) 8.13 (d, J=8.08 Hz, 1 H) 8.83 (s, 1 H).

Example 3.59 was made based on Scheme 9.

Example 3.59

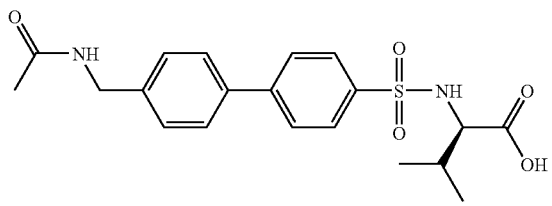

D-2-[4'-(Acetylamino-methyl)-biphenyl-4-sulfonylamino]-3-methyl-butyric acid

Step 9A: Combined 4-aminomethyl phenyl boronic acid (143 mg, 0.77 mmol, 1 eq), D-2-(4-Bromo-benzenesulfonylamino)-3-methyl-butyric acid tert-butyl ester (300 mg, 0.77 mmol, 1 eq), palladium tetrakis (44 mg, 0.038 mmol, 0.05 eq) in dimethoxy ethane (10 mL) and stirred at room temperature for 10 min. Potassium carbonate (212 mg, 1.53 mmol, 2 eq) in 4 mL of water was added to the reaction mixture and heated at 88° C. for 4 hrs. The reaction is then cool to room temperature and diluted with ethyl acetate, washed with brine, dried over magnesium sulfate and stripped to dryness. Residue is purified via flash chromatography on silica gel eluting with 4-10% MeOH in methylene chloride with 2% Et₃N to obtain 200 mg of D-2-(4'-Aminomethyl-biphenyl-4-sulfonylamino)-3-methyl-butyric acid tert-butyl ester. Yield: 63%. 1H NMR (400 MHz, DMSO-D6) δ ppm 0.9 (dd, J=8.1, 7.1 Hz, 6 H) 1.1 (s, 9 H) 1.9 (m, 1 H) 3.5 (d, J=6.3 Hz, 2 H) 3.8 (s, 2 H) 7.5 (d, J=8.3 Hz, 2 H) 7.6 (d, J=8.3 Hz, 2 H) 7.8 (d, J=2.0 Hz, 4 H).

Step 9B: To acetic anhydride (71 uL, 0.75 mmol, 1.05 eq.) in CH₂Cl₂ (5 mL) was added with pyridine (70 uL, 0.86 mmol, 1.2 eq.) under argon and stirred for 5 min, then D-2-(4'-Aminomethyl-biphenyl-4-sulfonylamino)-3-methyl-butyric acid tert-butyl ester (300 mg, 0.72 mmol, 1 eq.) was added and stirred for 16 hours. After work-up and flash column chromatography, D-2-[4'-(Acetylamino-methyl)-biphenyl-4-sulfonylamino]-3-methyl-butyric acid tert-butyl ester was obtained. Yield: 32%. 1H NMR (400 MHz, DMSO-D6) δ ppm 0.8 (dd, J=9.1, 6.8 Hz, 6 H) 0.9 (t, J=7.3 Hz, 3 H) 1.2 (s, 9 H) 1.3 (m, 2 H) 1.5 (m, 2 H) 1.9 (m, 1 H) 2.5 (m, 2 H) 3.4 (dd, J=9.6, 6.3 Hz, 1 H) 7.0 (dd, 4 H) 7.1 (m, 2 H) 7.5 (d, J=8.8 Hz, 2 H) 7.7 (d, J=9.6 Hz, 1 H) 8.6 (s, 1 H).

Step 9C: To a solution of D-2-[4'-(Acetylamino-methyl)-biphenyl-4-sulfonylamino]-3-methyl-butyric acid tert-butyl ester (300 mg, 0.65 mmol) in 6 mL of dichloroethane was added 3 mL of trifluoroacetic acid. The reaction mixture was stirred at room temperature for 4 hrs and reaction was complete as determined by TLC. Solvent removed and residue dried over vacuum oven to obtain 250 mg of D-2-[4'-(Acetylamino-methyl)-biphenyl-4-sulfonylamino]-3-methyl-butyric acid. Yield: 94%. 1H NMR (400 MHz, DMSO-D6) δ ppm 0.8 (dd, J=12.5, 6.7 Hz, 6 H) 1.9 (s, 3 H) 2.0 (m, 1 H) 3.6 (dd, J=9.3, 5.8 Hz, 1 H) 4.3 (d, J=5.8 Hz, 2 H) 7.4 (d, J=8.1 Hz, 2 H) 7.7 (d, J=8.3 Hz, 2 H) 7.8 (s, 4 H) 8.1 (d, J=9.3 Hz, 1 H) 8.4 (t, J=5.8 Hz, 1 H) 12.6 (s, 1 H).

Example 3.60 and 3.61 were made based on Scheme 10

Example 3.60

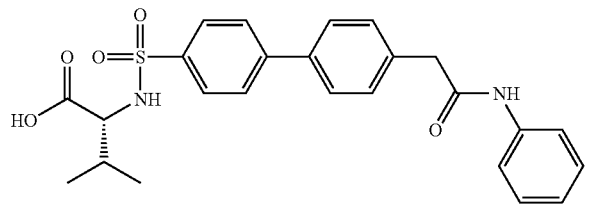

D-3-Methyl-2-(4'-phenylcarbamoylmethyl-biphenyl-4-sulfonylamino)-butyric acid

Step 10A: A mixture of 4-Bromophenylacetic acid (1.5 g, 7.0 mmol, 1 eq.), EDC (2.67 g, 14.0 mmol, 2 eq.), DMAP (846 mg, 7.0 mmol, 1 eq.), and phenylamine (0.765 mL, 8.4 mmol, 1.2 eq.) in 15 mL of DMF was stirred under nitrogen at room temperature for 3.5 hrs. After aqueous workup and recrystallization, 2-(4-Bromophenyl)-N-phenyl-acetamide was obtained in 69% yield (1.4 g). 1H NMR (400 MHz, DMSO-D6) δ ppm 3.6 (s, 2 H) 7.0 (m, 1 H) 7.3 (m, 4 H) 7.5 (m, 2 H) 7.6 (dd, J=8.7, 1.1 Hz, 2 H) 10.2 (s, 1 H).

Step 10B: A mixture of 2-(4-Bromophenyl)-N-phenyl-acetamide (107 mg, 0.37 mmol, 1.1 eq.), D-3-Methyl-2-(4-tributylstannanyl-benzenesulfonylamino)-butyric acid tert-butyl ester (202 mg, 0.34 mmol, 1 eq.), and Pd(PPh$_3$)$_4$ (38.5 mg, 0.033 mmol, 0.1 eq.) in 5 mL of toluene was heated to reflux under nitrogen. Reaction was complete after 5 hrs. Regular work-up and column purification, D-3-Methyl-2-(4'-phenylcarbamoylmethyl-biphenyl-4-sulfonylamino)-butyric acid tert-butyl ester was obtained in 34% yield (60 mg). 1H NMR (400 MHz, DMSO-D6) δ ppm 0.9 (dd, J=8.3, 6.8 Hz, 6 H) 1.1 (s, 9 H) 1.9 (m, 1 H) 3.5 (dd, J=9.6, 6.3 Hz, 1 H) 3.7 (s, 2 H) 7.0 (t, J=7.3 Hz, 1 H) 7.3 (m, 2 H) 7.5 (d, J=8.3 Hz, 2 H) 7.6 (dd, J=8.6, 1.0 Hz, 2 H) 7.7 (d, J=8.3 Hz, 2 H) 7.8 (d, J=2.5 Hz, 4 H) 8.1 (d, J=9.6 Hz, 1 H) 10.2 (s, 1 H).

Step 10C: Removal of t-butyl ester of D-3-Methyl-2-(4'-phenylcarbamoylmethyl-biphenyl-4-sulfonylamino)-butyric acid tert-butyl ester was done using TFA in dichloroethane (1:1). After evaporation of solvent, D-3-Methyl-2-(4'-phenylcarbamoyhmethyl-biphenyl-4-sulfonylamino)-butyric acid was obtained in quantitative yield. 1H NMR (400 MHz, MeOD) δ ppm 0.8 (dd, J=27.0, 6.8 Hz, 6 H) 2.0 (m, 1 H) 3.6 (d, J=5.6 Hz, 1 H) 3.6 (s, 2 H) 7.0 (m, 1 H) 7.2 (m, 2 H) 7.4 (d, J=8.3 Hz, 2 H) 7.5 (dd, J=8.7, 1.1 Hz, 2 H) 7.6 (d, J=8.3 Hz, 2 H) 7.7 (dd, J=48.0, 8.6 Hz, 4 H).

Example 3.61

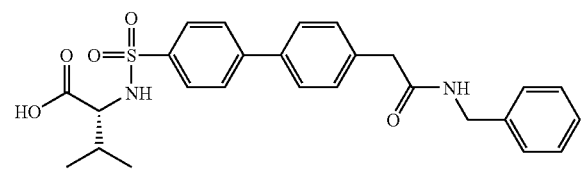

D-2-[4'-(Benzylcarbamoyl-methyl)-biphenyl-4-sulfonylamino]-3-methyl-butyric acid Step 10A: Amide coupling of 4-Bromophenylacetic acid with benzylamine was done according to procedures in Step 10A for Example 3.60 to give N-Benzyl-2-(4-bromo-phenyl)-acetamide in 82% yield. 1H NMR (400 MHz, DMSO-D6) δ ppm 3.5 (s, 2 H) 4.3 (d, J=5.8 Hz, 2 H) 7.2 (dd, J=7.8, 5.6 Hz, 5 H) 7.3 (m, 2 H) 7.5 (d, J=8.3 Hz, 2 H) 8.6 (t, J=5.9 Hz, 1 H).

Step 10B: Stille coupling of N-Benzyl-2-(4-bromo-phenyl)-acetamide with D-3-Methyl-2-(4-tributylstannanyl-benzenesulfonylamino)-butyric acid tert-butyl ester was carried out according to procedures in Step 10B for Example 3.60 to give D-2-[4'-(Benzylcarbamoyl-methyl)-biphenyl-4-sulfonylamino]-3-methyl-butyric acid tert-butyl ester in 31% yield. 1H NMR (400 MHz, CHLOROFORM-D) δ ppm 0.9 (d, J=6.8 Hz, 3 H) 1.0 (d, J=6.6 Hz, 3 H) 1.2 (s, 9 H) 2.1 (m, 1 H) 3.7 (m, 3 H) 4.5 (d, J=5.8 Hz, 2 H) 5.1 (d, J=9.9 Hz, 1 H) 5.7 (s, 1 H) 7.3 (m, 5 H) 7.4 (d, J=8.1 Hz, 2 H) 7.5 (d, J=8.3 Hz, 2 H) 7.7 (d, J=8.3 Hz, 2 H) 7.9 (d, J=8.3 Hz, 2 H).

Step 10C: Removal of t-butyl ester was done according to procedures in Step 10C for Example 3.60 in quantitative yield. 1H NMR (400 MHz, MeOD) δ ppm 0.8 (dd, J=26.3, 6.8 Hz, 6 H) 2.0 (m, 1 H) 3.5 (s, 2 H) 3.6 (d, J=5.6 Hz, 1 H) 4.3 (d, J=5.6 Hz, 2 H) 7.2 (m, 5 H) 7.3 (d, J=8.3 Hz, 2 H) 7.5 (d, J=8.3 Hz, 2 H) 7.7 (d, J=8.8 Hz, 2 H) 7.8 (d, J=8.8 Hz, 2 H) 8.5 (s, 1 H).

Examples 3.62, 3.63, 3.64, 3.65, 3.66, 3.67, 3.68, 3.69, 3.70, 3.71, 3.72, 3.73, 3.74, 3.75, 3.76, 3,77, 3,78, 3,79, 3.80 were made based on Scheme 11.

Example 3.62

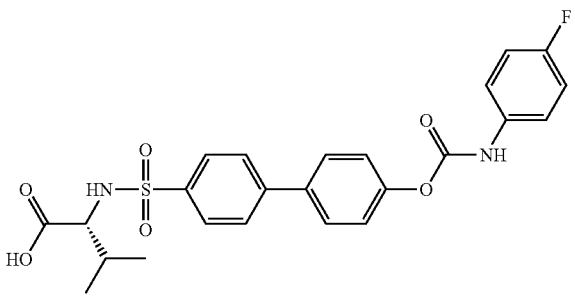

2-[4'-(4-Fluoro-phenylcarbamoyloxy)-biphenyl-4-sulfonylamino]-3-methyl-butyric acid Step 11A: 2-(4'-Hydroxy-biphenyl-4-sulfonylamino)-3-methyl-butyric acid tert-butyl ester (300 mg, 0.74 mmol, 1 equiv.) was dissolved in diethyl ether (7.5 mL), followed by the addition of 4-fluorophenylisocyanate (101 mg, 0.74 mmol, 1 equiv.) and Et$_3$N (1 mL). The reaction mixture was stirred at room temperature for 50 min. Solid precipitated from the reaction mixture. Solid was collected by filtration and washed with ether to yield 2-[4'-(4-Fluoro-phenylcarbamoyloxy)-biphenyl-4-sulfonylamino]-3-methyl-butyric acid tert-butyl ester in 57% yield (228 mg).

1H NMR (400 MHz, CHLOROFORM-D) δ ppm 0.87 (d, J=6.82 Hz, 3 H) 1.03 (d, J=6.82 Hz, 3 H) 1.20 (s, 9 H) 2.05 (m, 1 H) 3.67 (dd, J=9.98, 4.42 Hz, 1 H) 5.13 (d, J=9.85 Hz, 1 H) 6.95 (s, 1 H) 7.05 (d, J=9.09 Hz, 2 H) 7.30 (d, J=8.59 Hz, 2 H) 7.43 (m, 2 H) 7.57 (d, J=8.59 Hz, 2 H) 7.67 (s, 2 H) 7.90 (d, J=8.34 Hz, 2 H).

Step 11B: 2-[4'-(4-Fluoro-phenylcarbamoyloxy)-biphenyl-4-sulfonylamino]-3-methyl-butyric acid tert-butyl ester (223 mg) was dissolved in dichloroethane (7.5 mL) and added with TFA (2.5 mL). The mixture was stirred at room temperature for 5 hrs and TLC indicated the reaction was complete. Regular work-up and column chromatography to give 2-[4'-(4-Fluoro-phenylcarbamoyloxy)-biphenyl-4-sulfonylamino]-3-methyl-butyric acid in 89% yield (178 mg).

1H NMR (400 MHz, DMSO-D6) δ ppm 0.81 (d, J=6.57 Hz, 3 H) 0.84 (d, J=6.82 Hz, 3 H) 1.96 (m, 1 H) 3.56 (dd, J=9.35, 6.06 Hz, 1 H) 7.19 (t, J=8.84 Hz, 2 H) 7.37 (d, J=8.59 Hz, 2 H) 7.54 (dd, J=9.09, 4.80 Hz, 2 H) 7.79 (d, J=8.84 Hz, 2 H) 7.86 (d, J=4.29 Hz, 4 H) 8.08 (d, J=9.35 Hz, 1 H) 10.34 (s, 1 H).

Example 3.63

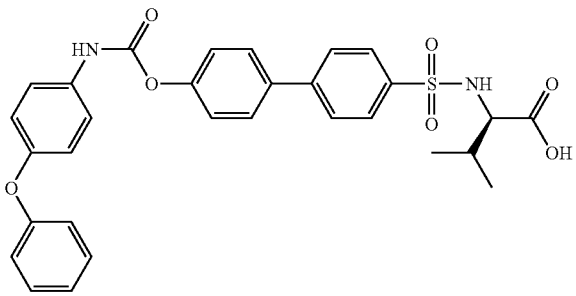

D-3-Methyl-2-[4'-(4-phenoxy-phenylcarbamoyloxy)-biphenyl-4-sulfonylamino]-butyric acid The title compound, D-3-Methyl-2-[4'-(4-phenoxy-phenylcarbamoyloxy)-biphenyl-4-sulfonylamino]-butyric acid, was prepared according to procedures similar to that of Example 3.62.

Step 11A: Reaction of 4-phenoxyphenyl isocyanate with D-2-(4'-Hydroxy-biphenyl-4-sulfonylamino)-3-methyl-butyric acid-tert-butyl ester to obtain D-3-Methyl-2-[4'-(4-phenoxy-phenylcarbamoyloxy)-biphenyl-4-sulfonylamino]-butyric acid tert-butyl ester was done according to procedures in Step 11A for Example 3.62. Yield: 36%. 1H NMR (400 MHz, DMSO-D6) □ ppm 0.9 (dd, J=8.2, 6.9 Hz, 6 H) 1.2 (s, 9 H) 1.9 (m, 1 H) 3.5 (dd, J=9.6, 6.3 Hz, 1 H) 7.0 (dd, J=8.6, 1.0 Hz, 2 H) 7.0 (d, J=9.1 Hz, 2 H) 7.1 (m, 1 H) 7.4 (m, 4 H) 7.5 (d, J=8.8 Hz, 2 H) 7.7 (d, J=8.8 Hz, 2 H) 7.9 (m, 4 H) 8.2 (d, J=9.6 Hz, 1 H) 10.3 (s, 1 H).

Step 11B: Conversion of D-3-Methyl-2-[4'-(4-phenoxy-phenylcarbamoyloxy)-biphenyl-4-sulfonylamino]-butyric acid tert-butyl ester to D-3-Methyl-2-[4'-(4-phenoxy-phenyl-carbamoyloxy)-biphenyl-4-sulfonylamino]-butyric acid was done according to procedures in Step 11B for Example 3.62. Yield: 87%. 1H NMR (400 MHz, DMSO-D6) δ ppm 0.8 (dd, J=12.1, 6.8 Hz, 6 H) 1.9 (m, 1 H) 3.6 (dd, J=9.3, 6.1 Hz, 1 H) 7.0 (m, 2 H) 7.0 (d, J=9.1 Hz, 2 H) 7.1 (t, J=7.3 Hz, 1 H) 7.4 (m, 4 H) 7.5 (d, J=8.8 Hz, 2 H) 7.8 (d, J=8.8 Hz, 2 H) 7.9 (d, J=4.8 Hz, 4 H) 8.1 (d, J=9.3 Hz, 1 H) 10.3 (s, 1 H).

Example 3.64

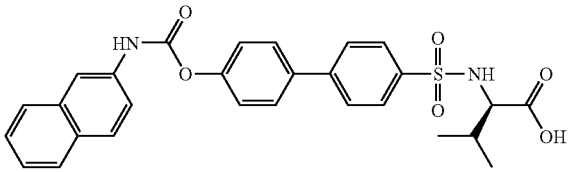

D-3-Methyl-2-[4'-(naphthalen-2-ylcarbamoyloxy)-biphenyl-4-sulfonylamino]-butyric acid The title compound, D-3-Methyl-2-[4'-(naphthalen-2-ylcarbamoyloxy)-biphenyl-4-sulfonylamino]-butyric acid, was prepared according to procedures similar to that of Example 3.62.

Step 11A: Reaction of 2-naphthyl isocyanate with D-2-(4'-Hydroxy-biphenyl-4-sulfonylamino)-3-methyl-butyric acid-tert-butyl ester to obtain D-3-Methyl-2-[4'-(naphthalen-2-ylcarbamoyloxy)-biphenyl-4-sulfonylamino]-butyric acid tert-butyl ester was done according to procedures in Step 11A for Example 3.62. Yield: 16%. 1H NMR (400 MHz, DMSO-D6) □ ppm 0.9 (dd, J=8.2, 6.9 Hz, 6 H) 1.2 (s, 9 H) 1.9 (m, 1 H) 3.5 (dd, J=9.9, 6.3 Hz, 1 H) 7.4 (m, 3 H) 7.5 (m, 1 H) 7.6 (dd, J=8.8, 2.3 Hz, 1 H) 7.8 (d, J=8.8 Hz, 2 H) 7.9 (m, 7 H) 8.1 (s, 1 H) 8.2 (d, J=9.9 Hz, 1 H) 10.5 (s, 1 H).

Step 11B: Conversion of D-3-Methyl-2-[4'-(naphthalen-2-ylcarbamoyloxy)-biphenyl-4-sulfonylamino]-butyric acid tert-butyl ester to D-3-Methyl-2-[4'-(naphthalen-2-ylcarbamoyloxy)-biphenyl-4-sulfonylamino]-butyric acid was done according to procedures in Step 11B for Example 3.62. Yield: 40%. 1H NMR (400 MHz, DMSO-D6) δ ppm 0.8 (dd, J=12.5, 6.7 Hz, 6 H) 2.0 (m, 1 H) 3.6 (dd, J=9.1, 5.8 Hz, 1 H) 7.4 (m, 3 H) 7.5 (m, 1 H) 7.6 (dd, J=8.8, 2.3 Hz, 1 H) 7.9 (m, 9 H) 8.1 (m, 2 H) 10.5 (s, 1 H) 12.6 (s, 1 H).

Example 3.65

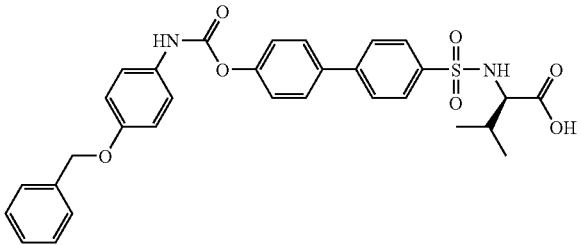

D-2-[4'-(4-Benzyloxy-phenylcarbamoyloxy)-biphenyl-4-sulfonylamino]-3-methyl-butyric acid The title compound, D-2-[4'-(4-Benzyloxy-phenylcarbamoyloxy)-biphenyl-4-sulfonylamino]-3-methyl-butyric acid, was prepared according to procedures similar to that of Example 3.62.

Step 11A: Reaction of 4-benzyloxyphenyl isocyanate with D-2-(4'-Hydroxy-biphenyl-4-sulfonylamino)-3-methyl-butyric acid-tert-butyl ester to obtain D-2-[4'-(4-Benzyloxy-phenylcarbamoyloxy)-biphenyl-4-sulfonylamino]-3-methyl-butyric acid tert-butyl ester was done according to procedures in Step 11A for Example 3.62. Yield: 37%. NMR: G8701-142. 1H NMR (400 MHz, DMSO-D6) δ ppm 0.9 (dd, J=8.1, 6.8 Hz, 6 H) 1.2 (s, 9 H) 1.9 (m, 1 H) 3.5 (dd, J=9.9, 6.3

Hz, 1 H) 5.1 (s, 2 H) 7.0 (d, J=9.1 Hz, 2 H) 7.4 (m, 9 H) 7.7 (d, J=8.8 Hz, 2 H) 7.9 (m, 4 H) 8.2 (d, J=9.6 Hz, 1 H) 10.1 (s, 1 H).

Step 11B: Conversion of D-2-[4'-(4-Benzyloxy-phenylcarbamoyloxy)-biphenyl-4-sulfonylamino]-3-methyl-butyric acid tert-butyl ester to D-2-[4'-(4-Benzyloxy-phenylcarbamoyloxy)-biphenyl-4-sulfonylamino]-3-methyl-butyric acid was done according to procedures in Step 11B for Example 3.62. Yield: 60%. NMR: G8701-151. 1H NMR (400 MHz, DMSO-D6) δ ppm 0.8 (dd, J=12.1, 6.8 Hz, 6 H) 1.9 (m, 1 H) 3.6 (dd, J=9.3, 6.1 Hz, 1 H) 5.1 (s, 2 H) 7.0 (d, J=9.1 Hz, 2 H) 7.4 (m, 9 H) 7.8 (d, J=8.8 Hz, 2 H) 7.9 (m, 4 H) 8.1 (d, J=9.3 Hz, 1 H) 10.1 (s, 1 H).

Example 3.66

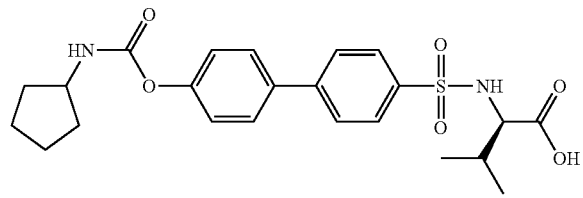

D-2-(4'-Cyclopentylcarbamoyloxy-biphenyl-4-sulfonylamino)-3-methyl-butyric acid

The title compound, D-2-(4'-Cyclopentylcarbamoyloxy-biphenyl-4-sulfonylamino)-3-methyl-butyric acid, was prepared according to procedures similar to that of Example 3.62.

Step 11A: Reaction of cyclopentyl isocyanate with D-2-(4'-Hydroxy-biphenyl-4-sulfonylamino)-3-methyl-butyric acid-tert-butyl ester to obtain D-2-(4'-Cyclopentylcarbamoyloxy-biphenyl-4-sulfonylamino)-3-methyl-butyric acid tert-butyl ester was done according to procedures in Step 11A for Example 3.62. Yield: 70%. 1H NMR (400 MHz, DMSO-D6) δ ppm 0.9 (dd, J=8.1, 7.1 Hz, 6 H) 1.2 (s, 9 H) 1.5 (m, 4 H) 1.7 (m, 2 H) 1.8 (m, 2 H) 1.9 (m, 1 H) 3.5 (dd, J=9.6,6.3 Hz, 1 H) 3.9 (m, 1 H) 7.2 (d, J=8.6 Hz, 2 H) 7.7 (d, J=8.6 Hz, 2 H) 7.8 (m, 5 H) 8.2 (d, J=9.6 Hz, 1 H).

Step 11B: Conversion of D-2-(4'-Cyclopentylcarbamoyloxy-biphenyl-4-sulfonylamino)-3-methyl-butyric acid tert-butyl ester to D-2-(4'-Cyclopentylcarbamoyloxy-biphenyl-4-sulfonylamino)-3-methyl-butyric acid was done according to procedures in Step 11B for Example 3.62. Yield: 91%. 1H NMR (400 MHz, DMSO-D6) δ ppm 0.8 (m, 6 H) 1.5 (m, 4 H) 1.7 (d, J=4.5 Hz, 2 H) 1.8 (m, 2 H) 1.9 (m, 1 H) 3.6 (dd, J=9.3, 6.1 Hz, 1 H) 3.9 (m, 1 H) 7.2 (d, J=8.6 Hz, 2 H) 7.7 (d, J=8.8 Hz, 2 H) 7.8 (s, 5 H) 8.1 (d, J=9.3 Hz, 1 H) 12.6 (s, 1 H).

Example 3.67

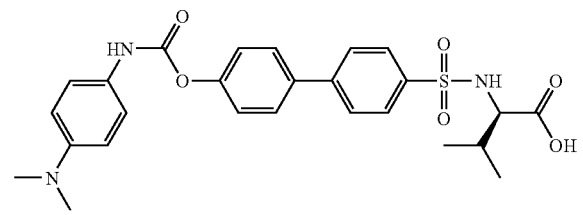

D-2-[4'-(4-Dimethylamino-phenylcarbamoyloxy)-biphenyl-4-sulfonylamino]-3-methyl-butyric acid The title compound, D-2-[4'-(4-Dimethylamino-phenylcarbamoyloxy)-biphenyl-4-sulfonylamino]-3-methyl-butyric acid, was prepared according to procedures similar to that of Example 3.62.

Step 11A: Coupling of 4-(dimethylamino)phenyl isocyanate with D-2-(4'-Hydroxy-biphenyl-4-sulfonylamino)-3-methyl-butyric acid-tert-butyl ester to obtain D-2-[4'-(4-Dimethylamino-phenylcarbamoyloxy)-biphenyl-4-sulfonylamino]-3-methyl-butyric acid tert-butyl ester was done according to procedures in Step 11A for Example 3.62. Yield: 28%. 1H NMR (400 MHz, DMSO-D6) δ ppm 0.9 (dd, J=8.1, 6.8 Hz, 6 H) 1.2 (s, 9 H) 1.9 (m, 1 H) 2.8 (s, 6 H) 3.5 (dd, J=9.6, 6.3 Hz, 1 H) 6.7 (d, J=9.1 Hz, 2 H) 7.3 (d, J=8.6 Hz, 4 H) 7.7 (d, J=8.6 Hz, 2 H) 7.8 (m, 4 H) 8.2 (d, J=9.9 Hz, 1 H) 9.9 (s, 1 H).

Step 11B: Conversion of D-2-[4'-(4-Dimethylamino-phenylcarbamoyloxy)-biphenyl-4-sulfonylamino]-3-methyl-butyric acid tert-butyl ester to D-2-[4'-(4-Dimethylamino-phenylcarbamoyloxy)-biphenyl-4-sulfonylamino]-3-methyl-butyric acid was done according to procedures in Step 11B for Example 3.62. Yield: 99%. NMR: G8701-161. 1H NMR (400 MHz, MeOD) δ ppm 0.8 (dd, J=23.7, 6.8 Hz, 6 H) 2.0 (m, 1 H) 3.1 (s, 6 H) 3.6 (d, J=5.6 Hz, 1 H) 7.2 (d, J=8.8 Hz, 2 H) 7.4 (d, J=9.1 Hz, 3 H) 7.6 (m, 6 H) 7.8 (d, J=8.8 Hz, 2 H).

Example 3.68

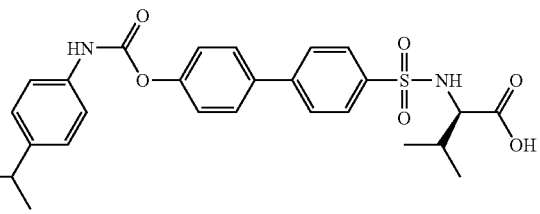

D-2-[4'-(4-Isopropyl-phenylcarbamoyloxy)-biphenyl-4-sulfonylamino]-3-methyl-butyric acid The title compound, D-2-[4'-(4-Isopropyl-phenylcarbamoyloxy)-biphenyl-4-sulfonylamino]-3-methyl-butyric acid, was prepared according to procedures similar to that of Example 3.62.

Step 11A: Reaction of 4-isopropylphenyl isocyanate with D-2-(4'-Hydroxy-biphenyl-4-sulfonylamino)-3-methyl-butyric acid-tert-butyl ester to obtain D-2-[4'-(4-Isopropyl-phenylcarbamoyloxy)-biphenyl-4-sulfonylamino]-3-methyl-butyric acid tert-butyl ester was done according to procedures in Step 11A for Example 3.62. Yield: 38%. NMR: G8701-158. 1H NMR (400 MHz, DMSO-D6) δ ppm 0.9 (dd, J=8.3, 6.8 Hz, 6 H) 1.2 (m, 15 H) 1.9 (m, 1 H) 2.8 (m, 1 H) 3.5 (dd, J=9.9, 6.3 Hz, 1 H) 7.2 (d, J=8.6 Hz, 2 H) 7.4 (d, J=8.6 Hz, 2 H) 7.4 (d, J=8.6 Hz, 2 H) 7.7 (d, J=8.6 Hz, 2 H) 7.9 (m, 4 H) 8.2 (d, J=9.9 Hz, 1 H) 10.2 (s, 1 H).

Step 11B: Conversion of D-2-[4'-(4-Isopropyl-phenylcarbamoyloxy)-biphenyl-4-sulfonylamino]-3-methyl-butyric acid tert-butyl ester to D-2-[4'-(4-Isopropyl-phenylcarbamoyloxy)-biphenyl-4-sulfonylamino]-3-methyl-butyric acid was done according to procedures in Step 11B for Example 3.62. Yield: 34%. NMR: G8701-165. 1H NMR (400 MHz, DMSO-D6) δ ppm 0.8 (dd, J=12.4, 6.8 Hz, 6 H) 1.2 (d, J=6.8 Hz, 6 H) 2.0 (m, 1 H) 2.8 (m, 1 H) 3.6 (dd, J=9.3, 6.1 Hz, 1 H) 7.2 (d, J=8.6 Hz, 2 H) 7.4 (d, J=8.8 Hz, 2 H) 7.4 (d, J=8.6 Hz, 2 H) 7.8 (d, J=8.8 Hz, 2 H) 7.9 (m, 4 H) 8.1 (d, J=9.3 Hz, 1 H) 10.2 (s, 1 H) 12.6 (s, 1 H).

Example 3.69

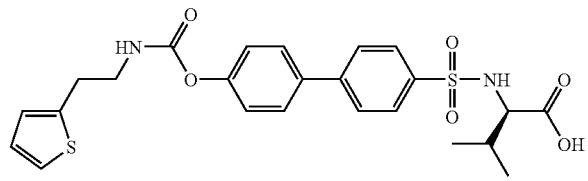

D-3-Methyl-2-[4'-(2-thiophen-2-yl-ethylcarbamoyloxy)-biphenyl-4-sulfonylamino]-butyric acid The title compound, D-3-Methyl-2-[4'-(2-thiophen-2-yl-ethylcarbamoyloxy)-biphenyl-4-sulfonylamino]-butyric acid, was prepared according to procedures similar to that of Example 3.62.

Step 11A: Reaction of 2-(2-thienyl)ethyl isocyanate with D-2-(4'-Hydroxy-biphenyl-4-sulfonylamino)-3-methyl-butyric acid-tert-butyl ester to obtain D-3-Methyl-2-[4'-(2-thiophen-2-yl-ethylcarbamoyloxy)-biphenyl-4-sulfonylamino]-butyric acid tert-butyl ester was done according to procedures in Step 11A for Example 3.62. Yield: 63%. NMR: G8701-169. 1H NMR (400 MHz, DMSO-D6) δ ppm 0.9 (dd, J=8.3, 7.1 Hz, 6 H) 1.2 (s, 9 H) 1.9 (m, 1 H) 3.0 (t, J=7.1 Hz, 2 H) 3.3 (m, 2 H) 3.5 (dd, J=9.6, 6.3 Hz, 1 H) 7.0 (m, 2 H) 7.2 (d, J=8.8 Hz, 2 H) 7.4 (dd, J=5.1, 1.3 Hz, 1 H) 7.7 (d, J=8.6 Hz, 2 H) 7.8 (d, J=2.3 Hz, 4 H) 8.0 (t, J=5.7 Hz, 1 H) 8.2 (d, J=9.9 Hz, 1 H).

Step 11B: Conversion of D-3-Methyl-2-[4'-(2-thiophen-2-yl-ethylcarbamoyloxy)-biphenyl-4-sulfonylamino]-butyric acid tert-butyl ester to D-3-Methyl-2-[4'-(2-thiophen-2-yl-ethylcarbamoyloxy)-biphenyl-4-sulfonylamino]-butyric acid was done according to procedures in Step 11B for Example 3.62. Yield: 43%. NMR: G8701-175. 1H NMR (400 MHz, DMSO-D6) δ ppm 0.8 (dd, J=12.4, 6.8 Hz, 6 H) 2.0 (m, 1 H) 3.0 (t, J=7.1 Hz, 2 H) 3.3 (m, 2 H) 3.6 (dd, J=9.2, 5.9 Hz, 1 H) 6.9 (d, J=3.3 Hz, 1 H) 7.0 (dd, J=5.1, 3.3 Hz, 1 H) 7.2 (d, J=8.8 Hz, 2 H) 7.4 (dd, J=5.1, 1.3 Hz, 1 H) 7.7 (d, J=8.6 Hz, 2 H) 7.8 (s, 4 H) 8.0 (t, J=5.8 Hz, 1 H) 8.1 (d, J=9.3 Hz, 1 H).

Example 3.70

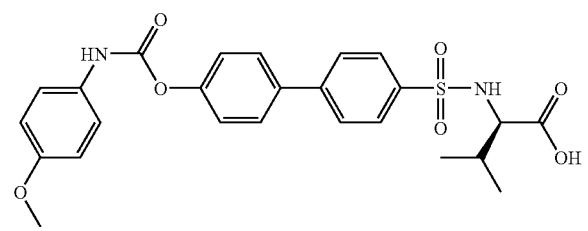

D-3-Methyl-2-[4'-(4-trifluoromethoxy-phenylcarbamoyloxy)-biphenyl4-sulfonylamino]-butyric acid The title compound, D-3-Methyl-2-[4'-(4-trifluoromethoxy-phenylcarbamoyloxy)-biphenyl-4-sulfonylamino]-butyric acid, was prepared according to procedures similar to that of Example 3.62.

Step 11A: Reaction of 4-methoxyphenyl isocyanate with D-2-(4'-Hydroxy-biphenyl-4-sulfonylamino)-3-methyl-butyric acid-tert-butyl ester to obtain D-2-[4'-(4-Methoxy-phenylcarbamoyloxy)-biphenyl-4-sulfonylamino]-3-methyl-butyric acid tert-butyl ester was done according to procedures in Step 11A for Example 3.62. Yield: 49%. NMR: G8701-199. 1H NMR (400 MHz, DMSO-D6) δ ppm 0.9 (dd, J=8.3, 6.8 Hz, 6 H) 1.2 (s, 9 H) 1.9 (m, 1 H) 3.5 (dd, J=9.9, 6.3 Hz, 1 H) 3.7 (s, 3 H) 6.9 (d, J=9.1 Hz, 2 H) 7.4 (d, J=8.8 Hz, 2 H) 7.4 (d, J=8.8 Hz, 2 H) 7.7 (d, J=8.6 Hz, 2 H) 7.9 (m, 4 H) 8.2 (d, J=9.9 Hz, 1 H) 10.1 (s, 1 H).

Step 11B: Reaction of D-2-[4'-(4-Methoxy-phenylcarbamoyloxy)-biphenyl-4-sulfonylamino]-3-methyl-butyric acid tert-butyl ester to D-3-Methyl-2-[4'-(4-trifluoromethoxy-phenylcarbamoyloxy)-biphenyl-4-sulfonylamino]-butyric acid was done according to procedures in Step 11B for Example 3.62. Yield: 91%. NMR: G9241-4. 1H NMR (400 MHz, DMSO-D6) δ ppm 0.8 (dd, J=12.6, 6.8 Hz, 6 H) 1.9 (m, 1 H) 3.6 (dd, J=9.3, 5.8 Hz, 1 H) 3.7 (s, 3 H) 6.9 (d, J=9.1 Hz, 2 H) 7.4 (d, J=8.8 Hz, 2 H) 7.4 (d, J=8.8 Hz, 2 H) 7.8 (d, J=8.6 Hz, 2 H) 7.9 (m, 4 H) 8.1 (d, J=9.3 Hz, 1 H) 10.1 (s, 1 H) 12.6 (s, 1 H).

Example 3.71

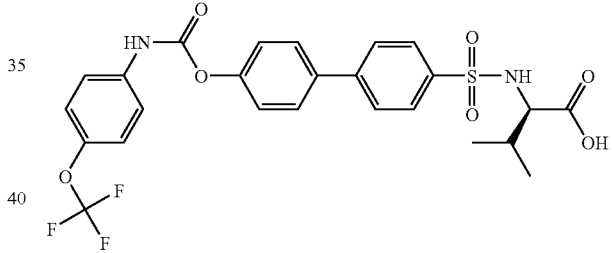

D-3-Methyl-2-[4'-(4-trifluoromethoxy-phenylcarbamoyloxy)-biphenyl4-sulfonylamino]-butyric acid The title compound, D-3-Methyl-2-[4'-(4-trifluoromethoxy-phenylcarbamoyloxy)-biphenyl-4-sulfonylamino]-butyric acid, was prepared according to procedures similar to that of Example 3.62.

Step 11A: To a solution of D-2-(4'-Hydroxy-biphenyl-4-sulfonylamino)-3-methyl-butyric acid-tert-butyl ester (300 mg, 0.74 mmol, 1 eq.) in diethyl ether (10 mL) were added with 4-(trifluoromethoxy)phenyl isocyanate (123 uL, 0.81 mmol, 1.1 eq.) and triethylamine (124 uL, 0.89 mmol, 1.2 eq.) under argon and stirred at room temperature. After reaction complete, regular work-up and flash column chromatography to provide D-3-Methyl-2-[4'-(4-trifluoromethoxy-phenylcarbamoyloxy)-biphenyl-4-sulfonylamino]-butyric acid tert-butyl ester in 37% yield. NMR: G8701-200. 1H NMR (400 MHz, DMSO-D6) □ ppm 0.9 (dd, J=8.1, 6.8 Hz, 6 H) 1.2 (s, 9 H) 1.9 (m, 1 H) 3.5 (dd, J=9.9, 6.3 Hz, 1 NMR: G8701-200. 1H NMR (400 MHz, DMSO-D6) δ ppm 0.9 (dd, J=8.1, 6.8 Hz, 6 H) 1.2 (s, 9 H) 1.9 (m, 1 H) 3.5 (dd, J=9.9, 6.3 Hz, 1 H) 7.4 (m, 4 H) 7.6 (d, J=9.3 Hz, 2 H) 7.8 (d, J=8.8 Hz, 2 H) 7.9 (m, 4 H) 8.2 (d, J=9.6 Hz, 1 H) 10.5 (s, 1 H).

Step 11B: Conversion of D-3-Methyl-2-[4'-(4-trifluoromethoxy-phenylcarbamoyloxy)-biphenyl-4-sulfonylamino]-butyric acid tert-butyl ester to D-3-Methyl-2-[4'-(4-trifluoromethoxy-phenylcarbamoyloxy)-biphenyl-4-sulfonylamino]-butyric acid was done according to procedures in Step 11B for Example 3.62. Yield: 76%. NMR: G9241-5. 1H NMR (400 MHz, DMSO-D6) δ ppm 0.8 (dd, J=12.4, 6.8 Hz, 6 H) 2.0 (m, 1 H) 3.6 (dd, J=9.3, 5.8 Hz, 1 H) 7.4 (m, 4 H) 7.6 (d, J=9.1 Hz, 2 H) 7.8 (d, J=8.6 Hz, 2 H) 7.9 (m, 4 H) 8.1 (d, J=9.3 Hz, 1 H) 10.5 (s, 1 H).

Example 3.72

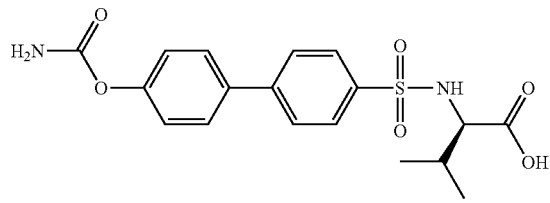

D-2-(4'-Carbamoyloxy-biphenyl-4-sulfonylamino)-3-methyl-butyric acid

The title compound, D-2-(4'-Carbamoyloxy-biphenyl-4-sulfonylamino)-3-methyl-butyric acid, was prepared according to procedures similar to that of Example 3.62.

Step 11A: To a solution of D-2-(4'-Hydroxy-biphenyl-4-sulfonylamino)-3-methyl-butyric acid-tert-butyl ester (500 mg, 1.23 mmol, 1 eq.) in CH2Cl2 (2 mL) were added with chlorosulfonyl isocyanate (107 uL, 1.23 mmol, 1 eq.) under argon and stirred at room temperature for 16 hours. Reaction was complete as determined by TLC. After work-up and flash column chromatography, D-2-(4'-Carbamoyloxy-biphenyl-4-sulfonylamino)-3-methyl-butyric acid tert-butyl ester was obtained. Yield: 45%. NMR: G9241-38. 1H NMR (400 MHz, DMSO-D6) δ ppm 0.9 (dd, J=8.3, 6.8 Hz, 6 H) 1.1 (s, 9 H) 1.9 (m, 1 H) 3.5 (dd, J=9.9, 6.3 Hz, 1 H) 7.2 (d, J=8.8 Hz, 2 H) 7.7 (d, J=8.8 Hz, 2 H) 7.8 (d, J=1.0 Hz, 4 ) 8.2 (d, J=9.6 Hz, 1 H).

Step 11B: Conversion of D-2-(4'-Carbamoyloxy-biphenyl-4-sulfonylamino)-3-methyl-butyric acid tert-butyl ester to D-2-(4'-Carbamoyloxy-biphenyl-4-sulfonylamino)-3-methyl-butyric acid was done according to procedures in Step 11B for Example 3.62. Yield: 85%. NMR: G9241-46. 1H NMR (400 MHz, DMSO-D6) δ ppm 0.8 (dd, J=12.4, 6.8 Hz, 6 H) 2.0 (m, 1 H) 3.6 (dd, J=9.3, 5.8 Hz, 1 H) 7.0 (s, 1 H) 7.2 (m, 3 H) 7.7 (d, J=8.8 Hz, 2 H) 7.8 (s, 4 H) 8.1 (d, J=9.3 Hz, 1 H).

Example 3.73

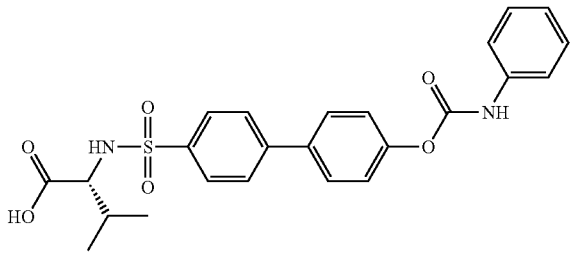

3-Methyl-2-(4'-phenylcarbamoyloxy-biphenyl-4-sulfonylamino)-butyric acid tert-butyl ester The title compound, 3-Methyl-2-(4'-phenylcarbamoyloxy-biphenyl-4-sulfonylamino)-butyric acid tert-butyl ester, was prepared according to procedures similar to that of Example 3.62.

Step 11A: 2-(4'-Hydroxy-biphenyl-4-sulfonylamino)-3-methyl-butyric acid tert-butyl ester (300 mg, 0.74 mmol, 1 equiv) was dissolved in diethyl ether (7.5 mL), added with phenylisocyanate (0.08 mL, 0.74 mmol, 1 equiv) followed by Et3N (1 mL). The reaction mixture was stirred for 4 hours. Solid precipitated from the reaction mixture was collected by filtration, washed with ether to afford with 76% yield (295 mg).

1H NMR (400 MHz, CHLOROFORM-D) δ ppm 0.87 (d, J=7.07 Hz, 3 H) 1.03 (d, J=6.82 Hz, 3 H) 1.20 (s, 9 H) 2.07 (m, 1 H) 3.67 (dd, J=9.98, 4.42 Hz, 1 H) 5.13 (d, J=9.85 Hz, 1 H) 6.96 (s, 1 H) 7.14 (m, 1 H) 7.31 (d, J=8.59 Hz, 2 H) 7.36 (m, 2 H) 7.47 (d, J=8.34 Hz, 2 H) 7.58 (d, J=8.59 Hz, 2 H) 7.66 (d, J=8.34 Hz, 2 H) 7.91 (m, 2 H).

Step 11B: 3-Methyl-2-(4'-phenylcarbamoyloxy-biphenyl-4-sulfonylamino)-butyric acid tert-butyl ester (200 mg) was hydrolyzed according procedures in Step 11B for Example 3.62 to afford 3-Methyl-2-(4'-phenylcarbamoyloxy-biphenyl-4-sulfonylamino)-butyric acid in 88% yield (158 mg).

1H NMR (400 MHz, DMSO-D6) δ ppm 0.82 (d, J=6.82 Hz, 3 H) 0.85 (d, J=6.57 Hz, 3 H) 1.95 (m, 1 H) 3.56 (dd, J=9.22, 5.94 Hz, 1 H) 3.90 (s, 1 H) 7.07 (m, 1 H) 7.35 (m, 4 H) 7.53 (d, J=7.83 Hz, 2 H) 7.80 (d, J=8.59 Hz, 2 H) 7.86 (d, J=22.23 Hz, 4 H) 8.08 (d, J=9.35 Hz, 1 H) 10.29 (s, 1 H).

Example 3.74

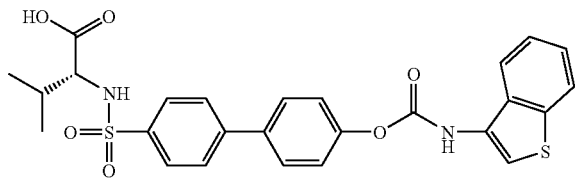

2-[4'-(Benzo[b]thiophen-3-ylcarbamoyloxy)-biphenyl-4-sulfonylamino]-3-methyl-butyric acid tert-butyl ester The title compound, 2-[4'-(Benzo[b]thiophen-3-ylcarbamoyloxy)-biphenyl-4-sulfonylamino]-3-methyl-butyric acid tert-butyl ester, was prepared according to procedures similar to that of Example 3.62.

Step 11A: 2-(4'-Hydroxy-biphenyl-4-sulfonylamino)-3-methyl-butyric acid tert-butyl ester (300 mg, 0.74 mmol, 1.0 equiv.) was dissolved in diethyl ether (7.5 mL), added with 1-Benzothiophene-3-yl isocyanate (129.6 mg, 0.74 mmol, 1.0 equiv.) and 0.5 mL of Et3N. Solid precipitated from the reaction mixture in 5 min. The mixture was continued to stir at room temperature for 2 hrs and the precipitate was collected by filtration, washed with ether to give in 43% yield (187 mg).

1H NMR (400 MHz, CHLOROFORM-D) δ ppm 0.87 (d, J=6.82 Hz, 3 H) 1.03 (d, J=6.82 Hz, 3 H) 1.20 (s, 9 H) 2.08 (m, 1 H) 3.68 (m, 1 H) 5.15 (d, J=10.11 Hz, 1 H) 7.35 (d, J=8.34 Hz, 2 H) 7.43 (m, 2 H) 7.60 (d, J=8.59 Hz, 2 H) 7.67 (d, J=8.34 Hz, 3 H) 7.74 (s, 1 H) 7.90 (t, J=9.09 Hz, 3 H).

Step 11B: 2-[4'-(Benzo[b]thiophen-3-ylcarbamoyloxy)-biphenyl-4-sulfonylamino]-3-methyl-butyric acid tert-butyl ester (180 mg, 0.31 mmol) was dissolved in methylene chloride under $N_2$ atmosphere, added with TFA (2 mL) at 0° C. and stirred for 4 hrs. Solvent was evaporated and the product dried under high vacuum to give 2-[4'-(Benzo[b]thiophen-3-ylcarbamoyloxy)-biphenyl-4-sulfonylamino]-3-methyl-butyric acid in 66% yield (108 mg).

1H NMR (400 MHz, MeOD) δ ppm 0.82 (d, J=6.82 Hz, 3 H) 0.89 (d, J=6.82 Hz, 3 H) 1.20 (s, 1 H) 3.54 (d, J=5.05 Hz, 1 H) 7.30 (m, 2 H) 7.35 (m, 2 H) 7.58 (s, 1 H) 7.66 (d, J=8.59 Hz, 2 H) 7.71 (d, J=8.59 Hz, 2 H) 7.78 (d, J=7.83 Hz, 1 H) 7.84 (d, J=8.59 Hz, 2 H) 7.92 (d, J=8.08 Hz, 1 H).

Example 3.75

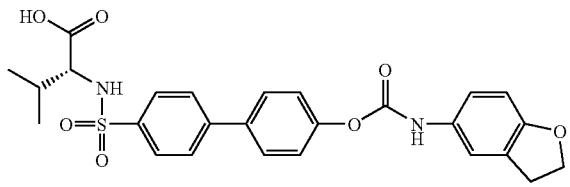

N-[(4'-{[2,3-dihydro-1-benzofuran-5-ylamino)carbonyl]oxy}-1,1'-biphenyl-4yl)sulfonyl]-D-valine The title compound, N-[(4'-{[2,3-dihydro-1-benzofuran-5-ylamino)carbonyl]oxy}-1,1'-biphenyl-4-yl)sulfonyl]-D-valine, was prepared according to procedures similar to that of Example 3.62.

Step 11A and 11B: Yield 40%. 1H NMR (400 MHz, DMSO-D6) δ ppm 0.80 (d, J=6.82 Hz, 3 H) 0.85 (d, J=6.82 Hz, 3 H) 1.98 (m, 1 H) 3.17 (t, J=8.97 Hz, 2 H) 3.39 (s, 1 H) 4.50 (t, J=8.59 Hz, 2 H) 6.72 (d, J=8.34 Hz, 1 H) 7.19 (d, J=8.84 Hz, 1 H) 7.34 (d, J=8.59 Hz, 2 H) 7.40 (s, 1 H) 7.78 (d, J=8.59 Hz, 2 H) 7.85 (d, J=1.77 Hz, 4 H) 10.05 (s, 1 H)

Example 3.76

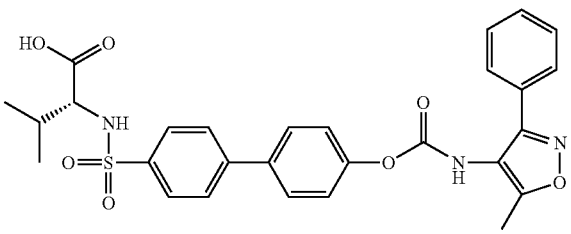

N-[(4'-{[(2,3-dihydro-1,4-benzodioxin-6-ylamino)carbonyl]oxy}-1,1'-biphenyl-4-yl)sulfonyl]-D-valine The title compound, N-[(4'-{[(2,3-dihydro-1,4-benzodioxin-6-ylamino)carbonyl]oxy}-1,1'-biphenyl-4-yl)sulfonyl]-D-valine, was prepared according to procedures similar to that of Example 3.62.

Step 11A and: Yield 62%. 1H NMR (400 MHz, DMSO-D6) δ ppm 0.80 (d, J=6.82 Hz, 3 H) 0.85 (d, J=6.82 Hz, 3 H) 1.98 (m, 1 H) 3.42 (s, 1 H) 4.21 (m, 4 H) 6.81 (d, J=8.84 Hz, 1 H) 6.94 (d, J=10.86 Hz, 1 H) 7.09 (s, 1 H) 7.34 (d, J=8.84 Hz, 2 H) 7.78 (d, J=8.84 Hz, 3 H) 7.85 (d, J=1.77 Hz,4 H) 10.11 (s, 1H).

Example 3.77

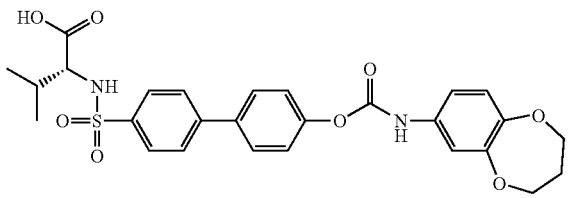

N-[(4'-{[(3,4-dihydro-2H-1,5-benzodioxepin-7-ylamino)carbonyl]oxy}-1,1'-biphenyl-4-yl)sulfonyl]-D-valine The title compound, N-[(4'-{[(3,4-dihydro-2H-1,5-benzodioxepin-7-ylamino)carbonyl]oxy}-1,1'-biphenyl-4-yl)sulfonyl]-D-valine, was prepared according to procedures similar to that of Example 3.62.

Step 11A and 11B: Yield 55%. 1H NMR (400 MHz, DMSO-D6) δ ppm 0.80 (d, J=6.82 Hz, 3 H) 0.85 (d, J=6.82 Hz, 3 H) 1.97 (m, 1 H) 2.08 (m, 2 H) 3.45 (s, 1 H) 4.08 (m, 4 H) 6.94 (d, J=8.59 Hz, 1 H) 7.06 (d, J=2.53 Hz, 1 H) 7.18 (d, J=2.27 Hz, 1 H) 7.35 (d, J=8.59 Hz, 2 H) 7.79 (d, J=8.59 Hz, 2 H) 7.85 (d, J=3.79 Hz, 4 H) 7.88 (s, 1 H) 10.21 (s, 1 H).

Example 3.78

N-[(4'-{[(5-methyl-3-phenylisoxazol-4-yl)amino)carbonyl]oxy}-1,1'-biphenyl-4-yl)sulfonyl]-D-valine The title compound, N-[(4'-{[(5-methyl-3-phenylisoxazol-4-yl)amino)carbonyl]oxy}-1,1'-biphenyl-4-yl)sulfonyl]-D-valine, was prepared according to procedures similar to that of Example 3.62.

Step 11B: Yield 75%.1H NMR (400 MHz, ACETONITRILE-D3) δ ppm 0.63 (d, J=6.82 Hz, 3 H) 0.74 (d, J=6.57 Hz, 3 H) 1.83-1.88 (m, 1 H) 2.20 (s, 1H) 2.34 (m, 3 H) 3.81 (s, 1 H) 6.56 (s, 1 H) 6.66 (s, 1 H) 7.12 (d, J=7.83 Hz, 1 H) 7.45 (d, J=4.80 Hz, 4 H) 7.59 (m, 4 H) 7.68 (d, J=3.54 Hz, 2 H) 7.80 (d, J=8.08 Hz, 2 H).

Example 3.79

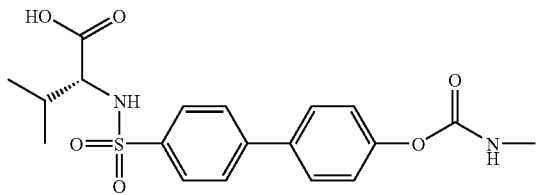

N-[(4'-{[(methylamino)carbonyl]oxy}-1,1'-biphenyl-4-yl)sulfonyl]-D-valine

The title compound, N-[(4'-{[(methylamino)carbonyl]oxy}-1,1'-biphenyl-4-yl)sulfonyl]-D-valine, was prepared according to procedures similar to that of Example 3.62.

Step 11B: Yield 90%. 1H NMR (400 MHz, MeOD) δ ppm 0.80 (d, J=8.34 Hz, 3 H) 0.87 (d, J=6.82 Hz, 3 H) 1.91-2.02 (m, 1 H) 2.71 (s, 3 H) 3.52 (d, J=5.05 Hz, 1 H) 7.11 (d, J=8.84 Hz, 2 H) 7.58 (d, J=8.84 Hz, 2 H) 7.66 (d, J=8.59 Hz, 2 H) 7.81 (d, J=8.59 Hz, 2 H).

Example 3.80

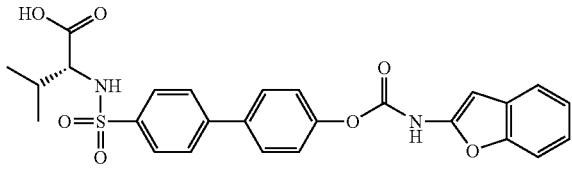

N-[(4'-{[(1-benzofuran-2-ylamino)carbonyl]oxy}-1,1'-biphenyl-4-yl)sulfonyl]-D-valine Step 12A: 2-(4'-Hydroxy-biphenyl-4-sulfonylamino)-3-methyl-butyric acid (314 mg, 0.9 mmol) dissolved in methylene chloride (10 mL) and diethyl ether (20 mL) was added with benzofuran isocyanate (143 mg, 0.9 mmol, 1 equiv) and triethyl amine (363 mg, 3.6 mmol, 4 equiv). The mixture was stirred at room temperature overnight. Solid precipitated from reaction mixture was collected by filtration followed by column chromatography (silica gel, 5% MeOH/CH2Cl2). 76 mg of white solid was obtained in 16% yield.

1H NMR (400 MHz, DMSO-D6) δ ppm 0.74-1.00 (m, 6 H) 1.90-2.07 (m, 1 H) 3.22-3.48 (m, 1 H) 6.86 (d, J=8.59 Hz, 2 H) 7.10-7.28 (m, 2 H) 7.33-7.62 (m, 4 H) 7.69-7.83 (m, 4 H) 7.86 (s, 1 H).

Examples 81 and 82 were made based on Scheme 13.

Example 81

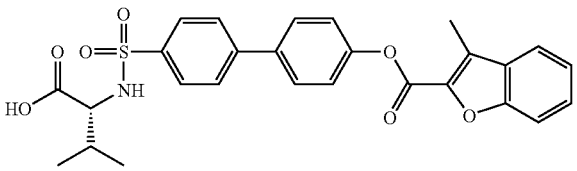

D-3-Methyl-benzofuran-2-carboxylic acid 4'-(1-carboxy-2-methyl-propylsulfamoyl)-biphenyl-4-yl ester Step 13A: A mixture of D-2-(4'-Hydroxy-biphenyl-4-sulfonylamino)-3-methyl-butyric acid tert-butyl ester (305 mg, 0.75 mmol, 1 eq), 3-Methyl-benzofuran-2-carboxylic acid (131 mg, 0.74 mmol, 1 eq), 4-dimethylaminopyridine (DMAP, 95 mg, 0.77 mol, 1 eq), and 1,3-Dicyclohexylcarbodiimide (DCC, 240 mg, 1.17 mmol, 1.6 eq) dissolved in 5 mL of dichloromethane under nitrogen atmosphere was allowed to react at room temperature for 3.5 hrs. Regular work-up and column chromatography (10% EtOAc in hexane) to give D-3-Methyl-benzofuran-2-carboxylic acid 4'-(1-tert-butoxycarbonyl-2-methyl-propylsulfamoyl)-biphenyl-4-yl ester (300 mg) in 71% yield. NMR: G8475-101. 1H NMR (400 MHz, CHLOROFORM-D) δ ppm 0.9 (d, J=7.1 Hz, 3 H) 1.0 (d, J=6.8 Hz, 3 H) 1.2 (s, 9 H) 2.1 (m, 1 H) 2.7 (s, 3 H) 3.7 (dd, J=10.0, 4.4 Hz, 1 H) 5.1 (d, J=9.9 Hz, 1 H) 7.4 (m, 3 H) 7.5 (m, 1 H) 7.6 (t, J=8.0 Hz, 3 H) 7.7 (m, 3 H) 7.9 (d, J=8.3 Hz, 2 H).

Step 13B: Removal of t-butyl ester was done according to procedures in Step 11B for Example 3.62 in quantitative yield. 1H NMR (400 MHz, DMSO-D6) δ ppm 0.8 (dd, J=12.1, 6.8 Hz, 6 H) 2.0 (m, 1 H) 2.7 (s, 3 H) 3.6 (dd, J=9.2, 5.9 Hz, 1 H) 7.4 (t, J=7.6 Hz, 1 H) 7.5 (d, J=8.8 Hz, 2 H) 7.6 (t, J=8.2 Hz, 1 H) 7.8 (d, J=8.3 Hz, 1 H) 7.9 (m, 7 H) 8.1 (d, J=9.3 Hz, 1 H).

Example 3.82

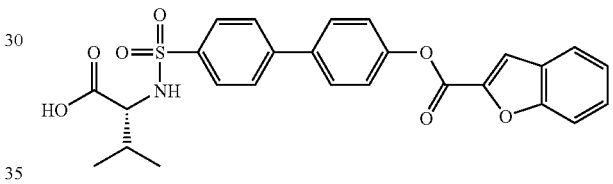

Benzofuran-2-carboxylic acid 4'-(1-tert-butoxycarbonyl-2-methyl-propylsulfamoyl)-biphenyl-4-yl ester The title compound, Benzofuran-2-carboxylic acid 4'-(1-tert-butoxycarbonyl-2-methyl-propylsulfamoyl)-biphenyl-4-yl ester, was prepared according to procedures similar to that of Example 3.81.

Step 13A: 2-Benzofuran carbocarboxylic acid (400.5 mg, 2.47 mmol, 1 equiv.) dissolved in dry CH$_2$Cl$_2$ (50 mL) was added with DCC (1.019 g, 4.94 mmol, 2 equiv) and stirred under N$_2$ for 15 min. Then 2-(4'-Hydroxy-biphenyl-4-sulfonylamino)-3-methyl-butyric acid tert-butyl ester (1.0 g, 2.47 mmol, 1 equiv.) was introduced to the reaction mixture, followed by the addition of DMAP (50 mg, 0.41 mmol,). The mixture was allowed to stir at room temperature overnight. The reaction mixture was then diluted with CH$_2$Cl$_2$, washed with H$_2$O and brine. Organic layer dried over MgSO$_4$ and solvent removed to yield crude product. Residue was dissolved in EtOAc and purified by column chromatograph (silica gel, 20% EtOAc/n-Hexane) to afford G9058-53-1 in 30.5% yield (325 mg).

1H NMR (400 MHz, CHLOROFORM-D) δ ppm 0.87 (d, J=6.82 Hz, 3 H) 1.03 (d, J=6.82 Hz, 3 H) 1.21 (s, 9 H) 2.07 (m, 1 H) 3.68 (dd, J=9.85, 4.55 Hz, 1 H) 5.15 (d, J=9.85 Hz, 1 H) 7.37 (m, 3 H) 7.53 (t, J=7.83 Hz, 1 H) 7.66 (m, 5H) 7.77 (m, 2H) 7.92 (d, J=8.34 Hz, 2 H).

Step 13B: Benzofuran-2-carboxylic acid 4'-(1-tert-butoxycarbonyl-2-methyl-propylsulfamoyl)-biphenyl-4-yl ester (325 mg) was dissolved in dichloromethane (15 mL) and added with TFA. The solution was stirred at room temperature for 7 hrs. Solvent was removed by rotovap and crude product purified by column chromatography (5-20% MeOH/EtOAc) to yield Benzofuran-2-carboxylic acid 4'-(1-carboxy-2-methyl-propylsulfamoyl)-biphenyl-4-yl ester in 76% yield (241 mg).

1H NMR (400 MHz, DMSO-D6) δ ppm 0.80 (d, J=6.57 Hz, 3 H) 0.87 (d, J=6.82 Hz, 3 H) 2.04 (m, 1 H) 3.24 (m, 1 H) 7.43 (t, J=7.58 Hz, 1 H) 7.49 (d, J=8.84 Hz, 2 H) 7.60 (t, J=7.96 Hz, 1 H) 7.70 (d, J=9.85 Hz, 1 H) 7.85 (m, 7 H) 8.08 (s, 1 H).

Examples 3.83, 3.84, 3.85, 3.86, 3.87, 3.88, 3.89 were made based on Scheme 14.

Example 3.83

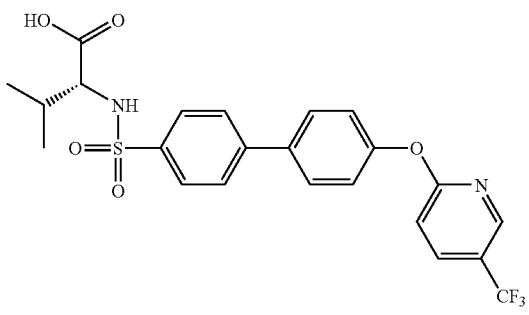

3-Methyl-2-[4'-(5-trifluoromethyl-pyridin-2-yloxy)-biphenyl-4-sulfonylamino]-butyric acid tert-butyl ester Step 14A: 2-(4'-Hydroxy-biphenyl-4-sulfonylamino)-3-methyl-butyric acid tert-butyl ester (100 mg, 0.25 mmol, 1.0 equiv.), 2-Chloro-5-trifluoro methyl pyridine (45.4 mg, 0.25 mmol, 1 equiv.), and $K_2CO_3$ (86.4 mg, 0.63 mmol, 2.5 equiv) were mixed in DMF (8 mL) and heat to 110° C. for 4.5 hr. Reaction was complete as determined by TLC. Then the reaction mixture was cool to room temperature, diluted with EtOAc, washed with brine and dried over $MgSO_4$. After removing solvent, crude product was purified by column chromatography (silica gel, 20% EtOAc/n-Hexane) to afford G9058-109-1 in 74% yield (100 mg).

1H NMR (400 MHz, CHLOROFORM-D) δ ppm 0.80 (d, J=6.82 Hz, 3 H) 0.96 (d, J=6.82 Hz, 3 H) 1.14 (s, 9 H) 2.01 (m, 1 H) 3.61 (m, 1 H) 5.07 (d, J=9.85 Hz, 1 H) 7.03 (d, J=8.59 Hz, 1 H) 7.19 (s, 1 H) 7.21 (s, 1 H) 7.55 (d, J=8.59 Hz, 2 H) 7.62 (d, J=8.59 Hz, 2 H) 7.85 (d, J=2.02 Hz, 2 H) 7.88 (d, J=6.06 Hz, 1 H) 8.40 (s, 1 H).

Step 14B: 3-Methyl-2-[4'-(5-trifluoromethyl-pyridin-2-yloxy)-biphenyl-4-sulfonylamino]-butyric acid tert-butyl ester (97 mg) was dissolved in $CH_2Cl_2$ (6 mL) and added with TFA (2 mL). Reaction was complete in 6 hrs as determined by TLC. After removing solvent, residue was purified by column chromatography (10% MeOH/$CH_2Cl_2$) to afford 3-Methyl-2-[4'-(5-trifluoromethyl-pyridin-2-yloxy)-biphenyl-4-sulfonylamino]-butyric acid in 66% yield (54.5 mg).

1H NMR (400 MHz, MeOD) δ ppm 0.81 (d, J=6.82 Hz, 3 H) 0.88 (d, J=6.82 Hz, 3 H) 1.97 (m, 1 H) 3.55 (d, J=5.31 Hz, 1 H) 7.09 (d, J=8.59 Hz, 1 H) 7.19 (d, J=8.59 Hz, 2 H) 7.68 (dd, J=14.65, 8.59 Hz, 4 H) 7.83 (d, J=8.34 Hz, 2 H) 8.02 (d, J=11.37 Hz, 1 H) 8.35 (d, J=2.53 Hz, 1 H).

Example 3.84

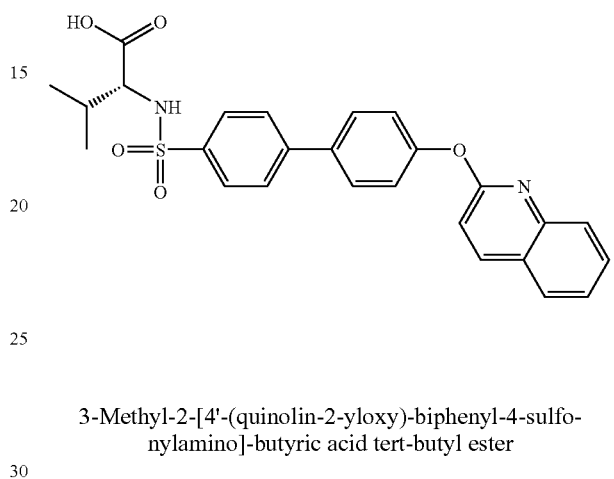

3-Methyl-2-[4'-(quinolin-2-yloxy)-biphenyl-4-sulfonylamino]-butyric acid tert-butyl ester The title compound, 3-Methyl-2-[4'-(quinolin-2-yloxy)-biphenyl-4-sulfonylamino]-butyric acid tert-butyl ester, was prepared according to procedures similar to that of Example 3.83.

Step 14A [9058-120-1]: 2-(4'-Hydroxy-biphenyl-4-sulfonylamino)-3-methyl-butyric acid tert-butyl ester (200 mg, 0.49 mmol, 1 equiv.), 2-Chloroquinoline (242 mg, 1.48 mmol, 3 equiv) and $Cs_2CO_3$ (402 mg, 1.235 mmol, 2.5 equiv.) were mixed in DMF (8 mL) and stirred at 100° C. for 7 hrs. Reaction mixture was cool to room temperature then placed in an ice bath and added with water. The solid precipitated from the mixture was collected by filtration and washed with water. After drying, 174 mg of yellow solid was obtained in 66% yield.

1H NMR (400 MHz, CHLOROFORM-D) δ ppm 0.88 (d, J=6.82 Hz, 3 H) 1.03 (d, J=6.82 Hz, 3 H) 1.22 (s, 9 H) 2.07 (m, 1 H) 3.68 (dd, J=9.85, 4.55 Hz, 1 H) 5.15 (d, J=9.85 Hz, 1 H) 7.15 (d, J=8.84 Hz, 1 H) 7.38 (d, J=8.84 Hz, 2 H) 7.45 (m, 1 H) 7.63 (m, 3 H) 7.71 (d, J=8.84 Hz, 2 H) 7.81 (t, J=8.72 Hz, 2 H) 7.91 (d, J=8.59 Hz, 2 H) 8.17 (d, J=8.34 Hz, 1 H).

Step 14B [9058-121-2]: 3-Methyl-2-[4'-(quinolin-2-yloxy)-biphenyl-4-sulfonylamino]-butyric acid tert-butyl ester (164 mg) was dissolved in dichloroethane (12 mL) and hydrolyzed with TFA (4 mL) at room temperature over a period of 4 hrs. Solvent was removed and crude was purified by column chromatography (Eluent 10% MeOH/DCE) to afford 3-Methyl-2-[4'-(quinolin-2-yloxy)-biphenyl-4-sulfonylamino]-butyric acid in 58% yield (84.8 mg).

1H NMR (400 MHz, MeOD) δ ppm 0.82 (d, J=6.82 Hz, 3 H) 0.88 (d, J=6.82 Hz, 3 H) 1.97 (m, 1 H) 3.60 (d, J=5.56 Hz, 1 H) 7.10 (d, J=8.84 Hz, 1 H) 7.25 (d, J=8.84 Hz, 2 H) 7.39 (t, J=6.82 Hz, 1 H) 7.56 (t, J=7.71 Hz, 1 H) 7.63 (d, J=0.51 Hz, 1 H) 7.65 (d, J=1.26 Hz, 1 H) 7.68 (m, 1 H) 7.69 (d, J=2.27 Hz, 1 H) 7.72 (m, 1 H) 7.74 (m, 1 H) 7.79 (dd, J=7.83, 1.26 Hz, 1 H) 7.82 (m, 1 H) 7.85 (m, 1 H) 8.23 (d, J=8.84 Hz, 1 H).

Example 3.85

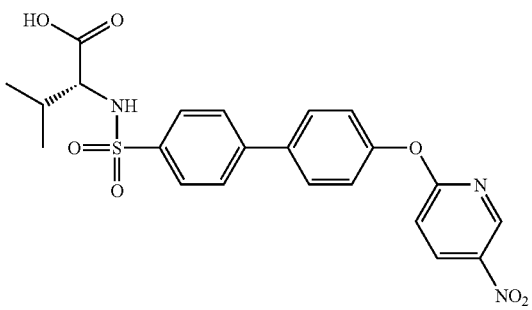

N-({4'-[(5-nitropyridin-2-yl)oxy]-1,1'-biphenyl-4-yl}sulfonyl)-D-valine

The title compound, N-({4'-[(5-nitropyridin-2-yl)oxy]-1,1'-biphenyl-4-yl}dulfonyl)-D-valine, was prepared according to procedures similar to that of Example 3.83.

Step 14A and 14B: Yield 60%. 1H NMR (400 MHz, MeOD) δ ppm 0.82 (d, J=6.82 Hz, 3 H) 0.88 (d, J=6.82 Hz, 3 H) 1.96 (m, 1 H) 3.58 (d, J=5.31 Hz, 1 H) 7.11 (d, J=9.09 Hz, 1 H) 7.22 (d, J=8.84 Hz, 2 H) 7.70 (dd, J=11.87, 8.84 Hz, 4 H) 7.83 (d, J=8.59 Hz, 2 H) 8.52 (dd, J=9.09, 2.78 Hz, 1 H) 8.91 (d, J=3.28 Hz, 1 H).

Example 3.86

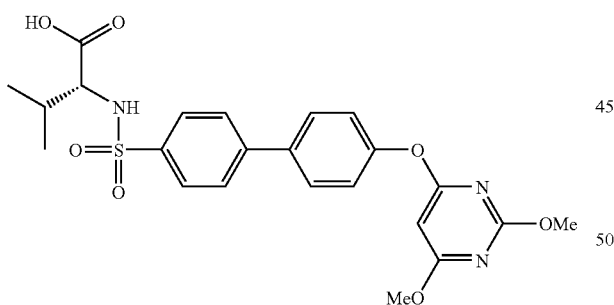

N-({4'-[(2,6-dimethoxypyrimidin-4-yl)oxy]-1,1'-biphenyl-4-yl}sulfonyl)-D-valine

The title compound, N-({4'-[(2,6-dimethoxypyrimidin-4-yl)oxy]-1,1'-biphenyl-4-yl}sulfonyl)-D-valine, was prepared according to procedures similar to that of Example 3.83.

Step 14A and 14B: Yield 82%. 1H NMR (400 MHz, MeOD) δ ppm 0.81 (d, J=6.82 Hz, 3 H) 0.88 (d, J=6.82 Hz, 3 H) 1.97 (m, 1 H) 3.56 (d, J=5.31 Hz, 1 H) 3.78 (s, 3 H) 3.85 (s, 3 H) 5.73 (s, 1 H) 7.18 (d, J=8.84 Hz, 2 H) 7.66 (d, J=8.84 Hz, 3 H) 7.70 (d, J=8.84 Hz, 3 H) 7.81 (s, 1 H) 7.83 (s, 1 H).

Example 3.87

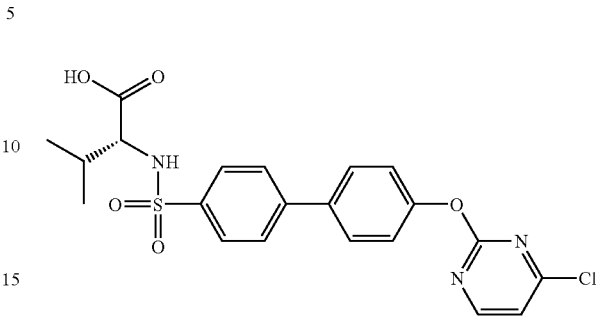

N-({4'-[(4-chloropyrimidin-2-yl)oxy]-1,1'-biphenyl-4-yl}sulfonyl)-D-valine

The title compound, N-({4'-[(4-chloropyrimidin-2-yl)oxy]-1,1'-biphenyl-4-yl}sulfonyl)-D-valine, was prepared according to procedures similar to that of Example 3.83.

Step 14A and 14B: Yield 59%. 1H NMR (400 MHz, DMSO-D6) δ ppm 0.80 (d, J=6.82 Hz, 3 H) 0.85 (d, J=6.82 Hz, 3 H) 1.97 (m, 1 H) 3.47 (s, 1 H) 7.24 (d, J=5.81 Hz, 1 H) 7.42 (d, J=8.84 Hz, 2 H) 7.87 (d, 7 H) 8.66 (d, J=5.56 Hz, 1 H).

Example 3.88

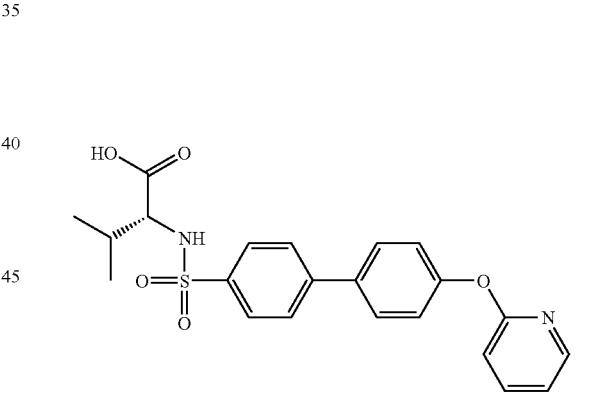

N-{[4'-(pyridin-2-yloxy)-1,1'-biphenyl-4-yl]sulfonyl}-D-valine

The title compound, N-{[4'-(pyridin-2-yloxy)-1,1'-biphenyl-4-yl]sulfonyl}-D-valine, was prepared according to procedures similar to that of Example 3.83.

Step 14A and 14B: Yield 83%. 1H NMR (400 MHz, DMSO-D6) δ ppm 0.82 (d, J=6.82 Hz, 3 H) 0.85 (d, J=6.82 Hz, 3 H) 1.85-2.02 (m, 1 H) 3.57 (dd, J=10.48, 4.67 Hz, 1 H) 7.10 (d, J=9.85 Hz, 1 H) 7.17 (dd, J=7.20, 4.93 Hz, 1 H) 7.26 (d, J=8.84 Hz, 2 H) 7.79 (d, J=8.84 Hz, 2 H) 7.82-7.95 (m, 4 H) 8.09 (d, J=9.35 Hz, 1 H) 8.13-8.28 (m, 1 H).

Example 3.89

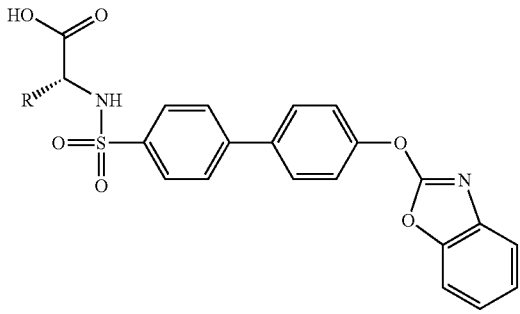

N-{[4'-(1,3-benzoxazol-2-yloxy)-1,1'-biphenyl-4-yl]sulfonyl}-D-valine

The title compound, N-{[4'-(1,3-benzoxazol-2-yloxy)-1,1'-biphenyl-4-yl]sulfonyl}-D-valine, was prepared according to procedures similar to that of Example 3.83.

Step 14A and 14B: Yield 85%. 1H NMR (400 MHz, DMSO-D6) δ ppm 0.82 (d, J=6.82 Hz, 3 H) 0.85 (d, J=6.82 Hz, 3 H) 1.86-2.05 (m, 1 H) 3.58 (dd, J=9.22, 5.94 Hz, 1 H) 7.32 (d, J=9.35 Hz, 1 H) 7.53 (d, J=7.33 Hz, 1 H) 7.61-7.73 (m, 3 H) 7.81-7.99 (m, 6 H) 8.10 (d, J=9.35 Hz, 1 H).

Example 3.90 was made based on Scheme 15.

Example 3.90

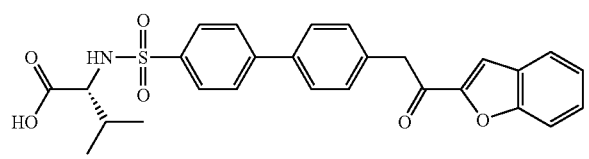

N-({4'-[2-(1-benzofuran-2-yl)-2-oxoethyl]-1,1'-biphenyl-4-yl}sulfonyl)-D-valine

Step 15A: (4-Bromophenyl)-acetic acid (5.0 g, 23.2 mmol, 1 eq.) dissolved in thionyl chloride (50 mL) was heat to reflux for 1 hr. under nitrogen atmosphere. The solution was cool to room temperature and solvent was evaporated. Residue thus obtained was dissolved in anhydrous methylene chloride and used in Step 15B.

Step 15B: Benzofuran-2-yl-trimethyl-silane (3.4 g, 17.86 mmol) was dissolved in methylene chloride (40 mL) and cool to −78° C. 4-Bromophenyl-acetyl chloride (19.65 mmol, 1.1 equiv.) was added at this temperature. Under vigorous stirring, a solution of TiCl₄ (23 mL, 1M, 23.2 mmol, 1.3 equiv.) in CH₂Cl₂ was added dropwise and stirring continued for 20 min. Then the reaction was quenched with H₂O (100 mL), cooling bath was removed and the mixture was allowed to warm up to room temperature. It was then diluted with H₂O (100 mL) and extracted with CH₂Cl₂ (3×). Organic layers were combined, washed with brine, dried over MgSO₄, solvent evaporated. Crude product thus obtained was subject to column purification. (silica gel, 10% EtOAC/Hexane). 980 mg of 1-Benzofuran-2-yl-2-(4-bromo-phenyl)-ethanone was obtained in 17% yield.

1H NMR (400 MHz, CHLOROFORM-D) δ ppm 4.34 (s, 2 H) 7.34 (d, J=8.59 Hz, 2 H) 7.44 (d, 1 H) 7.58 (d, J=8.59 Hz, 2 H) 7.62 (d, J=5.81 Hz, 1 H) 7.67 (s, 1 H) 7.71 (m, 1 H) 7.84 (t, J=6.19 Hz, 1 H).

Step 15C: A solution of 3-Methyl-2-(4-tributylstannanyl-benzenesulfonylamino)-butyric acid tert-butyl ester (347.5 mg, 0.58 mmol, 1.0 equiv.), 1-Benzofuran-2-yl-2-(4-bromophenyl)-ethanone (200 mg, 0.64 mmol, 1.1 equiv.) and Pd(PPh₃)₄ (66 mg, 0.06 mmol, 10%) in anhydrous toluene (10 mL) was heat to reflux for 7 hrs. Reaction was complete as determined by TLC. Solvent was removed by rotovap and crude product purified by column chromatography (silica gel, 20% EtOAc/n-Hexane) to afford 2-[4'-(2-Benzofuran-2-yl-2-oxo-ethyl)-biphenyl-4-sulfonylamino]-3-methyl-butyric acid tert-butyl ester in 20% yield (62 mg).

1H NMR (400 MHz, CHLOROFORM-D) δ ppm 0.79 (d, J=6.82 Hz, 3 H) 0.95 (d, J=6.82 Hz, 3 H) 1.11 (s, 9 H) 3.58 (dd, J=9.85, 4.55 Hz, 1 H) 4.26 (s, 2 H) 5.05 (d, J=9.85 Hz, 1 H) 7.26 (t, J=7.07 Hz, 1 H) 7.43 (m, 5 H) 7.56 (m, 4 H) 7.65 (d, J=7.83 Hz, 1 H) 7.81 (d, J=8.59 Hz, 2 H).

Step 15D: 2-[4'-(2-Benzofuran-2-yl-2-oxo-ethyl)-biphenyl-4-sulfonylamino]-3-methyl-butyric acid tert-butyl ester (62 mg) was dissolved in anhydrous CH₂Cl₂ (6 mL) and added with TFA (2 mL). The reaction mixture was stirred at room temperature for 3 hrs. Solvent was removed, crude product was purified by column chromatography (10% MeOH/CH₂Cl₂) to afford 2-[4'-(2-Benzofuran-2-yl-2-oxo-ethyl)-biphenyl-4-sulfonylamino]-3-methyl-butyric acid in 19% yield (10.7 mg).

1H NMR (400 MHz, DMSO-D6) δ ppm 0.79 (d, J=6.82 Hz, 3 H) 0.84 (m, J=6.82 Hz, 3 H) 1.97 (m, 1 H) 3.33 (s, 1 H) 4.42 (s, 2 H) 7.39 (t, J=7.07 Hz, 1 H) 7.74 (d, J=8.34 Hz, 2 H) 7.57 (t, J=8.59 Hz, 1 H) 7.73 (m, 3 H) 7.83 (d, 4 H) 7.88 (d, J=8.84 Hz, 1 H) 8.13 (s, 1 H) 10.08 (s, 1 H).

Example 3.91 was made based on Scheme 16.

Example 3.91

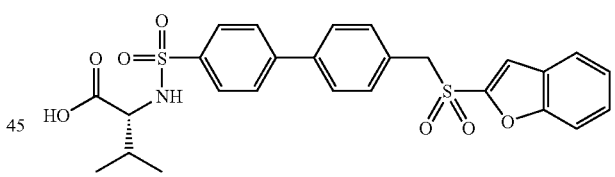

D-2-[4'-(Benzofuran-2-sulfonylmethyl)-biphenyl-4-sulfonylamino]-3-methyl-butyric acid Step 16A: Starting material 2-[1,2,3]Thiadiazol-4-yl-phenol was prepared according to literature procedure (M. A. Abramov, W. Dehaen, B. D'hooge, M. L. Petrov, S. Smeets, S. Toppet and M. Voets Tetrahedron, 2000, 56, 3933-3940). 2-[1,2,3]Thiadiazol-4-yl-phenol (241 mg, 1.35 mmol), 2-(4-Bromomethyl-phenyl)-4,4,5,5-tetramethyl-[1,3,2]dioxaborolane (406 mg, 1.37 mmol, 1 eq), and K₂CO₃ (396 mg, 2.87 mmol, 1.9 eq) was mixed in 8 mL of CH3CN and heat to 90° C. under nitrogen atmosphere. After reaction was complete as monitored by TLC, the mixture was cooled to room temperature and solvent evaporated. The resulting crude material was subject to column chromatography (20% EtOAc in hexane) to give 2-[4-(4,4,5,5-Tetramethyl-[1,3,2]dioxaborolan-2-yl)-benzylsulfanyl]-benzofuran (198 mg) in 40% yield. NMR: G8475-125. 1H NMR (400 MHz, CHLORO- FORM-D) δ ppm 1.3 (s, 12 H) 4.1 (s, 2 H) 6.6 (d, J=1.0 Hz, 1 H) 7.2 (m, 4 H) 7.4 (d, J=7.8 Hz, 2 H) 7.7 (d, J=8.1 Hz, 2 H).

Step 16B: Suzuki coupling of D-2-(4-Bromo-benzenesulfonylamino)-3-methyl-butyric acid methyl ester with 2-[4-(4,4,5,5-Tetramethyl-[1,3,2]dioxaborolan-2-yl)-benzylsulfanyl]-benzofuran was carried out according to procedures in Step 5B for Example 2A to give D-2-[4'-(Benzofuran-2-ylsulfanylmethyl)-biphenyl-4-sulfonylamino]-3-methyl-butyric acid methyl ester in 54% yield. NMR: G8475-165. 1H NMR (400 MHz, BENZENE-D6) δ ppm 0.7 (d, J=6.8 Hz, 3 H) 0.9 (d, J=6.8 Hz, 3 H) 1.9 (m, 1 H) 3.0 (s, 3 H) 4.0 (m, 3 H) 5.0 (d, J=10.1 Hz, 1 H) 6.6 (d, J=1.0 Hz, 1 H) 7.1 (m, 4 H) 7.3 (m, 6 H) 7.4 (m, 1 H).

Step 16C: A solution of D-2-[4'-(Benzofuran-2-ylsulfanylmethyl)-biphenyl-4-sulfonylamino]-3-methyl-butyric acid methyl ester (75 mg, 0.15 mmol, 1 eq) in 4 mL of THF was placed in ice bath. 125 mg of MCPBA (77%, 0.55 mmol, 3.7 eq) in 3 mL of THF was added dropwise. After addition complete, ice bath was removed and the reaction was allowed to warm to room temperature and stir for 12 hrs. TLC indicated reaction was complete. Regular work-up and column chromatography (20% EtOAc in hexane) to afford D-2-[4'-(Benzofuran-2-sulfonylmethyl)-biphenyl-4-sulfonylamino]-3-methyl-butyric acid methyl ester (56 mg) in 70% yield. NMR: G8475-166. 1H NMR (400 MHz, CHLOROFORM-D) □ ppm 0.9 (dd, J=33.3, 6.8 Hz, 6 H) 2.0 (m, 1 H) 3.4 (s, 3 H) 3.8 (dd, J=10.1, 5.3 Hz, 1 H) 4.6 (s, 2 H) 5.1 (d, J=10.1 Hz, 1 H) 7.4 (m, 4 H) 7.5 (m, 3 H) 7.6 (m, 1 H) 7.7 (m, 3 H) 7.9 (d, J=8.8 Hz,2H).

Step 16D [: Hydrolysis of D-2-[4'-(Benzofuran-2-sulfonylmethyl)-biphenyl-4-sulfonylamino]-3-methyl-butyric acid methyl ester was carried out according to procedures in Step 1D for Example 1A in quantitative yield. 1H NMR (400 MHz, DMSO-D6) δ ppm 0.8 (dd, J=12.1, 6.8 Hz, 6 H) 1.9 (m, 1 H) 3.5 (dd, J=9.3, 6.1 Hz, 1 H) 5.0 (s, 2 H) 7.4 (d, J=8.3 Hz, 2 H) 7.4 (m, 1 H) 7.6 (m, 1 H) 7.7 (d, J=1.O Hz, 1 H) 7.7 (d, J=8.3 Hz, 2 H) 7.8 (m, 6 H) 8.1 (d, J=9.1 Hz, 1 H).

The following compounds (3.92 and 3.93) were prepared according to Scheme 6.63.

Example 3.92

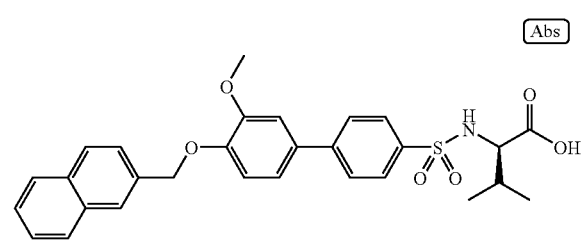

3-Methyl-2-[4'-(naphthalen-2-ylmethoxy)-3'-methoxy-biphenyl-4-sulfonylamino]-butyric acid ¹H NMR (400 MHz, DMSO): δ 0.806(d, 3H), 0.837(d, 3H), 1.94(m, 1H), 3.53(t, 1H), 3.90(s, 3H), 5.33(s, 2H), 7.20 (d, 1H), 7.27(m, 1H), 7.34(s, 1H), 7.54(d, 2H), 7.61(d, 1H), 7.89(m, 8H); ES⁺ m/z 518.2 (M–H); HRMS (C29H29NO6S): calcd; 520.17884; found; 520.17839 (M+H).

Example 3.93

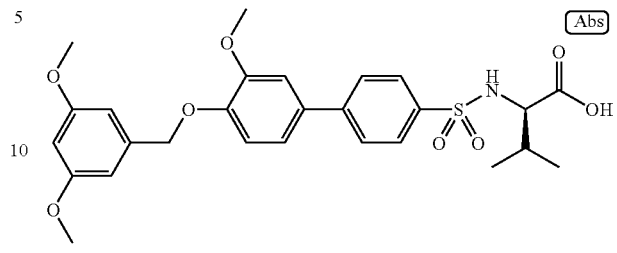

2-[4'-(3,5-Dimethoxy-benzyloxy)-3'-methoxy-biphenyl-4-sulfonylamino]-3-methyl-butyric acid ¹H NMR (400 MHz, DMSO): δ 0.808(d, 3H), 0.838(d, 3H), 1.94(m, 1H), 3.74(s, 6H), 3.89(s, 3H), 5.09(s, 2H), 6.45 (t, 1H), 6.62(d, 2H), 7.11(d, 1H), 7.25(d, 1H), 7.32(d, 1H), 7.79(d, 2H), 7.85(d, 2H), 8.02(d, 1H); ES⁺ m/z 528.2 (M–H); HRMS (C27H31NO8S): calcd; 530.18432; found; 530.18367 (M+H).

The following compounds (3.94-3.111) were made using procedures described in scheme 17.

Example 3.94

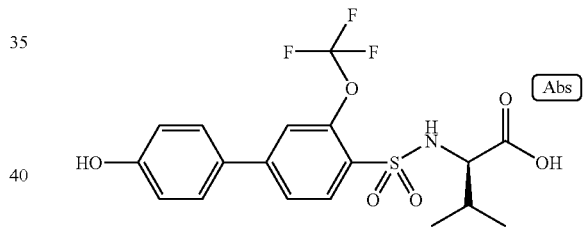

2-(4'-Hydroxy-3-trifluoromethoxy-biphenyl-4-sulfonylamino)-3-methyl-butyric acid ¹H NMR (400 MHz, DMSO): δ 0.825(d, 3H), 0.875(d, 3H), 2.04(m, 1H), 3.70(m, 1H), 6.89(d, 2H), 7.59(m, 2H), 7.75(dd, 1H), 7.94(d, 1H), 8.16(d, 1H); ES⁺ m/z 432.1 (M–H); HRMS (C18H18F3NO6S): calcd; 451.11451; found; 451.11461 (M+NH4).

Example 3.95

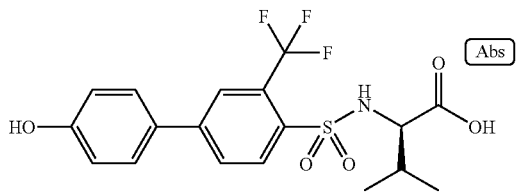

2-(4'-Hydroxy-3-trifluoromethyl-biphenyl-4-sulfonylamino)-3-methyl-butyric acid $^1$H NMR (400 MHz, DMSO): δ 0.850(m, 6H), 2.02(m, 1H), 3.60(m, 1H), 6.90(d, 2H), 7.67(d, 2H), 8.10(m, 3H); ES$^+$ m/z 416.0 (M−H); HRMS (C18H18F3NO5S): calcd; 435.11960; found; 435.11966 (M+NH4).

Example 3.96

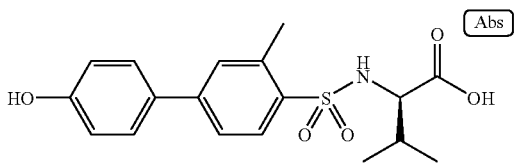

2-(4'-Hydroxy-3-methyl-biphenyl-4-sulfonylamino)-3-methyl-butyric acid $^1$H NMR (400 MHz, DMSO): δ 0.810(t, 6H), 1.93(m, 1H), 2.64(s, 3H), 3.39(m, 1H), 6.87(m, 2H), 7.56(m, 3H), 7.81(d, 1H), 8.00(d, 1H); ES$^+$ m/z 362.1 (M−H); HRMS (C18H21NO5S): calcd; 381.14786; found; 381.14808 (M+NH4).

Example 3.97

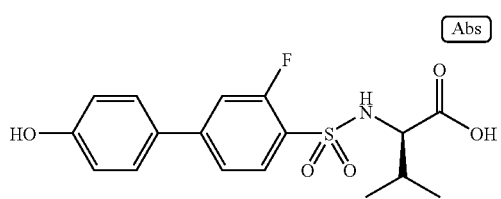

2-(3-Fluoro-4'-hydroxy-biphenyl-4-sulfonylamino)-3-methyl-butyric acid $^1$H NMR (400 MHz, DMSO): δ 0.850(m, 6H), 2.02(m, 1H), 3.63(m, 1H), 6.87(d, 2H), 7.61(m, 3H), 7.76(t, 1H), 8.22(d, 1H); ES$^+$ m/z 366.0 (M−H); HRMS (C17H18FNO5S): calcd; 385.12279; found; 385.12276 (M+NH4).

Example 3.98

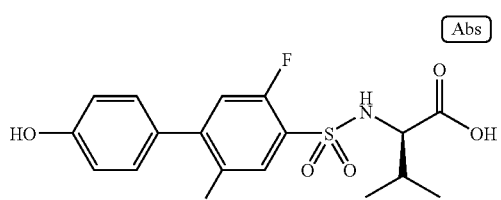

2-(2,5-Difluoro-4'-hydroxy-biphenyl-4-sulfonylamino)-3-methyl-butyric acid $^1$H NMR (400 MHz, DMSO): δ 0.880(m, 6H), 2.04(m, 1H), 3.69(m, 1H), 6.89(d, 1H), 7.45(m, 2H), 7.58(m, 2H), 8.45(d, 1H); ES$^+$ m/z 384.1 (M−H); HRMS (C17H17F2NO5S): calcd; 403.1137; found; 403.11328 (M+NH4).

Example 3.99

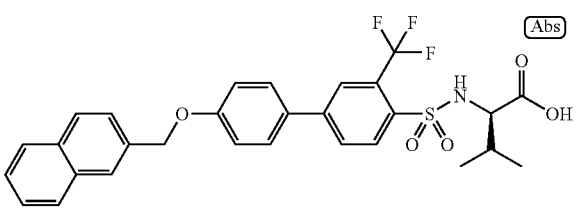

3-Methyl-2-[4'-(naphthalen-2-ylmethoxy)-3-trifluoromethyl-biphenyl-4-sulfonylamino]-butyric acid $^1$H NMR (400 MHz, DMSO): δ 0.900(d, 3H), 0.960(d, 3H), 2.06(m, 1H), 3.70(d, 1H), 4.19(s, 2H), 6.95(d, 1H), 7.43(m, 6H), 7.69(s, 1H), 7.75(m, 3H), 7.88 (m, 1H), 7.97 (s, 1H), 8.15(d, 1H); ES$^+$ m/z 556.1 (M−H); HRMS (C29H26F3NO5S): calcd; 558.15566; found; 558.15484 (M+H).

Example 3.100

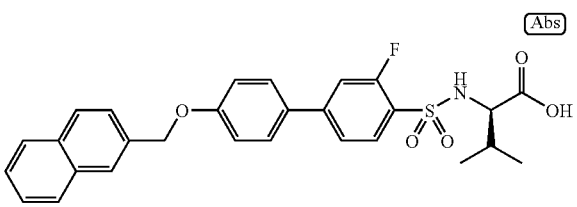

2-[3-Fluoro-4'-(naphthalen-2-ylmethoxy)-biphenyl-4-sulfonylamino]-3-methyl-butyric acid $^1$H NMR (400 MHz, MeOH): δ 0.920(d, 3H), 0.980(d, 3H), 2.10(m, 1H), 3.76(d, 1H), 4.19(s, 2H), 6.94(d, 1H), 7.43(m, 7H), 7.70(s, 1H), 7.78(m, 4H); ES$^+$ m/z 506.1 (M−H); HRMS (C28H26FNO5S): calcd; 508.15885; found; 508.15818 (M+H).

Example 3.101

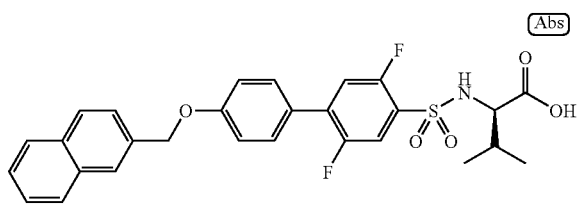

2-[2,5-Difluoro-4'-(naphthalen-2-ylmethoxy)-biphenyl-4-sulfonylamino]-3-methyl-butyric acid $^1$H NMR (400 MHz, MeOH): δ 0.910(d, 3H), 0.980(d, 3H), 2.09(m, 1H), 3.78(d, 1H), 4.16(s, 2H), 6.92(d, 1H), 7.37(m, 6H), 7.56(m, 1H), 7.67(s, 1H), 7.75(m, 4H) ES$^+$ m/z 524.1 (M−H); HRMS (C28H25F2NO5S): calcd; 526.14943; found; 526.14881 (M+H).

Example 3.102

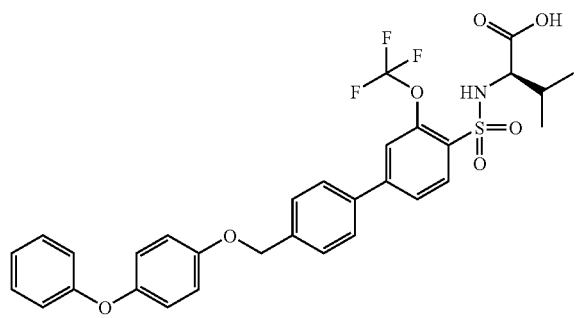

ES$^+$ m/z 614.1 (M−H)−HRMS: 616.16053 (M+H)+; 616.16114 Calc'd

H NMR (400 MHz, DMSO): δ 0.83 (d, 3H, J=6.8 Hz), .088 (d, 3H, J=6.8 Hz), 2.06 (m, 1H), 3.74 (dd, 1H, J=5.6, 10 Hz), 5.18 (s, 2H), 5.35 (d, 1H, J=10 Hz), 6.92 (d, J=8 Hz), 7.00 (d, 2H, J=8 Hz), 7.07 (d, 2H, J=8 Hz), 7.34 (d, 2H, J=8 Hz), 7.61 (d, 2H, J=8 Hz), 7.69 (s, 1H), 7.79 (d, 2H, J=8 Hz), 7.88 (m, 1H), 8.02 (d, 1H, J=8 Hz), 8.24 (m, 1H), 12.70 (s, 1H).

Example 3.103

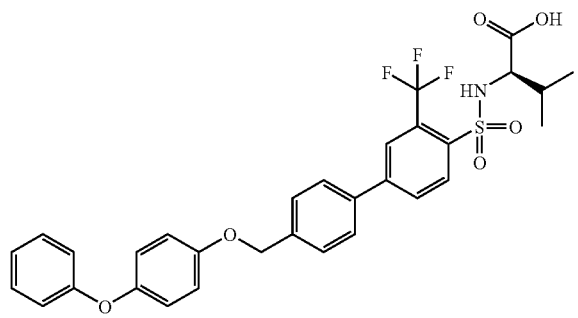

ES$^+$ m/z 598.1 (M−H)−HRMS: 600.16554 (M+H)+; 600.16622 Calc'd

H NMR (400 MHz, DMSO): δ 0.85 (d, 3H, J=6.8 Hz), .0.86 (d, 3H, J=6.8 Hz), 2.05 (m,

Example 3.104

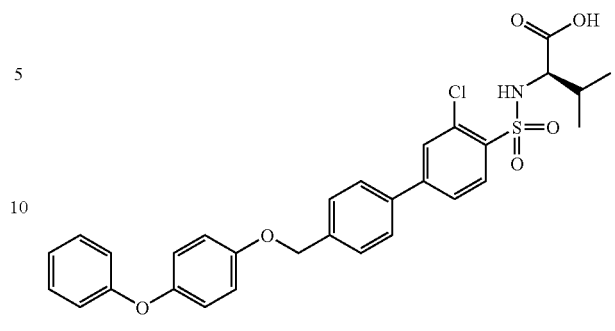

ES$^+$ m/z 564.1 (M−H)−HRMS: 566.13860 (M+H)+; 566.13987 Calc'd

H NMR (400 MHz, DMSO): δ 0.84 (d, 3H, J=6.8 Hz), .0.86 (d, 3H, J=6.8 Hz), 2.02 (m, 1H), 3.57 (dd, 1H, J=6, 9.2 Hz), 5.17 (s, 2H), 6.92 (d, 2H, J=8 Hz), 6.99 (d, 2H, J=8 Hz), 7.07 (m, 3H), 7.33 (m, 2H), 7.59 (d, 2H, J=8 Hz), 7.83 (m, 5H), 7.95 (d, 1H, J=1.6 Hz), 8.03 (d, 1H, J=8 Hz), 8.21 (m, 1H), 12.65 (s, 1H).

Example 3.105

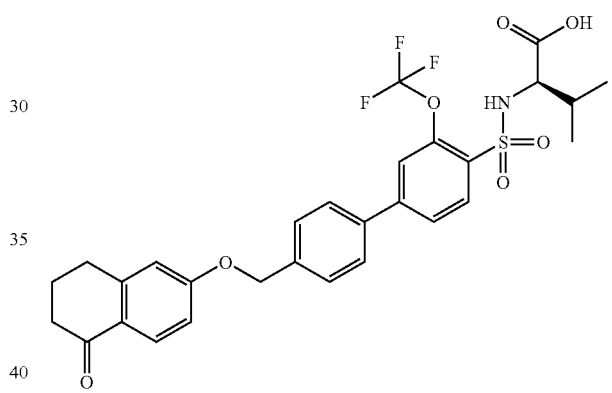

ES$^+$ m/z 590.1 (M−H)−HRMS: 592.16098 (M+H)+; 592.16114 Calc'd $^1$H NMR (400 MHz, DMSO): δ 0.83 (d, 3H, J=6.8 Hz), 0.88 (d, 3H, J=6.8 Hz), 2.05 (m, 3H), 2.53 (t, 2H, J=6 Hz), 2.91 (t, 2H, J=6 Hz), 3.74 (dd, 1H, J=5.6, 10 Hz), 5.28 (s, 2H), 6.98 (m, 2H), 7.60 (d, 2H, J=8 Hz), 7.69 (s, 1H), 7.85 (m, 4H), 8.02 (d, 1H, J=8 Hz), 8.25 (d, 1H, J=8 Hz), 12.70 (s, 1H).

Example 3.106

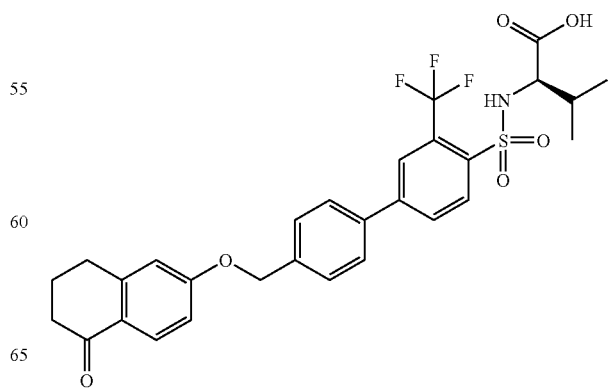

ES+ m/z 574.1 (M−H)−HRMS: 576.16522 (M+H)+; 576.16622 Calc'd

¹H NMR (400 MHz, DMSO): δ 0.85 (d, 3H, J=6.8 Hz), 0.86 (d, 3H, J=6.8 Hz), 2.04 (m, 3H), 2.53 (t, 2H, J=6 Hz), 2.91 (t, 2H, J=6 Hz), 3.63 (dd, 1H, J=6, 10 Hz), 5.29 (s, 2H), 6.98 (m, 2H), 7.61 (d, 2H, J=8 Hz), 7.85 (m, 3H), 8.20 (m, 4H), 12.70 (s, 1H).

Example 3.107

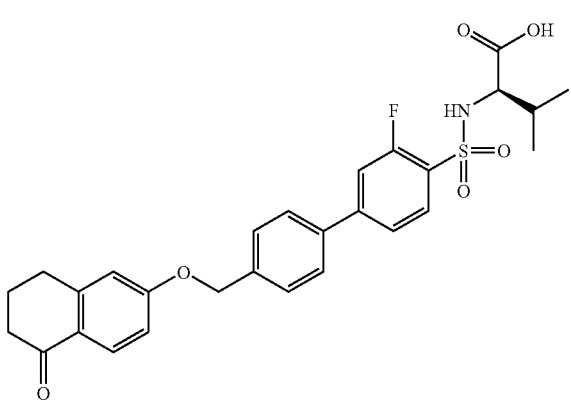

ES+ m/z 524.1 (M−H)−HRMS: 526.16859 (M+H)+; 526.16942 Calc'd

¹H NMR (400 MHz, DMSO): δ 0.84 (d, 3H, J=6.8 Hz), 0.87 (d, 3H, J=6.8 Hz), 2.02 (m, 3H), 2.53 (t, 2H, J=6 Hz), 2.91 (t, 2H, J=6 Hz), 3.66 (dd, 1H, J=6, 9.2 Hz), 5.27 (s, 2H), 6.98 (m, 2H), 7.58 (d, 2H, J=8 Hz), 7.70 (m, 1H), 7.83 (m, 5H), 8.30 (d, 1H, J=10 Hz), 12.65 (s, 1H).

Example 3.108

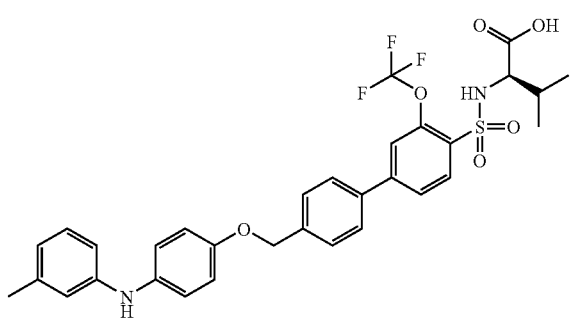

ES+ m/z 629.2 (M−H)−HRMS: 631.17159 (M+H)+; 631.17204 Calc'd

¹H NMR (400 MHz, DMSO): δ 0.83 (d, 3H, J=6.8 Hz), 0.88 (d, 3H, J=6.8 Hz), 2.07 (m, 1H), 2.30 (s, 3H), 3.74 (dd, J=5.6, 9.6 Hz), 5.20 (s, 2H), 6.68 (d, 1H, J=8 Hz), 6.95 (d, 1H, J=8 Hz), 7.06 (m, 4H), 7.62 (d, 2H, J=8 Hz), 7.69 (m, 2H), 7.80 (d, 2H, J=8 Hz), 7.87 (dd, 1H, J=1.6, 8 Hz), 8.03 (d, 1H, J=8 Hz), 8.25 (d, 2H, J=9.2 Hz), 12.70 (s, 1H).

Example 3.109

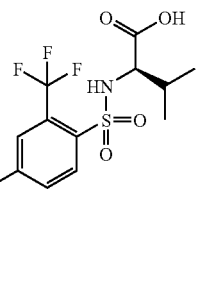

ES+ m/z 613.2 (M−H)−HRMS: 615.17639 (M+H)+; 615.17712 Calc'd

¹H NMR (400 MHz, DMSO): δ 0.85 (d, 3H, J=6.8 Hz), 0.87 (d, 3H, J=6.8 Hz), 2.05 (m, 1H), 2.30 (s, 3H), 3.63 (dd, 1H, J=6, 9.6 Hz), 5.20 (s, 2H), 6.68 (d, 1H, J=8 Hz), 6.95 (d, 1H, J=8 Hz), 7.06 (m, 4H), 7.63 (d, 2H, J=8 Hz), 7.69 (t, 1H, J=8 Hz), 7.87 (d, 2H, J=8 Hz), 8.21 (m, 4H), 12.70 (s, 1H).

Example 3.110

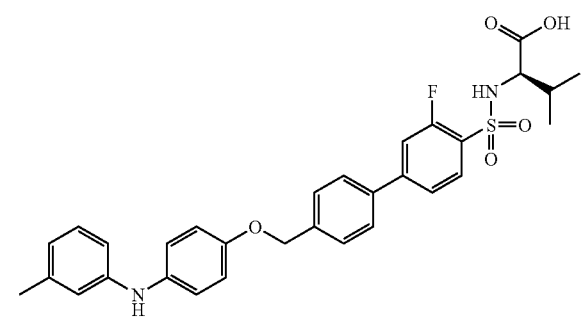

ES+ m/z 563.2 (M−H)−HRMS: 565.18038 (M+H)+; 565.18032 Calc'd

¹H NMR (400 MHz, DMSO): δ 0.84 (d, 3H, J=6.8 Hz), 0.87 (d, 3H, J=6.8 Hz), 2.04 (m, 1H), 2.30 (s, 3H), 3.66 (dd, 1H, J=6, 9.6 Hz), 5.19 (s, 2H), 6.68 (d, 1H, J=8 Hz), 6.95 (d, 1H, J=8 Hz), 7.06 (s, 4H), 7.60 (d, 2H, J=8 Hz), 7.70 (m, 2H), 7.83 (m, 4H), 8.31 (d, 1H, J=9.2 Hz), 12.70 (s, 1H).

Example 3.111

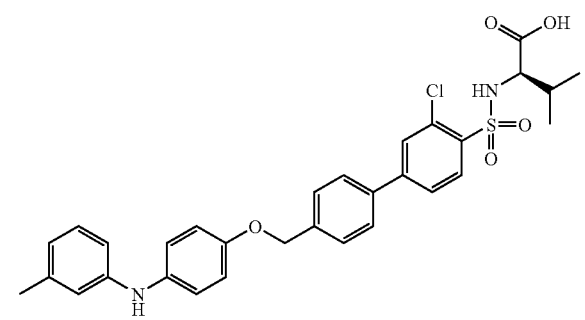

ES+ m/z 579.1 (M−H)−HRMS: 581.15050 (M+H)+; 581.15077 Calc'd

¹H NMR (400 MHz, DMSO): δ 0.84 (d, 3H, J=6.8 Hz), 0.86 (d, 3H, J=6.8 Hz), 2.02 (m, 1H), 2.30 (s, 3H), 3.58 (dd, 1H, J=6.4, 9.6 Hz), 5.20 (s, 2H), 6.68 (d, 1H, J=8 Hz), 6.95 (d, 1H, J=8 Hz), 7.06 (s, 4H), 7.60 (d, 2H, J=8 Hz), 7.62 (d, 2H, J=8 Hz), 7.83 (m, 3H), 7.95 (d, 1H, J=1.6), 8.03 (d, 1H, J=8 Hz), 8.22 (d, 1H, J=9.6 Hz), 12.70 (s, 1H).

Examples 112, 113, 114 were made based on Scheme 5.

Example 3.112

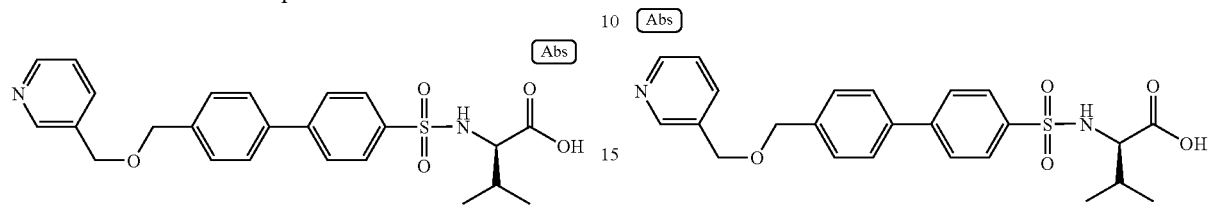

3-Methyl-2-[4'-(pyridin-3-ylmethoxymethyl)-biphenyl-4-sulfonylamino]-butyric acid ¹H NMR (400 MHz, MeOD): δ; ES⁺ m/z (M+H) 455.1; HRMS (M+H) m/z calcd 455.16352; found 455.16317; ($C_{24}H_{26}N_2O_5S$):

Example 3.113

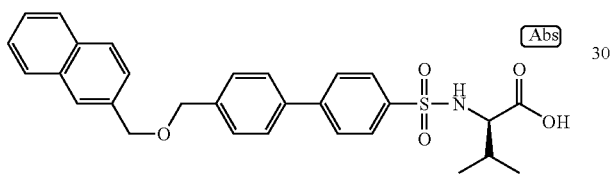

3-Methyl-2-[4'-(naphthalen-2-ylmethoxymethyl)-biphenyl-4-sulfonylamino]-butyric acid ¹H NMR (400 MHz, CDCl₃): δ0.85 (d, 3H), 0.95 (d, 3H), 2.10 (m, 1H), 3.83 (m, 1H), 4.63 (s, 2H), 4.74 (s, 2H), 5.25 (bs, 1H), 7.44-7.55 (m, 7H), 7.65 (d, 2H), 7.82-7.90 (m, 6H); ES⁺ m/z (M−H) 502.1; HRMS (M+H) m/z calcd 504.18392; found 504.18503; ($C_{29}H_{29}NO_5S$):

Example 3.114

3-Methyl-2-[4'-(pyridin-3-ylmethoxymethyl)-biphenyl-4-sulfonylamino]-butyric acid ¹H NMR (400 MHz, DMSO): δ 0.81 (d, 3H), 0.84 (d, 3H), 1.95 (m, 1H), 3.55 (dd, 1H), 4.56 (s, 2H), 4.63 (d, 2H), 7.44 (d, 2H), 7.50 (d, 1H), 7.70 (d, 2H), 7.74 (d, 1H), 7.84 (m, 4H), 8.08 (m, 2H); ES⁺ m/z (M+H) 455.1; HRMS (M+H) m/z calcd 455.16352; found 455.16290; ($C_{24}H_{26}N_2O_5S$).

Example 4

Inhibition of ADAMTS-5 Aggrecanase Activity Using the Biaryl Sulfonamide Compounds of the Present Invention The biaryl sulfonamide compounds of the present invention were tested for their ability to inhibit the aggrecanase activity of ADAMTS-4 (Agg-1) and ADAMTS-5 (Agg-2). The results are shown in Table 1 below, which shows the concentration of the compounds in µM that inhibits 50% of the aggrecanase activity of the enzyme (IC50). The compounds are listed from lowest to highest potency for ADAMTS-5, with the last being the most potent.

TABLE 1

| Compound | IC50 Agg-1 (uM) | Agg-2 (uM) |
|---|---|---|
|  | 0.1 | >200 |

TABLE 1-continued

| Compound | IC50 Agg-1 (uM) | Agg-2 (uM) |
| --- | --- | --- |
| (structure) Chiral | 0.3 | >100 |
| (structure) Chiral | 1.9 | 67.0 |
| (structure) Chiral | 1.1 | 13.0 |
| (structure) Chiral | 1.0 | 12.6 |
| (structure) Chiral | 1.9 | 12.0 |

TABLE 1-continued

| Compound | IC50 Agg-1 (uM) | Agg-2 (uM) |
|---|---|---|
| (4-fluorophenoxymethyl-biphenyl-sulfonyl-valine), Chiral | 1.7 | 11.3 |
| (tetrahydronaphthalenone-oxymethyl-biphenyl-methyl-sulfonyl-valine), Chiral | 0.9 | 11.2 |
| (4-methoxyphenoxymethyl-biphenyl-sulfonyl-valine), Chiral | 1.6 | 10.7 |
| (pyridyloxy-phenoxy-phenoxymethyl-biphenyl-sulfonyl-valine), Chiral | 0.9 | 10.6 |
| (isobutyryl-phenoxymethyl-biphenyl-sulfonyl-valine), Chiral | 0.1 | 8.4 |

TABLE 1-continued

| Compound | IC50 Agg-1 (uM) | Agg-2 (uM) |
|---|---|---|
| Chiral | 0.1 | 8.4 |
| Chiral | 1.2 | 8.2 |
| Chiral | 0.2 | 7.5 |
| Chiral | 0.4 | 7.0 |
| Chiral | 0.2 | 6.6 |

TABLE 1-continued

| Compound | IC50 Agg-1 (uM) | Agg-2 (uM) |
|---|---|---|
| (structure) | 0.4 | 6.5 |
| (structure) | 1.9 | 6.3 |
| (structure) | 1.8 | 5.8 |
| (structure) | 0.6 | 5.4 |
| (structure) | 2.6 | 5.0 |

TABLE 1-continued
| Compound | | IC50 Agg-1 (uM) | Agg-2 (uM) |
|---|---|---|---|
| 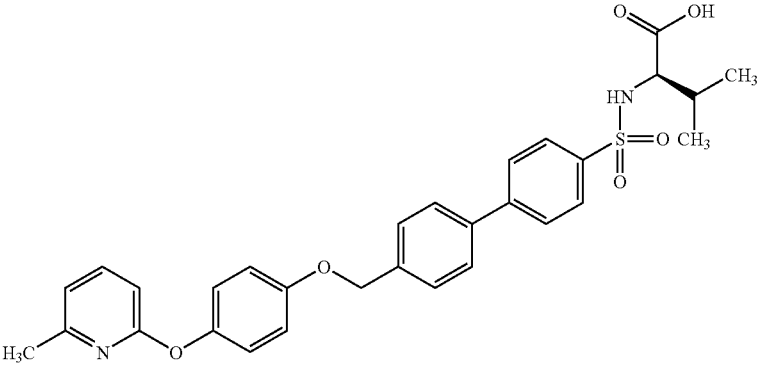 | Chiral | 0.7 | 4.0 |
| 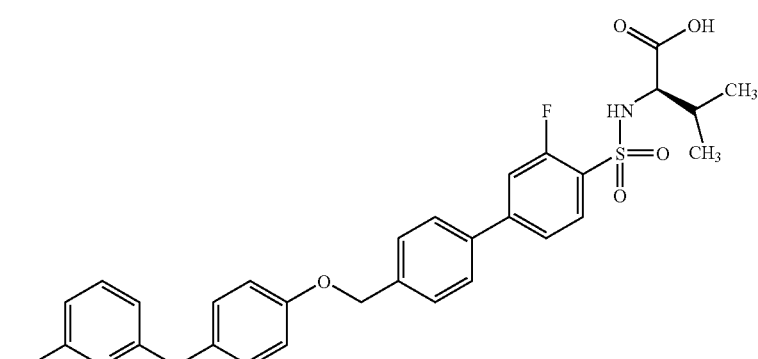 | Chiral | 0.9 | 3.5 |
| 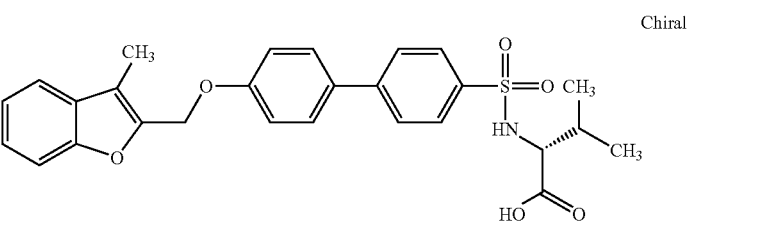 | Chiral | 1.1 | 3.4 |
| 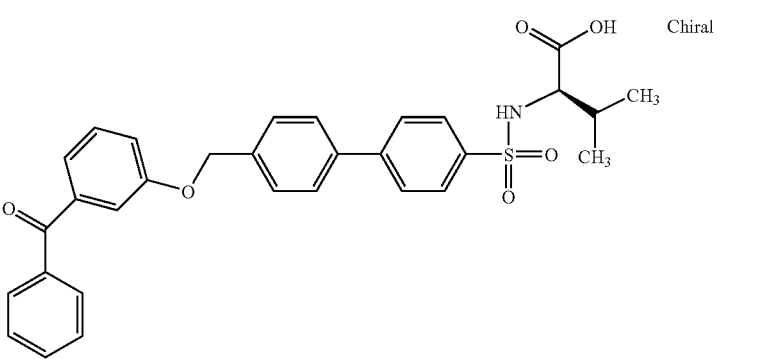 | Chiral | 0.2 | 3.4 |

TABLE 1-continued

| Compound | IC50 Agg-1 (uM) | Agg-2 (uM) |
|---|---|---|
| (Chiral structure) | 0.9 | 3.2 |
| (Chiral structure) | 1.9 | 3.2 |
| (Chiral structure) | 1.4 | 3.0 |
| (Chiral structure) | 0.2 | 2.8 |
| (Chiral structure) | 0.1 | 2.6 |
| (Chiral structure) | 0.1 | 2.5 |

TABLE 1-continued

| Compound | IC50 Agg-1 (uM) | Agg-2 (uM) |
|---|---|---|
| (structure: 4-fluorobenzoyl-phenoxymethyl-biphenyl-sulfonyl-valine, Chiral) | 0.1 | 2.4 |
| (structure: cyclohexyl ketone-phenoxymethyl-biphenyl-sulfonyl-valine, Chiral) | 0.4 | 2.4 |
| (structure: indanyl-oxy-methyl-biphenyl-sulfonyl-valine, Chiral) | 0.4 | 2.4 |
| (structure: benzoyl-phenoxymethyl-biphenyl-sulfonyl-valine, Chiral) | 0.2 | 2.0 |
| (structure: bis(trifluoromethyl)quinolinyloxy-methyl-biphenyl-sulfonyl-valine, Chiral) | 0.2 | 1.8 |
| (structure: cyclopentyl-phenoxymethyl-biphenyl-sulfonyl-valine, Chiral) | 0.4 | 0.8 |

TABLE 1-continued

| Compound | IC50 Agg-1 (uM) | Agg-2 (uM) |
|---|---|---|
| (Chiral structure: biaryl sulfonamide with threonine-like amino acid, biphenyl linked via -O-CH2- to 4-phenoxyphenyl ether) | 0.4 | 0.4 |

A continuous assay was used in which the substrate upon which Agg-1 and Agg-1 acts is a synthetic peptide containing a fluorescent group that is quenched by energy transfer. Cleavage of the peptide by the aggrecanase enzyme results in a large increase in fluorescence. The initial rates of the reaction are compared to the initial rates of reactions containing the biaryl sulfonamide compounds in order to assess the inhibitor potency of the compounds.

The source of enzyme in the assay is purified recombinant human Aggrecanase-2. More specifically, the form used is denoted as Ag2t-Phe$_{628}$-Strep (MW=41,737). This form is truncated relative to the full-length enzyme and contains an affinity tag. Aliquots of this enzyme were stored at −80° C. in 25 mM Tris (pH 8.0), 100 mM NaCl, 5 mM CaCl$_2$, 10 μM ZnCl$_2$, 10% glycerol.

The substrate in the assay is a synthetic peptide that is designed after a portion of brevican, one of the naturally occurring substrates of Aggrecanase-2. This peptide, denoted as WAKB-5, contains the fluorescent group 2-aminobenzoyl (Abz) that is quenched by energy transfer to a 2,4-dinitrophenyl group (Dnp). WAKB-5 (mass=1740) was custom synthesized by AnaSpec, Inc. (San Jose, Calif.) and was >95% pure based on HPLC analysis. WAKB-5 has the sequence of Abz-TESESRGAIY-Dap(Dnp)-KK-NH$_2$ (SEQ ID NO:11). Stock solutions of the substrate were prepared with MilliQ water and aliquots were stored at −80° C. The concentration of this substrate stock was spectrophotometrically determined using the extinction coefficient at 354 nm of 18,172 M$^{-1}$ cm$^{-1}$. The V$_{max}$ and K$_m$ for this enzyme/substrate reaction were determined to be insensitive to DMSO up to at least 10% (v/v).

The assay buffer (pH 7.4) consisted of 50 mM Hepes, 100 mM NaCl, 5 mM CaCl$_2$, 0.1% CHAPS, 5% glycerol. Each well of black polystyrene 96-well or 384-well plates contained a reaction consisting of assay buffer, purified Agg-2 (diluted with assay buffer), and varied concentrations of inhibitor (prepared by serial dilution in DMSO in 96-well polypropylene plates). The plates were then incubated at room temperature for 10 minutes. The enzymatic reactions were initiated by adding substrate to a final concentration of 25 μM and were mixed by pipetting up and down. The initial rates of the cleavage reactions were determined at room temperature with a fluorescence plate reader immediately after substrate addition.

A detailed procedure for 100 μl reactions in a 96-well plate with a final DMSO concentration of 4% and a final enzyme concentration of 0.5 μg/ml (a concentration found to be suitable in most cases) is as follows: (1) the compounds were diluted in a 96-well polypropylene plate with 100% DMSO to 25× final concentration in the assay, (2) the Agg-2 was diluted to 2.083×final concentration (i.e., 1.04 μg/ml) in assay buffer, (3) 48.0 μl of 2.083×Agg-2 was then added to the wells, (4) 4.0 μl of 25× compound was transferred to the assay plate and the reagents were mixed, (5) the plates were incubated for 10 minutes at room temperature, (6) the substrate was diluted to 52.075 μM (2.083× final concentration) with assay buffer, (7) after the 10 minute pre-incubation, 48.0 μl of 2.083× substrate was added and the reagents were mixed well, (8) the reactions were immediately monitored in a fluorescence plate reader at room temperature on the Tecan Safire with the excitation being 316 nm, bandwidth 12 nm and emission being 432 nm and bandwidth 12 nm.

Analysis of the results was conducted by generating a plot of time vs. RFU for each sample. This was used as the "progress curve" of the reaction. The slope for the portion of the progress curve that is most linear was then determined. This slope (RFU/min) was used as the initial rate of the reaction. Plots of the inhibitor concentration vs. the initial cleavage rate were then fit to the following equation: $y=V_{max}*(1-(x^n/(K^n+x^n)))$, whereby x=inhibitor concentration, y=initial rate, V$_{max}$=initial rate in the absence of inhibitor, n=slope factor, and K=IC$_{50}$ for the inhibition curve. Thus the IC50 calculations shown in Table 1 were determined.

Example 5

Inhibition of ADAMTS-5 Aggrecanase Activity Using the Anti-ADAMTS-5 Antibodies of the Present Invention The anti-ADAMTS-5 antibodies of the present invention were tested for their ability to inhibit the aggrecanase activity of ADAMTS-4 (Agg-1) and ADAMTS-5 (Agg-2). The results are shown in Table 2, which shows the characteristics of four monoclonal antibodies generated against recombinant human ADAMTS-5 demonstrated reactivity with ADAMTS-5, but not ADAMTS-4 or Bovine Serum Albumin (BSA) in an ELISA. All antibodies identified rhADAMTS-5 by western blot analysis.

TABLE 2

| Clone | ELISA Full Length RhADAMTS-5 Jun. 01, 2003 | ELISA Truncated RhADAMTS-5 Jun. 01, 2003 | ELISA Full Length RhADAMTS-5 Jun. 11, 2003 | ELISA Truncated RhADAMTS-5 Jun. 11, 2003 | ELISA Full Length RhADAMTS-4 Jun. 11, 2003 |
|---|---|---|---|---|---|
| 17 | 2.522 | 2.645 | 3.194 | 3.348 | 0.067 |
| 18 | 2.432 | 2.666 | 3.107 | 3.406 | 0.043 |
| 34 | 2.589 | 2.654 | 3.258 | 3.328 | 0.068 |
| 41 | 2.622 | 2.627 | 3.422 | 3.538 | 0.276 |

| Clone | ELISA Full Length RhADAMTS-5 Jun. 12, 2003 | ELISA Full Length RhADAMTS-4 Jun. 12, 2003 | ELISA BSA BSA | Western Blot 6/25 Reduced | Western Blot 6/26 non-red. |
|---|---|---|---|---|---|
| 17 | 3.758 | 0.115 | 0.094 | + | + |
| 18 | 3.839 | 0.291 | 0.122 | + | + |
| 34 | 3.786 | 0.207 | 0.064 | + | + |
| 41 | 4.000 | 0.374 | 0.104 | + | + |

While there have been described what are believed to be preferred embodiments of the invention, those skilled in the art will recognize that other and further modifications may be made thereto, e.g. to adapt the invention to various conditions, or other requirements, without departing from the spirit of the present invention as defined by the following claims.

What is claimed is:

1. A method for treating osteoarthritis, comprising administering to a subject in need thereof a therapeutically effective amount of an agent which inhibits ADAMTS-5, wherein the agent is a biaryl sulfonamide compound according to formula I:

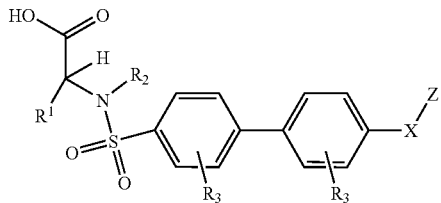

wherein:
$R^1$ is H or unsubstituted C1-C6 alkyl;
$R^2$ is H, C1-C6 alkyl, $(CH_2)_n R^{2'}$, phenyl, or benzyl;
n is 0-6;
$R^{2'}$ is aryl, heteroaryl, cycloalkyl, or heterocycloalkyl;
$R^3$ is, independently with respect to each occurrence, H, halogen, OC(halogen)$_3$, C(halogen)$_3$, alkoxy, or C1-C6 alkyl;
X is selected from $CH_2O$, $OCH_2$, $C(R^3)=C(R^3)_2-C(R^3)_2$, $CH_2NHC(=O)$, $O(C=O)NH$, O, $C(=O)CH_2$, $SO_2CH_2C(=O)NH$, $SO_2NH$, $OC(=O)$, $CH_2S(O)$, and $CH_2S(O)_2$; and
Z is at least one aryl or heteroaryl moiety.

2. The method of claim 1, wherein the agent inhibits the metalloprotease activity of ADAMTS-5.

3. The method of claim 1, wherein the agent inhibits the aggrecanase activity of ADAMTS-5.

4. The method of claim 1, wherein Z is pyridine, pyrimidine, pyrazine, pyridazine, phenyl, naphthalene, furan, thiophene, pyrrole, pyrazole, imidazole, oxazole, isoxazole, thiazole, benzothiazole, quinoline, or isoquinoline, or

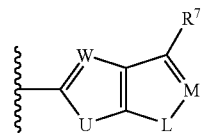

wherein:
U is selected from S, O, $C(R^3)=C(R^3)$, $C(R^3)=N$, and $N(R^4)$;
W is selected from $C(R^3)$, and N;
M is selected from $C(R^3)$, and N;
L is selected from S, O, $C(R^3)=C(R^3)$, $C(R^3)=N$, and $N(R^4)$;
$R^4$ and $R^5$ are, independently with respect to each occurrence, a bond to the other, H, C1-C6 alkyl, or phenyl;
$R^7$ is selected from a bond to $R^3$, H, halogen, C(halogen)$_3$, $NR^4R^5$, $N[(CH_2)_2]_2O$, $N[(CH_2)_2]_2NR^4$, $NHSO_2R^4$, $NR^4C(=O)R^5$, $NHC(=O)OR^4$, $NO_2$, $SO_2NR^4R^5$, $SO_2R^4$, $OR^4$, $C(=O)R^4$, $COOR^4$, $CONR^4R^5$, CN, phenyl, heteroaryl, C1-C6 alkyl, C2-C6 alkenyl, or C2-C6 alkynyl.

5. The method of claim 4 wherein $R^7$ is substituted with $NR^4R^5$, $N[(CH_2)_2]_2O$, $N[(CH_2)_2]_2NR^4$, $NHSO_2R^4$, $NR^4C(=O)R^5$, $NHC(=O)OR^4$, $NO_2$, $SO_2NR^4R^5$, $SO_2R^4$, $C(=O)R^4$, $COOR^4$, $CONR^4R^5$, CN, phenyl, or heteroaryl, wherein $R^8$ is H, phenyl, heteroaryl, or C1-C6 alkyl.

6. The method of claim 5 wherein $R^8$ is substituted with $NR^4R^5$, $N[(CH_2)_2]_2O$, $N[(CH_2)_2]_2NR^4$, $NR^4SO_2R^5$, $NR^4C(=O)R^5$, $NHC(=O)OR^4$, $NO_2$, $SO_2NR^4R^5$, $SO_2R^4$, $C(=O)R^4$, $COOR^4$, $CONR^4R^5$, CN, phenyl, or heteroaryl.

7. The method of claim 1 wherein $R^1$ is H or branched alkyl.

8. The method of claim 1 wherein $R^1$ is isopropyl.

9. The method of claim 1 wherein $R^3$ is halogen, $CF_3$, $OCH_3$, or $CH_3$.

10. The method of claim 1 wherein X is $CH_2O$, $OCH_2$, $C(R^3)=C(R^3)$, or $CH_2NHC(=O)$.

11. The method of claim 4 wherein $R^7$ is $CH_3$, ethyl, isopropyl, $CF_3$, CN, or $OCH_3$.

12. The method of claim 5 wherein $R^8$ is $CH_3$, phenyl, and benzyl.

13. The method of claim 1 wherein Z is bicyclic.

14. The method of claim 6 wherein $R^8$ is $CH_3$, phenyl, or benzyl.

15. A method for modulating the activity of ADAMTS-5 comprising contacting ADAMTS-5 with a biaryl sulfonamide compound according to formula I:

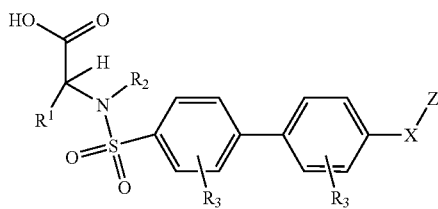

wherein:
$R^1$ is H or unsubstituted C1-C6 alkyl;
$R^2$ is H, C1-C6 alkyl, $(CH_2)_nR^{2'}$, phenyl, or benzyl;
n is 0-6;
$R^{2'}$ is aryl, heteroaryl, cycloalkyl, or heterocycloalkyl;
$R^3$ is, independently with respect to each occurrence, H, halogen, $OC(halogen)_3$, $C(halogen)_3$, alkoxy, or C1-C6 alkyl;
X is selected from $CH_2O$, $OCH_2$, $C(R^3)=C(R^3)$, $C(R^3)_2-C(R^3)_2$, $CH_2NHC(=O)$, $O(C=O)NH$, O, $C(=O)CH_2$, $SO_2CH_2C(=O)NH$, $SO_2NH$, $OC(=O)$, $CH_2S(O)$, and $CH_2S(O)_2$; and
Z is at least one aryl or heteroaryl moiety.

16. The method of claim 15, wherein Z is pyridine, pyrimidine, pyrazine, pyridazine, phenyl, naphthalene, furan, thiophene, pyrrole, pyrazole, imidazole, oxazole, isoxazole, thiazole, benzothiazole, quinoline, or isoquinoline, or

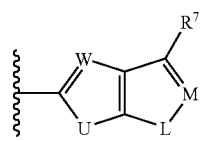

wherein:
U is selected from S, O, $C(R^3)=C(R^3)$, $C(R^3)=N$, and $N(R^4)$;
W is selected from $C(R^3)$, and N;
M is selected from $C(R^3)$, and N;
L is selected from S, O, $C(R^3)=C(R^3)$, $C(R^3)=N$, and $N(R^4)$;
$R^4$ and $R^5$ are, independently with respect to each occurrence, a bond to the other, H, C1-C6 alkyl, or phenyl;
$R^7$ is selected from a bond to $R^3$, H, halogen, $C(halogen)_3$, $NR^4R^5$, $N[(CH_2)_2]_2O$, $N[(CH_2)_2]_2NR^4$, $NHSO_2R^4$, $NR^4C(=O)R^5$, $NHC(=O)OR^4$, $NO_2$, $SO_{NR}{}^4R^5$, $SO_2NR^4R^5$, $SO_2R^4$, $OR^4$, $C(=O)R^4$, $COOR^4$, $CONR^4R^5$, CN, phenyl, heteroaryl, C1-C6 alkyl, C2-C6 alkenyl, or C2-C6 alkynyl.

17. The method of claim 16 wherein $R^7$ is substituted with $NR^4R^5$, $N[(CH_2)_2]_2O$, $N[(CH_2)_2]_2NR^4$, $NHSO_2R^4$, $NR^4C(=O)R^5$, $NHC(=O)OR^4$, $NO_2$, $SO_2NR^4R^5$, $SO_2R^4$, $OR^8$, $C(=O)R^4$, $COOR^4$, $CONR^4R^5$, CN, phenyl, or heteroaryl, wherein $R^8$ is H, phenyl, heteroaryl, or C1-C6 alkyl.

18. The method of claim 17 wherein $R^8$ is substituted with $NR^4R^5$, $N[(CH_2)_2]_2O$, $N[(CH_2)_2]_2NR^4$, $NR^4SO_2R^5$, $NR^4C(=O)R^5$, $NHC(=O)OR^4$, $NO_2$, $SO_2NR^4R^5$, $SO_2R^4$, $C(=O)R^4$, $COOR^4$, $CONR^4R^5$, CN, phenyl, or heteroaryl.

19. The method of claim 15 wherein $R^1$ is H or branched alkyl.

20. The method of claim 15 wherein $R^1$ is isopropyl.

21. The method of claim 15 wherein $R^3$ is halogen, $CF_3$, $OCH_3$, or $CH_3$.

22. The method of claim 15 wherein X is $CH_2O$, $OCH_2$, $C(R^3)=C(R^3)$, or $CH_2NHC(=O)$.

23. The method of claim 16 wherein $R^7$ is $CH_3$, ethyl, isopropyl, $CF_3$, CN, or $OCH_3$.

24. The method of claim 17 wherein $R^8$ is $CH_3$, phenyl, and benzyl.

25. The method of claim 15 wherein Z is bicyclic.

26. The method of claim 15, wherein the activity is metalloproteinase activity.

27. The method of claim 26, wherein the activity is aggrecanase activity.

28. The method of claim 1 or 15, wherein the biaryl sulfonamide compound is selected from the group consisting of

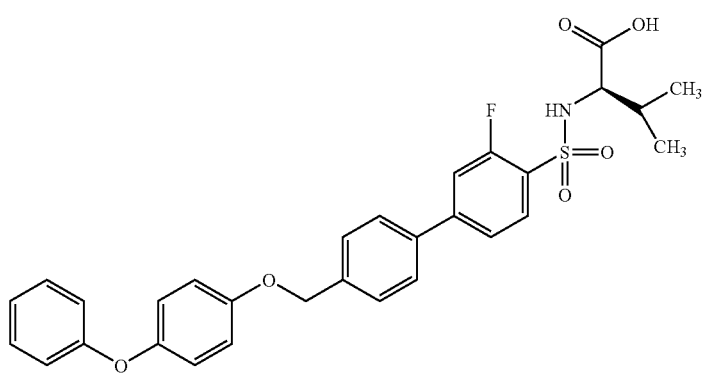

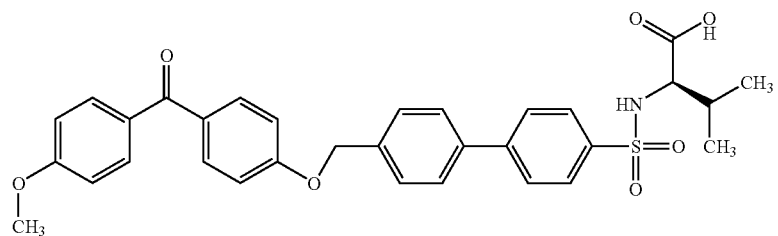
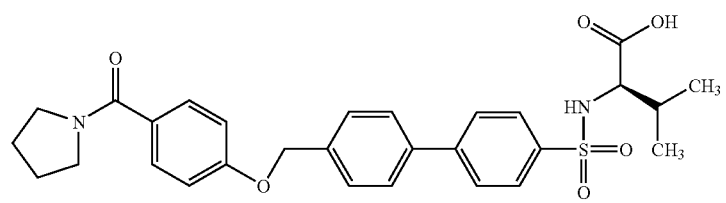
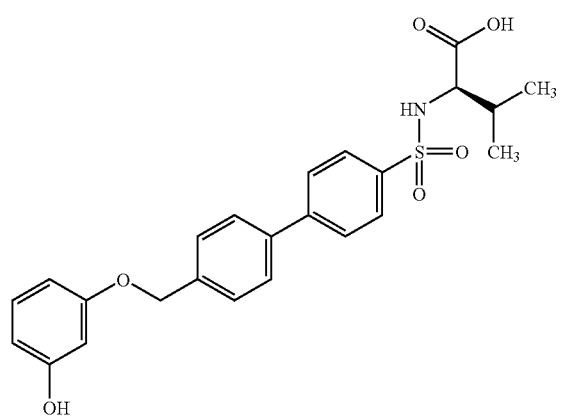
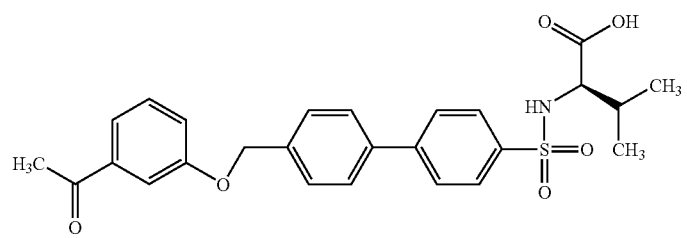
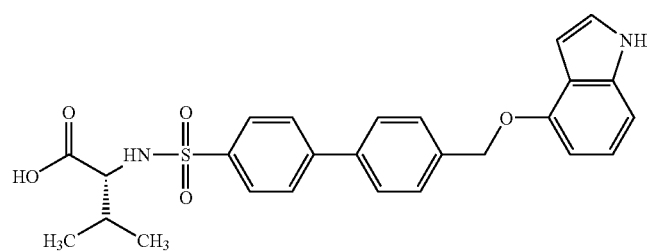
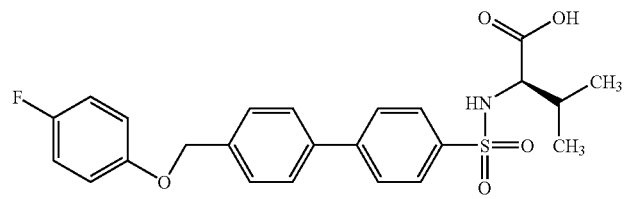

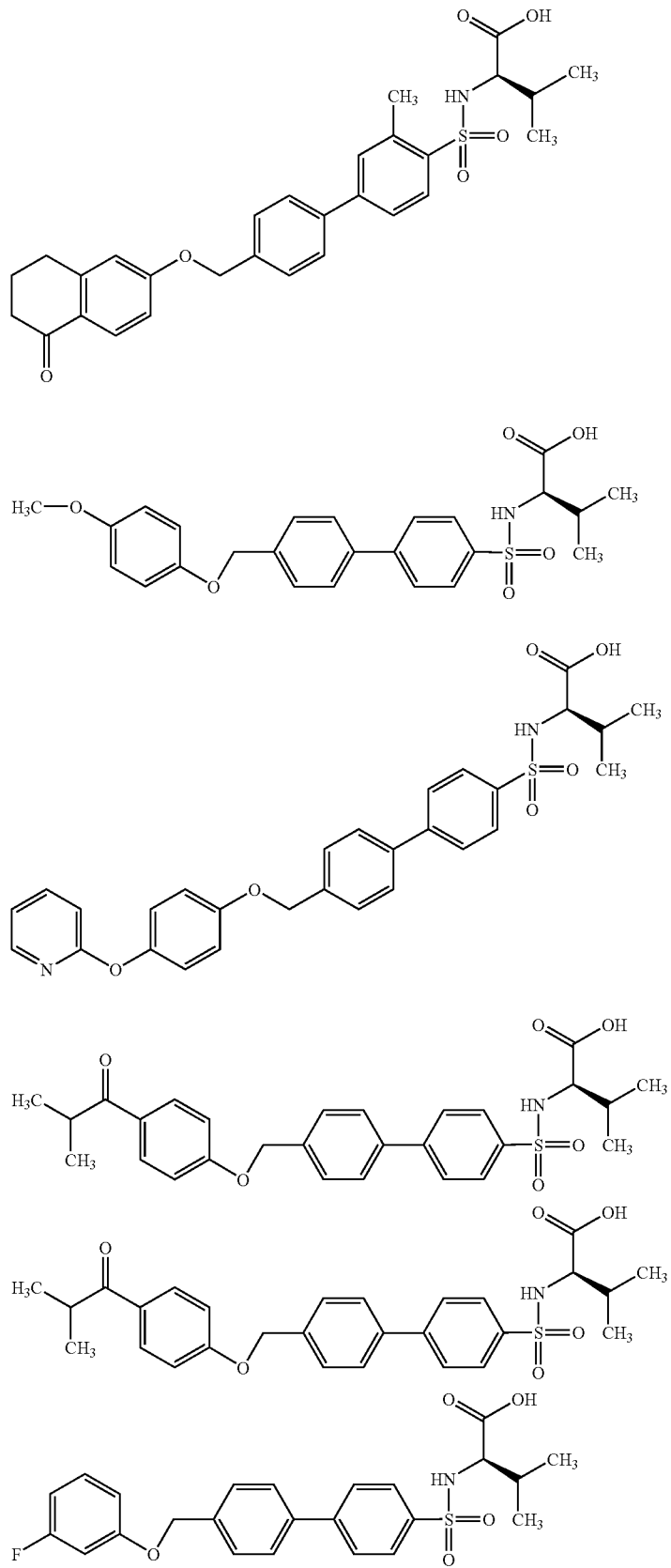

-continued
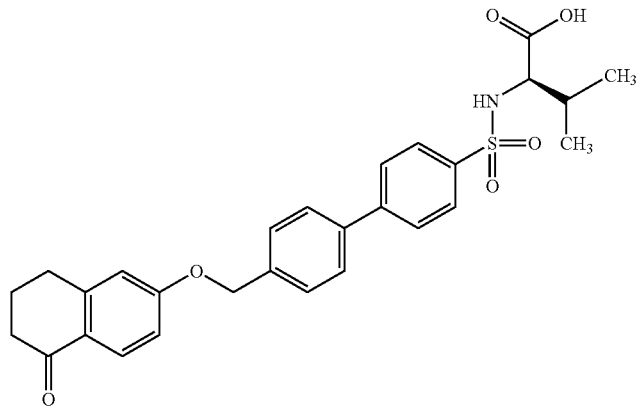
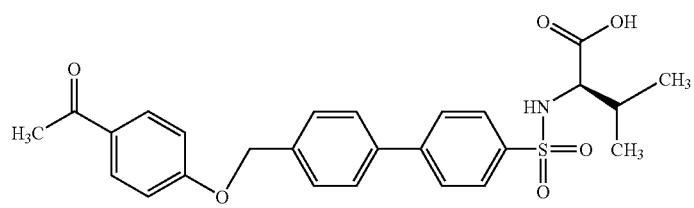
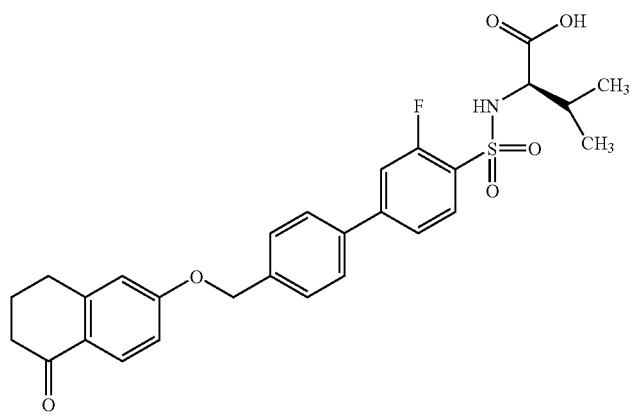
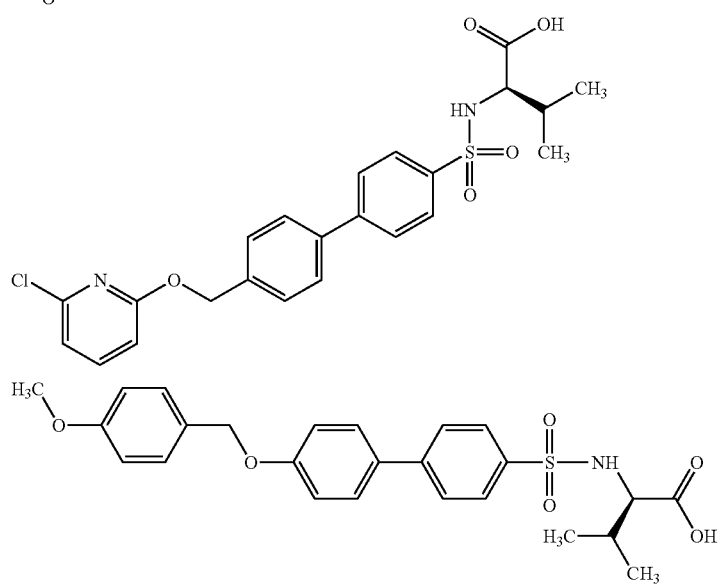

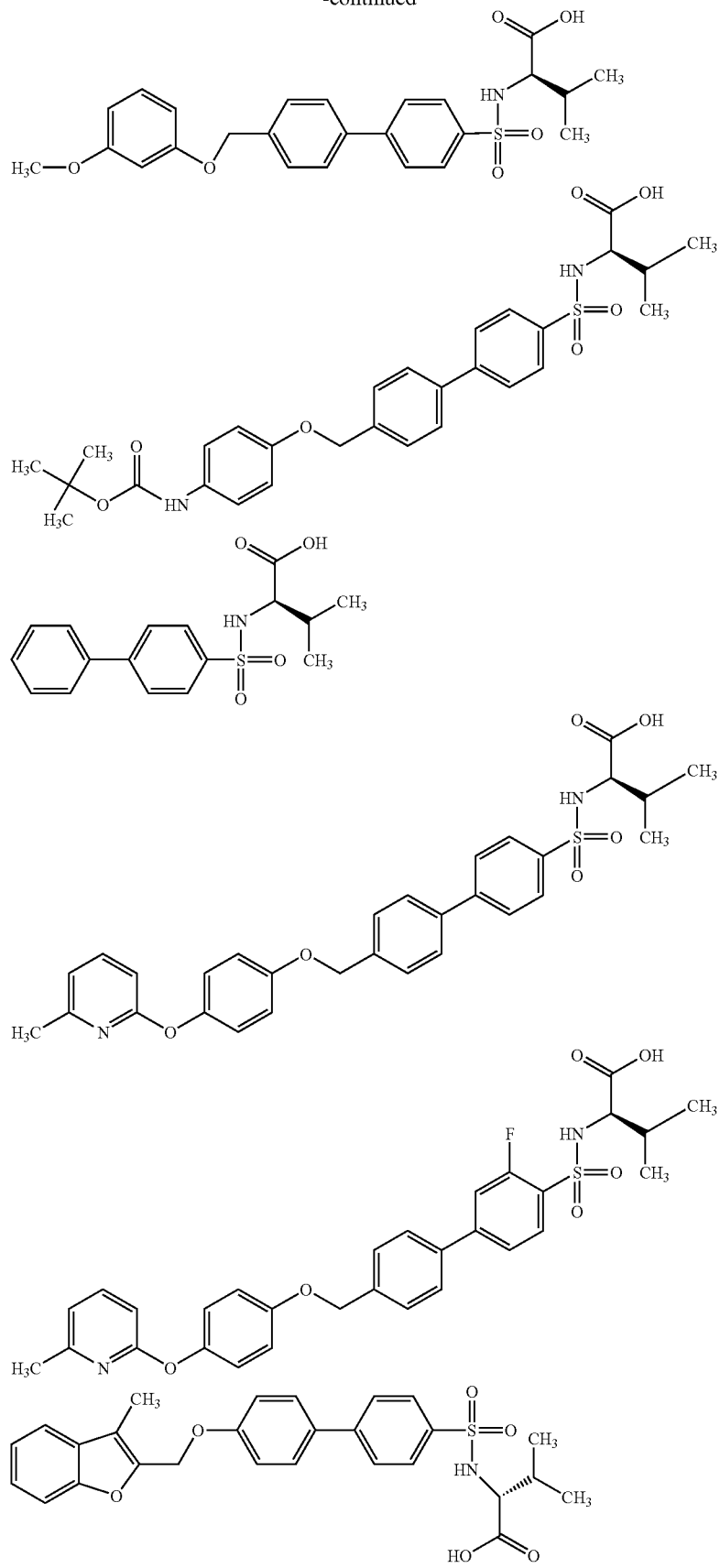

-continued
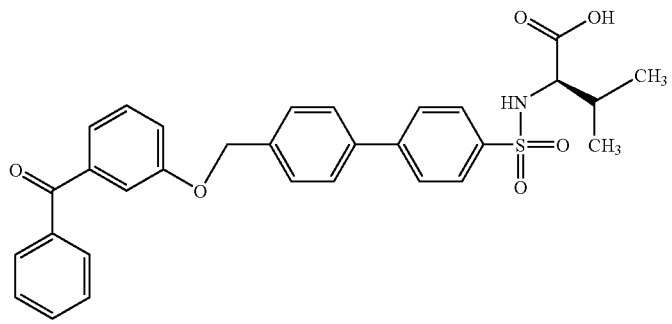
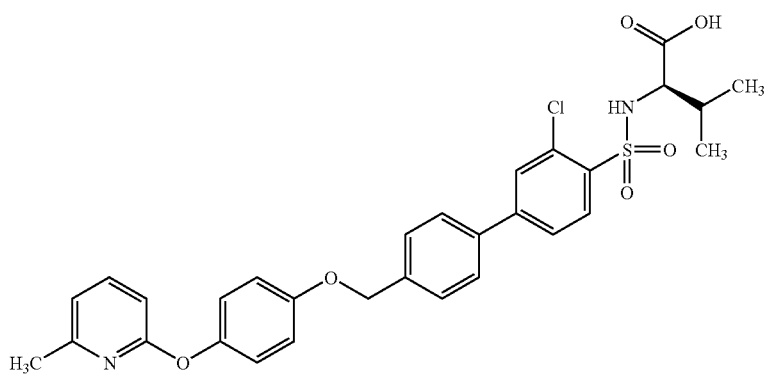
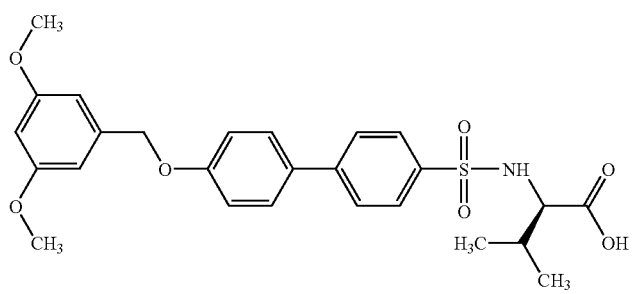
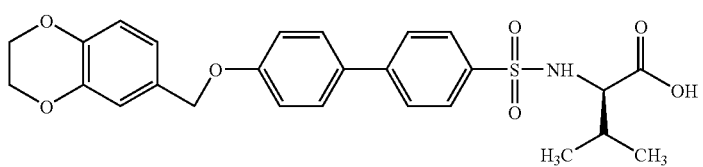
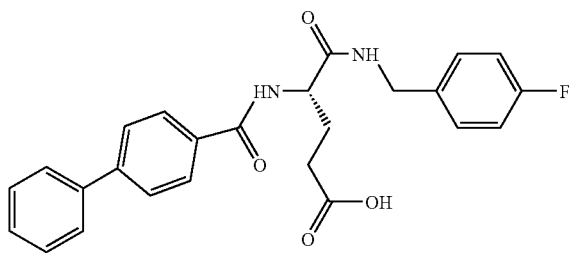
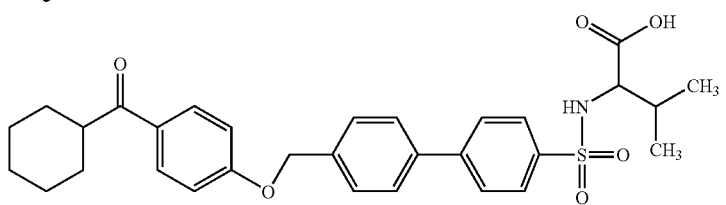

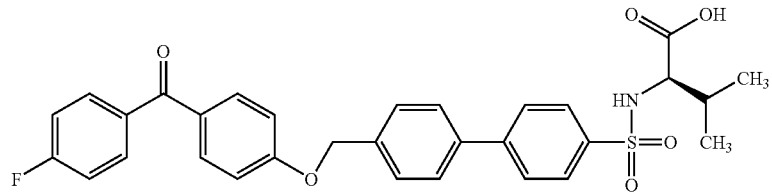
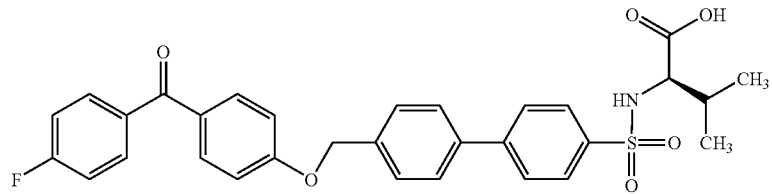
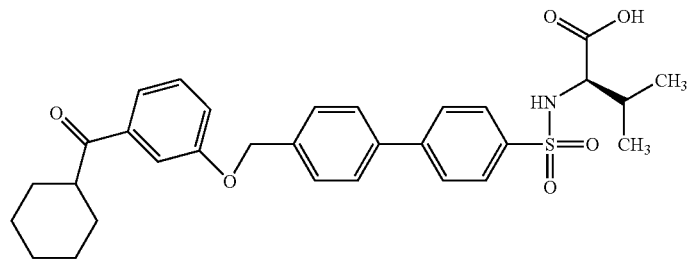
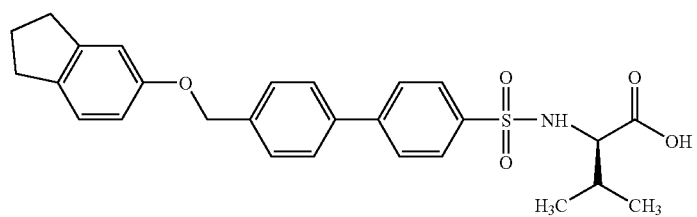
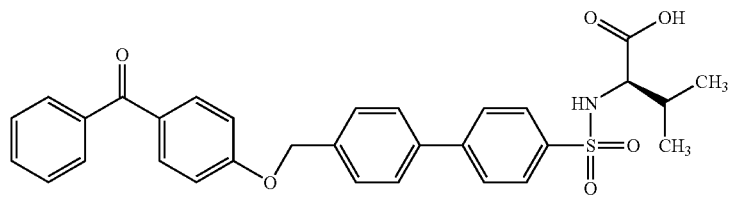
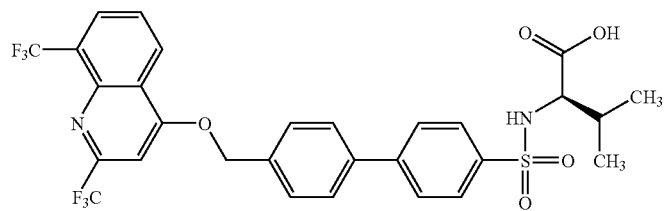
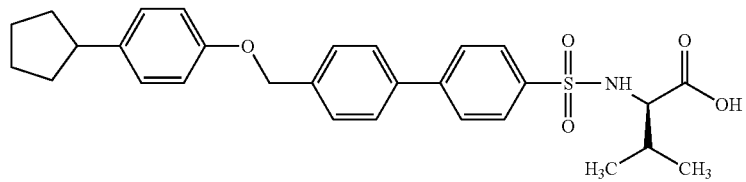

-continued
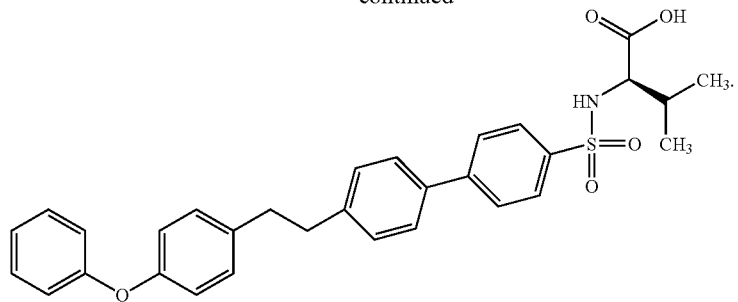
29. The method of claim 18, wherein $R^8$ is $CH_3$, phenyl, or benzyl.
* * * * *

UNITED STATES PATENT AND TRADEMARK OFFICE
CERTIFICATE OF CORRECTION

PATENT NO.        : 7,390,833 B2
APPLICATION NO.   : 10/983981
DATED             : June 24, 2008
INVENTOR(S)       : Elisabeth A. Morris et al.

It is certified that error appears in the above-identified patent and that said Letters Patent is hereby corrected as shown below:

COLUMN 1:

Line 28, "2" should read --two--.

COLUMN 2:

Line 67, "particularly" should read --particular--.

COLUMN 3:

Line 55, "form" should read --from--.

COLUMN 5:

Line 47, "CH3," should read --$CH_3$,--.

COLUMN 8:

Line 5, "form" should read --from--.

COLUMN 10:

Line 18, "may" should read --may be--.

COLUMN 14:

Line 53, "thefinal" should read --the final--.

COLUMN 16:

Line 6, "resulted" should read --resulted in--.

COLUMN 17:

Line 60, "a boronate ester." should read --(a boronate ester).--.

UNITED STATES PATENT AND TRADEMARK OFFICE
CERTIFICATE OF CORRECTION

| | |
|---|---|
| PATENT NO. | : 7,390,833 B2 |
| APPLICATION NO. | : 10/983981 |
| DATED | : June 24, 2008 |
| INVENTOR(S) | : Elisabeth A. Morris et al. |

It is certified that error appears in the above-identified patent and that said Letters Patent is hereby corrected as shown below:

COLUMN 19:

Line 19, "$^1$The" should read --1 The--.

COLUMN 30:

Line 1, "art recognized" should read --art-recognized--.

COLUMN 31:

Line 50, "would" should read --wound--; and
    Line 58, "Alternatively" should read --Alternatively,--.

COLUMN 32:

Line 33, "ADAMTS5" should read --ADAMTS-5--;
    Line 36, "ADAMTS5" should read --ADAMTS-5--;
    Line 52, "ADAMTS5" should read --ADAMTS-5--.

COLUMN 33:

Line 53, "art recognized" should read --art-recognized--.

COLUMN 35:

Line 45, "[is this $\gamma$ or $\propto$]" should be deleted.

COLUMN 36:

Line 8, "doe" should read --due--.

COLUMN 38:

Line 45, "(m, 4 H" should read --(m, 4H).--; and
    Line 53, "heat" should read --heated--.

UNITED STATES PATENT AND TRADEMARK OFFICE
CERTIFICATE OF CORRECTION

PATENT NO. : 7,390,833 B2
APPLICATION NO. : 10/983981
DATED : June 24, 2008
INVENTOR(S) : Elisabeth A. Morris et al.

It is certified that error appears in the above-identified patent and that said Letters Patent is hereby corrected as shown below:

COLUMN 39:

Line 20, "IN NaOH" should read --1N NaOH--; and
Line 59, "heat" should read --heated--.

COLUMN 40:

Line 61, "heat" should read --heated--.

COLUMN 42:

Line 46, "heat" should read --heated--; and
Line 63, "heat" should read --heated--.

COLUMN 43:

Line 11, "cool" should read --cooled--;
Line 48, "heat" should read --heated--; and
Line 64, "(3 mL)" should read --(3 mL).--.

COLUMN 52:

Line 32, "heat" should read --heated--; and
Line 48, "heat" should read --heated-- and "cool" should read --cooling--.

COLUMN 53:

Line 33, "D-$^2$-[$^{4'}$-(Benzofuran-2-yl-" should read --D-2-[4'-(Benzofuran-2-yl- --; and
Line 41, "Step 5C: D-$^2$-[$^{4'}$-(Benzofuran-2-ylmethoxy)-biphenyl-4-" should read --D-2-[4'-(Benzofuran-2-ylmethoxy)-biphenyl-4- --.

UNITED STATES PATENT AND TRADEMARK OFFICE
CERTIFICATE OF CORRECTION

| | |
|---|---|
| PATENT NO. | : 7,390,833 B2 |
| APPLICATION NO. | : 10/983981 |
| DATED | : June 24, 2008 |
| INVENTOR(S) | : Elisabeth A. Morris et al. |

It is certified that error appears in the above-identified patent and that said Letters Patent is hereby corrected as shown below:

COLUMN 59:

Line 45, "heat" should read --heated--.

COLUMN 67:

Line 14, "cool" should read --cooling--.

COLUMN 68:

Line 43, "cool" should read --cooling--.

COLUMN 69:

Line 25, "N-[(4'-ethyny-1," should read --N-[(4'-ethynyl-1,--.

COLUMN 70:

Line 30, "cool" should read --cooled--.

COLUMN 89:

Line 48, "heat" should read --heated--;
Line 49, "cool" should read --cooled--;
Line 54, "cool" should read --cooled--; and
Line 65, "purification." should read --purification--.

COLUMN 90:

Line 10, "heat" should read --heated--; and
Line 60, "heat" should read --heated--.

COLUMN 121:

Line 54, "$C(R^3)=C(R^3)_2-$" should read --$C(R^3)=C(R^3)$, $C(R^3)_2-$ --.

UNITED STATES PATENT AND TRADEMARK OFFICE
CERTIFICATE OF CORRECTION

PATENT NO. : 7,390,833 B2
APPLICATION NO. : 10/983981
DATED : June 24, 2008
INVENTOR(S) : Elisabeth A. Morris et al.

It is certified that error appears in the above-identified patent and that said Letters Patent is hereby corrected as shown below:

COLUMN 122:

Line 54, "$SO_2R^4$, C(=O)" should read --$SO_2R^4$, $OR^8$, C(=O)--.

COLUMN 124:

Line 13, "$SO_{NR}{}^4R^5$," should be deleted; and
Line 38, "and" should read --or--.

Signed and Sealed this

Tenth Day of February, 2009

JOHN DOLL
*Acting Director of the United States Patent and Trademark Office*

SEQUENCE LISTING

```
<160> NUMBER OF SEQ ID NOS: 11

<210> SEQ ID NO 1
<211> LENGTH: 7
<212> TYPE: PRT
<213> ORGANISM: Murine

<400> SEQUENCE: 1

Phe Thr Val Ala His Glu Ile
  1               5

<210> SEQ ID NO 2
<211> LENGTH: 56
<212> TYPE: PRT
<213> ORGANISM: Murine

<400> SEQUENCE: 2

Gly His Leu Leu Gly Leu Ser His Asp Asp Ser Lys Phe Cys Glu Glu
  1               5                  10                  15

Asn Phe Gly Thr Thr Glu Asp Lys Arg Leu Met Ser Ser Ile Leu Thr
              20                  25                  30

Ser Ile Asp Ala Ser Lys Pro Trp Ser Lys Cys Thr Ser Ala Thr Ile
          35                  40                  45

Thr Glu Phe Leu Asp Asp Gly His
      50                  55

<210> SEQ ID NO 3
<211> LENGTH: 8
<212> TYPE: PRT
<213> ORGANISM: Murine

<400> SEQUENCE: 3

Gly Asn Cys Leu Leu Asp Leu Pro
  1               5

<210> SEQ ID NO 4
<211> LENGTH: 20
```

-continued

```
<212> TYPE: DNA
<213> ORGANISM: Artificial Sequence
<220> FEATURE:
<222> LOCATION:
<223> OTHER INFORMATION: Primer

<400> SEQUENCE: 4
tgttcaccca aagcaactac                                               20

<210> SEQ ID NO 5
<211> LENGTH: 19
<212> TYPE: DNA
<213> ORGANISM: Artificial Sequence
<220> FEATURE:
<222> LOCATION:
<223> OTHER INFORMATION: Primer

<400> SEQUENCE: 5
tagaggagag gagaggagg                                                19

<210> SEQ ID NO 6
<211> LENGTH: 20
<212> TYPE: DNA
<213> ORGANISM: Artificial Sequence
<220> FEATURE:
<222> LOCATION:
<223> OTHER INFORMATION: Primer

<400> SEQUENCE: 6
gtgaaccaca tggactttgg                                               20

<210> SEQ ID NO 7
<211> LENGTH: 20
<212> TYPE: DNA
<213> ORGANISM: Artificial Sequence
<220> FEATURE:
<222> LOCATION:
<223> OTHER INFORMATION: Primer

<400> SEQUENCE: 7
tcgtagcaaa cacccacctg                                               20

<210> SEQ ID NO 8
<211> LENGTH: 20
<212> TYPE: DNA
<213> ORGANISM: Artificial Sequence
<220> FEATURE:
<222> LOCATION:
<223> OTHER INFORMATION: Primer

<400> SEQUENCE: 8
cgaccctcaa gaacttttgc                                               20

<210> SEQ ID NO 9
<211> LENGTH: 20
<212> TYPE: DNA
<213> ORGANISM: Artificial Sequence
<220> FEATURE:
<222> LOCATION:
<223> OTHER INFORMATION: Primer

<400> SEQUENCE: 9
ctcaggccca aatgtcaagt                                               20

<210> SEQ ID NO 10
<211> LENGTH: 20
<212> TYPE: DNA
```

```
<213> ORGANISM: Artificial Sequence
<220> FEATURE:
<222> LOCATION:
<223> OTHER INFORMATION: Primer

<400> SEQUENCE: 10
cgtcatgaga aaggccaagt                                          20

<210> SEQ ID NO 11
<211> LENGTH: 14
<212> TYPE: PRT
<213> ORGANISM: Artificial Sequence
<220> FEATURE:
<221> NAME/KEY: misc_feature
<222> LOCATION: 1
<223> OTHER INFORMATION: Xaa is o-aminobenzoic acid
<220> FEATURE:
<221> NAME/KEY: misc_feature
<222> LOCATION: 12
<223> OTHER INFORMATION: Xaa is 3-(2,4-dinitrophenyl)-(2,3-diamino
      propionic acid)

<400> SEQUENCE: 11

Xaa Thr Glu Ser Glu Ser Arg Gly Ala Ile Tyr Xaa Lys Lys
  1               5                  10
```